US012215333B2

(12) United States Patent
Parks et al.

(10) Patent No.: US 12,215,333 B2
(45) Date of Patent: Feb. 4, 2025

(54) PESTICIDAL GENES AND METHODS OF USE

(71) Applicant: AgBiome, Inc., Durham, NC (US)

(72) Inventors: Jessica Parks, Apex, NC (US); Kira Bulazel Roberts, Bahama, NC (US); Rebecca E. Thayer, Morrisville, NC (US)

(73) Assignee: AgBiome, Inc., Durham, NC (US)

( * ) Notice: Subject to any disclaimer, the term of this patent is extended or adjusted under 35 U.S.C. 154(b) by 0 days.

(21) Appl. No.: 18/466,111

(22) Filed: Sep. 13, 2023

(65) Prior Publication Data

US 2024/0043865 A1 Feb. 8, 2024

Related U.S. Application Data

(62) Division of application No. 17/398,575, filed on Aug. 10, 2021, now Pat. No. 11,898,153, which is a division of application No. 16/426,332, filed on May 30, 2019, now Pat. No. 11,118,190, which is a division of application No. 15/530,267, filed on Dec. 16, 2016, now Pat. No. 10,358,654.

(60) Provisional application No. 62/412,619, filed on Oct. 25, 2016, provisional application No. 62/270,742, filed on Dec. 22, 2015.

(51) Int. Cl.
| | |
|---|---|
| *C12N 15/82* | (2006.01) |
| *A01N 37/46* | (2006.01) |
| *A01N 63/50* | (2020.01) |
| *C07K 14/195* | (2006.01) |
| *C07K 14/32* | (2006.01) |
| *C07K 14/325* | (2006.01) |

(52) U.S. Cl.
CPC ......... *C12N 15/8286* (2013.01); *A01N 37/46* (2013.01); *A01N 63/50* (2020.01); *C07K 14/195* (2013.01); *C07K 14/32* (2013.01); *C07K 14/325* (2013.01); *C12N 15/8261* (2013.01); *C12N 15/8285* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 5,596,071 | A * | 1/1997 | Payne | C12N 15/82 |
| | | | | 435/252.5 |
| 5,616,495 | A | 4/1997 | Payne et al. | |
| 5,824,792 | A | 10/1998 | Payne et al. | |
| 6,077,937 | A | 6/2000 | Payne et al. | |
| 9,567,381 | B2 | 2/2017 | Kennedy et al. | |
| 10,059,959 | B2 * | 8/2018 | Baum | C12N 15/8286 |
| 2014/0007292 | A1 * | 1/2014 | Cerf | C12N 15/8286 |
| | | | | 435/254.11 |
| 2014/0283208 | A1 | 9/2014 | Abad et al. | |
| 2017/0175134 | A1 | 6/2017 | Parks et al. | |

FOREIGN PATENT DOCUMENTS

| | | |
|---|---|---|
| CA | 2878263 | 1/2014 |
| CL | 2019/002973 | 1/2020 |
| CN | 102395679 | 3/2012 |
| CN | 102421905 | 4/2012 |
| EA | 20327 B1 | 10/2014 |
| RU | 2478710 C2 | 4/2013 |
| WO | WO 2007/107302 | 9/2007 |
| WO | WO 2010/027793 | 3/2010 |
| WO | WO 2010/027799 | 3/2010 |
| WO | WO 2014/008054 | 1/2014 |
| WO | WO 2014/159836 | 10/2014 |

OTHER PUBLICATIONS

Heckel, David G. "Learning the ABCs of Bt: ABC transporters and insect resistance to Bacillus thuringiensis provide clues to a crucial step in toxin mode of action." Pesticide Biochemistry and Physiology 104.2 (2012): 103-110. (Year: 2012).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
GenBank Accession No. AAA68598.1, "delta endotoxin, partial [Bacillus thuringiensis]," Jun. 21, 1995, via internet at https://www.ncbi.nlm.nih.gov/protein/862637/.
GenBank Accession No. AAB46298.1, Sequence 8 from U.S. Pat. No. 5,596,071, Feb. 7, 1997, via internet at https://www.ncbi.nlm.nih.gov/protein/AAB46298.1.

(Continued)

*Primary Examiner* — Weihua Fan
(74) *Attorney, Agent, or Firm* — Womble Bond Dickinson (US) LLP

(57) ABSTRACT

Compositions having pesticidal activity and methods for their use are provided. Compositions include isolated and recombinant polypeptides having pesticidal activity, recombinant and synthetic nucleic acid molecules encoding the polypeptides, DNA constructs and vectors comprising the nucleic acid molecules, host cells comprising the vectors, and antibodies to the polypeptides. Polynucleotide sequences encoding the polypeptides can be used in DNA constructs or expression cassettes for transformation and expression in organisms of interest. The compositions and methods provided are useful for producing organisms with enhanced pest resistance or tolerance. Transgenic plants and seeds comprising a nucleotide sequence that encodes a pesticidal protein of the invention are also provided. Such plants are resistant to insects and other pests. Methods are provided for producing the various polypeptides disclosed herein, and for using those polypeptides for controlling or killing a pest. Methods and kits for detecting polypeptides of the invention in a sample are also included.

20 Claims, 9 Drawing Sheets

Specification includes a Sequence Listing.

(56) References Cited

OTHER PUBLICATIONS

GenBank Accession No. AAB55098.1, "Sequence 8 from U.S. Pat. No. 5,616,495," May 14, 1997, via internet at https://www.ncbi.nlm.nih.gov/protein/AAB55098.1.
GenBank Accession No. AAE12606.1, "Sequence 8 from U.S. Pat. No. 5,824,792," Sep. 29, 1999, via internet at https://www.ncbi.nlm.nih.gov/protein/ME 12606.1.
GenBank Accession No. AAE44105.1, "Sequence 8 from U.S. Pat. No. 6,077,937," Feb. 14, 2001, via internet at https://www.ncbi.nlm.nih.gov/protein/AAE44105.1.
GenBank Accession No. ABW88931.1, "Cry5B-like protein [Bacillus thuringiensis YBT-1518]," Nov. 17, 2008, via internet at https://www.ncbi.nlm.nih.gov/protein/159137703.1.
GenBank Accession No. AEH31432.1, "Cry1D-like protein, partial [Bacillus thuringiensis]," Jul. 25, 2016, via internet at https://www.ncbi.nlm.nih.gov/protein/335355188.
GenBank Accession No. AFJ04417.1, "Cry5B-like delta endotoxin [Bacillus thuringiensis]," May 8, 2012, via internet at https://www.ncbi.nlm.nih.gov/protein/AFJ04417.1.
GenBank Accession No. AHA70031.1, "pesticidal crystal protein cry5Ba [Bacillus thuringiensis YBT-1518]," Feb. 13, 2015, via internet at https://www.ncbi.nlm.nih.gov/protein/AHA70031.1.
GenBank Accession No. ATK48782.1, "Sequence 432 from U.S. Pat. No. 9,567,381," Oct. 13, 2017, via internet at https://www.ncbi.nlm.nih.gov/protein/ATK48782.1.
GenBank Accession No. ATK48783.1, "Sequence 433 from U.S. Pat. No. 9,567,381," Oct. 13, 2017, via internet at https://www.ncbi.nlm.nih.gov/protein/ATK48783.1.
GenBank Accession No. ATK48784.1, "Sequence 434 from U.S. Pat. No. 9,567,381," Oct. 13, 2017, via internet at https://www.ncbi.nlm.nih.gov/protein/ATK48784.1.
NCBI Reference Sequence: WP_000405159.1, "hypothetical protein [Bacillus thuringiensis]," May 14, 2013, via internet at https://www.ncbi.nlm.nih.gov/protein/WP_000405159.1.
NCBI Reference Sequence: WP_020294695.1, "monalysin family beta-barrel pore-forming toxin [*Pseudomonas* sp. CF161]," Jun. 20, 2019.
NCBI Reference Sequence: WP_023521141.1, "pesticidal crystal protein cry5Ba [Bacillus thuringiensis]," Jan. 27, 2016, via internet at https://www.ncbi.nlm.nih.gov/protein/WP_023521141.1.
UniProtKB/Swiss-Prot (GenBank) Accession No. Q45712.1, "RecName: Full=Pesticidal crystal protein Cry5Ba; AltName: Full= 140 kDa crystal protein; AltName: Full=Crystaline entomocidal protoxin; AltName: Full=Insecticidal delta-endotoxin CryVB(a)," Jul. 18, 2018, via internet https://www.ncbi.nlm.nih.gov/protein/Q45712.1.
Appell et al., "Nucleic Acids from A to Z: A Concise Encyclopedia," Wiley-VCH Verlag GmbH & Co. KGaA, Oct. 30, 2007, 19:17, edited by S. Muller, translated from English, M. Bionom, Laboratory of Knowledge, 2013, 413 pp, p. 216, machine translation.
Argôlo-Filho et al., "*Bacillus thuringiensis* Is an Environmental Pathogen and Host-Specificity Has Developed as an Adaptation to Human-Generated Ecological Niches," Insects, 2014, 5:62-91.
Devyatkin et al., "Crop Entomology," Electronic lecture course, 2012, 301 pp, including machine translation.
Guo et al., "Protein tolerance to random amino acid change," PNAS, Jun. 22, 2004, 101(25):9205-9210.
Heckel, "Learning the ABCs of Bt: ABC transporters and insect resistance to Bacillus thuringiensis provide clues to a crucial step in toxin mode of action," Pesticide Biochemistry and Physiology, Oct. 2012, 104(2):103-110.
Mozolevskaya et al., "Forest Entomology: manual for university students," published by "the Academy," 2010, ISBN 978-5-7695-5997, pp. 105-213, including machine translation.
Popova et al., "Chemical plant protectants: manual/SPbGTURP," Saint Petersburg, 2009, 96 pages, pp. 8-12, including machine translation.
Invitation to Pay Additional Fees of PCT/US2016/067146 mailed May 19, 2017, 11 pp.
International Preliminary Report on Patentability of PCT/US2016/067146 mailed Jul. 5, 2018, 12 pp.
International Search Report and Written Opinion of PCT/US2016/067146 mailed Aug. 9, 2017, 16 pp.

\* cited by examiner

FIGURE 1

| | b | m,b | s,b | s,m,b | s,m | s |
|---|---|---|---|---|---|---|
| 0-50% | - | - | - | - | +/- | +/- |
| 50-80% | - | - | - | +/- | +/- | +/- |
| 80-100% | +/- | +/- | +/- | +/- | + | + | increasing size phenotype →

Increasing mortality →

FIGURE 2

```
                            20                          40                          60
                             |                           |                           |
APG01037.1  ----------  ----------  -MPIQEKFSF  SELSAVGSNP  NSVREKFKER  FGVLPDGIAV 39
APG01037.0  ----------  ----------  LMPIQEKFSF  SELSAVGSNP  NSVREKFKER  FGVLPDGIAV 40
APG01037.4  ----------  ----------  -MPIQEKFSF  SELSAVGSNP  NSVREKFKER  FGVLPDGIAV 39
APG01037.5  ----------  ----------  -MPIQEKFSF  SELSAVGSNP  NSVREKFKER  FGVLPDGIAV 39
APG01037.6  ----------  ----------  -MPIQEKFSF  SELSAVGSNP  NSVREKFKER  FGVLPDGIAV 39
APG01037.7  ----------  ----------  -MPIQEKFSF  SELSAVGSNP  NSVREKFKER  FGVLPDGIAV 39
APG01037.8  ----------  ----------  -MPIQEKFSF  SELSAVGSNP  NSVREKFKER  FGVLPDGIAV 39
APG00556.0  MLFLVLSFRG  FLLKNQRSV   LMPIQEKFSF  SELSAVGSNP  NSVREKFKER  FGILPDGIAV 60
APG00556.1  ----------  ----------  -MPIQEKFSF  SELSAVGSNP  NSVREKFKER  FGILPDGIAV 39
APG00623.0  ----------  ----------  -MPIQEKFSF  SELSAVGSNP  NSIREKFKER  FGVLPDGIAV 39

80                         100                         120
                             |                           |                           |
APG01037.1  NSETYYNAEK  PAITEQYGHP  CYKTLGEFTY  QIGNGQPPSE  AILGSNYAVN  HGDEEASISL 99
APG01037.0  NSETYYNAEK  PAITEQYGHP  CYKTLGEFTY  QIGNGQPPSE  AILGSNYAVN  HGDEEASISL 100
APG01037.4  NSETYYNAEK  PAITEQYGHP  CYKTLGEFTY  QIGNGQPPSE  AILGSNYAVN  HGDEEASISL 99
APG01037.5  NSETYYNAEK  PAITEQYGHP  CYKTLGEFTY  QIGNGQPPSE  AILGSNYAVN  HGDEEASISL 99
APG01037.6  NSETYYNAEK  PAITEQYGHP  CYKTLGEFTY  QIGNGQPPSE  AILGSNYAVN  HGDEEASISL 99
APG01037.7  NSETYYNAEK  PAITEQYGHP  CYKTLGEFTY  QIGNGQPPSE  AILGSNYAVN  HGDEEASISL 99
APG01037.8  NSETYYNAEK  PAITEQYGHP  CYKTLGEFTY  QIGNGQPPSE  AILGSNYAVN  HGDEEASISL 99
APG00556.0  NSETYYDAVK  PAITEQYGHP  CYKTLGEFTY  QVGNGKPPSE  AILGSNYAVN  HGDEEASISL 120
APG00556.1  NSETYYDAVK  PAITEQYGHP  CYKTLGEFTY  QVGNGKPPSE  AILGSNYAVN  HGDEEASISL 99
APG00623.0  NSETYYDAAK  PAITEQYGHP  CYKTLGEFTY  QIGNGKPPSE  AILGSNYAVN  HGDEEASISL 99

140                         160                         180
                             |                           |                           |
APG01037.1  SVQGNWTETK  TWSSQTTTGL  TISSKFTLEG  VFESGAEFSV  STTVGESSST  SISRSASSTV 159
APG01037.0  SVQGNWTETK  TWSSQTTTGL  TISSKFTLEG  VFESGAEFSV  STTVGESSST  SISRSASSTV 160
APG01037.4  SVQGNWTETK  TWSSQTTTGL  TISSKFTLEG  VFESGAEFSV  STTVGESSTT  SISRSASSTV 159
APG01037.5  SVQGNWTETK  TWSSQTTTGL  TISSKFTLEG  VFESGAEFSV  STTVGETSST  SISRSASSTV 159
APG01037.6  SVQGNWTETK  TWSSQTTTGL  TISSKFTLEG  VFESGAEFSV  STTVGESKST  SISRSASSTV 159
APG01037.7  SVQGNWTETK  TWSSQTTTGL  TISSKFTLEG  VFESGAEFSV  STTVGESSSE  SISRSASSTV 159
APG01037.8  SVQGNWTETK  TWSSQTTTGL  TISSKFTLEG  VFESGAEFSV  STTVGESSST  SESRSASSTV 159
APG00556.0  SVQGNWTETK  TWSSETTTGL  TISSKFTLEG  VFESGAEFSV  STTVGESSST  SVSRSASSTV 180
APG00556.1  SVQGNWTETK  TWSSETTTGL  TISSKFTLEG  VFESGAEFSV  STTVGESSST  SVSRSASSTV 159
APG00623.0  SVQGNWTETK  TWSSQTTTGL  TISSKFTLEG  VFESGAEFSV  STTVGESSST  SISRSASSTV 159

200                         220                         240
                             |                           |                           |
APG01037.1  TVNVPPRSKK  KISMVGTMKQ  ETMNFQAPLS  VQGSFGANFP  RKVEDHYFWF  LGADNVLNST 219
APG01037.0  TVNVPPRSKK  KISMVGTMKQ  ETMNFQAPLS  VQGSFGANFP  RKVEDHYFWF  LGADNVLNST 220
APG01037.4  TVNVPPRSKK  KISMVGTMKQ  ETMNFQAPLS  VQGSFGANFP  RKVEDHYFWF  LGADNVLNST 219
APG01037.5  TVNVPPRSKK  KISMVGTMKQ  ETMNFQAPLS  VQGSFGANFP  RKVEDHYFWF  LGADNVLNST 219
APG01037.6  TVNVPPRSKK  KISMVGTMKQ  ETMNFQAPLS  VQGSFGANFP  RKVEDHYFWF  LGADNVLNST 219
APG01037.7  TVNVPPRSKK  KISMVGTMKQ  ETMNFQAPLS  VQGSFGANFP  RKVEDHYFWF  LGADNVLNST 219
APG01037.8  TVNVPPRSKK  KISMVGTMKQ  ETMNFQAPLS  VQGSFGANFP  RKVEDHYFWF  LGADNVLNST 219
APG00556.0  TVIVPPRSKK  KVSMVGTMKQ  ETMNFQAPLS  VQGSFGANFP  RKVEDHYFWF  LGADNVLNST 240
APG00556.1  TVIVPPRSKK  KVSMVGTMKQ  ETMNFQAPLS  VQGSFGANFP  RKVEDHYFWF  LGADNVLNST 219
APG00623.0  TVNVPPRSKK  KISMVGTMKQ  ETMNFQAPLS  VQGSFGANFP  RKVEDHYFWF  LGADNVLNST 219

260
                             |
APG01037.1  TGTLTGKIKN  TAVFDVQTEV  GAAEPLDAKT  PV 251
APG01037.0  TGTLTGKIKN  TAVFDVQTEV  GAAEPLDAKT  PV 252
APG01037.4  TGTLTGKIKN  TAVFDVQTEV  GAAEPLDAKT  PV 251
APG01037.5  TGTLTGKIKN  TAVFDVQTEV  GAAEPLDAKT  PV 251
APG01037.6  TGTLTGKIKN  TAVFDVQTEV  GAAEPLDAKT  PV 251
APG01037.7  TGTLTGKIKN  TAVFDVQTEV  GAAEPLDAKT  PV 251
APG01037.8  TGTLTGKIKN  TAVFDVQTEV  GAAEPLDAKT  PV 251
APG00556.0  TGTLTGKIKN  TAVFNVQTEV  GAAEPLDAKT  PV 272
APG00556.1  TGTLTGKIKN  TAVFNVQTEV  GAAEPLDAKT  PV 251
APG00623.0  TGTLTGKIKN  TAVFDVQTEV  GAAEPLDAKT  PV 251
```

FIGURE 8

Pairwise sequence comparison showing global percent identity relationship of each recited sequence.

| | APG01037.1 | APG01037.0 | APG01037.4 | APG01037.5 | APG01037.6 | APG01037.7 | APG01037.8 | APG00556.0 | APG00556.1 | APG00632.0 |
|---|---|---|---|---|---|---|---|---|---|---|
| APG01037.1 | | 99.60 | 99.60 | 99.60 | 99.60 | 99.60 | 99.60 | 88.60 | 96.02 | 98.41 |
| APG01037.0 | 99.60 | | 99.21 | 99.21 | 99.21 | 99.21 | 99.21 | 88.97 | 95.63 | 98.02 |
| APG01037.4 | 99.60 | 99.21 | | 99.20 | 99.20 | 99.20 | 99.20 | 88.24 | 95.62 | 98.01 |
| APG01037.5 | 99.60 | 99.21 | 99.20 | | 99.20 | 99.20 | 99.20 | 88.24 | 95.62 | 98.01 |
| APG01037.6 | 99.60 | 99.21 | 99.20 | 99.20 | | 99.20 | 99.20 | 88.24 | 95.62 | 98.01 |
| APG01037.7 | 99.60 | 99.21 | 99.20 | 99.20 | 99.20 | | 99.20 | 88.24 | 95.62 | 98.01 |
| APG01037.8 | 99.60 | 99.21 | 99.20 | 99.20 | 99.20 | 99.20 | | 88.60 | 95.62 | 98.01 |
| APG00556.0 | 88.60 | 88.97 | 88.24 | 88.24 | 88.24 | 88.24 | 88.60 | | 92.28 | 88.97 |
| APG00556.1 | 96.02 | 95.63 | 95.62 | 95.62 | 95.62 | 95.62 | 96.02 | 92.28 | | 96.41 |
| APG00632.0 | 98.41 | 98.02 | 98.01 | 98.01 | 98.01 | 98.01 | 98.01 | 88.97 | 96.41 | |

FIGURE 9

SEQUENCE LISTING

```
Sequence total quantity: 218
SEQ ID NO: 1        moltype = AA  length = 1202
FEATURE             Location/Qualifiers
REGION              1..1202
                    note = Unknown organism from environmental sample
source              1..1202
                    mol_type = protein
                    organism = unidentified
SEQUENCE: 1
```

```
LLQQKKSVSK LSMGGTNMNP YQNKNEYEIL NASQKNLNIS NSYPRYPMEN SPKQLLQSTN   60
YKDWLNMCQQ NQQYGGDFET FIDTAELSAY TIVVGTMLTG FGLTTPIGLV LISFGTLIPV  120
LFPNQDQSNT WSDFITQTKD IIKKEIASTY INNANQILNR SFNVINTYYN HLKTWENNPN  180
PQNTQDVRTQ IQLVHYHFQN VIPELVNSCP PNDCDYYNIL VLSSYAQVAN LHLTVLNQAV  240
KFEAYLKNNR QFDYLEPLPT AIDYYPVLTK AIEDYTNHCV TTYKKGLNLI KTTPDSNLNG  300
NINWNTYNTY RTKMTTSVLD LVALFPNYDV GKYPIGIQSE LTREIYQVLN FEESPYKYYD  360
FQYQEDSLTR RPHLFTWLDS LNFYEKAQTT PNNFFTSHYN MPHYTLDNNS QKSSVFGNQN  420
VTDRLKSLDL ATNIYIFLLN VTSLDNKYLN DYNNISKMDF FITNGTRLLE KDLTAGSGQI  480
NSDVNKNIFG LPILKRRENQ GIPTLFPTYD NYSHILSFIK SLSIPATYKT QVYTFAWTHS  540
SVDPKNIIYT HLTTQIPAVK ATLLGTATTE LSKVVQGPGH TGGDLIDFKD RFKIICQHSN  600
SQQSYFVRIR YASNGSANTR ATINLSIPGV AELDMALNPT FSGTDYTNLK YKDFQYLEFL  660
DEVKFGPNQN LSLVFNRSDV YTNTTVLIDK IEFLPITRSI REDREKQKLE TVQQIINTFF  720
VNPIKNTLKS EIADYDIDQA AKLVESLSEE IYPQKKIILL DEIKYAKQLS YSRNLLQNGD  780
FNDLIDWKTS NDITIKTGNP IFKASYLDMS ETRNTLFPTY IHQKIDESKL KPYTRYQVRG  840
FVRRSKDLEL TVTRYGKEID VIMNVPNDLV FMQSNSSYGD YNSCETLPNP VMDQGNSTLL  900
TDGYATDISS CQPKLGKKHV TCHDRHPFDF HIDTGELDIN TNLGIWVLFK ISNPDGYATL  960
GNLEVIEEGP LTGEALAHVK QKEKKWKQHM EKKRMETQQA YDPAKQAVDA LFTNTQGEEL 1020
HYHTTLDQIK NADHLVRSIP YVHHAWLPDV PGMNDDLYNN LKVRIEQARY LYDARNVITN 1080
GDFAQGLTGW HATGKAAVQQ MDGASVLVLS NWSAEVSQNL HVQDHCGYVL RVIAKKEGPG 1140
KGYVTMMDCN GNQETLTFTS CEEGYMTKTV EVFPESDRVR IEIGETEGTF YIESIELLCM 1200
KG                                                                1202

SEQ ID NO: 2            moltype = AA   length = 1185
FEATURE                 Location/Qualifiers
REGION                  1..1185
                        note = variant of native sequence
source                  1..1185
                        mol_type = protein
                        organism = synthetic construct
SEQUENCE: 2
MNPYQNKNEY EILNASQKNL NISNSYPRYP MENSPKQLLQ STNYKDWLNM CQQNQQYGGD   60
FETFIDTAEL SAYTIVVGTM LTGFGLTTPI GLVLISFGTL IPVLFPNQDQ SNTWSDFITQ  120
TKDIIKKEIA STYINNANQI LNRSFNVINT YYNHLKTWEN NPNPQNTQDV RTQIQLVHYH  180
FQNVIPELVN SCPPNDCDYY NILVLSSYAQ VANLHLTVLN QAVKFEAYLK NNRQFDYLEP  240
LPTAIDYYPV LTKAIEDYTN HCVTTYKKGL NLIKTTPDSN LNGNINWNTY NTYRTKMTTS  300
VLDLVALFPN YDVGKYPIGI QSELTREIYQ VLNFEESPYK YYDFQYQEDS LTRRPHLFTW  360
LDSLNFYEKA QTTPNNFFTS HYNMPHYTLD NNSQKSSVFG NQNVTDRLKS LDLATNIYIF  420
LLNVTSLDNK YLNDYNNISK MDFFITNGTR LLEKDLTAGS GQINSDVNKN IFGLPILKRR  480
ENQGIPTLFP TYDNYSHILS FIKSLSIPAT YKTQVYTFAW THSSVDPKNI IYTHLTTQIP  540
AVKATLLGTA TTELSKVVQG PGHTGGDLID FKDRFKIICQ HSNSQQSYFV RIRYASNGSA  600
NTRATINLSI PGVAELDMAL NPTFSGTDYT NLKYKDFQYL EFLDEVKFGP NQNLSLVFNR  660
SDVYTNTTVL IDKIEFLPIT RSIREDREKQ KLETVQQIIN TFFVNPIKNT LKSEIADYDI  720
DQAAKLVESL SEEIYPQKKI ILLDEIKYAK QLSYSRNLLQ NGDFNDLIDW KTSNDITIKT  780
GNPIFKASYL DMSETRNTLF PTYIHQKIDE SKLKPYTRYQ VRGFVRRSKD LELTVTRYGK  840
EIDVIMNVPN DLVFMQSNSS YGDYNSCETL PNPVMDQGNS TLLTDGYATD ISSCQPKLGK  900
KHVTCHDRHP FDFHIDTGEL DINTNLGIWV LFKISNPDGY ATLGNLEVIE EGPLTGEALA  960
HVKQKEKKWK QHMEKKRMET QQAYDPAKQA VDALFTNTQG EELHYHTTLD QIKNADHLVR 1020
SIPYVHHAWL PDVPGMNDDL YNNLKVRIEQ ARYLYDARNV ITNGDFAQGL TGWHATGKAA 1080
VQQMDGASVL VLSNWSAEVS QNLHVQDHCG YVLRVIAKKE GPGKGYVTMM DCNGNQETLT 1140
FTSCEEGYMT KTVEVFPESD RVRIEIGETE GTFYIESIEL LCMKG                 1185

SEQ ID NO: 3            moltype = AA   length = 679
FEATURE                 Location/Qualifiers
REGION                  1..679
                        note = variant of native sequence
source                  1..679
                        mol_type = protein
                        organism = synthetic construct
SEQUENCE: 3
MNPYQNKNEY EILNASQKNL NISNSYPRYP MENSPKQLLQ STNYKDWLNM CQQNQQYGGD   60
FETFIDTAEL SAYTIVVGTM LTGFGLTTPI GLVLISFGTL IPVLFPNQDQ SNTWSDFITQ  120
TKDIIKKEIA STYINNANQI LNRSFNVINT YYNHLKTWEN NPNPQNTQDV RTQIQLVHYH  180
FQNVIPELVN SCPPNDCDYY NILVLSSYAQ VANLHLTVLN QAVKFEAYLK NNRQFDYLEP  240
LPTAIDYYPV LTKAIEDYTN HCVTTYKKGL NLIKTTPDSN LNGNINWNTY NTYRTKMTTS  300
VLDLVALFPN YDVGKYPIGI QSELTREIYQ VLNFEESPYK YYDFQYQEDS LTRRPHLFTW  360
LDSLNFYEKA QTTPNNFFTS HYNMPHYTLD NNSQKSSVFG NQNVTDRLKS LDLATNIYIF  420
LLNVTSLDNK YLNDYNNISK MDFFITNGTR LLEKDLTAGS GQINSDVNKN IFGLPILKRR  480
ENQGIPTLFP TYDNYSHILS FIKSLSIPAT YKTQVYTFAW THSSVDPKNI IYTHLTTQIP  540
AVKATLLGTA TTELSKVVQG PGHTGGDLID FKDRFKIICQ HSNSQQSYFV RIRYASNGSA  600
NTRATINLSI PGVAELDMAL NPTFSGTDYT NLKYKDFQYL EFLDEVKFGP NQNLSLVFNR  660
SDVYTNTTVL IDKIEFLPI                                               679

SEQ ID NO: 4            moltype = AA   length = 677
FEATURE                 Location/Qualifiers
REGION                  1..677
                        note = Unknown organism from environmental sample
source                  1..677
                        mol_type = protein
                        organism = unidentified
```

```
SEQUENCE: 4
MHAFYLRMEE FSMTTIENND ENKNESIDES SSTSVSNASS RYPLANNQTT VLQNINYKDY    60
LRVTEGGDSK FLGNPETLIS SSSVQTGIGI VGEILGALGV PFAGAIAGFY SFIVGLLWPS   120
STVSIWEMIM EQVEELVNQK ITEHAREEAL AKLRGLGDGL DVYQRSLENW LENRNNTKAR   180
SVVATQFIAL ELDFVSSIPS FAVGGQEVPL LAIYAQAANL HLLLLRDASI FGEEWGFTSG   240
EISTFYNRQM TRTAQYSDHC VRWYNNGLDK LKDTSAASWL RYHQFRRNMT LLVLDLVALF   300
PSYDTHTYQI KTTAQLTRDV YTDPLAFNKK TSSGFCNPWS THNGVLFSEV ESAVIRPPHL   360
FDILSSVEIS TARGKIALNN KAFLDYWIGH SLKYRHANNT SLLHSNYGRI TSEKNSFTLE   420
DKDIVEINST TANLANTYQK AYGVPESRFH MVNRDNSVTS DYLYSKTHTT LEACTHDYES   480
SNEIPLDKNA AVAESYSHRL SHITHHSFSK HSAAYYGSFP VFSWSHVSAD INNTVYTDKI   540
TQLPLTKSYS IEDNVEIINS CYVGGSLLKV ERNMLKSNQV CSIRLSIPKS PKYIVRVRYA   600
STGNGFLGIT GISSDTYFNE TMSKNSDLKY DSFKYVTLGT INNSTYAYYS LYLPRPGNVG   660
DEQYTIYIDR IEFIPVS                                                 677

SEQ ID NO: 5          moltype = AA   length = 665
FEATURE               Location/Qualifiers
REGION                1..665
                      note = variant of native sequence
source                1..665
                      mol_type = protein
                      organism = synthetic construct
SEQUENCE: 5
MTTIENNDEN KNESIDESSS TSVSNASSRY PLANNQTTVL QNINYKDYLR VTEGGDSKFL    60
GNPETLISSS SVQTGIGIVG EILGALGVPF AGAIAGFYSF IVGLLWPSST VSIWEMIMEQ   120
VEELVNQKIT EHAREEALAK LRGLGDGLDV YQRSLENWLE NRNNTKARSV VATQFIALEL   180
DFVSSIPSFA VGGQEVPLLA IYAQAANLHL LLLRDASIFG EEWGFTSGEI STFYNRQMTR   240
TAQYSDHCVR WYNNGLDKLK DTSAASWLRY HQFRRNMTLL VLDLVALFPS YDTHTYQIKT   300
TAQLTRDVYT DPLAFNKKTS SGFCNPWSTH NGVLFSEVES AVIRPPHLFD ILSSVEISTA   360
RGKIALNNKA FLDYWIGHSL KYRHANNTSL LHSNYGRITS EKNSFTLEDK DIVEINSTTA   420
NLANTYQKAY GVPESRFHMV NRDNSVTSDY LYSKTHTTLE ACTHDYESSN EIPLDKNAAV   480
AESYSHRLSH ITHHSFSKHS AAYYGSFPVF SWSHVSADIN NTVYTDKITQ LPLTKSYSIE   540
DNVEIINSCY VGGSLLKVER NMLKSNQVCS IRLSIPKSPK YIVRVRYAST GNGFLGITGI   600
SSDTYFNETM SKNSDLKYDS FKYVTLGTIN NSTYAYYSLY LPRPGNVDE QYTIYIDRIE   660
FIPVS                                                              665

SEQ ID NO: 6          moltype = AA   length = 846
FEATURE               Location/Qualifiers
REGION                1..846
                      note = Unknown organism from environmental sample
source                1..846
                      mol_type = protein
                      organism = unidentified
SEQUENCE: 6
MNSLQTLQAQ PIIPYNVLAN PLSGNADAQP GSLGDLIASL KEAWVEFQKT GSDKLLQTVF    60
QNGFSAASGG SFNYLAVLQA VIGVLGTVLG AEIPGVAVAA PILSMVIGWI WPSKKKDETQ   120
QLINLIDAEI QKQLNQALSN QDKNDWTGYL NAIFQISHDA ARAVVDAQFT GSEGDTNRQP   180
RTPGVSDYEN VYNHLLATTG SLIVALSQMI NGNFDTLAIP FFVIGATVQL STYQTFIQFA   240
NKWLPIVYPD YQIQGTAGYT QQQNLINAKS DMRAAIHDHT QKVFNAFKTG MPSLGSDKNS   300
VNAYNRYVRG MVLNGLDMLA TWPSMYPDDY PSQTELEQTR VIFSDLVGKD QTVNNAVTLI   360
NMVDKSGPDA WNQHSSIDIN SISYTRRELQ QVQFPIHDGN RGNTTNCPYP AVILNYPDNS   420
YFYGDLYAPQ FSGNPTFGGD NDILTVLNAR TQHTRYVDSE SLQMNYYPYA SNDCHILGYC   480
TGGTCLAPSG CSDGYGKSCN ETLPNQKINA LYPFRMDLGH SGTPDKLGVM SSHVPFNLIP   540
NNVFGAIDSD TNNISGKGFP AEKGYWSNGG DRPIPSSNIA KEWVNGANAV KVEYGAFLAM   600
KANNMTTGKY YIRVRYANPS NKDVNMWQEV WAGNQKLQGG GWTFKSTSDD NVADNFPKQV   660
YVTGQQGNYI IQDITWPTGG KQGDPLNLPS GEIMVKLSGQ NSGDSIYVDR IEFIPISETE   720
NINYMITSTV PLLPSGQYVP SLSNYPTIWT ADSGQQAISA TLTFSGLNST LFLLAKTNPG   780
DDDNDENNWDW MCPDGFLGSV LNGTYTFPIN NHDSACAKKP FTAIKIGAEL IPVSAGTITG   840
SITHQR                                                             846

SEQ ID NO: 7          moltype = AA   length = 716
FEATURE               Location/Qualifiers
REGION                1..716
                      note = variant of native sequence
source                1..716
                      mol_type = protein
                      organism = synthetic construct
SEQUENCE: 7
MNSLQTLQAQ PIIPYNVLAN PLSGNADAQP GSLGDLIASL KEAWVEFQKT GSDKLLQTVF    60
QNGFSAASGG SFNYLAVLQA VIGVLGTVLG AEIPGVAVAA PILSMVIGWI WPSKKKDETQ   120
QLINLIDAEI QKQLNQALSN QDKNDWTGYL NAIFQISHDA ARAVVDAQFT GSEGDTNRQP   180
RTPGVSDYEN VYNHLLATTG SLIVALSQMI NGNFDTLAIP FFVIGATVQL STYQTFIQFA   240
NKWLPIVYPD YQIQGTAGYT QQQNLINAKS DMRAAIHDHT QKVFNAFKTG MPSLGSDKNS   300
VNAYNRYVRG MVLNGLDMLA TWPSMYPDDY PSQTELEQTR VIFSDLVGKD QTVNNAVTLI   360
NMVDKSGPDA WNQHSSIDIN SISYTRRELQ QVQFPIHDGN RGNTTNCPYP AVILNYPDNS   420
YFYGDLYAPQ FSGNPTFGGD NDILTVLNAR TQHTRYVDSE SLQMNYYPYA SNDCHILGYC   480
TGGTCLAPSG CSDGYGKSCN ETLPNQKINA LYPFRMDLGH SGTPDKLGVM SSHVPFNLIP   540
NNVFGAIDSD TNNISGKGFP AEKGYWSNGG DRPIPSSNIA KEWVNGANAV KVEYGAFLAM   600
KANNMTTGKY YIRVRYANPS NKDVNMWQEV WAGNQKLQGG GWTFKSTSDD NVADNFPKQV   660
YVTGQQGNYI IQDITWPTGG KQGDPLNLPS GEIMVKLSGQ NSGDSIYVDR IEFIPI       716
```

```
SEQ ID NO: 8            moltype = AA  length = 295
FEATURE                 Location/Qualifiers
REGION                  1..295
                        note = Unknown organism from environmental sample
source                  1..295
                        mol_type = protein
                        organism = unidentified
SEQUENCE: 8
VAILDTSQRH LALRTHSSRD VTMTIKEELS LPQSHSIDVD ELKQEHEHGS ARAVLTSNFS    60
GSFDQFPTKR GGFAIDSYLL DYSAPKQGCW VDGITVYGDI YIGKQNWGTY TRPVFAYLQY   120
MDTISIPQQV TQTRSYQLTK GHTKTFTTSV NAKYSVGGSI GIVNVGSEIS VGFSSSESWS   180
TTQTFTESTQ LTGPGTFIVY QVVLVYAHNA TSAGRQNGNV FAYNKTSTVG SRLDLYYLSA   240
ITQNSTVIVE SSKAIAPLDW DTVQRNVLME NYNPASNSGH FRFDWSAYDD PHRRY        295

SEQ ID NO: 9            moltype = AA  length = 273
FEATURE                 Location/Qualifiers
REGION                  1..273
                        note = variant of native sequence
source                  1..273
                        mol_type = protein
                        organism = synthetic construct
SEQUENCE: 9
MTIKEELSLP QSHSIDVDEL KQEHEHGSAR AVLTSNFSGS FDQFPTKRGG FAIDSYLLDY    60
SAPKQGCWVD GITVYGDIYI GKQNWGTYTR PVFAYLQYMD TISIPQQVTQ TRSYQLTKGH   120
TKTFTTSVNA KYSVGGSIGI VNVGSEISVG FSSSESWSTT QTFTESTQLT GPGTFIVYQV   180
VLVYAHNATS AGRQNGNVFA YNKTSTVGSR LDLYYLSAIT QNSTVIVESS KAIAPLDWDT   240
VQRNVLMENY NPASNSGHFR FDWSAYDDPH RRY                                273

SEQ ID NO: 10           moltype = AA  length = 373
FEATURE                 Location/Qualifiers
REGION                  1..373
                        note = Unknown organism from environmental sample
source                  1..373
                        mol_type = protein
                        organism = unidentified
SEQUENCE: 10
VGKSMTFKVG MKYMFKNKNS RKYLDISKNS TANNANVQQY EYLADAPSER FFLHPLDNNY    60
YAMINVNSGK VLDISENSTA NNANIQQYEW LGDAPSEYWF FHREADGYYV IESKLSGKVL   120
DISKNSTANN ANVQQYEFLH DAPSERFAAE EAGSVPLPSI NTQPLAPVPQ YETINDQLPE   180
ETERVVTSFT IVPSISVRDP HYGRDTARQI KENPYYMVVK KQWWKKQESY VLAPGETYNF   240
VTTTGIRVTD QETATKTVSW SIGADMGFSF KGFSLGMSSQ YSQELQTSIS HTTEQLKEET   300
HTHEIKNPFS ERMAYSRYIL TTEYSVQRKN GTIVNSPWTM TDKTKAHAVT FPKSAGNVLN   360
ENKKKISKNE SVN                                                     373

SEQ ID NO: 11           moltype = AA  length = 369
FEATURE                 Location/Qualifiers
REGION                  1..369
                        note = variant of native sequence
source                  1..369
                        mol_type = protein
                        organism = synthetic construct
SEQUENCE: 11
MTFKVGMKYM FKNKNSRKYL DISKNSTANN ANVQQYEYLA DAPSERFFLH PLDNNYYAMI    60
NVNSGKVLDI SENSTANNAN IQQYEWLGDA PSEYWFFHRE ADGYYVIESK LSGKVLDISK   120
NSTANNANVQ QYEFLHDAPS ERFAAEEAGS VPLPSINTQP LAPVPQYETI NDQLPEETER   180
VVTSFTIVPS ISVRDPHYGR DTARQIKENP YYMVVKKQWW KKQESYVLAP GETYNFVTTT   240
GIRVTDQETA TKTVSWSIGA DMGFSFKGFS LGMSSQYSQE LQTSISHTTE QLKEETHTHE   300
IKNPFSERMA YSRYILTTEY SVQRKNGTIV NSPWTMTDKT KAHAVTFPKS AGNVLNENKK   360
KISKNESVN                                                          369

SEQ ID NO: 12           moltype = AA  length = 326
FEATURE                 Location/Qualifiers
REGION                  1..326
                        note = Unknown organism from environmental sample
source                  1..326
                        mol_type = protein
                        organism = unidentified
SEQUENCE: 12
VKSNILLIDT YNGGYCKMKK RVMLCSLLAG TLLGNVTLST NVSAAEIEGD KNNIINTPTN    60
TSQQAMKDIN QEAIQDIDQK INKMIDSLPL DMFGFKYTRT DRYGESLTYS GINLKENNIT   120
NAEPLFFGTN TFYNNGEDTQ SYYTASFSEA ITTSTTTQVQ NGFKSGITTG GKVGIPFVAE   180
GEVKINLEYN FTHTNSNTTS TTRTLTAPSQ KVDVPRGKVY KADVYLEKKS TSGNVELYAD   240
VLTGVVAGGR TSFIGVSLNK ATDQQGLTQS PHDPNQVRAV GKGTFKVEHG TNFIVKTYDV   300
TSGTKAAKLV DTKIIPIKGH HTGTST                                       326

SEQ ID NO: 13           moltype = AA  length = 283
FEATURE                 Location/Qualifiers
REGION                  1..283
```

```
                        note = variant of native sequence
source                  1..283
                        mol_type = protein
                        organism = synthetic construct
SEQUENCE: 13
MAEIEGDKNN IIINTPTNTSQ QAMKDINQEA IQDIDQKINK MIDSLPLDMF GFKYTRTDRY    60
GESLTYSGIN LKENNITNAE PLFFGTNTFY NNGEDTQSYY TASFSEAITT STTTQVQNGF   120
KSGITTGGKV GIPFVAEGEV KINLEYNFTH TNSNTTSTTR TLTAPSQKVD VPRGKVYKAD   180
VYLEKKSTSG NVELYADVLT GVVAGGRTSF IGSVLNKATD QQGLTQSPHD PNQVRAVGKG   240
TFKVEHGTNF IVKTYDVTSG TKAAKLVDTK IIPIKGHHTG TST                     283

SEQ ID NO: 14           moltype = AA  length = 347
FEATURE                 Location/Qualifiers
REGION                  1..347
                        note = Unknown organism from environmental sample
source                  1..347
                        mol_type = protein
                        organism = unidentified
SEQUENCE: 14
MKKYCNPNKV NPNEVNPREV VLYDLDTYLH NLPENITGSP VGLRNRVADG SVSVDQYYVP    60
TPTSDQLINP CNNYGDLPCT YYPFNGSRWA VDSAGLIAEG IDSFQEVNAV ALSTPIIADK   120
HEYQNNSSLE QPYVTPSYTE AVTTTTNTT THGCKVNPKI SYSRKSKLKV RINDVEKGFN   180
LEIGAEYSFN DTNTYTSTTT RTVVFPSFTT YVPPYTTAIV TVTLNRGTYS QSNLPIQTNL   240
YGRYNIYDPE GYAPEIYYFD LYPVIELVNL CCSSSCSQCV TDMVQPIPET EKVRFNGTGG   300
IIADFASNNF VVTTDFIDNA TGATVSKKVE YVPATYGPAT TAVTTSK                 347

SEQ ID NO: 15           moltype = AA  length = 677
FEATURE                 Location/Qualifiers
REGION                  1..677
                        note = Unknown organism from environmental sample
source                  1..677
                        mol_type = protein
                        organism = unidentified
SEQUENCE: 15
MHDYYLRMEE FIMKKTENNL VNKRKSVDKA PSTSVSNVSS RYPLANDQTT VLQNIHYKDY    60
LRLTEGRDSK IFGNPETLIS SSSVQTGIDI VGQILGALGV PFAGAIAGFY SPIVGLLWPS   120
STVSIWEMIM EQVEELVDQK ITEHAREQAL AKLKGLGDGL EVYQQSLEIW LENRNNTRAR   180
SVVAAQFIAL ELDFVSSIPS FAVGGQEVPL LAIYAQAANL HLLLLRDASI FGEEWGFTSG   240
EISTFYNRQM TRTAQYSDHC VRWYNIGLDK LKDTSAASWL RYHQFRRDMT LLVLDLVALF   300
PSYDTHTYQI KTTAQLTRDV YTDPLAFNKK TSSGFCNPWS THSGVLFSEV ESAVIRPPHL   360
FDILSSVEIS TARGKIALNN KAYLDYWIGH SLKYRHANNT SLIQSNYGRI TSEKNSFTLE   420
DKDIFEINST TANLANAYQK AYGVPESRFH MVKRGSSVTS DYLYSKTHTT LEGCTQDYES   480
SDEIPLDKTV AVAESYSHRL SHITYHSFSF NSAAYYGGFP VFAWSHVSAD INNTIYVDKI   540
TQLPVTKSYS IEDNVKIVNS CYVGGSLLKV ERNMLKSNGV CGIRLSIPKS QKYIVRVRYA   600
STGNGFMHMT GVSGDTYFKE TMLKNSDLKY DSFKYLTLGT IYDTTYSVYS LYLPRPGNVG   660
DEQYTIYIDR IEFIPVS                                                  677

SEQ ID NO: 16           moltype = AA  length = 665
FEATURE                 Location/Qualifiers
REGION                  1..665
                        note = variant of native sequence
source                  1..665
                        mol_type = protein
                        organism = synthetic construct
SEQUENCE: 16
MKKTENNLVN KRKSVDKAPS TSVSNVSSRY PLANDQTTVL QNIHYKDYLR LTEGRDSKIF    60
GNPETLISSS SVQTGIDIVG QILGALGVPF AGAIAGYSF IVGLLWPSST VSIWEMIMEQ   120
VEELVDQKIT EHAREQALAK LKGLGDGLEV YQQSLEIWLE NRNNTRARSV VAAQFIALEL   180
DFVSSIPSFA VGGQEVPLLA IYAQAANLHL LLLLRDASIG EEWGFTSGEI STFYNRQMTR   240
TAQYSDHCVR WYNIGLDKLK DTSAASWLRY HQFRRDMTLL VLDLVALFPS YDTHTYQIKT   300
TAQLTRDVYT DPLAFNKKTS SGFCNPWSTH SGVLFSEVES AVIRPPHLFD ILSSVEISTA   360
RGKIALNNKA YLDYWIGHSL KYRHANNTSL IQSNYGRITS EKNSFTLEDK DIFEINSTTA   420
NLANAYQKAY GVPESRFHMV KRGSSVTSDY LYSKTHTTLE GCTQDYESSD EIPLDKTVAV   480
AESYSHRLSH ITYHSFSKNS AAYYGGFPVF AWSHVSADIN NTIYVDKITQ LPVTKSYSIE   540
DNVKIVNSCY VGGSLLKVER NMLKSNGVCG IRLSIPKSQK YIVRVRYAST GNGFMHMTGV   600
SGDTYFKETM LKNSDLKYDS FKYLTLGTIY DTTYSVYSLY LPRPGNVGDE QYTIYIDRIE   660
FIPVS                                                               665

SEQ ID NO: 17           moltype = AA  length = 1282
FEATURE                 Location/Qualifiers
REGION                  1..1282
                        note = Unknown organism from environmental sample
source                  1..1282
                        mol_type = protein
                        organism = unidentified
SEQUENCE: 17
LATLNELYPS YYNVLAKPPV SNLSSATDQL SDIAESMKKA WEEFQKTGSF SLEALKQGFS    60
AANGGAFNYL TLLQSGISLA GSFIPGGSFV APILNMVIGW LWPNKKKDDS QALIDLIDQE   120
VKKELNKALS EQDKNNWVGF LSSIFDNSNT VNNALIDAQW SGTADDPNRQ TVSPTVSDYK   180
```

```
NVVGKFDAAD TSIVTAQSQI MNGNFDVAAS SYFVIGATVR IALYQSYIRF CNHWIDQVGF   240
NSDDHKTQLD NLTRAKETMR NTITSYTQRI REVFKDNLPK LDSTKFGINA YNVYVKGMTI   300
NVLDMVATWP SLYPNDYDSQ TQLEQTRVIF SNMVGQEQGT DGTVKIYNTF DSGSHQHGQI   360
NNNNVDLISY FPDELQNLQL AVYTPKGGSG YAYPYGFILN YINSAYKYGD NDPSSGGLST   420
ISAPIQQINA TTQHTKYLDG ETINGIGASL PGYCDPTYSP KTIPCSEVEK PPSCISAENA   480
LKNSCNSVYS SQKINALYPF TQTGVQGNQG KLGVMASHVP YDLNPINIIG EVDSDTKNII   540
LKGIPAEKGT LDNNTRPSVV KEWMNGANAV KLSSNQTLRM KISNETPHNY QIRLRYATEN   600
DVGASIWFHL MDPSNRDLTN GNHSFPAPSD KQVSVQGENG NYILNTVIDS IGLPPGQQTI   660
LIQNTSSQDL FLDRIEFAPI PTDPTQPFEI PVPETITTPN KINPLWSSNQ FFADVISITG   720
TVTNYGSIKI QLLNDKKIVK EFPVEGNGPT MGMGRCRDAS YGINNLQNIQ IPEKFNQIQI   780
LELSDNHYNC FRGDGNNTYT TNITVAIQPS QFMAPEDLEK ITAQVNQLFS SSSQTELANT   840
VTDYVIDQVV LKVDALSDDV FGVEKKALRK LVNKAKQLSK DRNVLVGGNF ETFNEWFLGR   900
NVIRRSGNDL FKGDHLFLPP AVLYPSYAYQ KVDESKLKPY TRYIVSGFVA QSEHLELVVS   960
RYGKEIETVL NVSYGEALPI SAGNQSNCCK PGPCQCPSCD GSQPDSHFFS YSIDVGTLYP  1020
DLNPGIQFGL RIVKSNGLAS VSNMEIREDC QLTEKEIKKV QRKEQKWKKA LEKERSEISA  1080
ILQPVINQIN AFYENENWNS DVLPHVTYQD LYNVVLPELP NLRHWFMEDQ EGEHYGILQR  1140
FKQAVERVFT HLEEKNLMHN GSFANGLTDW LVDGNAQIIN LGNGNLALQL SHWDSSVSQT  1200
VDISDFDEDK EYKLRVRANG KGTITIQHGE EMETMSLDKN DFYFQEQPFY FEEPSFYLQI  1260
QSEANEFIVD SIEIIEVPEE DE                                         1282

SEQ ID NO: 18          moltype = AA  length = 680
FEATURE                Location/Qualifiers
REGION                 1..680
                       note = variant of native sequence
source                 1..680
                       mol_type = protein
                       organism = synthetic construct
SEQUENCE: 18
MATLNELYPS YYNVLAKPPV SNLSSATDQL SDIAESMKKA WEEFQKTGSF SLEALKQGFS    60
AANGGAFNYL TLLQSGISLA GSFIPGGSFV APILNMVIGW LWPNKKKDDS QALIDLIDQE   120
VKKELNKALS EQDKNNWVGF LSSIFDNSNT VNNALIDAQW SGTADDPNRQ TVSPTVSDYK   180
NVVGKFDAAD TSIVTAQSQI MNGNFDVAAS SYFVIGATVR IALYQSYIRF CNHWIDQVGF   240
NSDDHKTQLD NLTRAKETMR NTITSYTQRI REVFKDNLPK LDSTKFGINA YNVYVKGMTI   300
NVLDMVATWP SLYPNDYDSQ TQLEQTRVIF SNMVGQEQGT DGTVKIYNTF DSGSHQHGQI   360
NNNNVDLISY FPDELQNLQL AVYTPKGGSG YAYPYGFILN YINSAYKYGD NDPSSGGLST   420
ISAPIQQINA TTQHTKYLDG ETINGIGASL PGYCDPTYSP KTIPCSEVEK PPSCISAENA   480
LKNSCNSVYS SQKINALYPF TQTGVQGNQG KLGVMASHVP YDLNPINIIG EVDSDTKNII   540
LKGIPAEKGT LDNNTRPSVV KEWMNGANAV KLSSNQTLRM KISNETPHNY QIRLRYATEN   600
DVGASIWFHL MDPSNRDLTN GNHSFPAPSD KQVSVQGENG NYILNTVIDS IGLPPGQQTI   660
LIQNTSSQDL FLDRIEFAPI                                              680

SEQ ID NO: 19          moltype = AA  length = 1282
FEATURE                Location/Qualifiers
REGION                 1..1282
                       note = variant of native sequence
source                 1..1282
                       mol_type = protein
                       organism = synthetic construct
SEQUENCE: 19
MATLNELYPS YYNVLAKPPV SNLSSATDQL SDIAESMKKA WEEFQKTGSF SLEALKQGFS    60
AANGGAFNYL TLLQSGISLA GSFIPGGSFV APILNMVIGW LWPNKKKDDS QALIDLIDQE   120
VKKELNKALS EQDKNNWVGF LSSIFDNSNT VNNALIDAQW SGTADDPNRQ TVSPTVSDYK   180
NVVGKFDAAD TSIVTAQSQI MNGNFDVAAS SYFVIGATVR IALYQSYIRF CNHWIDQVGF   240
NSDDHKTQLD NLTRAKETMR NTITSYTQRI REVFKDNLPK LDSTKFGINA YNVYVKGMTI   300
NVLDMVATWP SLYPNDYDSQ TQLEQTRVIF SNMVGQEQGT DGTVKIYNTF DSGSHQHGQI   360
NNNNVDLISY FPDELQNLQL AVYTPKGGSG YAYPYGFILN YINSAYKYGD NDPSSGGLST   420
ISAPIQQINA TTQHTKYLDG ETINGIGASL PGYCDPTYSP KTIPCSEVEK PPSCISAENA   480
LKNSCNSVYS SQKINALYPF TQTGVQGNQG KLGVMASHVP YDLNPINIIG EVDSDTKNII   540
LKGIPAEKGT LDNNTRPSVV KEWMNGANAV KLSSNQTLRM KISNETPHNY QIRLRYATEN   600
DVGASIWFHL MDPSNRDLTN GNHSFPAPSD KQVSVQGENG NYILNTVIDS IGLPPGQQTI   660
LIQNTSSQDL FLDRIEFAPI PTDPTQPFEI PVPETITTPN KINPLWSSNQ FFADVISITG   720
TVTNYGSIKI QLLNDKKIVK EFPVEGNGPT MGMGRCRDAS YGINNLQNIQ IPEKFNQIQI   780
LELSDNHYNC FRGDGNNTYT TNITVAIQPS QFMAPEDLEK ITAQVNQLFS SSSQTELANT   840
VTDYVIDQVV LKVDALSDDV FGVEKKALRK LVNKAKQLSK DRNVLVGGNF ETFNEWFLGR   900
NVIRRSGNDL FKGDHLFLPP AVLYPSYAYQ KVDESKLKPY TRYIVSGFVA QSEHLELVVS   960
RYGKEIETVL NVSYGEALPI SAGNQSNCCK PGPCQCPSCD GSQPDSHFFS YSIDVGTLYP  1020
DLNPGIQFGL RIVKSNGLAS VSNMEIREDC QLTEKEIKKV QRKEQKWKKA LEKERSEISA  1080
ILQPVINQIN AFYENENWNS DVLPHVTYQD LYNVVLPELP NLRHWFMEDQ EGEHYGILQR  1140
FKQAVERVFT HLEEKNLMHN GSFANGLTDW LVDGNAQIIN LGNGNLALQL SHWDSSVSQT  1200
VDISDFDEDK EYKLRVRANG KGTITIQHGE EMETMSLDKN DFYFQEQPFY FEEPSFYLQI  1260
QSEANEFIVD SIEIIEVPEE DE                                         1282

SEQ ID NO: 20          moltype = AA  length = 425
FEATURE                Location/Qualifiers
REGION                 1..425
                       note = Unknown organism from environmental sample
source                 1..425
                       mol_type = protein
                       organism = unidentified
```

-continued

```
SEQUENCE: 20
MVRIYPDFDE MVWEAAQKWA AANGLLFQKS SYADPVDNTD TISLNVKFTD IGCPEECVEL    60
EKIRISQAFS NNTEQKQKET FENITYVENH FTWENEYQFV LPGQSFLTIP RLPMSAHEDI   120
HPGFLVNLFG MNQQFHTKLR ERRPLRADVF VEPSSSATVQ LKVEKQHISQ PYQIELSIQG   180
SIIVTAQDRQ EQSKEYYVRL TELMPFFCSH KNLSWEGQAL VFREKGKFTG ILSRAIHAYV   240
TQTCYNGGKT LEYEIPLLGP ASERESVSAQ QPMPARRLSD EASSTLPSIS SNPAAYSQQP   300
ITTTSTPCGC ASYEPPVSTY THPSNPTSYS QQPMTTDSTS CGCASYEPPV STYTHPSNPT   360
SYSQQPMTTT STPCGCASYE PPVSTYTHPS NPTPHSQQPM TTDSTSCGCS SCMSTKSNGN   420
LYTDQ                                                              425

SEQ ID NO: 21           moltype = AA  length = 741
FEATURE                 Location/Qualifiers
REGION                  1..741
                        note = Unknown organism from environmental sample
source                  1..741
                        mol_type = protein
                        organism = unidentified
SEQUENCE: 21
MLMENNSLNV LANNNMSSFP LFNNKIEPSI APALIAVEPI AKYLATALAK WVAKEAFAKL    60
KSVIFPGNTP ATMEKVRLEV QTLLNQRLQD DRVLILNAEY QGFINLGRVF TDYVSQSTYT   120
PDTAKTHFLS MSNQLIQRLP QFEIAGYEGV SIALFTQMCT LHLGLLKDGI LAGSDWGFTP   180
ADKDSLICQF NRYVNEYHTR MMGLYSKEFG RLLSINLNQA LNFRNMCSLY VFPFSEAWSL   240
LRYEGTKLEN TLSLWNFVGL PIANISPYDW GGALYKLLMG APNQRLNQVQ FNYSYFSNAG   300
PTLDGEKIIG TLPRYNGGPT ITGWIGNGRL GGFSSPCNNE LEITKIKQEI TYNGKGGNSN   360
SIAPANAFNE ILTATVPTSP EPFFKTADIN MTYNVPRGWN IKFDNQVILR TRMPINIPPN   420
SLEYEGYYIR AVSACPQGLP LSYNHDFLTL TYNTLEYVAP TTQNIIVGFS PNITKHFYSR   480
NSHYLSATDD AYVIPALQFA TVSDRSFLED TPDQATDGSI KFNNNFLGNE AKYSIRLNTG   540
FNTATRYRLI IRFKAPARLA SGIRVRSQNS GNNRLLAAIP VEGNSGWVNY VTDSFTFNDL   600
GITPTSTNAF FSIDSDGVNA SQQWYLSKLI LVKDFVNNSG FRNQVPFNPL VITRCPETLF   660
VSNNSSSTYE QGNNYNYDQN SSSAYEQGDN YNYDQNSSSA YEQGDNYNYD QNLCCACNQN   720
YDGSHKQSVG CTCNRNYKNN Y                                            741

SEQ ID NO: 22           moltype = AA  length = 857
FEATURE                 Location/Qualifiers
REGION                  1..857
                        note = Unknown organism from environmental sample
source                  1..857
                        mol_type = protein
                        organism = unidentified
SEQUENCE: 22
MNQNDNNNEF EILDSKGKEG QPRYPFAEAP GVMTSGMEKT YTTGQSANIS NATSTTIDVT    60
SQMLRGGKKV AGAIIKMLIK ILWPTGTQQE WENFMDAVEQ LINEKLDIYA RNKATADLVG   120
LQRVLSEYID RLTIYTDDPN AAHAQSLRTQ VITTDNLFEY SMPSFAIRDY EMQLLTVYAQ   180
AANLHLAFLE DIVRFGDEWG FTPTEIADPH RSMKERTNEY TNHCVNTYKQ GLEKAKTLAA   240
NLCNHNTYPW TRYNQGWREE EKPNCTSQLD SGDPQLDERI EQENPYMGDF RWSIGEYQKL   300
EDWNLYNAYR RDMTLMVLDI VSLWPTYDPK LYPTSFGVKS ELTRELYTDI RGTTYRSDES   360
QNSLTAIEGR MIPQPSLFRW LFSITISMRQ FIGTGGSNDW TSGNIMTAMR IMWRKTLTEQ   420
LEELRFGSSG PISINLHPLD HAEGITHVNT RQWFEPRWFE FYSGGYDTEL KFQNKCGTIE   480
EKNPFWAAGP YNYIYQPGVR TSQIPEHRLS WITYEPVREN APFVYPQDKQ LGAVALGWTN   540
NSVDQKNAID IDKITSLPAV KGNEIRGPGS VVRGPGSTGG NLVQLNPTGE VSIKVSQPIL   600
NKPGAGYYHV RIRYAAIANG KLNVKRSVNS STQESVTYDY KQTNALDLTY SSFQYLEVYD   660
FSPVTTASQF EVLLTNESGG PIYIDKIEFI PFQGTTGPEA PGIPADIYYS MSPAIDENYY   720
TIGGSNSVWL ALKEIHPTPP RDGQWRFVYD TSKKAYQIGT RLGEYPEEGV LNGVLTSFNP   780
NDLIVFRNES SDQQYWFVKD AGDGYVTLEN YRYPGYVVTA PPTTYHGATV TLSPFNGSMN   840
QKFKLTKLSG NDAVILG                                                 857

SEQ ID NO: 23           moltype = AA  length = 692
FEATURE                 Location/Qualifiers
REGION                  1..692
                        note = variant of native sequence
source                  1..692
                        mol_type = protein
                        organism = synthetic construct
SEQUENCE: 23
MNQNDNNNEF EILDSKGKEG QPRYPFAEAP GVMTSGMEKT YTTGQSANIS NATSTTIDVT    60
SQMLRGGKKV AGAIIKMLIK ILWPTGTQQE WENFMDAVEQ LINEKLDIYA RNKATADLVG   120
LQRVLSEYID RLTIYTDDPN AAHAQSLRTQ VITTDNLFEY SMPSFAIRDY EMQLLTVYAQ   180
AANLHLAFLE DIVRFGDEWG FTPTEIADPH RSMKERTNEY TNHCVNTYKQ GLEKAKTLAA   240
NLCNHNTYPW TRYNQGWREE EKPNCTSQLD SGDPQLDERI EQENPYMGDF RWSIGEYQKL   300
EDWNLYNAYR RDMTLMVLDI VSLWPTYDPK LYPTSFGVKS ELTRELYTDI RGTTYRSDES   360
QNSLTAIEGR MIPQPSLFRW LFSITISMRQ FIGTGGSNDW TSGNIMTAMR IMWRKTLTEQ   420
LEELRFGSSG PISINLHPLD HAEGITHVNT RQWFEPRWFE FYSGGYDTEL KFQNKCGTIE   480
EKNPFWAAGP YNYIYQPGVR TSQIPEHRLS WITYEPVREN APFVYPQDKQ LGAVALGWTN   540
NSVDQKNAID IDKITSLPAV KGNEIRGPGS VVRGPGSTGG NLVQLNPTGE VSIKVSQPIL   600
NKPGAGYYHV RIRYAAIANG KLNVKRSVNS STQESVTYDY KQTNALDLTY SSFQYLEVYD   660
FSPVTTASQF EVLLTNESGG PIYIDKIEFI PF                                692

SEQ ID NO: 24           moltype = AA  length = 835
FEATURE                 Location/Qualifiers
```

| | | |
|---|---|---|
| REGION | 1..835 | |
| | note = Unknown organism from environmental sample | |
| source | 1..835 | |
| | mol_type = protein | |
| | organism = unidentified | |

SEQUENCE: 24

```
VINLSKIRID VSIIWISCLR VYSFRNLCFY NVCTIAIKNK NYMRDEKMNS NQNKNEYEVL   60
NTSGNNVNTL TKYPFANDPD SSVLSSCQRS GPGNWINILG NAVSQAVSNS QDILSLLRQP  120
SLSGIISMAF SLLNRMTGSN GRSISELSMC DLLAIIDLRV NQSVLDAGVA DPNGSLVVYR  180
NYLEALQRWN NNPNSATAED VRARFRNSDT TFDFILTRGS LTNGGSLARN NAQILLLPSF  240
ANAAYPHLLL LRDANVYGDN WGLFRDTPNI NYKSKLLDLI KLYTNYCTHW YNQGLNELRN  300
RGNNATAWLE FHRFRRDMTL MVLDIVASFS NFDITRYPRA TDIQLSRVIY TDPIGFVNRS  360
DPSAGRTWFS FHNQANFSAL ESGIPIPSFS QFLDSMRIST GPLSLPASPN IHRAGVWYGN  420
QNNFNGSSSQ TFGEVTNENQ TISGLNIFRI DSQAVNLNNT TFGVSRSEFY HDTSQGSQRS  480
IYQGFVDTSG TSTAVAQNIQ TFFPGENSNI PTPHDYTHIL SRSTNLTGGL RQVASGRRSS  540
LVLHGWTHTS LSRQNRVEPN RITQVPAVKV STDSNCTVIA GPGFTGGDVV RMNSNGSVSY  600
NITPANQQVV IRLRYACQGI ASLRMTFGNG SSQVIPLVST TSSINNLQYE NFSFVTGPNS  660
VNFLSAGTSV TIQNISTNSN VVLDRIELVP ELPEPPIIPG EYQIVTAINN SSVLDLNSGT  720
RVTLWSNSRG AHQIWSFMYD HQRNAYVIRN VSNPSLVLTW DFTSSNNIVF AAPFSPGRDE  780
QYWIAENFQN GFVLGNLRNP NMVLDVSGGS TSNGTNIIAY PRHNGNAQRF FIRRP       835
```

| | | |
|---|---|---|
| SEQ ID NO: 25 | moltype = AA   length = 644 | |
| FEATURE | Location/Qualifiers | |
| REGION | 1..644 | |
| | note = variant of native sequence | |
| source | 1..644 | |
| | mol_type = protein | |
| | organism = synthetic construct | |

SEQUENCE: 25

```
MNSNQNKNEY EVLNTSGNNV NTLTKYPFAN DPDSSVLSSC QRSGPGNWIN ILGNAVSQAV   60
SNSQDILSLL RQPSLSGIIS MAFSLLNRMT GSNGRSISEL SMCDLLAIID LRVNQSVLDA  120
GVADFNGSLV VYRNYLEALQ RWNNNPNSAT AEDVRARFRN SDTTFDFILT RGSLTNGGSL  180
ARNNAQILLL PSFANAAYFH LLLLRDANVY GDNWGLFRDT PNINYKSKLL DLIKLYTNYC  240
THWYNQGLNE LRNRGNNATA WLEPHRFRRD MTLMVLDIVA SFSNFDITRY PRATDIQLSR  300
VIYTDPIGFV NRSDPSAGRT WFSFHNQANF SALESGIPIP SFSQFLDSMR ISTGPLSLPA  360
SPNIHRAGVW YGNQNNFNGS SSQTFGEVTN ENQTISGLNI FRIDSQAVNL NNTTFGVSRS  420
EFYHDTSQGS QRSIYQGFVD TSGTSTAVAQ NIQTFFPGEN SNIPTPHDYT HILSRSTNLT  480
GGLRQVASGR RSSLVLHGWT HTSLSRQNRV EPNRITQVPA VKVSTDSNCT VIAGPGFTGG  540
DVVRMNSNGS VSYNITPANQ QVVIRLRYAC QGIASLRMTF GNGSSQVIPL VSTTSSINNL  600
QYENFSFVTG PNSVNFLSAG TSVTIQNIST NSNVVLDRIE LVPE                    644
```

| | | |
|---|---|---|
| SEQ ID NO: 26 | moltype = AA   length = 788 | |
| FEATURE | Location/Qualifiers | |
| REGION | 1..788 | |
| | note = variant of native sequence | |
| source | 1..788 | |
| | mol_type = protein | |
| | organism = synthetic construct | |

SEQUENCE: 26

```
MNSNQNKNEY EVLNTSGNNV NTLTKYPFAN DPDSSVLSSC QRSGPGNWIN ILGNAVSQAV   60
SNSQDILSLL RQPSLSGIIS MAFSLLNRMT GSNGRSISEL SMCDLLAIID LRVNQSVLDA  120
GVADFNGSLV VYRNYLEALQ RWNNNPNSAT AEDVRARFRN SDTTFDFILT RGSLTNGGSL  180
ARNNAQILLL PSFANAAYFH LLLLRDANVY GDNWGLFRDT PNINYKSKLL DLIKLYTNYC  240
THWYNQGLNE LRNRGNNATA WLEFHRFRRD MTLMVLDIVA SFSNFDITRY PRATDIQLSR  300
VIYTDPIGFV NRSDPSAGRT WFSFHNQANF SALESGIPIP SFSQFLDSMR ISTGPLSLPA  360
SPNIHRAGVW YGNQNNFNGS SSQTFGEVTN ENQTISGLNI FRIDSQAVNL NNTTFGVSRS  420
EFYHDTSQGS QRSIYQGFVD TSGTSTAVAQ NIQTFFPGEN SNIPTPHDYT HILSRSTNLT  480
GGLRQVASGR RSSLVLHGWT HTSLSRQNRV EPNRITQVPA VKVSTDSNCT VIAGPGFTGG  540
DVVRMNSNGS VSYNITPANQ QVVIRLRYAC QGIASLRMTF GNGSSQVIPL VSTTSSINNL  600
QYENFSFVTG PNSVNFLSAG TSVTIQNIST NSNVVLDRIE LVPELPEPPI IPGEYQIVTA  660
INNSSVLDLN SGTRVTLWSN SRGAHQIWSF MYDHQRNAYV IRNVSNPSLV LTWDFTSSNN  720
IVFAAPFSPG RDEQYWIAEN FQNGFVLGNL RNPNMVLDVS GGSTSNGTNI IAYPRHNGNA  780
QRFFIRRP                                                            788
```

| | | |
|---|---|---|
| SEQ ID NO: 27 | moltype = AA   length = 680 | |
| FEATURE | Location/Qualifiers | |
| REGION | 1..680 | |
| | note = Unknown organism from environmental sample | |
| source | 1..680 | |
| | mol_type = protein | |
| | organism = unidentified | |

SEQUENCE: 27

```
VKGMNSYQNK NEYEILDASQ NNSNMSTHYP RYPLAKDPQA SMQNTNYKDW LNLCDTPNME   60
NPEFQSVGRS ALSILINLSS RILSLLGIPF AAQIGQLWSY TLNLLWPVAN NATQWEIFMR  120
TIEELINIHI ETSVRNRALA ELAGLGNILE DYKVALQRWD LNPTNPVLQS EVVRQFEIVH  180
AFFRAQMPVF AISGFEVPLL PVYASAANLH LLLLRDVVIN GSRWGLSAAR INDYHDLQLH  240
LTSTYTDHCV TWYNTGLNRL IGTNARQWVV YNQFRREMTI SVLDIISLFS NYDARRYPTK  300
IQSELTRMIY TDPIGTEGNQ FIPGWVDNAP SFSVIENSVV RSPEAFTWLE RVGIFTGVLH  360
GWSSRSEFWA AHRLFSRRTL GWLFESAVFG NPQNNIGYQE VDFTNFDVFS INSRATSHMF  420
```

```
PSGGGRLFGV PRVTFDLSNI TNNSLAQRTY NRPFTFGGQD IVSRLSGETT EIPNSSNYSH    480
RLAHISSFPV GNNGSVLSYG WTHRSVNRHN RLNPNSITQI PYIKGHGGLW GPRRGPGHTG    540
GDIVFIGWSN GASIPIQSNS AQRYRIRVRY ASSMSIPLTV GIRDESTQST HVVELNLVGR    600
GPLPNQLRYA DFLYTDLTEN TTLFETPNRE TFYTVFTSVR DGDVRLDRIE FIPENTITIE    660
YEEERNLEKE KKAVDDLFTN                                                680

SEQ ID NO: 28             moltype = AA   length = 677
FEATURE                   Location/Qualifiers
REGION                    1..677
                          note = variant of native sequence
source                    1..677
                          mol_type = protein
                          organism = synthetic construct
SEQUENCE: 28
MNSYQNKNEY EILDASQNNS NMSTHYPRYP LAKDPQASMQ NTNYKDWLNL CDTPNMENPE    60
FQSVGRSALS ILINLSSRIL SLLGIPFAAQ IGQLWSYTLN LLWPVANNAT QWEIFMRTIE    120
ELINIHIETS VRNRALAELA GLGNILEDYK VALQRWDLNP TNPVLQSEVV RQFEIVHAFF    180
RAQMPVFAIS GFEVPLLPVY ASAANLHLLL LRDVVINGSR WGLSAARIND YHDLQLHLTS    240
TYTDHCVTWY NTGLNRLIGT NARQWVVYNQ FRREMTISVL DIISLFSNYD ARRYPTKIQS    300
ELTRMIYTDP IGTEGNQFIP GWVDNAPSFS VIENSVVRSP EAFTWLERVG IFTGVLHGWS    360
SRSEFWAAHR LFSRRTLGWL FESAVFGNPQ NNIGYQEVDF TNFDVFSINS RATSHMPSG    420
GGRLFGVPRV TFDLSNITNN SLAQRTYNRP FTFGGQDIVS RLSGETTEIP NSSNYSHRLA    480
HISSFPVGNN GSVLSYGWTH RSVNRHNRLN PNSITQIPYI KGHGGLWGPR RGPGHTGGDI    540
VFIGWSNGAS IPIQSNSAQR YRIRVRYASS MSIPLTVGIR DESTQSTHVV ELNLVGRGPL    600
PNQLRYADFL YTDLTENTTL FETPNRETFY TVFTSVRDGD VRLDRIEFIP ENTITIEYEE    660
ERNLEKEKKA VDDLFTN                                                  677

SEQ ID NO: 29             moltype = AA   length = 651
FEATURE                   Location/Qualifiers
REGION                    1..651
                          note = variant of native sequence
source                    1..651
                          mol_type = protein
                          organism = synthetic construct
SEQUENCE: 29
MNSYQNKNEY EILDASQNNS NMSTHYPRYP LAKDPQASMQ NTNYKDWLNL CDTPNMENPE    60
FQSVGRSALS ILINLSSRIL SLLGIPFAAQ IGQLWSYTLN LLWPVANNAT QWEIFMRTIE    120
ELINIHIETS VRNRALAELA GLGNILEDYK VALQRWDLNP TNPVLQSEVV RQFEIVHAFF    180
RAQMPVFAIS GFEVPLLPVY ASAANLHLLL LRDVVINGSR WGLSAARIND YHDLQLHLTS    240
TYTDHCVTWY NTGLNRLIGT NARQWVVYNQ FRREMTISVL DIISLFSNYD ARRYPTKIQS    300
ELTRMIYTDP IGTEGNQFIP GWVDNAPSFS VIENSVVRSP EAFTWLERVG IFTGVLHGWS    360
SRSEFWAAHR LFSRRTLGWL FESAVFGNPQ NNIGYQEVDF TNFDVFSINS RATSHMPSG    420
GGRLFGVPRV TFDLSNITNN SLAQRTYNRP FTFGGQDIVS RLSGETTEIP NSSNYSHRLA    480
HISSFPVGNN GSVLSYGWTH RSVNRHNRLN PNSITQIPYI KGHGGLWGPR RGPGHTGGDI    540
VFIGWSNGAS IPIQSNSAQR YRIRVRYASS MSIPLTVGIR DESTQSTHVV ELNLVGRGPL    600
PNQLRYADFL YTDLTENTTL FETPNRETFY TVFTSVRDGD VRLDRIEFIP E             651

SEQ ID NO: 30             moltype = AA   length = 556
FEATURE                   Location/Qualifiers
REGION                    1..556
                          note = Unknown organism from environmental sample
source                    1..556
                          mol_type = protein
                          organism = unidentified
SEQUENCE: 30
VNNMYTNNMK TTLKLETTDY EIDQAAISIE CMSDEQDLQE KMMLWDEVKL AKQLSQSRNL    60
LYNVNFEDSS NGWKTSNNIT IQLDNPIFKG KYLNMPGARD IYGTIFPTYV YQKIEESKLK    120
SYTRYRVRGF VGSSKDLKLM VTRYGKEIDA SMDVPNDLAY MQPNLSCGDY RCDSSSPSMM    180
SQGYPTPYTD GYASDMYACP SNFGKKHVKC HDRHPFDPHN LGCIELDINTN LGICILFKIS    240
NPDGYATLGN LEVIEEGPLT GEALAHVKQK EKKWNQQMEK KRSETQQAYD PAKQAVDALF    300
TNAQGEELHY HITLDYIQNA NQLVQSIPYV HHAWLPDAPG MNYDLYNNLK VRIEQARYLY    360
DARNVITNGD FTQGLQGWHT TGKAAVQQMD GASVLVLSNW SAGVSQNLHA QDHHGYVLRV    420
IAKKEGPGKG YVTMMDCNGN QETLKFTSCE EGYMTKTVEV FPESDRVRIE IGETEGTFYI    480
DSIELLCMKG YNNPHTGNMY EQSYNGIYNQ NTSDVYHQDS SSMYNQNYTN NDDQHSACTC    540
NQGHNSGCTC NQGYNR                                                   556

SEQ ID NO: 31             moltype = AA   length = 781
FEATURE                   Location/Qualifiers
source                    1..781
                          mol_type = protein
                          organism = Bacillus sp.
SEQUENCE: 31
MNPYQNKNEY EILDAKRNNC HMSNGYPRYP LANDPQMYLR NTHYTDWLTM CNNTNLAGWI    60
PPGSFEFTWL NATVAALTII SVTTALLIAP PLLVGGVIAA GAAILAGTLP LLWPADSKPE    120
DNTFNEIMNA TELLINTKIS EFVRQTADTK ITSLQSLMFY YNNALDNWKK NPNDSAAINT    180
VSTRFQIVNA FFVEAMPALS MPGYELAQLG AYAQAANLHL LLLRDGILYA DKWNLAKEAT    240
YKQGDLHYQE FLNYRNQYIN HCSTWYNEGQ IEANNKGNGL VYQRTMTILV LDLIAMFSTY    300
DPRLYTMPIK TEILTRTIYT DGVNRNQTSS IYNPGLFRRL EQMEFHIYEY QGSQFLSGHQ    360
NIFRSMNYTH PLIYGPLQGY RSSNINKITT INLGDYDKIY SIKTESRDRI VQGSITFDKI    420
```

```
NFYGTFNKSW LFSVYNQNGP IIKHSNIPGV EAPSATLDYR NYTHYLSNCI FQSKQNVVSE   480
PDYNTQSYIF GWNHYTIDPT GNYVTDASWV DNNLPAGRYV PQISQVPAVK ASDIYNPGRV   540
VNATVEDGPH FTGGDVIVSK AQLDGSGLAR TLITFPIIPK RYQASGFRVR MYYAANHTGQ   600
LSYRAKDISV TGYASFTKTF DGWEYFRARH EHFKYIEFDT TFNLRNSGQL EEHELLIYYP   660
NTSRVSGDQL LIIDKIEFIP VGIPLNQTLE GYDDSYNQNP NANYNQNYTD TYDSGYNSSQ   720
NTDYNYDQEY NTYNQSYNNY NLGNNNYNQN SDCMCNQGYN GNYNQSGCR CNQGDNGNYP   780
K                                                                  781

SEQ ID NO: 32           moltype = AA   length = 681
FEATURE                 Location/Qualifiers
REGION                  1..681
                        note = variant of native sequence
source                  1..681
                        mol_type = protein
                        organism = synthetic construct
SEQUENCE: 32
MNPYQNKNEY EILDAKRNNC HMSNGYPRYP LANDPQMYLR NTHYTDWLTM CNNTNLAGWI    60
PPGSFEFTWL NATVAALTII SVTTALLIAP PLLVGGVIAA GAAILAGTLP LLWPADSKPE   120
DNTFNEIMNA TELLINTKIS EFVRQTADTK ITSLQSLMFY YNNALDNWKK NPNDSAAINT   180
VSTRFQIVNA FFVEAMPALS MPGYELAQLG AYAQAANLHL LLLRDGILYA DKWNLAKEAT   240
YKQGDLHYQE FLNYRNQYIN HCSTWYNEGQ IEANNKGNGL VYQRTMTILV LDLIAMFSTY   300
DPRLYTMPIK TEILTRTIYT DGVNRNQTSS IYNPGLFRRL EQMEFHIYEY QGSQFLSGHQ   360
NIFRSMNYTH PLIYGPLQGY RSSNINKITT INLGDYDKIY SIKTESRDRI VQGSITFDKI   420
NFYGTFNKSW LFSVYNQNGP IIKHSNIPGV EAPSATLDYR NYTHYLSNCI FQSKQNVVSE   480
PDYNTQSYIF GWNHYTIDPT GNYVTDASWV DNNLPAGRYV PQISQVPAVK ASDIYNPGRV   540
VNATVEDGPH FTGGDVIVSK AQLDGSGLAR TLITFPIIPK RYQASGFRVR MYYAANHTGQ   600
LSYRAKDISV TGYASFTKTF DGWEYFRARH EHFKYIEFDT TFNLRNSGQL EEHELLIYYP   660
NTSRVSGDQL LIIDKIEFIP V                                            681

SEQ ID NO: 33           moltype = AA   length = 679
FEATURE                 Location/Qualifiers
REGION                  1..679
                        note = Unknown organism from environmental sample
source                  1..679
                        mol_type = protein
                        organism = unidentified
SEQUENCE: 33
VKKMNSYQNK NDYEILDTSP NNSNMSTLHP RYPLANDPQM PMRNTNYKDW LTMCDSNTQF    60
VGDISTYSSP EAALSARDAV FTGINVAGSI LSYFGVPFAS FSFGLIGRLL GILWPGPDPF   120
AALIVLVEEL IKREIDTLVR RGALDALGGL QEILDVYRTR LNTWRNAKTD ENLKRLLEQH   180
DIVENFFTFN MVRFRSPGYE ILLLPVYAQA ANMHLILLRD FDVFGAEWRV GPDQIRDNYE   240
RLKGKIREYK DHCVTVYNQG LNLFNRSTAQ DWVSFNRFRT DMTLTVLDIA TLFPNYDSRI   300
YPSAVKTELT REIYTDPVGY TERGLPWYNP NNTTFATMEN SARRPPSYTT WLNRIFVYTG   360
HLGNFSAVRN VWGGHTLIEN GNDGSEIIHN FGNPNSITPI QYLNFQNVSV FSIDSIAHVL   420
VVGSQPYRES QYGVSRVTFH TSNINNVPGS LSYEVPNVNQ SQTILSELPG KDEQRPDART   480
FSHRLSYISN FDARRGGSGG NVSLLTYGWT HISMDRNNRL EPNGITQIDA VKGFGDDLVI   540
PGPTGGNLVR LSDRGDRGYS LRVQAPEIST SYRIRLRYAC LANFGDAIFV EHSGSSHIVS   600
FFDCSNAPGR PSNTLEESDF RYIDVPGTFT PSINPEIRFR TNSFDGPNAL DKIEFIPLDI   660
YNEHFVEERA KTINDLFIN                                               679

SEQ ID NO: 34           moltype = AA   length = 676
FEATURE                 Location/Qualifiers
REGION                  1..676
                        note = variant of native sequence
source                  1..676
                        mol_type = protein
                        organism = synthetic construct
SEQUENCE: 34
MNSYQNKNDY EILDTSPNNS NMSTLHPRYP LANDPQMPMR NTNYKDWLTM CDSNTQFVGD    60
ISTYSSPEAA LSARDAVFTG INVAGSILSY FGVPFASFSF GLIGRLLGIL WPGPDPFAAL   120
IVLVEELIKR EIDTLVRRGA LDALGGLQEI LDVYRTRLNT WRNAKTDENL KRLLEQHDIV   180
ENFFTFNMVR FRSPGYEILL LPVYAQAANM HLILLRDFDV FGAEWRVGPD QIRDNYERLK   240
GKIREYKDHC VTVYNQGLNL FNRSTAQDWV SFNRFRTDMT LTVLDIATLF PNYDSRIYPS   300
AVKTELTREI YTDPVGYTER GLPWYNPNNT TFATMENSAR RPPSYTTWLN RIFVYTGHLG   360
NFSAVRNVWG GHTLIENGND GSEIIHNFGN PNSITPIQYL NFQNVSVFSI DSIAHVLVVG   420
SQPYRESQYG VSRVTFHTSN INNVPGSLSY EVPNVNQSQT ILSELPGKDE QRPDARTFSH   480
RLSYISNFDA RRGGSGGNVS LLTYGWTHIS MDRNNRLEPN GITQIDAVKG FGDDLVIPGP   540
TGGNLVRLSD RGDRGYSLRV QAPEISTSYR IRLRYACLAN FGDAIFVEHS GSSHIVSFFD   600
CSNAPGRPSN TLEESDFRYI DVPGTFTPSI NPEIRFRTNS FDGPNALDKI EFIPLDIYNE   660
HFVEERAKTI NDLFIN                                                  676

SEQ ID NO: 35           moltype = AA   length = 655
FEATURE                 Location/Qualifiers
REGION                  1..655
                        note = variant of native sequence
source                  1..655
                        mol_type = protein
                        organism = synthetic construct
SEQUENCE: 35
```

```
MNSYQNKNDY EILDTSPNNS NMSTLHPRYP LANDPQMPMR NTNYKDWLTM CDSNTQFVGD    60
ISTYSSPEAA LSARDAVFTG INVAGSILSY FGVPFASFSF GLIGRLLGIL WPGPDPFAAL   120
IVLVEELIKR EIDTLVRRGA LDALGGLQEI LDVYRTRLNT WRNAKTDENL KRLLEQHDIV   180
ENFFTFNMVR FRSPGYEILL LPVYAQAANM HLILLRDFDV FGAEWRVGPD QIRDNYERLK   240
GKIREYKDHC VTVYNQGLNL FNRSTAQDWV SFNRFRTDMT LTVLDIATLF PNYDSRIYPS   300
AVKTELTREI YTDPVGYTER GLPWYNPNNT TFATMENSAR RPPSYTTWLN RIFVYTGHLG   360
NFSAVRNVWG GHTLIENGND GSEIIHNFGN PNSITPIQYL NFQNVSVFSI DSIAHVLVVG   420
SQPYRESQYG VSRVTFHTSN INNVPGSLSY EVPNVNQSQT ILSELPGKDE QRPDARTFSH   480
RLSYISNFDA RRGGSGGNVS LLTYGWTHIS MDRNNRLEPN GITQIDAVKG FGDDLVIPGP   540
TGGNLVRLSD RGDRGYSLRV QAPEISTSYR IRLRYACLAN FGDAIFVEHS GSSHIVSFFD   600
CSNAPGRPSN TLEESDFRYI DVPGTFTPSI NPEIRFRTNS FDGPNALDKI EFIPL        655

SEQ ID NO: 36              moltype = AA  length = 404
FEATURE                    Location/Qualifiers
source                     1..404
                           mol_type = protein
                           organism = Bacillus sp.
SEQUENCE: 36
MATYKKDEVM NYTSTENMDV NLKSKNDKKP CDCEPVGYAT PNLSEESRKF LVITIPTGSR    60
YAFAQNSNAP GESIGSEKCQ QLKFHDHLIY DEFVKNDNRF LFIFYQLDTG DFIIANKKTG   120
EVISHVRDSG SDGIVLRPYI TMDEEDEVMQ WHKFYRADGE FTLDYVDAKM SLVPCGYHNV   180
EAKQIAAYGG TEGAWPVRYL KEGEQNINIP SLPPTSELGP VPEVTGFNDP LPTNDEAKRA   240
IKGSVLIPSI LVNDYLLLAD RIKKNPYYVL EHRQYWHLLW SDLFTAGSNQ LKTEVTGISS   300
DAQEKMKAAV GMSIGSDLGL NFIETSDPFK QQIISGLNSK LSHTKDLNET TTIRDVENPE   360
DFTVRFARYA RAHEFVLKDS DGNVVGAPWV VVDGNEMYLK RYKK                    404

SEQ ID NO: 37              moltype = AA  length = 395
FEATURE                    Location/Qualifiers
REGION                     1..395
                           note = variant of native sequence
source                     1..395
                           mol_type = protein
                           organism = synthetic construct
SEQUENCE: 37
MNYTSTENMD VNLKSKNDKK PCDCEPVGYA TPNLSEESRK FLVITIPTGS RYAFAQNSNA    60
PGESIGSEKC QQLKFHDHLI YDEFVKNDNR FLFIFYQLDT GDFIIANKKT GEVISHVRDS   120
GSDGIVLRPY ITMDEEDEVM QWHKFYRADG EFTLDYVDAK MSLVPCGYHN VEAKQIAAYG   180
GTEGAWPVRY LKEGEQNINI PSLPPTSELG PVPEVTGFND PLPTNDEAKR AIKGSVLIPS   240
ILVNDYLLLA DRIKKNPYYV LEHRQYWHLL WSDLFTAGSN QLKTEVTGIS SDAQEKMKAA   300
VGMSIGSDLG LNFIETSDPF KQQIISGLNS KLSHTKDLNE TTTIRDVENP EDFTVRFARY   360
ARAHEFVLKD SDGNVVGAPW VVVDGNEMYL KRYKK                              395

SEQ ID NO: 38              moltype = AA  length = 750
FEATURE                    Location/Qualifiers
source                     1..750
                           mol_type = protein
                           organism = Bacillus sp.
SEQUENCE: 38
LDSYPKKNEH GILDASSNYS NMTNNYPRYP VANNSQTSMQ NTNYKDWMNM WDSNTINYRR    60
IDSSPEAYVS AKSAISTGIS IFSKLLSYLG LGLVADSINI TMSLVNTLWN EQNNIWDNLL   120
RHVEDLMDQK ISDLVLSNAI VELTNLKRSL NEYAASLENW KKNPGNPNAI EHIKSQFTNT   180
HNSFVERLAV FAHPGYEVLL LSVYVQAANL HLLLLRDASI YGNQWGLARS NSNYFYGRQL   240
YYTNEYTNHC VNWYHNGLNR LRGTTGAHWL NFNRFRTEMT LTVLDIIALF PTYDYRKYPA   300
FTKVELSRVI YTDPVIYDGF SQLPSNNAGN FNDEREAIG  IPSLTKWLKK IEISTGEIRF   360
ATNPHTGDWV TNVWNGNTNT FAFTESSSEV VESHGIMTNN RTSLNMNNFD NFRVDLRSHC   420
FSQGAPFYDV FGIGRSQFFN GRTNIIYDNE IGITDRYNRH RHQTTTISLP GANSEQATAN   480
DYSHRLADVR NLTGGLRQNP PQQNMGRSSL IGHGWTHVSM KRENILELDK ITQIPAVKSN   540
GWMFSGDLLR GPGHTGGDLV TLGNGDRYTL NIIFPAQAYR IRVRYASNGD GEMGIDVNGV   600
GYTRFSIKCT FSHNNYNNLN SQDFCLVDTS FIYNATYTGS KTIWLYSYST TRVIIDKIEF   660
IPVGIFANQS FEETEGYNQN YSHYDQNMDT TYQPNYDNGY EQNNYDSYDQ SCNNTYESNH   720
DCNCNQEYTN NYNQNSGCTC NQKYNNNYPK                                    750

SEQ ID NO: 39              moltype = AA  length = 750
FEATURE                    Location/Qualifiers
REGION                     1..750
                           note = variant of native sequence
source                     1..750
                           mol_type = protein
                           organism = synthetic construct
SEQUENCE: 39
MDSYPKKNEH GILDASSNYS NMTNNYPRYP VANNSQTSMQ NTNYKDWMNM WDSNTINYRR    60
IDSSPEAYVS AKSAISTGIS IFSKLLSYLG LGLVADSINI TMSLVNTLWN EQNNIWDNLL   120
RHVEDLMDQK ISDLVLSNAI VELTNLKRSL NEYAASLENW KKNPGNPNAI EHIKSQFTNT   180
HNSFVERLAV FAHPGYEVLL LSVYVQAANL HLLLLRDASI YGNQWGLARS NSNYFYGRQL   240
YYTNEYTNHC VNWYHNGLNR LRGTTGAHWL NFNRFRTEMT LTVLDIIALF PTYDYRKYPA   300
FTKVELSRVI YTDPVIYDGF SQLPSNNAGN FNDEREAIG  IPSLTKWLKK IEISTGEIRF   360
ATNPHTGDWV TNVWNGNTNT FAFTESSSEV VESHGIMTNN RTSLNMNNFD NFRVDLRSHC   420
FSQGAPFYDV FGIGRSQFFN GRTNIIYDNE IGITDRYNRH RHQTTTISLP GANSEQATAN   480
DYSHRLADVR NLTGGLRQNP PQQNMGRSSL IGHGWTHVSM KRENILELDK ITQIPAVKSN   540
```

```
GWMFSGDLLR GPGHTGGDLV TLGNGDRYTL NIIFPAQAYR IRVRYASNGD GEMGIDVNGV    600
GYTRFSIKCT FSHNNYNNLN SQDFCLVDTS FIYNATYTGS KTIWLYSYST TRVIIDKIEF    660
IPVGIFANQS FEETEGYNQN YSHYDQNMDT TYQPNYDNGY EQNNYDSYDQ SCNNTYESNH    720
DCNCNQEYTN NYNQNSGCTC NQKYNNNYPK                                    750

SEQ ID NO: 40           moltype = AA  length = 663
FEATURE                 Location/Qualifiers
REGION                  1..663
                        note = variant of native sequence
source                  1..663
                        mol_type = protein
                        organism = synthetic construct
SEQUENCE: 40
MDSYPKKNEH GILDASSNYS NMTNNYPRYP VANNSQTSMQ NTNYKDWMNM WDSNTINYRR     60
IDSSPEAYVS AKSAISTGIS IFSKLLSYLG LGLVADSINI TMSLVNTLWN EQNNIWDNLL    120
RHVEDLMDQK ISDLVLSNAI VELTNLKRSL NEYAASLENW KKNPGNPNAI EHIKSQFTNT    180
HNSFVERLAV FAHPGYEVLL LSVYVQAANL HLLLLRDASI YGNQWGLARS NSNYFYGRQL    240
YYTNEYTNHC VNWYHNGLNR LRGTTGAHWL NFNRFRTEMT LTVLDIIALF PTYDYRKYPA    300
FTKVELSRVI YTDPVIYDGF SQLPSNNAGN FNDFEREAIG IPSLTKWLKK IEISTGEIRF    360
ATNPHTGDWV TNVWNGNTNT FAFTESSSEV VESHGIMTNN RTSLNMNNFD NFRVDLRSHC    420
FSQGAPFYDV FGIGRSQFFN GRTNIIYDNE IGITDRYNRH RHQTTTISLP GANSEQATAN    480
DYSHRLADVR NLTGGLRQNP PQQNMGRSSL IGHGWTHVSN KRENILELDK ITQIPAVKSN    540
GWMFSGDLLR GPGHTGGDLV TLGNGDRYTL NIIFPAQAYR IRVRYASNGD GEMGIDVNGV    600
GYTRFSIKCT FSHNNYNNLN SQDFCLVDTS FIYNATYTGS KTIWLYSYST TRVIIDKIEF    660
IPV                                                                 663

SEQ ID NO: 41           moltype = AA  length = 700
FEATURE                 Location/Qualifiers
REGION                  1..700
                        note = Unknown organism from environmental sample
source                  1..700
                        mol_type = protein
                        organism = unidentified
SEQUENCE: 41
MFRVLYIRNY EHTGGIKMNP YQNTNEYEIL DALPNYSKMV NAYSRYPLAN NPQVPLQNTS     60
YKDWLNMCQT INPLCTPIDP DINSVAAAIG VIGSILGLIP GPGEAIGLIL GTFSSIIPFL    120
WPENKTIIWE EFTHRGLHLI RPELTPAEIE IIVNPLKGYY NALREQLENF EREFAIWDRN    180
KNAATTGDVL RRFSAIDAAI ITLKHQLTVD VRNKPALLSL YAQTANIDLI LFQRGAKYGD    240
EWVRYARNQP IPFKTSQEYY DSLKAKIEIY TNDIAETYRN GLNIIKNIPK ISWDVFNLYR    300
REMTLSALDL VALFPNYDIC RYPISTKTEL TRKVYMSSFY LQALEQNESI ESLENKLTHP    360
PSLFTWLKRL KLYTISENFS PPLRVSSLSG LQAAYSHTHQ QQVLYSHPPQ GITVGEAPEK    420
RIDGFVYKLF MSQNISPNDC YPIGGIPQMS FYISDYSGSL RPNIDYYSAS ASIYFINSYM    480
NGPQNATKSN NISIRETKHI LSDIKMNYSR TGGFYPFHTF GYSFAWTHTS VDTNNLIVPN    540
RITQIPAVKA HVLSATAKVI AGPGHTGGDL VALINDGSRT GSMNIECKTG SFTQPSRRYG    600
LRMRYAANNL FTVYISLNNQ GVGRFDTERT FSRTNNIIPT DLKYNEFKYN NYDKIIMDLP    660
PNTIININIQ QTNALSINQF IIDRIEFYPM DQGVEACKME                         700

SEQ ID NO: 42           moltype = AA  length = 673
FEATURE                 Location/Qualifiers
REGION                  1..673
                        note = variant of native sequence
source                  1..673
                        mol_type = protein
                        organism = synthetic construct
SEQUENCE: 42
MNPYQNTNEY EILDALPNYS KMVNAYSRYP LANNPQVPLQ NTSYKDWLNM CQTINPLCTP     60
IDPDINSVAA AIGVIGSILG LIPGPGEAIG LILGTFSSII PFLWPENKTI IWEEFTHRGL    120
HLIRPELTPA EIEIIVNPLK GYYNALREQL ENFEREFAIW DRNKNAATTG DVLRRFSAID    180
AAIITLKHQL TVDVRNKPAL LSLYAQTANI DLILFQRGAK YGDEWVRYAR NQPIPFKTSQ    240
EYYDSLKAKI EIYTNDIAET YRNGLNIIKN IPKISWDVFN LYRREMTLSA LDLVALFPNY    300
DICRYPISTK TELTRKVYMS SFYLQALEQN ESIESLENKL THPPSLFTWL KRLKLYTISE    360
NFSPPLRVSS LSGLQAAYSH THQQQVLYSH PPQGITVGEA PEKRIDGFVY KLFMSQNISP    420
NDCYPIGGIP QMSFYISDYS GSLRPNIDYY SASASIYFIN SYMNGPQNAT KSNNISIRET    480
KHILSDIKMN YSRTGGFYPF HTFGYSFAWT HTSVDTNNLI VPNRITQIPA VKAHVLSATA    540
KVIAGPGHTG GDLVALINDG SRTGSMNIEC KTGSFTQPSR RYGLRMRYAA NNLFTVYISL    600
NNQGVGRFDT ERTFSRTNNI IPTDLKYNEF KYNNYDKIIM DLPPNTIINI NIQQTNALSI    660
NQFIIDRIEF YPM                                                      673

SEQ ID NO: 43           moltype = AA  length = 683
FEATURE                 Location/Qualifiers
REGION                  1..683
                        note = variant of native sequence
source                  1..683
                        mol_type = protein
                        organism = synthetic construct
SEQUENCE: 43
MNPYQNTNEY EILDALPNYS KMVNAYSRYP LANNPQVPLQ NTSYKDWLNM CQTINPLCTP     60
IDPDINSVAA AIGVIGSILG LIPGPGEAIG LILGTFSSII PFLWPENKTI IWEEFTHRGL    120
HLIRPELTPA EIEIIVNPLK GYYNALREQL ENFEREFAIW DRNKNAATTG DVLRRFSAID    180
```

```
AAIITLKHQL TVDVRNKPAL LSLYAQTANI DLILFQRGAK YGDEWVRYAR NQPIPFKTSQ    240
EYYDSLKAKI EIYTNDIAET YRNGLNIIKN IPKISWDVFN LYRREMTLSA LDLVALFPNY    300
DICRYPISTK TELTRKVYMS SFYLQALEQN ESIESLENKL THPPSLFTWL KRLKLYTISE    360
NFSPPLRVSS LSGLQAAYSH THQQQVLYSH PPQGITVGEA PEKRIDGFVY KLFMSQNISP    420
NDCYPIGGIP QMSFYISDYS GSLRPNIDYY SASASIYFIN SYMNGPQNAT KSNNISIRET    480
KHILSDIKMN YSRTGGFYPF HTFGYSFAWT HTSVDTNNLI VPNRITQIPA VKAHVLSATA    540
KVIAGPGHTG GDLVALINDG SRTGSMNIEC KTGSFTQPSR RYGLRMRYAA NNLFTVYISL    600
NNQGVGRFDT ERTFSRTNNI IPTDLKYNEF KYNNYDKIIM DLPPNTIINI NIQQTNALSI    660
NQFIIDRIEF YPMDQGVEAC KME                                           683

SEQ ID NO: 44           moltype = AA  length = 306
FEATURE                 Location/Qualifiers
source                  1..306
                        mol_type = protein
                        organism = Bacillus sp.
SEQUENCE: 44
VERRLKFMAI FDLDAYLMEL AKKYFPSPFN QFISRIDTTS LLKVKNAESY GFEIKNSKPQ     60
GTMFMGESVL KNDTNETQTI KSDSFTKTIT DSITLSVTNG IKTGIEINVG GKVFGIGVET    120
SMSFEVSTST TREQTSTEGV AYTVPSQDVV VPAKKIYYVY TALQRSQLEG TIRLRADLFN    180
AFGVYMNMGG KEIPLGSYWI YDFIKENQSL HPLSGISLN HNDRSVHFEG VAEYLYGTGT     240
KFNVTITDTP SSQGTQEHKP FDAKTGLGTY ELRLDGKKLG FDLNDLKEHM DPKDFEKLKE    300
MQSEIV                                                              306

SEQ ID NO: 45           moltype = AA  length = 299
FEATURE                 Location/Qualifiers
REGION                  1..299
                        note = variant of native sequence
source                  1..299
                        mol_type = protein
                        organism = synthetic construct
SEQUENCE: 45
MAIFDLDAYL MELAKKYFPS PFNQFISRID TTSLLKVKNA ESYGFEIKNS KPQGTMFMGE     60
SVLKNDTNET QTIKSDSFTK TITDSITLSV TNGIKTGIEI NVGGKVFGIG VETSMSFEVS    120
TSTTREQTST EGVAYTVPSQ DVVVPAKKIY YVYTALQRSQ LEGTIRLRAD LFNAFGVYMN    180
MGGKEIPLGS YWIYDFIKEN QSLHPLSGI SLNHNDRSVH FEGVAEYLYG TGTKFNVTIT     240
DTPSSQGTQE HKPFDAKTGL GTYELRLDGK KLGFDLNDLK EHMDPKDFEK LKEMQSEIV     299

SEQ ID NO: 46           moltype = AA  length = 977
FEATURE                 Location/Qualifiers
source                  1..977
                        mol_type = protein
                        organism = Bacillus sp.
SEQUENCE: 46
MQENVSGMIC NVRGFSLECI GNKLLIKAVY HKKIDNKELQ TVSWQWNDSP IYGYGVKEGR     60
YKYDLTEMRD TGKTYEVTSE WSVIDGESIN DELPVTETVD TRDSIQYWGN TESEALNAEL    120
YNEKSYRYEM SDTSITDKYN FIFKNYYDDG SLIVYEFEYN ISDCTIQFKN VSSDLFPLSS    180
VEAAIKDEHQ FDGWAMGTCS NTEDIYVKDL SSYTIGLYFK NVSAYTLDQV TKYRVSIDQK    240
EPVTKIRYNP EPDGRMKLDL LPYHKGLGIT EGSLITVWAI TVNGYAIKVF EGLTNGGEQS    300
IQSNENGYAY DSSIGYSNPN WVGKINGERT ISEVSFAGTH GSIALHGVTP FDEDWVRNQR    360
MTITTQLNSG IRYFDIRARR TQNSFAMHHG SVFQKLMFGD VLDAMALFLR QNPYETILMR    420
LKEEHPETG SASFETILTR YWNLYNSYFW DPKSSNPKLK DVRGKIIIIQ NFSASKSFGI     480
SYNSLVIQDY DNVDDAPDAM YDKWNRVKSH LQSANNSNKT QIYLNHLSGN GGYNGAKPWF    540
VSSGYNSRGT DSIKKLIQES NSSKWPDYPR GYYGQVFYGG TNLLTKEFIP RLGLQHVGII    600
AADFPGKGLI DTVVKLNGRL STSDIQYVRL NANKEIEVGF TGDVYRKHY QIKRNGSYIA     660
SLENGTAYYS YWQQTSFGHQ LTRKGITLFT GDKIQVYLVG GGKETLLATL TVEIKEEELE    720
IIQVPDGPYK IISELNKSSV VDLSKTSSQN VALWTYNNQL EGEWDFKYDS TQKAYRIYNR    780
WNSSLVMARN AYDEGINVFG TPYEGKLEHL WIIRRTGDND GTVYLQNKKD ETKQLMLDVQ    840
AGGTSNGTNI NIWPLNRLKQ QKFKLVARRE TLESQIDSSY RPLSGQKNRS SSNFSLGHLA    900
DGTRVRVSIE GAGSVNLSFR VMRDKPADTD PTIWSDVKNG SILTVQSGAN KKDLYIANPS    960
GYSSNGTFKV KFYTLEN                                                  977

SEQ ID NO: 47           moltype = AA  length = 606
FEATURE                 Location/Qualifiers
REGION                  1..606
                        note = Unknown organism from environmental sample
source                  1..606
                        mol_type = protein
                        organism = unidentified
SEQUENCE: 47
MKYKNRKHAK RKYKQALLAT VATMTLGVST LGSTASALAA EDITETRKVT PQLRSADPIA     60
DGIFKIAADG TITLLNANLF DSATAKAIAS LGGNLLKQLY LDAYNNDFTG SAKTLVLGAT    120
ALVPYVGSFV SPIIGLLWPA NTSNNIAKQT EALVKMMHQE ITNYDLEALA QEVKTLAELT    180
SRFDDLLNGK PLSAKEYAET GTIQETLRTK ASAINDQFIR LNQCQKSSF KSEELPIYTT     240
VATARLLFLN VIELHGQGPK MQMDDATYGE YVKDFKNLPT EFTNYIEATH KKTIDEMQKQ    300
MKPILDEAKK DPMSVSGNEQ ENIKNMEKRL AHWRDEVATS KDPTIKEYAK FRRDKMQGYL    360
NAYRGLVNAK SDYIKKTVDN TAFKLVKESL SAPVEIRVPD GNYRLQSALD TNMSVGLSDD    420
QKNIELRKNN DQLNTDFILT YSSLRKTYEI RSSRLDSNLY MTGSYGHDIN NVFTMARQYS    480
DSQHWKVLKA RGSEFMYLKN YKTSQVLDIF NANPNNGANI ITWPLKPQDQ NPNNQQFKLV    540
PLELESKEQK LGPEEQILLW DSHKPYKKGD IVKHQDKTYK CIQDYNGDGN PEWIFAKSLW    600
```

KPISNQ                                                                        606

SEQ ID NO: 48           moltype = AA  length = 568
FEATURE                 Location/Qualifiers
REGION                  1..568
                        note = variant of native sequence
source                  1..568
                        mol_type = protein
                        organism = synthetic construct
SEQUENCE: 48
MAEDITETRK VTPQLRSADP IADGIFKIAA DGTITLLNAN LFDSATAKAI ASLGGNLLKQ  60
LYLDAYNNDF TGSAKTLVLG ATALVPYVGS FVSPIIGLLW PANTSNNIAK QTEALVKMMH  120
QEITNYDLEA LAQEVKTLAE LTSRFDDLLN GKPLSAKEYA ETGTIQETLR TKASAINDQF  180
IRVLNQCQKS SFKSEELPIY TTVATARLLF LNVIELHGQG PKMQMDDATY GEYVKDFKNL  240
PTEFTNYIEA THKKTIDEMQ KQMKPILDEA KKDPMSVSGN EQENIKNMEK RLAHWRDEVA  300
TSKDPTIKEY AKFRRDKMQG YLNAYRGLVN AKSDYIKKTV DNTAFKLVKE SLSAPVEIRV  360
PDGNYRLQSA LDTNMSVGLS DDQKNIELRK NNDQLNTDFI LTYSSLRKTY EIRSSRLDSN  420
LYMTGSYGHD INNVFTMARQ YSDSQHWKVL KARGSEFMYL KNYKTSQVLD IFNANPNNGA  480
NIIITWPLKPQ DQNPNNQQFK LVPLELESKE QKLGPEEQIL LWDSHKPYKK GDIVKHQDKT  540
YKCIQDYNGD GNPEWIFAKS LWKPISNQ                                    568

SEQ ID NO: 49           moltype = AA  length = 959
FEATURE                 Location/Qualifiers
REGION                  1..959
                        note = Unknown organism from environmental sample
source                  1..959
                        mol_type = protein
                        organism = unidentified
SEQUENCE: 49
MIMQMVTKVM TPKLGALPDF IDDFNGIFGF MDNITGVMST IFGVDTGDSS IDDVLNNEEL  60
LQEMLDQMNT MQISIRDILE QQGISADIEK QILALTTDLA TSINTELGKI EGILNTYLPA  120
ISNMLSNIYE QTSVIDQKVD KLLALMTFAL KELDYIKDNV VLNSSIVEIT PHVQKLVYVN  180
KKFLTLTRGF LQGEDVSIDS MQEIQEWAKS ILATEMNSFE FSVDTLHSII IGDNLYKRSA  240
LKTFSDVLLD DADQYGDFGT PLAKFYTFFS SLATLQINAY LCLTFARKVL GLSEIDYQVT  300
MQDRIEQQNQ MFVNLIQDKN YSNALEITGI YPMSLDRGDC KSTDLQADAG CALIGLEFFM  360
DNGIYKAKAY QGEIGKNFSV SADTVTELIS DDLSTLFHDT TNDNPELDVV YPLSGELTGP  420
PNTIITRIGL GTKYDKTRES SVQAFAYIDA DFSPYDYISG TISKGGTQTV SLEGNDHKNR  480
GYSNWPIGLI GDLYMTPLKS LSLNVEDTGT TLNMSGESYF STILSREYNT NFILFPYTNN  540
SSPIAENLIQ NGNFEDGDKY WEIVTGAAVI AEGEGIYGSN AISISMDDSG PALKQELKLK  600
PYTSYELTAY IKSKTNKLQQ GHISITYNNN DITWITETFS TSYKQIKLNF RTGADNQDFH  660
VTFEEQNSDY LLLDNIQLHE IPQTDNLIDR GDFGVYEGDT NDYRLWQTPY LWELDGGAEL  720
TDKETLFKPK CLKIIQRGGA NQKVQLKANT NYILTAYVKV DDPTTTAQIG CGSNQIPCNS  780
TSYTPLKLKF RTGEDPSTTE SSVYCSNSND SGTVWADNFV LYEVPNLIVN GDFEQFDQSY  840
WTFSPSEGGR IYLQSGLGMS HSNAVVLQGQ NGQISQKVPL KPFTKYRLTA YVKVSRGSIA  900
HIGYGDNTCA CAVDDFRQAL VDFTTGANPM QSDDAIYLSS GNSKYTVADN FELYELDQI   959

SEQ ID NO: 50           moltype = AA  length = 957
FEATURE                 Location/Qualifiers
REGION                  1..957
                        note = variant of native sequence
source                  1..957
                        mol_type = protein
                        organism = synthetic construct
SEQUENCE: 50
MQMVTKVMTP KLGALPDFID DFNGIFGFMD NITGVMSTIF GVDTGDSSID DVLNNEELLQ  60
EMLDQMNTMQ ISIRDILEQQ GISADIEKQI LALTTDLATS INTELGKIEG ILNTYLPAIS  120
NMLSNIYEQT SVIDQKVDKL LALMTFALKE LDYIKDNVVL NSSIVEITPH VQKLVYVNKK  180
FLTLTRGFLQ GEDVSIDSMQ EIQEWAKSIL ATEMNSFEFS VDTLHSIIIG DNLYKRSALK  240
TFSDVLLDDA DQYGDFGTPL AKFYTFFSSL ATLQINAYLC LTFARKVLGL SEIDYQVTMQ  300
DRIEQQNQMF VNLIQDKNYS NALEITGIYP MSLDRGDCKS TDLQADAGCA LIGLEFFMDN  360
GIYKAKAYQG EIGKNFSVSA DTVTELISDD LSTLFHDTTN DNPELDVVYP LSGELTGPPN  420
TIITRIGLGT KYDKTRESSV QAFAYIDADF SPYDYISGTI SKGGTQTVSL EGNDHKNRGY  480
SNWPIGLIGD LYMTPLKSLS LNVEDTGTTL NMSGESYFST ILSREYNTNF ILFPYTNNSS  540
PIAENLIQNG NFEDGDKYWE IVTGAAVIAE GEGIYGSNAI SISMDDSGPA LKQELKLKPY  600
TSYELTAYIK SKTNKLQQGH ISITYNNNDI TWITETFSTS YKQIKLNFRT GADNQDFHVT  660
FEEQNSDYLL LDNIQLHEIP QTDNLIDRGD FGVYEGDTND YRLWQTPYLW ELDGGAELTD  720
KETLFKPKCL KIIQRGGANQ KVQLKANTNY ILTAYVKVDD PTTTAQIGCG SNQIPCNSTS  780
YTPLKLKFRT GEDPSTTESS VYCSNSNDSG TVWADNFVLY EVPNLIVNGD FEQFDQSYWT  840
FSPSEGGRIY LQSGLGMSHS NAVVLQGQNG QISQKVPLKP FTKYRLTAYV KVSRGSIAHI  900
GYGDNTCACA VDDFRQALVD FTTGANPMQS DDAIYLSSGN SKYTVADNFE LYELDQI    957

SEQ ID NO: 51           moltype = AA  length = 669
FEATURE                 Location/Qualifiers
REGION                  1..669
                        note = Unknown organism from environmental sample
source                  1..669
                        mol_type = protein
                        organism = unidentified
SEQUENCE: 51

```
VKNMNSYQNT NEYEILDASQ NNSTMSNRYP RYPLANDPQA SMQNTNYKDW LNLCDTPNME   60
NPEFQSVGRS ALSILINLSS RILSLLGIPF AAQIGQLWSY TLNLLWPVAN NATQWEIFMR  120
TIEELINIRI ETSVRNRALA ELAGLGNILE DYKVALQRWD LNPTNLVLQS EVVRQFEIVH  180
AFFRAQMPVF AIRDFEVPLL PVYASAANLH LLLLRDVVIN GSRWGLEDDR INDYHDLQLR  240
LTSTYTDHCV NWYNTGLNRL IGTNARQWVT YNQFRREMTI SVLDIISLFS NYDVRRYPTK  300
IQSELTRMIY TDPVGTEGNQ FIPGWLDNAP SFSAIENSVV QMPQFFTFLE RVGIFTGFLH  360
GWSSRSEFWS AHRLFSRWTL GGLFESAVFG NTQNNIGYQE VDFTNFDVFS INSRATSHMF  420
PNGSARLFGV PQVTFNLSNI NNNSLAQRSY NRPFTFGGQD IVSRLPGETT ETPNSSNYSH  480
RLAHISSFPV GNNGSVLSYG WTHRSVNRHN RLDPTSITQI PAVKGWGGVT GSVIPGPTGG  540
NLVSLPMSPW SVSLRVQAPQ IQTDYRIRLR FACVWPGTHH MWVSHGGISH PVQILCNNTS  600
GRPSNNLLVS DFGYVVVPGT FSPSINPEIR FSSISGSPVL DKIEFIPLDM YNDLFLGDRE  660
KTVSDLFIN                                                         669

SEQ ID NO: 52           moltype = AA   length = 645
FEATURE                 Location/Qualifiers
REGION                  1..645
                        note = variant of native sequence
source                  1..645
                        mol_type = protein
                        organism = synthetic construct
SEQUENCE: 52
MNSYQNTNEY EILDASQNNS TMSNRYPRYP LANDPQASMQ NTNYKDWLNL CDTPNMENPE   60
FQSVGRSALS ILINLSSRIL SLLGIPFAAQ IGQLWSYTLN LLWPVANNAT QWEIFMRTIE  120
ELINIRIETS VRNRALAELA GLGNILEDYK VALQRWDLNP TNLVLQSEVV RQFEIVHAFF  180
RAQMPVFAIR DFEVPLLPVY ASAANLHLLL LRDVVINGSR WGLEDDRIND YHDLQLRLTS  240
TYTDHCVNWY NTGLNRLIGT NARQWVTYNQ FRREMTISVL DIISLFSNYD VRRYPTKIQS  300
ELTRMIYTDP VGTEGNQFIP GWLDNAPSFS AIENSVVQMP QFFTFLERVG IFTGFLHGWS  360
SRSEFWSAHR LFSRWTLGGL FESAVFGNTQ NNIGYQEVDF TNFDVFSINS RATSHMFPNG  420
SARLFGVPQV TFNLSNINNN SLAQRSYNRP FTFGGQDIVS RLPGETTETP NSSNYSHRLA  480
HISSFPVGNN GSVLSYGWTH RSVNRHNRLD PTSITQIPAV KGWGGVTGSV IPGPTGGNLV  540
SLPMSPWSVS LRVQAPQIQT DYRIRLRFAC VWPGTHHMWV SHGGISHPVQ ILCNNTSGRP  600
SNNLLVSDFG YVVVPGTFSP SINPEIRFSS ISGSPVLDKI EFIPL                  645

SEQ ID NO: 53           moltype = AA   length = 666
FEATURE                 Location/Qualifiers
REGION                  1..666
                        note = variant of native sequence
source                  1..666
                        mol_type = protein
                        organism = synthetic construct
SEQUENCE: 53
MNSYQNTNEY EILDASQNNS TMSNRYPRYP LANDPQASMQ NTNYKDWLNL CDTPNMENPE   60
FQSVGRSALS ILINLSSRIL SLLGIPFAAQ IGQLWSYTLN LLWPVANNAT QWEIFMRTIE  120
ELINIRIETS VRNRALAELA GLGNILEDYK VALQRWDLNP TNLVLQSEVV RQFEIVHAFF  180
RAQMPVFAIR DFEVPLLPVY ASAANLHLLL LRDVVINGSR WGLEDDRIND YHDLQLRLTS  240
TYTDHCVNWY NTGLNRLIGT NARQWVTYNQ FRREMTISVL DIISLFSNYD VRRYPTKIQS  300
ELTRMIYTDP VGTEGNQFIP GWLDNAPSFS AIENSVVQMP QFFTFLERVG IFTGFLHGWS  360
SRSEFWSAHR LFSRWTLGGL FESAVFGNTQ NNIGYQEVDF TNFDVFSINS RATSHMFPNG  420
SARLFGVPQV TFNLSNINNN SLAQRSYNRP FTFGGQDIVS RLPGETTETP NSSNYSHRLA  480
HISSFPVGNN GSVLSYGWTH RSVNRHNRLD PTSITQIPAV KGWGGVTGSV IPGPTGGNLV  540
SLPMSPWSVS LRVQAPQIQT DYRIRLRFAC VWPGTHHMWV SHGGISHPVQ ILCNNTSGRP  600
SNNLLVSDFG YVVVPGTFSP SINPEIRFSS ISGSPVLDKI EFIPLDMYND LFLGDREKTV  660
SDLFIN                                                            666

SEQ ID NO: 54           moltype = AA   length = 757
FEATURE                 Location/Qualifiers
REGION                  1..757
                        note = Unknown organism from environmental sample
source                  1..757
                        mol_type = protein
                        organism = unidentified
SEQUENCE: 54
MLMENNSLNV LANNNMSSFP LFNNKIEPSI APALIAVEPI AKYLATALAK WVAKEAFAKL   60
KSVIFPGNTP ATMEKVRLEV QTLLNQRLQD DRVLILNAEY QGFINLGRVF TDYVSQSTYT  120
PDTAKTHFLS MSNQLIQRLP QFEIAGYEGV SIALFTQMCT LHLGLLKDGI LAGSDWGFTP  180
ADKDSLICQF NRYVNEYHTR MMGLYSKEFG RLLSINLNQA LNFRNMCSLY VPFSEAWSL   240
LRYEGTKLEN TLSLWNFVGL PIANISPYDW GGALYKLLMG APNQRLNVQ FNYSYFSNAG  300
PTLDGEKIIG TLPRYNGGPT ITGWIGNGRL GGFSSPCNNE LEITKIKQEI TYNGKGGNSN  360
SIAPANAFNE ILTATVPTSP EPFFKTADIN MTYNVPRGWN IKFDNQVILR TRMPINIPPN  420
SLEYEGYYIR AVSACPQGLP LSYNHDFLTL TYNTLEYVAP TTQNIIVGFS PNITKNFYSR  480
NSHYLSATDD AYVIPALQFA TVSDRSFLED TPDQATDGSI KFNNNFLGNE AKYSIRLNTG  540
FNTATRYRLI IRFKAPARLA SGIRVRSQNS GNNRLLAAIP VEGNSGWVNY VTDSFTFNDL  600
GITPTSTNAF FSIDSDGVNA SQQWYLSKLI LVKDFVNNSG FRNQVPFNPL VITRCPETLF  660
VSNNSSSTYE QGNNYNYDQN SSSAYEQGRG YNYDQNSSSA YEQGDNYNYD QNSSSAYEQG  720
DNYNYDQNLC CACNQNYDGS HKQSVGCTCN RNYKNNY                          757

SEQ ID NO: 55           moltype = AA   length = 853
FEATURE                 Location/Qualifiers
REGION                  1..853
```

```
                    note = Unknown organism from environmental sample
source              1..853
                    mol_type = protein
                    organism = unidentified
SEQUENCE: 55
MAQLRELQTQ SIIPYNVLVN PPISNINLNN DPCVGTDSAS LAKCLADAWS TFQKTGVLNY   60
DAFKQGLTVA AGGKLNYLAL VQSAIGLAGV LGAEIPGVAI AAPILSLLIG AFWPFGKPAA  120
QNIITIVDQE VQRLLNQDLG DALIKTLNQH LSDLNEFVTD LSDKMHNALF TNNQAISLVA  180
PSDYENVDQS FTAITAAGTN AMSEFLANVS TCTFKEKTPP PCFTQQVFPL FVMAATLDLS  240
IYQSYIKFGN VWLDKIQWTA DQQTQGKPKT MADNLNLAKQ KMREKIRDFT NQALTAFNDP  300
SIKPKVGTNK NSINSYNRYV RFMQINGLDL VAMWPTMYPD NYTTQMKMEH TRVVFSDLVG  360
QDQSKDGDVT IYTMLDKPGP DVWKQHPQTS IDSIAYFKDE LGQIQLAQHY SRQSNGIQCY  420
PYGIILNYPS NTYVYGQLYN PWGEQNMAVS KAPLIDVNAQ TQHNSSTSIT YEHLDFTGDG  480
TPGTGGSAGC NPIGYCTGGD CYHPTGCSSD FGYSCNTPLP GQKINAFYPF VQSNTEGTAD  540
RIGLMSSNVP LDLSPNNVFG ELDTETRNII GKGFPAEKGT LASGNVPTVV REWVNGANAV  600
KLSDVPLTLK MTNMTSGKYY IRVRYANTSN AEISINQSVS AGNQNIQNGP WGLPSTIAGN  660
VAANFPNQLY ITGINGNYVL EDITWGVDGQ GKPITIPSGD VTVTLSRTNM SQSGDLFIDR  720
VELVPSSPQN LTYIVTKPLV AFTNQSLDTF PTIWTAGPEG SGLKANLQLG NLNSTVSFLV  780
KTKDGADSDR NNWEQMCSGG FTRFGNGNLH FKPGDSYPAG CYKSSFTAIK LLNNPSDGRS  840
LLTQGIITGS VFV                                                    853

SEQ ID NO: 56       moltype = AA  length = 726
FEATURE             Location/Qualifiers
REGION              1..726
                    note = variant of native sequence
source              1..726
                    mol_type = protein
                    organism = synthetic construct
SEQUENCE: 56
MAQLRELQTQ SIIPYNVLVN PPISNINLNN DPCVGTDSAS LAKCLADAWS TFQKTGVLNY   60
DAFKQGLTVA AGGKLNYLAL VQSAIGLAGV LGAEIPGVAI AAPILSLLIG AFWPFGKPAA  120
QNIITIVDQE VQRLLNQDLG DALIKTLNQH LSDLNEFVTD LSDKMHNALF TNNQAISLVA  180
PSDYENVDQS FTAITAAGTN AMSEFLANVS TCTFKEKTPP PCFTQQVFPL FVMAATLDLS  240
IYQSYIKFGN VWLDKIQWTA DQQTQGKPKT MADNLNLAKQ KMREKIRDFT NQALTAFNDP  300
SIKPKVGTNK NSINSYNRYV RFMQINGLDL VAMWPTMYPD NYTTQMKMEH TRVVFSDLVG  360
QDQSKDGDVT IYTMLDKPGP DVWKQHPQTS IDSIAYFKDE LGQIQLAQHY SRQSNGIQCY  420
PYGIILNYPS NTYVYGQLYN PWGEQNMAVS KAPLIDVNAQ TQHNSSTSIT YEHLDFTGDG  480
TPGTGGSAGC NPIGYCTGGD CYHPTGCSSD FGYSCNTPLP GQKINAFYPF VQSNTEGTAD  540
RIGLMSSNVP LDLSPNNVFG ELDTETRNII GKGFPAEKGT LASGNVPTVV REWVNGANAV  600
KLSDVPLTLK MTNMTSGKYY IRVRYANTSN AEISINQSVS AGNQNIQNGP WGLPSTIAGN  660
VAANFPNQLY ITGINGNYVL EDITWGVDGQ GKPITIPSGD VTVTLSRTNM SQSGDLFIDR  720
VELVPS                                                            726

SEQ ID NO: 57       moltype = AA  length = 348
FEATURE             Location/Qualifiers
REGION              1..348
                    note = Unknown organism from environmental sample
source              1..348
                    mol_type = protein
                    organism = unidentified
SEQUENCE: 57
MKTCSNQNEV NPRALSLFDL EYYLTRTMYN VSATPISLGW RYQKNADLGS WRFSENAIPT   60
PTSGQIPNPC QSIYAAYPYN CTWGSQDYAY TVDTSGLIAG GVDVYQQINS IPLQTPIIAD  120
RHEYRNTSSL QQAYVSPSYS ESVTTTTTNT TTNGCKFNTK ASYSKKSKYK VAIRDIERGF  180
NLEVGAEYNF SNTQTTTAST IRTVTFPSFT TQVPPRTTAI VSIILNRGYY TNYNVPEVD   240
LTGRFNQGWT SQPPTYVAAR YDLYPFVELV QTCCKSCVDC NPKEIRALPS TGTVRFNGTG  300
TFIADVASNN FVVTTSFIDN DTGATVAEQV EYVPAIYEGP AIQTVTTS              348

SEQ ID NO: 58       moltype = AA  length = 1422
FEATURE             Location/Qualifiers
source              1..1422
                    mol_type = protein
                    organism = Bacillus sp.
SEQUENCE: 58
MATINELYPV PYNVLARPVS QNNDALSDFM DIFNDLKGAY DEFSKTGAKD PLQNHLMLAW   60
NAYQTGKIDY LALTKATISL AGLIPGVGAA VPIVNMVVDM VWPSLFGAPK ADPYAELFKQ  120
IMKAVEDYVG QQFNNFEISW LQTSLQSLRD ALAKFQNSIQ VAVCQGRAPE SGFLATSDAD  180
CPSTPIPCEP CSTHLTAVKT AFGDANTTFT TYLPHFKNPA SNQTTDDNGF YGDLIAVTLP  240
MFTTAATLQM VMKGYIQFM EKWGGLTSGE LNDVKAELQE LIRDNTKVVR DTFKKYLPTL  300
DTGRKQSINK YNRYVRNMVL NVFDLAVIWP SFDGTYYSSS LQLDQTRLVF SDIAGPWEGN  360
ENIGANVIDI FSPVSTWVGY QEGSDLRNFT YPRMDLQNVQ FHQQSVASHS VTHCYSDGLK  420
LTYNDNQVIT AGQNNTDESN QSNKHGYGAL VQSPVTDINV YSQNTMYLDV SSISVNGGWA  480
VAGCSPLSSQ GNSNNEALTG QKINVIYPVQ SNDKSEKHAD TSTKWGYMST HIPFDLVPEN  540
IIGDIDQNTK LPSTQIKGFP FEKYGTEYNN RGIVLVPEWI NGNHSVKLSS GQSVGIHITN  600
QRKQKYEVRC RYASNGTNNV YFNVDLSENP FRNTVSFDST ANRQMAVGGE NGKYVVKSIT  660
TVEIPAGNQG FYVHITNQGS SDLFLDRIEF VPPIPLPLPS PSSGLKFDAP GPYILVSKEN  720
FVIWKAPVTK ICDDSLQVDL SFKFAGYGEL QYLGDNDTIL TKQTIAWSSE APYSFSKAFS  780
ANDLKEIRFV ALDDDAVSISQ VVGEILCFEG NCHAVLPEPL VVEHASDTTI WPNAGTNVKG  840
NLIVTAETSD FRWSLLDDYD FIALSTSVPP PTFNNGIYTW NVPIASSRPF KYLNFRNLSY  900
```

```
NKTTISGTLS ACTSDNRSMS INTSINQNNM FSNPTDLANI TTQVNALFAS NTQNTLATDV    960
SDYKIEEVVL KVDALSDEVF GKEKKALRKL VNQAKRLSKA RNLLVGGNFD NLDAWYRGRN   1020
VVNVSDHELF KSDHVLLPPP TLYPSYIFQK LEESKLKANT RYTVSGFIAH AEDLEIIVSR   1080
YGGQEIKKVVQ VPYGEAFPLT SSGPVCCVPR STRNGTPADP HFFSYSIDVG ALDMAVGPGI  1140
EFGLRIVERT GMARVSNLEI REDRPLKTNE LRKVQRAARD WRQKYDQERA EVTALIQPVL   1200
NQINALYENE DWNGAIRSGV SYHDLEAIVL PTLPKLNHWF MSDMLGEQGS ILAQFQEALD   1260
RAYTQLEGRT ILHNGHFTTD AANWTIEGDA HHAILEDGRR VLRLPDWSSS VSQTIEIEDF   1320
DPDKEYQLVF HAQGEGTVSL QHGEEGEYVE THPHKFANFT TSQRQGVTFE TNKVTVEIAS   1380
EDGEFLVDHI ALVEAPLPTD DQNSEGNTTS STNSNTSMNN NQ                     1422

SEQ ID NO: 59           moltype = AA   length = 693
FEATURE                 Location/Qualifiers
REGION                  1..693
                        note = variant of native sequence
source                  1..693
                        mol_type = protein
                        organism = synthetic construct
SEQUENCE: 59
MATINELYPV PYNVLARPVS QNNDALSDFM DIFNDLKGAY DEFSKTGAKD PLQNHLMLAW    60
NAYQTGKIDY LALTKATISL AGLIPGVGAA VPIVNMVVDM VWPSLFGAPK ADPYAELFKQ   120
IMKAVEDYVG QQFNNFEISW LQTSLQSLRD ALAKFQNSIQ VAVCQGRAPE SGFLATSDAD   180
CPSTPIPCEP CSTHLTAVKT AFGDANTTFT TYLPHFKNPA SNQTTDDNGF YGDLIAVTLP   240
MFTTAATLQM VMYKGYIQFM EKWGGLTSGE LNDVKAELQE LIRDNTKVVR DTFKKYLPTL   300
DTGRKQSINK YNRYVRNMVL NVFDLAVIWP SFDGTYYSSS LQLDQTRLVF SDIAGPWEGN   360
ENIGANVIDI FSPVSTWVGY QEGSDLRNFT YPRMDLQNVQ FHQQSVASHS VTHCYSDGLK   420
LTYNDNQVIT AGQNNTDESN QSNKHGYGAL VQSPVTDINV YSQNTMYLDV SSISVNGGWA   480
VAGCSPLSSQ GNSNNEALTG QKINVIYPVQ SNDKSEKHAD TSTKWGYMST HIPFDLVPEN   540
IIGDIDQNTK LPSTQIKGFP FEKYGTEYNN RGIVLVPEWI NGNHSVKLSS GQSVGIHITN   600
QRKQKYEVRC RYASNGTNNV YFNVDLSENP FRNTVSFDST ANRQMAVQGE NGKYVVKSIT   660
TVEIPAGNQG FYVHITNQGS SDLFLDRIEF VPP                               693

SEQ ID NO: 60           moltype = AA   length = 573
FEATURE                 Location/Qualifiers
source                  1..573
                        mol_type = protein
                        organism = Bacillus sp.
SEQUENCE: 60
LHYCCTRTIK NKRMLKIILQ VPLSIYKKGY IKTAKLFLNY TGNLNYLYKR GINMNQLELI    60
QNPWKSRQSS ARVVILQVNN PAQTNNSLDI TQIENLNHLQ QAIDLSNAFQ DALVPTSSEF   120
GNNTLRFDIS RGLQIANHLI PKAVTIDDKY SILTQNNNQV GTMVDRVTFE LKTLFGISLS   180
HSVSQQLTAA IRETFTNLNI QKNSAWIFWG KTTSAQTNYT YNILFAIQNA ETGHFMAAIP   240
IGFEITAHAV REKVLFFTVK DYASYSVKIE GIKVAQPLSN ENNIAFTGVY NIVSALNNKS   300
VINMSTISYN NVDYKVNLWE KTNTNNQNWA FIYDKDKKAY QIENLFFPGL VLAWNNYGDS   360
NIVFATSNKK YAEHYWILQE AGNNYFYLVN MKNTNLVLDV SDSDNSNGTN VIVHPKNGGT   420
NQKFSIQENH GIQSGTYQLV TALNNSSVVD LNQSNNNVTL WSNNQGNNQK WNFIYDSTRS   480
AYQIKNVANE SLVLTWTYYS SDRDNIAAIS NQHRPEQYWI PEYIGAGYYR FKNYMNPQGA   540
MDVKGSGTKN GTNILYYSYH GSNNQKFKLL TTK                               573

SEQ ID NO: 61           moltype = AA   length = 520
FEATURE                 Location/Qualifiers
REGION                  1..520
                        note = variant of native sequence
source                  1..520
                        mol_type = protein
                        organism = synthetic construct
SEQUENCE: 61
MNQLELIQNP WKSRQSSARV VILQVNNPAQ TNNSLDITQI ENLNHLQQAI DLSNAFQDAL    60
VPTSSEFGNN TLRFDISRGL QIANHLIPKA VTIDDKYSIL TQNNQVGTM VDRVTFELKT    120
LFGISLSHSV SQQLTAAIRE TFTNLNIQKN SAWIFWGKTT SAQTNYTYNI LFAIQNAETG   180
HFMAAIPIGF EITAHAVREK VLFFTVKDYA SYSVKIEGIK VAQPLSNENN IAFTGVYNIV   240
SALNNKSVIN MSTISYNNVD YKVNLWEKTN TNNQNWAFIY DKDKKAYQIE NLFFPGLVLA   300
WNNYGDSNIV FATSNKKYAE HYWILQEAGN NYFYLVNMKN TNLVLDVSDS DNSNGTNVIV   360
HPKNGGTNQK FSIQENHGIQ SGTYQLVTAL NNSSVVDLNQ SNNNVTLWSN NQGNNQKWNF   420
IYDSTRSAYQ IKNVANESLV LTWTYYSSDR DNIAAISNQH RPEQYWIPEY IGAGYYRFKN   480
YMNPQGAMDV KGSGTKNGTN ILYYSYHGSN NQKFKLLTTK                        520

SEQ ID NO: 62           moltype = AA   length = 1395
FEATURE                 Location/Qualifiers
REGION                  1..1395
                        note = Unknown organism from environmental sample
source                  1..1395
                        mol_type = protein
                        organism = unidentified
SEQUENCE: 62
MGGLLMNQYY NNNEYEILDN GDRGYQPRYP LAQAPGSEFQ QMNYKDWMDR YTGEEQAGGL    60
IRAEIDANTA LTATFGVAWA VLGVSNPVGS AVAGILNVVT PIIFNQVDPN SPLKVWESMI   120
GYAQALIKKE LTETVRNLAL DHIDRINDYQ IDYKNKAKIW ETNPTPGNTS QLLDAFRNLK   180
RSCQDAMPHL DTRGYETILL PLYAQAANIH LIVLRDGLMH GRSWGMTNEE YEDLYSGFFG   240
FTNRIATYTN YCTNTFNQGA TMDYVADMED CTKYPWVRYN QDEFYSGFFG PENSCKQASL   300
```

```
TNEYTQSQNG FNPSFAGNAR YSNGEYKDVE AWNLRNEFIS SMTIQVLDTV ALWPTYDPKV  360
YTAAVKTEFT REIYTSIRGT TYRSDPAQNT MSAIEARMIR PPHLFEWPQT MTFFFEDVNV  420
RYTWVGNSWT KGQALIGLKT ESTRTLDTNM ITALQGLTDE YEYYHIPLDV STGQKDITNI  480
RTKQWFEPRE FIFYRSGGQQ VLALGTIEED IPGYSVYLVN DYIYTPSIRQ NTFPPIEVPE  540
GTPPPSHRLS WVKFEPVRDN ATTFVDPKQI GATIFGWTHT SVDPNNTIDT TKITQIPAVK  600
ASGGTDYQVI KGPGSTGGDL VSLPTYAKIE IPLTSSAGQL YTIRIRYAAA EQKRIRIGKK  660
YRDMQWRYTD YDVPSTPYSG GNLTYNAFRY RELGTSQGVL ELSIERIDPF DEPIIIDKIE  720
FIPIQGSVET YEADQDLEKA RKAVNALFTS DAKNALQLKV TDYLVDQAAK LVECMSDKIY  780
PQEKMCLLDQ VKVAKRLSQL RNLLNHGDFE FPDWSGENGW KTSNHVSVMS GNPIFKGRYL  840
HMPGADNPQL SDQVYPTYAY QKIDESKLKP YTRYMIRGFV GSSKDLEVFI TRYDKEVHKN  900
MNVPHDILPT DPCTGTHQLG QEPMITNHTI PQDMSCDPCD AGTVMKVQQT FVKCEDPHAF  960
SFHIDTGELD MNQNLGIWVG FKIGTTDGRA TFDNLEVIEA NPLTGEALAR VKKREHKWKQ 1020
KWMEKRTKID KAVQTAQGAI QALFTDSNQN RLKPDITLNH ILQAETEVQK IPYVYNAFLQ 1080
GALPPVPGET SDIFQQLSSA VAIARLLYEQ RNVLRNGDFM AGLSNWRGAK NAIVQKIGNA 1140
SVLVISDWSA NLSQDVPVNP GHGYILRVTA KKEGSGEGYV TISDGTEDNT ETLKFTVGEV 1200
ATRLAQSDMR SPMQERYQER NMANAPLEAY GTNGYTNNPM TNYPSDNAGA NAYPGNHNRN 1260
YQPESFGITP YGDENPMMNY PSNDYEANPY PGSTNMTNYN GGCNCGCGTN AYAGENMMRN 1320
NPSNENGSDY GCGCRTHTNN KTDSYPMTAH SSSLSGYVTK TFEIFPETNR ICIEIGEISG 1380
TFKVESIELI RMDCE                                                 1395

SEQ ID NO: 63          moltype = AA  length = 719
FEATURE                Location/Qualifiers
REGION                 1..719
                       note = variant of native sequence
source                 1..719
                       mol_type = protein
                       organism = synthetic construct
SEQUENCE: 63
MNQYYNNNEY EILDNGDRGY QPRYPLAQAP GSEFQQMNYK DWMDRYTGEE QAGGLIRAEI   60
DANTALTATF GVAWAVLGVS NPVGSAVAGI LNVVTPIIFN QVDPNSPLKV WESMIGYAQA  120
LIKKELTETV RNLALDHIDR INDYQIDYKN KAKIWETNPT PGNTSQLLDA FRNLKRSCQD  180
AMPHLDTRGY ETILLPLYAQ AANIHLIVLR DGLMHGRSWG MTNEEYEDLY SGFFGFTNRI  240
ATYTNYCTNT FNQGATMDYV ADMEDCTKYP WVRYNQDEFY SGFFGPENSC KQASLTNEYT  300
QSQNGFNPSF AGNARYSNGE YKDVEAWNLR NEFISSMTIQ VLDTVALWPT YDPKVYTAAV  360
KTEFTREIYT SIRGTTYRSD PAQNTMSAIE ARMIRPPHLF EWPQTMTFFF EDVNVRYTWV  420
GNSWTKGQAL IGLKTESTRT LDTNMITALQ GLTDEYEYYH IPLDVSTGQK DITNIRTKQW  480
FEPREFIFYR SGGQQVLALG TIEEDIPGYS VYLVNDYIYT PSIRQNTFPP IEVPEGTPPP  540
SHRLSWVKFE PVRDNATTFV DPKQIGATIF GWTHTSVDPN NTIDTTKITQ IPAVKASGGT  600
DYQVIKGPGS TGGDLVSLPT YAKIEIPLTS SAGQLYTIRI RYAAAEQKRI RIGKKYRDMQ  660
WRYTDYDVPS TPYSGGNLTY NAFRYRELGT SQGVLELSIE RIDPFDEPII IDKIEFIPI   719

SEQ ID NO: 64          moltype = AA  length = 1390
FEATURE                Location/Qualifiers
REGION                 1..1390
                       note = variant of native sequence
source                 1..1390
                       mol_type = protein
                       organism = synthetic construct
SEQUENCE: 64
MNQYYNNNEY EILDNGDRGY QPRYPLAQAP GSEFQQMNYK DWMDRYTGEE QAGGLIRAEI   60
DANTALTATF GVAWAVLGVS NPVGSAVAGI LNVVTPIIFN QVDPNSPLKV WESMIGYAQA  120
LIKKELTETV RNLALDHIDR INDYQIDYKN KAKIWETNPT PGNTSQLLDA FRNLKRSCQD  180
AMPHLDTRGY ETILLPLYAQ AANIHLIVLR DGLMHGRSWG MTNEEYEDLY SGFFGFTNRI  240
ATYTNYCTNT FNQGATMDYV ADMEDCTKYP WVRYNQDEFY SGFFGPENSC KQASLTNEYT  300
QSQNGFNPSF AGNARYSNGE YKDVEAWNLR NEFISSMTIQ VLDTVALWPT YDPKVYTAAV  360
KTEFTREIYT SIRGTTYRSD PAQNTMSAIE ARMIRPPHLF EWPQTMTFFF EDVNVRYTWV  420
GNSWTKGQAL IGLKTESTRT LDTNMITALQ GLTDEYEYYH IPLDVSTGQK DITNIRTKQW  480
FEPREFIFYR SGGQQVLALG TIEEDIPGYS VYLVNDYIYT PSIRQNTFPP IEVPEGTPPP  540
SHRLSWVKFE PVRDNATTFV DPKQIGATIF GWTHTSVDPN NTIDTTKITQ IPAVKASGGT  600
DYQVIKGPGS TGGDLVSLPT YAKIEIPLTS SAGQLYTIRI RYAAAEQKRI RIGKKYRDMQ  660
WRYTDYDVPS TPYSGGNLTY NAFRYRELGT SQGVLELSIE RIDPFDEPII IDKIEFIPIQ  720
GSVETYEADQ DLEKARKAVN ALFTSDAKNA LQLKVTDYLV DQAAKLVECM SDKIYPQEKM  780
CLLDQVKVAK RLSQLRNLLN HGDFEFPDWS GENGWKTSNH VSVMSGNPIF KGRYLHMPGA  840
DNPQLSDQVY PTYAYQKIDE SKLKPYTRYM IRGFVGSSKD LEVFITRYDK EVHKNMNVPH  900
DILPTDPCTG THQLGQEPMI TNHTIPQDMS CDPCDAGTVM KVQQTFVKCE DPHAFSFHID  960
TGELDMNQNL GIWVGFKIGT TDGRATFDNL EVIEANPLTG EALARVKKRE HKWKQKWMEK 1020
RTKIDKAVQT AQGAIQALFT DSNQNRLKPD ITLNHILQAE TEVQKIPYVY NAFLQGALPP 1080
VPGETSDIFQ QLSSAVAIAR LLYEQRNVLR NGDFMAGLSN WRGAKNAIVQ KIGNASVLVI 1140
SDWSANLSQD VPVNPGHGYI LRVTAKKEGS GEGYVTISDG TEDNTETLKF TVGEVATRLA 1200
QSDMRSPMQE RYQERNMANA PLEAYGTNGY TNNPMTNYPS DNAGANAYPG NHNRNYQPES 1260
FGITPYGDEN PMMNYPSNDY EANPYPGSTN MTNYNGGCNC GCGTNAYAGE NMMRNNPSNE 1320
NGSDYGCGCR THTNNKTDSY PMTAHSSSLS GYVTKTFEIF PETNRICIEI GEISGTFKVE 1380
SIELIRMDCE                                                       1390

SEQ ID NO: 65          moltype = AA  length = 496
FEATURE                Location/Qualifiers
REGION                 1..496
                       note = Unknown organism from environmental sample
source                 1..496
```

```
                            mol_type = protein
                            organism = unidentified
SEQUENCE: 65
MEIYNNQKSC  IDSPSIRAAY  PNYVDSNGRL  TMDRNGFNVN  QSVHYTNQDW  MNYIPDSRRI   60
SELSIPGTHG  SMALYGGVLG  HILINQTMNL  GIQLSSGIRY  IDIRCRHYYN  TFTIHHDLVF  120
QDAYFDSDVL  TPVISFLNQN  PRETILMRVK  EEYDPIGNTR  TFGQTFESYW  RGREQYFWNP  180
SNSPDDPRNPT LGEVRGKIIL  LQDFTADRLF  GMHWYWLNVK  DMWELDGSSQ  IYAKWESVRE  240
HFFSAMRNRN  LIFLNHLSAN  GRISTLGDPR  PWFVASGFAD  RENNSLAYQL  SSNPSSNWPD  300
NPRLSPTSGP  IFYGGTNVLT  TRRIRDGRFT  HTGIIAADFP  GKGLIDGTIA  LNFPGTLSGD  360
FQIVTALNNS  SVVDLNVGSR  NVTLWSNDYT  DNKRWNFTYD  RSENAYVIRS  VSNPDLALAW  420
DTSSPNRNVF  AAPPGLIRGN  EYYWILEKNG  DGYIFKNKRD  TNMVLDVTAG  GIINGTNLQV  480
SPRTGGNAQT  FFNRFI                                                     496

SEQ ID NO: 66               moltype = AA  length = 302
FEATURE                     Location/Qualifiers
source                      1..302
                            mol_type = protein
                            organism = Bacillus sp.
SEQUENCE: 66
MGGIMMSILD  MRTIAEQYAR  YWYEPQAVPG  SVTNFQMYEG  VLYEDVATPT  QTNFKVTPAL   60
ARTAVQTLKN  GTDVPQNQTV  KFSETKTLTT  KTTTTEGIKN  TESTKTSTKF  SAGFKVDWFN  120
AGMDFTIEVT  STGEYSYTTS  TEQSFSNSSL  WEVTQPVTVP  PHSTVRAILY  IYEATFNVNY  180
DLNTKIRGTK  TSPIPSYYKY  FSIQYRRKSD  NSLRTVWFDA  ANLYDSQWPA  RPSSFVGREV  240
GGYYPLYYKG  KGVSTVATGL  YTEVEFIQSP  LSGYAGETKI  WKTGPILAPS  DKKLTLDCSG  300
QY                                                                     302

SEQ ID NO: 67               moltype = AA  length = 297
FEATURE                     Location/Qualifiers
REGION                      1..297
                            note = variant of native sequence
source                      1..297
                            mol_type = protein
                            organism = synthetic construct
SEQUENCE: 67
MSILDMRTIA  EQYARYWYEP  QAVPGSVTNF  QMYEGVLYED  VATPTQTNFK  VTPALARTAV   60
QTLKNGTDVP  QNQTVKFSET  KTLTTKTTTT  EGIKNTESTK  TSTKFSAGFK  VDWFNAGMDF  120
TIEVTSTGEY  SYTTSTEQSF  SNSSLWEVTQ  PVTVPPHSTV  RAILYIYEAT  FNVNYDLNTK  180
IRGTKTSPIP  SYYKYFSIQY  RRKSDNSLRT  VWFDAANLYD  SQWPARPSSF  VGREVGGYYP  240
LYYKGKGVST  VATGLYTEVE  FIQSPLSGYA  GETKIWKTGP  ILAPSDKKLT  LDCSGQY     297

SEQ ID NO: 68               moltype = AA  length = 649
FEATURE                     Location/Qualifiers
source                      1..649
                            mol_type = protein
                            organism = Bacillus sp.
SEQUENCE: 68
MNSNNKNKHN  VIDTLSNNPL  STNSVEYPLA  NDQSTPLQNV  NYKEYLRMSE  GNENYPNHEV   60
LISTPGLVDI  TANITSVILS  ALGVPILGTV  VKLYSKLFSF  LWGATPGQDP  WKELMDRVEI  120
LIDQKLTEYA  RNKALAELEG  LQNVMNSYVD  ALESWQNNSR  NSQTRLLVQQ  RLVAADSHFK  180
KTMPSFAIKN  YEVSLLPVYA  QAANLHLLLL  RDSQIFGKEW  GMPQNEIDLF  YKEQLDCIEK  240
YSDHCVEWYH  TGLKQLKDRG  ATAKNWVDYN  RFRREITLSV  LDIVALFPHY  STHMYPMPIH  300
AELTREIYTD  PVGSYLPYKG  NFRDVMSWYE  MKRYRQPTFQ  DLENLIRKPN  RFTWLKDLKM  360
YTRKRQNGQY  EYYNYWVGHE  LKKALIDEAY  IRETTTSGEI  TSEEDTFTFE  DYNIHRVLCN  420
YIGRYDNSLV  GVNQVEFHYL  DNNTPRKKEY  KKDIRVSNQS  QKIIDSEEEL  HSHRLSYVES  480
FGLYWDHKNE  KGGTIPIFGW  THHSVAPQNT  IYEDKITSIP  ATKANGYFTS  EVIQGPGYTG  540
GDLIQGSQNM  GSIKITPPRN  ANNKKYRLRV  RYAAHFDGVL  TMTFTSSSGP  GTHKINFNAT  600
MKNGDSFKYN  SFQYVEKEVP  ISFVDNGILC  KASSGFYLDK  LEFIPLNES              649

SEQ ID NO: 69               moltype = AA  length = 646
FEATURE                     Location/Qualifiers
REGION                      1..646
                            note = variant of native sequence
source                      1..646
                            mol_type = protein
                            organism = synthetic construct
SEQUENCE: 69
MNSNNKNKHN  VIDTLSNNPL  STNSVEYPLA  NDQSTPLQNV  NYKEYLRMSE  GNENYPNHEV   60
LISTPGLVDI  TANITSVILS  ALGVPILGTV  VKLYSKLFSF  LWGATPGQDP  WKELMDRVEI  120
LIDQKLTEYA  RNKALAELEG  LQNVMNSYVD  ALESWQNNSR  NSQTRLLVQQ  RLVAADSHFK  180
KTMPSFAIKN  YEVSLLPVYA  QAANLHLLLL  RDSQIFGKEW  GMPQNEIDLF  YKEQLDCIEK  240
YSDHCVEWYH  TGLKQLKDRG  ATAKNWVDYN  RFRREITLSV  LDIVALFPHY  STHMYPMPIH  300
AELTREIYTD  PVGSYLPYKG  NFRDVMSWYE  MKRYRQPTFQ  DLENLIRKPN  RFTWLKDLKM  360
YTRKRQNGQY  EYYNYWVGHE  LKKALIDEAY  IRETTTSGEI  TSEEDTFTFE  DYNIHRVLCN  420
YIGRYDNSLV  GVNQVEFHYL  DNNTPRKKEY  KKDIRVSNQS  QKIIDSEEEL  HSHRLSYVES  480
FGLYWDHKNE  KGGTIPIFGW  THHSVAPQNT  IYEDKITSIP  ATKANGYFTS  EVIQGPGYTG  540
GDLIQGSQNM  GSIKITPPRN  ANNKKYRLRV  RYAAHFDGVL  TMTFTSSSGP  GTHKINFNAT  600
MKNGDSFKYN  SFQYVEKEVP  ISFVDNGILC  KASSGFYLDK  LEFIPL                 646

SEQ ID NO: 70               moltype = AA  length = 882
```

```
FEATURE                    Location/Qualifiers
source                     1..882
                           mol_type = protein
                           organism = Bacillus sp.
SEQUENCE: 70
MEECKLKYKD RTSAKRRFKK AVLIAATTIT LGLSTAGGTT SAFAEETSTQ KFEIIPDGSI   60
KILENNPNLQ NLVADLSGPL FKEAVLTGNS SIQDLQNLGK HMALASTGLL PFGGSFVYEF  120
ISAVWPEAGP SQMDLIMKTV PAMIDEKISQ YDLDSIQSDM ETLRDDLKVF ERSINNAPKN  180
IPSGAQAAPG DIQRSNQELA KDINRLFKSL INTCRKSSQK EAELPFYTVV ATSHLQFLRF  240
MELNAQSHPR IKMEPDVLNQ LFSEPLKVIA QNYKKHINET SQSAQKKIYS KMNSIIDVSI  300
NPLENLEHMY VPRGVPTPNY NDKKIEELKT EYTNLFNNMH AYAYVTENNE AFKVISESIT  360
GKEMLHMGSQ GNVTINAKDQ NGFVKYLTAK SDLSQVHCEG YSAGSEQEFM FEAVNAEENI  420
FALKSKINGH YATFDYSYKK IAGLGSFEAT DKNDKRTHVK LISLGDSKYA MRSIYDDNNF  480
IYADFDHGGA LTAHSKYIGD WEVFTIKGVG GNSPASSIVM PSLNYTSEG YRYQVLPTE  540
ETTTPILSSG DLKEIDGKWY YGDSGKVVTG QEIINGEWRY LEDGKIVTGW RRINSTGPRY  600
YFNSDGSRFE KTGWQTIEGK VYYFNSDHSM FESKGLQELG GLYYIDLDYT RFEKTGWQTI  660
EGKVYYLNTD HTVFEKIGTQ KVEDKLYYFT EEHARFEKTG AQKVEGKLYY FNADHTLYGS  720
IKNQEIGGKS YYVNADYSLF TGLFKAGDGR LFYYDPETGI MAKDKTITIE GYAYKFDSNG  780
TCINPPDGFT GWVNLPSAPD RNHYKIGYKE NGEFVTGLKQ IENAWYYFDD NHYEVIGWKV  840
IDGKSYYFDP FYENQMTRGE TITIKEKSYT FDSNGVCMNP PS                    882

SEQ ID NO: 71              moltype = AA   length = 877
FEATURE                    Location/Qualifiers
REGION                     1..877
                           note = variant of native sequence
source                     1..877
                           mol_type = protein
                           organism = synthetic construct
SEQUENCE: 71
MKYKDRTSAK RRFKKAVLIA ATTITLGLST AGGTTSAFAE ETSTQKFEII PDGSIKILEN   60
NPNLQNLVAD LSGPLFKEAV LTGNSSIQDL QNLGKHMALA STGLLPFGGS FVYEFISAVW  120
PEAGPSQMDL IMKTVPAMID EKISQYDLDS IQSDMETLRD DLKVFERSIN NAPKNIPSGA  180
QAAPGDIQRS NQELAKDINR LFKSLINTCR KSSQKEAELP FYTVVATSHL QFLRFMELNA  240
QSHPRIKMEP DVLNQLFSEP LKVIAQNYKK HINETSQSAQ KKIYSKMNSI IDVSINPLEN  300
LEHMYVPRGV PTPNYNDKKI EELKTEYTNL FNNMHAYAYV TENNEAFKVI SESITGKEML  360
HMGSQGNVTI NAKDQNGFVK YLTAKSDLSQ VHCEGYSAGS EQEFMFEAVN AEENIFALKS  420
KINGHYATFD YSYKKIAGLG SFEATDKNDK RTHVKLISLG DSKYAMRSIY DDNNFIYADF  480
DHGGALTAHS KYIGDWEVFT IKGVGGNSPA SSIVMPSLNL YTSEGYRYQV VLPTEETTTP  540
ILSSGDLKEI DGKWYYGDSG KVVTGQEIIN GEWRYLEDGK IVTGWRRINS TGPRYYFNSD  600
GSRFEKTGWQ TIEGKVYYFN SDHSMFESKG LQELGGLYYI DLDYTRFEKT GWQTIEGKVY  660
YLNTDHTVFE KIGTQKVEDK LYYFTEEHAR FEKTGAQKVE GKLYYFNADH TLYGSIKNQE  720
IGGKSYYVNA DYSLFTGLFK AGDGRLFYYD PETGIMAKDK TITIEGYAYK FDSNGTCINP  780
PDGFTGWVNL PSAPDRNHYK IGYKENGEFV TGLKQIENAW YYFDDNHYEV IGWKVIDGKS  840
YYFDPFYENQ MTRGETITIK EKSYTFDSNG VCMNPPS                          877

SEQ ID NO: 72              moltype = AA   length = 839
FEATURE                    Location/Qualifiers
REGION                     1..839
                           note = variant of native sequence
source                     1..839
                           mol_type = protein
                           organism = synthetic construct
SEQUENCE: 72
MEETSTQKFE IIPDGSIKIL ENNPNLQNLV ADLSGPLFKE AVLTGNSSIQ DLQNLGKHMA   60
LASTGLLPFG GSFVYEFISA VWPEAGPSQM DLIMKTVPAM IDEKISQYDL DSIQSDMETL  120
RDDLKVFERS INNAPKNIPS GAQAAPGDIQ RSNQELAKDI NRLFKSLINT CRKSSQKEAE  180
LPFYTVVATS HLQFLRFMEL NAQSHPRIKM EPDVLNQLFS EPLKVIAQNY KKHINETSQS  240
AQKKIYSKMN SIIDVSINPL ENLEHMYVPR GVPTPNYNDK KIEELKTEYT NLFNNMHAYA  300
YVTENNEAFK VISESITGKE MLHMGSQGNV TINAKDQNGF VKYLTAKSDL SQVHCEGYSA  360
GSEQEFMFEA VNAEENIFAL KSKINGHYAT FDYSYKKIAG LGSFEATDKN DKRTHVKLIS  420
LGDSKYAMRS IYDDNNFIYA DFDHGGALTA HSKYIGDWEV FTIKGVGGNS PASSIVMPSL  480
NLYTSEGYRY QVLPTEETT TPILSSGDLK EIDGKWYYGD SGKVVTGQEI INGEWRYLED  540
GKIVTGWRRI NSTGPRYYFN SDGSRFEKTG WQTIEGKVYY FNSDHSMFES KGLQELGGLY  600
YIDLDYTRFE KTGWQTIEGK VYYLNTDHTV FEKIGTQKVE DKLYYFTEEH ARFEKTGAQK  660
VEGKLYYFNA DHTLYGSIKN QEIGGKSYYV NADYSLFTGL FKAGDGRLFY YDPETGIMAK  720
DKTITIEGYA YKFDSNGTCI NPPDGFTGWV NLPSAPDRNH YKIGYKENGE FVTGLKQIEN  780
AWYYFDDNHY EVIGWKVIDG KSYYFDPFYE NQMTRGETIT IKEKSYTFDS NGVCMNPPS   839

SEQ ID NO: 73              moltype = AA   length = 399
FEATURE                    Location/Qualifiers
source                     1..399
                           mol_type = protein
                           organism = Bacillus sp.
SEQUENCE: 73
MKSWKIKKFP FSKKIVTGLF AGTMALSIGV PASHAATPEK NAYYSIHLAA KPSIAWDVFR   60
GWTSDDAGIV LWNGSLGDNE QFVFFPLDGG AYAIVNKNSG KPVGLGGGIN FTDGVRNMSV  120
ADNNGLGQNN WTGASTDQWY LRDKGNNNYE IVNQGNGRVA SWAGAGGTVA GYIDYVDLDE  180
SDPSDKNRLF QISAARSTFS LPRLPAIGTR PTAPEYNPAG RVDQQLPQTS ESAVVAATLI  240
PCIMVKDNSL SDYTKIHNSP YYVLEKEEYW EKVSSEIVPA GGTSKYTVKR GVSTVDQQKM  300
```

```
TDTLAMNFGA DLGLKFGNQS LALKYGISKT LQTEVSKTST DATEEGRDKQ YVSAASTDTG    360
LTVYQLVTRY TLKRTDGSAV SSSWSVRDNL QTTERTIKK                          399

SEQ ID NO: 74           moltype = AA  length = 365
FEATURE                 Location/Qualifiers
REGION                  1..365
                        note = variant of native sequence
source                  1..365
                        mol_type = protein
                        organism = synthetic construct
SEQUENCE: 74
MATPEKNAYY SIHLAAKPSI AWDVFRGWTS DDAGIVLWNG SLGDNEQFVF FPLDGGAYAI     60
VNKNSGKPVG LGGGINFTDG VRNMSVADNN GLGQNNWTGA STDQWYLRDK GNNNYEIVNQ    120
GNGRVASWAG AGGTVAGYID YVDLDESDPS DKNRLFQISA ARSTFSLPRL PAIGTRPTAP    180
EYNPAGRVDQ QLPQTSESAV VAATLIPCIM VKDNSLSDYT KIHNSPYYVL EKEEYWEKVS    240
SEIVPAGGTS KYTVKRGVST VDQQKMTDTL AMNFGADLGL KFGNQSLALK YGISKTLQTE    300
VSKTSTDATE EGRDKQYVSA ASTDTGLTVY QLVTRYTLKR TDGSAVSSSW SVRDNLQTTE    360
RTIKK                                                                365

SEQ ID NO: 75           moltype = AA  length = 381
FEATURE                 Location/Qualifiers
source                  1..381
                        mol_type = protein
                        organism = Bacillus sp.
SEQUENCE: 75
VCMANDKSNN ENNMNIPKVN NEDSIPSEIM ASGARVSFPD FNFYNIRTFC GKYVDIAKGS     60
TADRAGAVQY AGNNSDNQKF LIFTLDDDNYS VIAAKHSGKV LDIARIPPFN NDLLIQYYFQ   120
NSDNQKFFIS NDGVISIKIS GQVWDIPNGS TSNDIPITSF RYQGSPNQKF SLVKNGSVSI    180
NPPARGTLPP APDFKTNDIN EQLPNETTPV NTHFTYLPYF MVKDPYYNPQ QQMKNSPYYI    240
LVRRQYWEKK TQRILAPSEF HEYSETIGVS RTNQTSMTNT TEISIGADLG FSFKGFSAGL    300
STSITKTLSV TESTSQTDST ETTRKVGYTN PFTYLIAYAK YMLINEYYVT RADGQTITAG    360
TTTYWKVPDQ DHTVSRTIPR S                                              381

SEQ ID NO: 76           moltype = AA  length = 379
FEATURE                 Location/Qualifiers
REGION                  1..379
                        note = variant of native sequence
source                  1..379
                        mol_type = protein
                        organism = synthetic construct
SEQUENCE: 76
MANDKSNNEN NMNIPKVNNE DSIPSEIMAS GARVSFPDFN FYNIRTFCGK YVDIAKGSTA     60
DRAGAVQYAG NNSDNQKFLI FTLDDNYSVI AAKHSGKVLD IARIPPFNND LLIQYYFQNS    120
DNQKFFISND GVISIKISGQ VWDIPNGSTS NDIPITSFRY QGSPNQKFSL VKNGSVSINP    180
PARGTLPPAP DFKTNDINEQ LPNETTPVNT HFTYLPYFMV KDPYYNPQQQ MKNSPYYILV    240
RRQYWEKKTQ RILAPSEFHE YSETIGVSRT NQTSMTNTTE ISIGADLGFS FKGFSAGLST    300
SITKTLSVTE STSQTDSTET TRKVGYTNPF TYLIAYAKYM LINEYYVTRA DGQTITAGTT    360
TYWKVPDQDH TVSRTIPRS                                                 379

SEQ ID NO: 77           moltype = AA  length = 1245
FEATURE                 Location/Qualifiers
REGION                  1..1245
                        note = Unknown organism from environmental sample
source                  1..1245
                        mol_type = protein
                        organism = unidentified
SEQUENCE: 77
MVNSSEFYPS YYNVLATPVS NFSSTFDQFS DIAEEMKKAW EQFQKTGSFS LEALKQGFSA     60
ANGGAFNYLT LLQSGISLAG SFIPGGSFVA PILNMVIGWL WPNKKKDDSQ ALIDLIDKEI    120
QKELNKALTE QDKNNWTGFL TSIFDNSNTV NNAIIDAQWS GTADDTNRQT VSPTVSDYKN    180
VVGKFDSADT SIVTAQSQIM NGNFDVAASS YFVIGATVRL ALYQSYIRFC NHWIDQVGFD    240
SADHKTQLDN LTRAKETMRN TITSYTQRIR KVFKDNLPKL DSTKFGINAY NVYVKGMTIN    300
VLDMVATWSS LYPNDYDSQT QLEQTRVIFS NMVGQEQATD GTVKIYNTFD SGSHQHGQIT    360
NNNVDLISYF PDELQNLELA VYTPKGGSGY AYPYGFILNY TNSNYKYGDN DPTGGVLSKQ    420
NGPIQQMNAA TQTSKYVDGE TINGIGASLP GYCTTSCSEI ASPFSCTSTA NSYKASCNSV    480
YTSQKINALY PFTQTGVKGS TGKLGVMASH VPYDLNPINI IGEVDPDTNN MILKGMPAEK    540
GTFENNTRPN VVKEWMNGAN AVKLSSNQVL KMNITNVTAH KYQIRLRYAT QGDVGASIWF    600
HLIDPSNKDL TNGNHSFPAP SDKQVKVQGE NGNYILTTVI DSIDLPTGQQ TILIQNTSSQ    660
DLFLDRIEFA PVPGPPPNPN QIPAQDFYIP FKGHTPFWNS DNGKIVTQAT FEQPVQRNYL    720
RLYLKGNYVG LVPENGIVTT PFDSIVLYNS TEPSSVTAHF AGATLTFATT NEIYFDNPGD    780
LEKITNQVNQ LFTSSSQTEL SPTVTDYRID QVILKVDALS NDVFVVEKNA LRKLVNKAKQ    840
LSKARNVLVG GNFENFDEWS LGRNVIRRSG NDLFKGDHLF LPPAALYPSY AYQKVDESKL    900
KPYTRYTVSG FVAQSEHLEL VVSRYSKEIE TVLNVPYEES LPITSDDQPN CCKKSPCQCS    960
SCDGSQPDSH FFSYSIDVGA LHLALNPGIE FGLRIVKPNG LAFVSNMEIR EDRPLTEREI   1020
KKLQRKEQKW KKAFEKERAE ISALLQPIIN RINTFYKNED WNSDILPHVT YQDVFSVVLP   1080
ELPNLRHWFM EDREGEHNEI LKKLQQAIDR VFTHLEEQNL LHNGSFTNGL TDWLVEGDAR   1140
IIDLGNGNLA LQLSHWDASA SQSIDISDFD DEKEYKLRVR GKGKGTITIQ HGEEMETMSF   1200
DKTGFYFQEQ PFYFEEPSFY LQVQSEANEF IVDSIEIIEV PEEDE                  1245
```

```
SEQ ID NO: 78              moltype = AA   length = 672
FEATURE                    Location/Qualifiers
REGION                     1..672
                           note = variant of native sequence
source                     1..672
                           mol_type = protein
                           organism = synthetic construct
SEQUENCE: 78
MVNSSEFYPS YYNVLATPVS NFSSTFDQFS DIAEEMKKAW EQFQKTGSFS LEALKQGFSA   60
ANGGAFNYLT LLQSGISLAG SFIPGGSFVA PILNMVIGWL WPNKKKDDSQ ALIDLIDKEI  120
QKELNKALTE QDKNNWTGFL TSIFDNSNTV NNAIIDAQWS GTADDTNRQT VSPTVSDYKN  180
VVGKFDSADT SIVTAQSQIM NGNFDVAASS YFVIGATVRL ALYQSYIRFC NHWIDQVGFD  240
SADHKTQLDN LTRAKETMRN TITSYTQRIR KVFKDNLPKL DSTKFGINAY NVYVKGMTIN  300
VLDMVATWSS LYPNDYDSQT QLEQTRVIFS NMVGQEQATD GTVKIYNTFD SGSHQHGQIT  360
NNNVDLISYF PDELQNLELA VYTPKGGSGY AYPYGFILNY TNSNYKYGDN DPTGGVLSKQ  420
NGPIQQMNAA TQTSKYVDGE TINGIGASLP GYCTTSCSEI ASPFSCTSTA NSYKASCNSV  480
YTSQKINALY PFTQTGVKGS TGKLGVMASH VPYDLNPINI IGEVDPDTNN MILKGMPAEK  540
GTFENNTRPN VVKEWMNGAN AVKLSSNQVL KMNITNVTAH KYQIRLRYAT QGDVGASIWF  600
HLIDPSNKDL TNGNHSFPAP SDKQVKVQGE NGNYILTTVI DSIDLPTGQQ TILIQNTSSQ  660
DLFLDRIEFA PV                                                     672

SEQ ID NO: 79              moltype = AA   length = 947
FEATURE                    Location/Qualifiers
REGION                     1..947
                           note = Unknown organism from environmental sample
source                     1..947
                           mol_type = protein
                           organism = unidentified
SEQUENCE: 79
MIMQMVTKAM TTKLGALPDF IDDFNGIFGF MDSITGVMST IFGVDTGDSS IDDVINNQEL   60
LQEMQAQMQQ MQDSITDMAN NQIISENIER QILALTNDLS TSITTEFKKI EGILNTYLPA  120
ISKMLGEVYE QTSEINEKVD KLLAMMTFAL KELDYIKDNV VLNSSIVEIT PHVQKLVYVN  180
KKFLSLTKSF FQNEDLSIDS MQEMLEWAKS ILATEMNSFE FSVDTLHSII IGDNLYKRSA  240
LKTFSDVLLD DADQYGDFGT PLAKFYTFFS SLATLQINAY LCLTFARKVL GLSEFDYQVT  300
MEDRIEQQNQ LFVNLIQDKN YSNVLEIDGI YPMPMKAGEC KGLDLQADDG YALIGLEFFM  360
DNGIYKAKAY QGKLDKNFSV HADTVTEIIS DDLSTVFLHN TDTPPVLNIV YPLSGELTGP  420
PNTIITRIGL GTKYDNTRQS GVQAFAYIDA DFSPYDYKSG TISKHGKNTV SLEGSDTRNS  480
FYSKWPIGLI GDLYMTPLKS LALNVDVDNG FLNMGGESYF STILSREYNS NFILFPHANN  540
SSPIVENLIQ NGDFENGDTN WKVTGGTAVI AKGEGVYGSN AMQLNMDAIT QDVTLKPYTN  600
YELTLYGKID YSVLLISIYE ASKNTFIAEA QFTSTIYKQT KLTLKTGEYT TFTISVSGLE  660
PNDGFIDNIQ LCEVPETDNI IDCGGFGGQV DPSLHTNPYL WELNGGGKVV GNEGLFDDKV  720
LKITKSGGAN QKIKLERNTN YILSAYVKVD ASTTTAQIGC GSHQEICNST SYTPIEVKFR  780
TGDDPVTTEN SIYCSNPNDS GTVWADNFVL YKVPNLVVNG DFENVDLSSW NLSPSESGTI  840
SLGIAKGISN SNAIVLRGKG QISQKVALKP YTKYRLTAYV KVSKGSTAYI GYGENECACA  900
VDDFRQAHVE FTTGANPMQT DNVIYLSTGD SQYTVADNFE LYEFDQI             947

SEQ ID NO: 80              moltype = AA   length = 945
FEATURE                    Location/Qualifiers
REGION                     1..945
                           note = variant of native sequence
source                     1..945
                           mol_type = protein
                           organism = synthetic construct
SEQUENCE: 80
MQMVTKAMTT KLGALPDFID DFNGIFGFMD SITGVMSTIF GVDTGDSSID DVINNQELLQ   60
EMQAQMQQMQ DSITDMANNQ IISENIERQI LALTNDLSTS ITTEFKKIEG ILNTYLPAIS  120
KMLGEVYEQT SEINEKVDKL LAMMTFALKE LDYIKDNVVL NSSIVEITPH VQKLVYVNKK  180
FLSLTKSFFQ NEDLSIDSMQ EMLEWAKSIL ATEMNSFEFS VDTLHSIIIG DNLYKRSALK  240
TFSDVLLDDA DQYGDFGTPL AKFYTFFSSL ATLQINAYLC LTFARKVLGL SEFDYQVTME  300
DRIEQQNQLF VNLIQDKNYS NVLEIDGIYP MPMKAGECKG LDLQADDGYA LIGLEFFMDN  360
GIYKAKAYQG KLDKNFSVHA DTVTEIISDD LSTVFLHNTD TPPVLNIVYP LSGELTGPPN  420
TIITRIGLGT KYDNTRQSGV QAFAYIDADF SPYDYKSGTI SKHGKNTVSL EGSDTRNSFY  480
SKWPIGLIGD LYMTPLKSLA LNVDVDNGFL NMGGESYFST ILSREYNSNF ILFPHANNSS  540
PIVENLIQNG DFENGDTNWK VTGGTAVIAK GEGVYGSNAM QLNMDAITQD VTLKPYTNYE  600
LTLYGKIDYS VLLISIYEAS KNTFIAEAQF TSTIYKQTKL TLKTGEYTTF TISVSGLEPN  660
DGFIDNIQLC EVPETDNIID CGGFGGQVDP SLHTNPYLWE LNGGGKVVGN EGLFDDKVLK  720
ITKSGGANQK IKLERNTNYI LSAYVKVDAS TTTAQIGCGS HQEICNSTSY TPIEVKFRTG  780
DDPVTTENSI YCSNPNDSGT VWADNFVLYK VPNLVVNGDF ENVDLSSWNL SPSESGTISL  840
GIAKGISNSN AIVLRGKGQI SQKVALKPYT KYRLTAYVKV SKGSTAYIGY GENECACAVD  900
DFRQAHVEFT TGANPMQTDN VIYLSTGDSQ YTVADNFELY EFDQI                 945

SEQ ID NO: 81              moltype = AA   length = 296
FEATURE                    Location/Qualifiers
REGION                     1..296
                           note = Unknown organism from environmental sample
source                     1..296
                           mol_type = protein
                           organism = unidentified
SEQUENCE: 81
```

```
LNIHQCLQYS PALSGTLPEP TRETTMTIKE ELGQPQSHSI ELDSLSGEAG DIRAALTSNL    60
AGSFDQYPTK SGDFQIDSYL LDYSAPKQGC WVNGITVYGD IYIGKQNWGT YTRPVFAYLQ   120
YMDTISIPQQ VTQTRSYQLT KGHTQSFTTS VSAKYSVGAK IDIVNIGSEI STGFSQTESW   180
STTQTFTEST QLTGPGTFMV YQIVMVYAHN ATSAGRQNSN AFAYSKTQDV GSRVDLYYLS   240
AITLDKKVIV QSGQAISPLD WNTVQRNVLM ENYNTGSNNG HFSFDWSAYN DPHRRY       296

SEQ ID NO: 82           moltype = AA   length = 271
FEATURE                 Location/Qualifiers
REGION                  1..271
                        note = variant of native sequence
source                  1..271
                        mol_type = protein
                        organism = synthetic construct
SEQUENCE: 82
MTIKEELGQP QSHSIELDSL SGEAGDIRAA LTSNLAGSFD QYPTKSGDFQ IDSYLLDYSA    60
PKQGCWVNGI TVYGDIYIGK QNWGTYTRPV FAYLQYMDTI SIPQQVTQTR SYQLTKGHTQ   120
SFTTSVSAKY SVGAKIDIVN IGSEISTGFS QTESWSTTQT FTESTQLTGP GTFMVYQIVM   180
VYAHNATSAG RQNSNAFAYS KTQDVGSRVD LYYLSAITLD KKVIVQSGQA ISPLDWNTVQ   240
RNVLMENYNT GSNNGHFSFD WSAYNDPHRR Y                                  271

SEQ ID NO: 83           moltype = AA   length = 334
FEATURE                 Location/Qualifiers
REGION                  1..334
                        note = Unknown organism from environmental sample
source                  1..334
                        mol_type = protein
                        organism = unidentified
SEQUENCE: 83
MVRVYPDFDE MIREAAQKWS EANGLLFQNV SYSDPLTNTD TFSLSVEFKD IGCLEECVEL    60
EKINVSQAFT NNTGQQQKET FETITYYEDE YTWENDYHFV LPGQNFLTMP RLPRSAHKDI   120
NPGFLVNFFG ENQQFHTKMR ERRPIRGELF LEPSSSATIQ LQVEKYHISQ PYEIELSILG   180
SIIVTAQDRG QEQGTDRYVR LTDLIPFLCP HKNFFSKGRA LIFLEQGTFT GILSRAIRAY   240
ATQTLHCDGK TLEYEIPLNN PLPESALQPK PMTTNATSCG CSSDRPSVVS TYSTYSHPAN   300
PTAYSQQPMT TDSTSCGCSS CMSARSNKTL YTNQ                               334

SEQ ID NO: 84           moltype = AA   length = 1247
FEATURE                 Location/Qualifiers
REGION                  1..1247
                        note = Unknown organism from environmental sample
source                  1..1247
                        mol_type = protein
                        organism = unidentified
SEQUENCE: 84
VTGMNGGKNV NKNNQNEVQI VDSSSNDFNQ SNSYPRYPLA EESNYKDWLA NGKESNLDRL    60
STPSTVQDAI VTSLSIASYI ISFLDGTIGA GLGILSVLFG QFWPSNTNTV WDNFLHVVEE   120
LINRRIDIVE RERILRQFDG LRAVISNYNT AFRNWNENET TRNDPALQSE VRSRFDNADD   180
AFANRMPEFR ITGFETQSLA VYAQAATLHL LVLRDAVVNG RAWGFAQATI ESLYTKLVCL   240
INAYADHCTS VYRQGLQELR NRGNWRNFNN YRRDMTITVL DVISLFSNYD PRIYYYSTNT   300
QLTREVCTEP IASSTWLNRY SNPDEFQQIE NDLNPPPSLF SILTTLFART AFFYYNDLHT   360
PRDAISKTSM RLTRTDGTTI ITTPWQGAFP PNISQELPRN FSGYKVYNVD SILANTAVQF   420
TGIQRVVFHM VNEAGTGVPS QSIDLPLTTY YFNKSSNIPG IRSENPTGTD YTHILSSIRS   480
TSVGTPYRDR SNIMVYGWTH TSAERTNRLL SSYGITQIPV VKANQLSNNA RVISGPGHTG   540
GALISMSGDS SIAMSLYVPK ERYYIIRIRF VNDFNDVEGI LEFQGTGITL NVKFPGSGAA   600
VNPDLSVGDF RYVTIPAYPL IRGNTTYQVI LKTRNATGTC LIDKIEFIPN SARALEYEGK   660
QNLEKTKKAV ADLFTNTGKE ALKVDTTDYD VDQAANLVEC VPEEPYAKEK MILLDEVKHA   720
KQLSASRNLI QNGSFEFYTD EWTTSNNVSI QADNPIFKGN YLKMPGARET EGGTTRFPTY   780
VLQKIDESKL KPYTRYKARG FVGSSHDVKL IVERYGKEVD ALLNVRNNLA LNTVAPSRIE   840
ANQCQSQPYP IIQDGCLTNV IDTNSYEEAQ SGHANFKKEQ GMCHQSHQFD FHIDTGEVHL   900
NKNPGIWVLF KISSPEGHAT LDNIELIEEG PLVGESLALV KKREKKWNNE METRWIQTKE   960
VYEKAKGAID ALFTDAQDQA LKFDTNISHI ISAEHLVQSM PYVYNKWISD VPGMNYDIYT  1020
ELERRITQAY SLYERRNIIR NGDFNHDLNH WHATPHAKVQ QIDGTAVLVI PNWSSNVSQN  1080
LCVEQNRGYV LRVTAKKEDP GKGYVTISDC NGNQETLTFT SCDNYVSNKI TNDQSEYHFN  1140
QEMNEQRSYN PTEINEQLG YRLGQVSNEQ RCYTRNAITN DQSEYHFSQE MNEQRSYNPI  1200
ETMNEHRNYI TRTIDFFPDT DQVRIDIGET EGTFKVESIE LICRKSQ               1247

SEQ ID NO: 85           moltype = AA   length = 1238
FEATURE                 Location/Qualifiers
REGION                  1..1238
                        note = variant of native sequence
source                  1..1238
                        mol_type = protein
                        organism = synthetic construct
SEQUENCE: 85
MNKNNQNEVQ IVDSSSNDFN QSNSYPRYPL AEESNYKDWL ANGKESNLDR LSTPSTVQDA    60
IVTSLSIASY IISFLDGTIG AGLGILSVLF GQFWPSNTNT VWDNFLHVVE ELINRRIDIV   120
ERERILRQFD GLRAVISNYN TAFRNWNENE TTRNDPALQS EVRSRFDNAD DAFANRMPEF   180
RITGFETQSL AVYAQAATLH LLVLRDAVVN GRAWGFAQAT IESLYTKLVC LINAYADHCT   240
SVYRQGLQEL RNRGNWRNFN NYRRDMTITV LDVISLFSNY DPRIYYYSTN TQLTREVCTE   300
PIASSTWLNR YSNPDEFQQI ENDLNPPPSL FSILTTLFAR TAFFYYNDLH TPRDAISKTS   360
```

```
MRLTRTDGTT IIITTPWQGAF PPNISQELPR NFSGYKVYNV DSILANTAVQ FTGIQRVVFH    420
MVNEAGTGVP SQSIDLPLTT YYFNKSSNIP GIRSENPTGT DYTHILSSIR STSVGTPYRD    480
RSNIMVYGWT HTSAERTNRL LSSYGITQIP VVKANQLSNN ARVISGPGHT GGALISMSGD    540
SSIAMSLYVP KERYYIIRIR FVNDFNDVEG ILEFQGTGIT LNVKFPGSGA AVNPDLSVGD    600
FRYVTIPAYP LIRGNTTYQV ILKTRNATGT CLIDKIEFIP NSARALEYEG KQNLEKTKKA    660
VADLFTNTGK EALKVDTTDY DVDQAANLVE CVPEEPYAKE KMILLDEVKH AKQLSASRNL    720
IQNGSFEFYT DEWTTSNNVS IQADNPIFKG NYLKMPGARE TEGGTTRFPT YVLQKIDESK    780
LKPYTRYKAR GFVGSSHDVK LIVERYGKEV DALLNVRNNL ALNTVAPSRI EANQCQSQPY    840
PIIQDGCLTN VIDTNSYEEA QSGHANFKKE QGMCHQSHQF DPHIDTGEVH LNKNPGIWVL    900
FKISSPEGHA TLDNIELIEE GPLVGESLAL VKKREKKWNN EMETRWIQTK EVYEKAKGAI    960
DALFTDAQDQ ALKFDTNISH IISAEHLVQS MPYVYNKWIS DVPGMNYDIY TELERRITQA   1020
YSLYERRNII RNGDFNHDLN HWHATPHAKV QQIDGTAVLV IPNWSSNVSQ NLCVEQNRGY   1080
VLRVTAKKED PGKGYVTISD CNGNQETLTF TSCDNYVSNK ITNDQSEYHF NQEMNEQRSY   1140
NPTETINEQL GYRLGQVSNE QRCYTRNAIT NDQSEYHFSQ EMNEQRSYNP IETMNEHRNY   1200
ITRTIDFFPD TDQVRIDIGE TEGTFKVESI ELICRKSQ                           1238

SEQ ID NO: 86              moltype = AA  length = 641
FEATURE                    Location/Qualifiers
REGION                     1..641
                           note = variant of native sequence
source                     1..641
                           mol_type = protein
                           organism = synthetic construct
SEQUENCE: 86
MNKNNQNEVQ IVDSSSNDFN QSNSYPRYPL AEESNYKDWL ANGKESNLDR LSTPSTVQDA     60
IVTSLSIASY IISFLDGTIG AGLGILSVLF GQFWPSNTNT VWDNFLHVVE ELINRRIDIV    120
ERERILRQFD GLRAVISNYN TAFRNWNENE TTRNDPALQS EVRSRFDNAD DAFANRMPEF    180
RITGFETQSL AVYAQAATLH LLVLRDAVVN GRAWGFAQAT IESLYTKLVC LINAYADHCT    240
SVYRQGLQEL RNRGNWRNFN NYRRDMTITV LDVISLFSNY DPRIYYYSTN TQLTREVCTE    300
PIASSTWLNR YSNPDEFQQI ENDLNPPPSL FSILTTLFAP TAFFYYNDLH TPRDAISKTS    360
MRLTRTDGTT IIITTPWQGAF PPNISQELPR NFSGYKVYNV DSILANTAVQ FTGIQRVVFH   420
MVNEAGTGVP SQSIDLPLTT YYFNKSSNIP GIRSENPTGT DYTHILSSIR STSVGTPYRD    480
RSNIMVYGWT HTSAERTNRL LSSYGITQIP VVKANQLSNN ARVISGPGHT GGALISMSGD    540
SSIAMSLYVP KERYYIIRIR FVNDFNDVEG ILEFQGTGIT LNVKFPGSGA AVNPDLSVGD    600
FRYVTIPAYP LIRGNTTYQV ILKTRNATGT CLIDKIEFIP N                       641

SEQ ID NO: 87              moltype = AA  length = 1294
FEATURE                    Location/Qualifiers
source                     1..1294
                           mol_type = protein
                           organism = Bacillus sp.
SEQUENCE: 87
MATLNELYPV PYNVLANPPM RLSTTDPNVL DAIEKGGLF TDYSKDKKFG EIASTISEFY      60
KAFSGDSVKW LEFTKGLLGI AGFYPPIGAA MPFINLFLNI FWPAEDKTAH LFKIIMEAVQ    120
KLVEQTFQSE ILGNLQSEIT GFQSNLQHFS DAISDAIVTI GTPPTVNKLI DVKSKFEVAR    180
GIIEAALPKF KNPLDSVSSN PTFQRESILL TLPLYTIAAT MNLTLHQSYI NFMDHWGILT    240
YGSHEAYEDA IGMHRVKIDL RKRISTDSST ILSAFSQYMP PKQSTTKSAI NTYIRYVRSM    300
TTNSLDLVAL WPTLYPDLYP KRTELDQTRS VFGDIIGPTE YNSNINIQVI DIYNNNRISS    360
EIPSYSYPSS YSRLELSESN FHGYSSTSGP YTICAVDGVK LKYDGGAIFE YGPASNSKTI    420
QNLQSLNMKS QIGATTQPHS DVDNTALYVN DSTWTVTSGC YDFLEDQMAS SHNSSNNTVI    480
SNHKINTIYP VKTDSDDGGT QTSSKIGFLY SLILNDIAPT NSLDNKIQIS NSSDLAIKAF    540
PAEKGSLNNN IGTLQYVQEP LNGAAAVKLT SRQILQLPII NSNNLHYSIR IRYASNSNID    600
AYIHIETDNY SQGSGPISLP KTQVSVNDDD IYKDEKVMYT PGVDNKQYTS LLVMDSIEMF    660
PGSSTVYIQN NSQEDLFLDR IEFIPISRLE FQDLSFSADR DDVKQIDGFI SYYADLWQRK    720
DTELGYVINI NPTSLESRCT YQFFNGENLV HEERNTASWA QGQTITVPEG FTKVRLNDFS    780
ASDAQLLYIT GTININKPTF FALARDLEVI TTQVNALFAS GTQNKLTTDV SDYEIEEAVL    840
KVDALSDEVF GNEKKALRKL VNQAKRLSKA RNLLIGGSFD KLNAWYRGRH VVAVSDHELL    900
KSDHILLPPP TLYPSYIFQK VEESKLKANT RYTVSGFIAH AIDLEIVVSR YGQEVKKVVQ    960
VPYGEAFPLT SSGPICCRPR SRVNGKPADP HFFSYSIDYA ALDVEANPGI ELGLRIVEPT   1020
GMARVSNLEI REDRPLTANE LRKVQRAARD WRTAYDQERA EVTALIQPVL NQINALYENE   1080
DWNGTIRSRV SYHDLEAIVL PTLPKLNHWF MSDMLGEQGS ILAQFQEALN RAYTQLEGST   1140
LLHNGHFTTD AANWTIEGDA HHAILEDGRR VLRLPDWSSS ISQTIEIENF DPDKEYQLVF   1200
HAQGEGTVTL EHGEETKYIE THTHHFANFT TSQRQGITFE SNKVTVTISS EDGEFLADNI   1260
AIVEVPMFNK NQMVNENRGV NINSNTNMNS SNNQ                              1294

SEQ ID NO: 88              moltype = AA  length = 686
FEATURE                    Location/Qualifiers
REGION                     1..686
                           note = variant of native sequence
source                     1..686
                           mol_type = protein
                           organism = synthetic construct
SEQUENCE: 88
MATLNELYPV PYNVLANPPM RLSTTDPNVL DAIEKGGLF TDYSKDKKFG EIASTISEFY      60
KAFSGDSVKW LEFTKGLLGI AGFYPPIGAA MPFINLFLNI FWPAEDKTAH LFKIIMEAVQ    120
KLVEQTFQSE ILGNLQSEIT GFQSNLQHFS DAISDAIVTI GTPPTVNKLI DVKSKFEVAR    180
GIIEAALPKF KNPLDSVSSN PTFQRESILL TLPLYTIAAT MNLTLHQSYI NFMDHWGILT    240
YGSHEAYEDA IGMHRVKIDL RKRISTDSST ILSAFSQYMP PKQSTTKSAI NTYIRYVRSM    300
TTNSLDLVAL WPTLYPDLYP KRTELDQTRS VFGDIIGPTE YNSNINIQVI DIYNNNRISS    360
```

```
                                          -continued

EIPSYSYPSS YSRLELSESN FHGYSSTSGP YTICAVDGVK LKYDGGAIFE YGPASNSKTI    420
QNLQSLNMKS QIGATTQPHS DVDNTALYVN DSTWTVTSGC YDFLEDQMAS SHNSSNNTVI    480
SNHKINTIYP VKTDSDDGGT QTSSKIGFLY SLILNDIAPT NSLDNKIQIS NSSDLAIKAF    540
PAEKGSLNNN IGTLQYVQEP LNGAAAVKLT SRQILQLPII NSNNLHYSIR IRYASNSNID    600
AYIHIETDNY SQGSGPISLP KTQVSVNDDD IYKDEKVMYT PGVDNKQYTS LLVMDSIEMF    660
PGSSTVYIQN NSQEDLFLDR IEFIPI                                        686

SEQ ID NO: 89           moltype = AA  length = 713
FEATURE                 Location/Qualifiers
REGION                  1..713
                        note = Unknown organism from environmental sample
source                  1..713
                        mol_type = protein
                        organism = unidentified
SEQUENCE: 89
MNQNNDNKYE IIDSHASPYP SNRNIDQSRY PFTNNPNQPL QNTNYKNWIN MCQQNQQCNG     60
DIETLASADT ISGVSAGIIV VGTLLGAFAA PIISSFIISF GTLLPLFWKS SEDKTIWEQF    120
LIIGNRPFDS VVDQAIINLL SDKAKSLKAQ FEDYQRYFDL WNQNKNSQNA GEVLRRFSSL    180
DSDITRELEQ LKGNYYITLL PGYANVANWH LNLLQHAAIN YDKWISNSST QNIYPEDYIS    240
DIDKECLDKC STASGGSVSS AYYKCRLKCK IAAYTNYCSK TYQEGLNLKL KNSNNIKWNIY   300
NTYRREMTLT VLDLIALFPN YDIENYPIEI GTNTELTREI YTDALIANYA NSHFSIEKIE    360
NSLTRYPDLV TWLHSIFFYT RTIFSPVPGQ YEIGFTANAV RVSYTNGPIQ PPSPIYGYYD    420
GIDDKSEKVF SNQYIYKNRI TYFRDDPGMV QEIHLDLTNR GTVSFTDTSP FPPNFQTNIT    480
LAIPGKDRSN PPTFNEYSHV LSYMKTAIGD ERPFYSRARS ICFGWMHFSV NNRNTISDKK    540
ITQIPAVKAN RLDLPSFVMP GPGHTGGNLV VLSDRIEFQC NVPILAKYKI RMRYVAYSPN    600
KSINLTLSIQ GGGGSYIVQI PNIGSTVHSE QDTVNPKYQD FQYLYFNDPT GQPIIAQLFS    660
TTNITLSTNR LASNTLIIDK IEFIPTTEAF EQTYEKQKLE KNQQTVNNLF EKR           713

SEQ ID NO: 90           moltype = AA  length = 686
FEATURE                 Location/Qualifiers
REGION                  1..686
                        note = variant of native sequence
source                  1..686
                        mol_type = protein
                        organism = synthetic construct
SEQUENCE: 90
MNQNNDNKYE IIDSHASPYP SNRNIDQSRY PFTNNPNQPL QNTNYKNWIN MCQQNQQCNG     60
DIETLASADT ISGVSAGIIV VGTLLGAFAA PIISSFIISF GTLLPLFWKS SEDKTIWEQF    120
LIIGNRPFDS VVDQAIINLL SDKAKSLKAQ FEDYQRYFDL WNQNKNSQNA GEVLRRFSSL    180
DSDITRELEQ LKGNYYITLL PGYANVANWH LNLLQHAAIN YDKWISNSST QNIYPEDYIS    240
DIDKECLDKC STASGGSVSS AYYKCRLKCK IAAYTNYCSK TYQEGLNLKL KNSNNIKWNIY   300
NTYRREMTLT VLDLIALFPN YDIENYPIEI GTNTELTREI YTDALIANYA NSHFSIEKIE    360
NSLTRYPDLV TWLHSIFFYT RTIFSPVPGQ YEIGFTANAV RVSYTNGPIQ PPSPIYGYYD    420
GIDDKSEKVF SNQYIYKNRI TYFRDDPGMV QEIHLDLTNR GTVSFTDTSP FPPNFQTNIT    480
LAIPGKDRSN PPTFNEYSHV LSYMKTAIGD ERPFYSRARS ICFGWMHFSV NNRNTISDKK    540
ITQIPAVKAN RLDLPSFVMP GPGHTGGNLV VLSDRIEFQC NVPILAKYKI RMRYVAYSPN    600
KSINLTLSIQ GGGGSYIVQI PNIGSTVHSE QDTVNPKYQD FQYLYFNDPT GQPIIAQLFS    660
TTNITLSTNR LASNTLIIDK IEFIPT                                        686

SEQ ID NO: 91           moltype = AA  length = 859
FEATURE                 Location/Qualifiers
source                  1..859
                        mol_type = protein
                        organism = Bacillus sp.
SEQUENCE: 91
MKNKKKYMKP LAVGLLATNI IGFGTQTVAF AATDKAGSKE QIQQQMKTQN KSFNPTVLAS     60
MPSDTSELQK MLEDAIKNKD TQITPELIKK LQDKGFDYLS IVKGLTGGLL KQIPYAGSIL    120
SPLVVGLFPG KGYVTKANVW GEIQDRVSNL IDQKLEESQV NNLIGKLTGI QDNLGIYQTR    180
VGLVNGIKPP IANFIQKDAN SDKNKENLRS TIDSLDKDLG RVIPEFAVKG YEAASLPYYV    240
QVANVHLFLL KDALTHADEW GLTDDEKRGY LSRLQQKIQE YSSVVYDSFN KGVEAAKSKG    300
GSTADNWNRT NAYVRTMTLY GLDFVAFWPA FDTKHYNQPV KLQQTRELYS NMIGRPINWQ    360
DYDTTLQQIH NSGYAGYPGE LKQINVSQWD RIDGIKEVFD WTGDGSRDYT QQWGKPNKSG    420
YSTSSPTVDD PAIGISAYES NDANHYNMST ITYKQNNAYR WLSGPFATKG DSKDGSRIDS    480
KAPAGHKLSR VKVQEKRSDL NTISSFVAAY VPEEVHPQNI LEATAITGVP AEKYLAHAGF    540
ENKIEYMNGS NAMVSSKNGD TIDYNVQSQG KQKYKIRLRV ATNNDTSVGI SINGNSQQVN    600
IKNTEAATKL EDGITVKGVN GKYMLIEGPT VELNQGTNTI QLKNSGGAKI TLDRIEFQPI    660
GGDIRHWKQE GDKWYLYDEN NKKLTGWQEI NGLKYYLGKT GDGSGMNTEG EMATGWKKID    720
GVQYFGKTG DGVGMRAEGE VAIGWKKIDG VQYYFGKTGD GSGMEHEGEM AKGFKKIDGV    780
KYYFGKTGDG SGLNHEGEMA KGWRTIDGLK YYFNKTGDGS GMEHEGEMAI GDMTIDGVKH   840
HFNKTGDGTG RDHEGELVW                                                859

SEQ ID NO: 92           moltype = AA  length = 660
FEATURE                 Location/Qualifiers
REGION                  1..660
                        note = variant of native sequence
source                  1..660
                        mol_type = protein
                        organism = synthetic construct
SEQUENCE: 92
```

```
MKNKKKYMKP LAVGLLATNI IGFGTQTVAF AATDKAGSKE QIQQQMKTQN KSFNPTVLAS    60
MPSDTSELQK MLEDAIKNKD TQITPELIKK LQDKGFDYLS IVKGLTGGLL KQIPYAGSIL   120
SPLVVGLFPG KGYVTKANVW GEIQDRVSNL IDQKLEESQV NNLIGKLTGI QDNLGIYQTR   180
VGLVNGIKPP IANFIQKDAN SDKNKENLRS TIDSLDKDLG RVIPEFAVKG YEAASLPYYV   240
QVANVHLFLL KDALTHADEW GLTDDEKRGY LSRLQQKIQE YSSVVYDSFN KGVEAAKSKG   300
GSTADNWNRT NAYVRTMTLY GLDFVAFWPA FDTKHYNQPV KLQQTRELYS NMIGRPINWQ   360
DYDTTLQQIH NSGYAGYPGE LKQINVSQWD RIDGIKEVFD WTGDGSRDYT QQWGKPNKSG   420
YSTSSPTVDD PAIGISAYES NDANHYNMST ITYKQNNAVR WLSGPFATKG DSKDGSRIDS   480
KAPAGHKLSR VKVQEKRSDL NTISSFVAAY VPEEVHPQNI LEATAITGVP AEKYLAHAGF   540
ENKIEYMNGS NAMVSSKNGD TIDYNVQSQG KQKYKIRLRV ATNNDTSVGI SINGNSQQVN   600
IKNTEAATKL EDGITVKGVN GKYMLIEGPT VELNQGTNTI QLKNSGGAKI TLDRIEFQPI   660

SEQ ID NO: 93            moltype = AA  length = 1291
FEATURE                  Location/Qualifiers
source                   1..1291
                         mol_type = protein
                         organism = Bacillus sp.
SEQUENCE: 93
LKHHEAILIC SIYKRPQLLR NIKNIGGLYM NNNEFEIMDN GAMSYQSRYP LARKPGSEWQ    60
QMNYKDWMDM CTNGEAGDIF NDTAGAVRTG LIVGTGIAWA LLGLIPVYGT AASAIAGLFN   120
VLIPYWWPEQ PGVQPGSPQA QFTWDQLMTA VEDLTDKKIL ESKRSNAIAR WQGLQILGHD   180
FYVALCDWTK DQDNDRKKEV LRQEFNDLND ALKLAMPHFG AQGFELPMLS MYAQAANMHL   240
LVLKEVVQNG LRWGFEQYQV DRFYFDSTTP QGQGLLQLQA NYTNYCVEWY ERGLQEQYNT   300
GNWHKFNDFR RNMTIMVLDT VAVWPTYDPR RYPYPTQSQL TRTVYTNPVG GAIRSRPDPI   360
DIMENNMVSP PRLFSWLRKW EITTRKAGRE GEQPCMSVKT LQNTLSSMQW SITQGESKPP   420
IIKTLTLDIP NPYYQDDIWK VDTFRFDGIN DGIAGWDFYF TKSADQHFPI FVVHPDSYVH   480
RFNGLPCRGK DSGICDPCNF ENPCRKETPN TSVPCEDKIQ YSHRLSDIGA IFVASRYFDT   540
DRLKSFGYGW THVSADAKNL IDGSKKIIQI PAVKGKALYG EASVVRGPGS TGGDLVSLRP   600
GGELVVTVTL PPPDQPGDFK SYVLGIRFAN DLTTRLKVSY SDGYGESRSV IGTFGATSNP   660
GPDGRLRFQS FAYRDFDTMW ITQKEGLNEF DFTFENLGAV DGDGISNFQI DKLEFIPIER   720
SLAEYQANQD IEKARKAVNA LFTSDAKNAL KLNVTDYAVD QAANLVECVS EEFHAQEKMI   780
LLDQVKYGKR LSQARNLLNY GDFESSDWSG ENGWRTSHV HVASDNPIFK GRYLHIPGAM   840
SPQFSNKTYP TYAYQKVDES KLKSYTRYLV RGFVGNSKDL ELLVERYGKD VHVEMDVPND   900
ITYSLPINEC GGSDRCKPAS YQASPPHTCT CKDKENRNLT NRYTTEPTGS AVYLNRPDHK   960
SCGCKNDDMY QNGTHLHKSC GCKDPHVFTY HIDTGYVDQE ENLGLFFALK IASENGIANI  1020
DNLEIIEAQP LTGEALARVK KREQKWKQDM VQKRAQTEKA VQAAQGAIQT LFTNVQYNYL  1080
KFETLFPQIV HAEKLVQQIP YAYHPFLGEA LPTVPGMNFE IIQQLLAVIG NAHALYEQRN  1140
LVRNGTFSSG TGNWHVTEGV KVQLLQDTSV LVLSEWSHGA SQQLHIDPDR GYVLRVTARK  1200
EGGGKGTVTM SDCAAYTETV TFTSCDYNTV GSQMMTSGTL SGFVTKTLEI FPDTDRIQID  1260
IGETEGTFQV ESVELLCMKQ MENAGNFEDE M                                 1291

SEQ ID NO: 94            moltype = AA  length = 689
FEATURE                  Location/Qualifiers
REGION                   1..689
                         note = variant of native sequence
source                   1..689
                         mol_type = protein
                         organism = synthetic construct
SEQUENCE: 94
MNNNEFEIMD NGAMSYQSRY PLARKPGSEW QQMNYKDWMD MCTNGEAGDI FNDTAGAVRT    60
GLIVGTGIAW ALLGLIPVYG TAASAIAGLF NVLIPYWWPE QPGVQPGSPQ AQFTWDQLMT   120
AVEDLTDKKI LESKRSNAIA RWQGLQILGH DFYVALCDWT KDQDNDRKKE VLRQEFNDLN   180
DALKLAMPHF GAQGFELPML SMYAQAANMH LLVLKEVVQN GLRWGFEQYQ VDRFYFDSTT   240
PQGQGLLQLQ ANYTNYCVEW YERGLQEQYN TGNWHKFNDF RRNMTIMVLD TVAVWPTYDP   300
RRYPYPTQSQ LTRTVYTNPV GGAIRSRPDP IDIMENNMVS PPRLFSWLRK WEITTRKAGR   360
EGEQPCMSVK TLQNTLSSMQ WSITQGESKP PIIKTLTLDI PNPYYQDDIW KVDTFRFDGI   420
NDGIAGWDFY FTKSADQHFP IFVVHPDSYV HRFNGLPCRG KDSGICDPCN FENPCRKETP   480
NTSVPCEDKI QYSHRLSDIG AIFVASRYFD TDRLKSFGYG WTHVSADAKN LIDGSKKIIQ   540
IPAVKGKALY GEASVVRGPG STGGDLVSLR PGGELVVTVT LPPPDQPGDF KSYVLGIRFA   600
NDLTTRLKVS YSDGYGESRS VIGTFGATSN PGPDGRLRFQ SFAYRDFDTM WITQKEGLNE   660
FDFTFENLGA VDGDGISNFQ IDKLEFIPI                                    689

SEQ ID NO: 95            moltype = AA  length = 1262
FEATURE                  Location/Qualifiers
REGION                   1..1262
                         note = variant of native sequence
source                   1..1262
                         mol_type = protein
                         organism = synthetic construct
SEQUENCE: 95
MNNNEFEIMD NGAMSYQSRY PLARKPGSEW QQMNYKDWMD MCTNGEAGDI FNDTAGAVRT    60
GLIVGTGIAW ALLGLIPVYG TAASAIAGLF NVLIPYWWPE QPGVQPGSPQ AQFTWDQLMT   120
AVEDLTDKKI LESKRSNAIA RWQGLQILGH DFYVALCDWT KDQDNDRKKE VLRQEFNDLN   180
DALKLAMPHF GAQGFELPML SMYAQAANMH LLVLKEVVQN GLRWGFEQYQ VDRFYFDSTT   240
PQGQGLLQLQ ANYTNYCVEW YERGLQEQYN TGNWHKFNDF RRNMTIMVLD TVAVWPTYDP   300
RRYPYPTQSQ LTRTVYTNPV GGAIRSRPDP IDIMENNMVS PPRLFSWLRK WEITTRKAGR   360
EGEQPCMSVK TLQNTLSSMQ WSITQGESKP PIIKTLTLDI PNPYYQDDIW KVDTFRFDGI   420
NDGIAGWDFY FTKSADQHFP IFVVHPDSYV HRFNGLPCRG KDSGICDPCN FENPCRKETP   480
NTSVPCEDKI QYSHRLSDIG AIFVASRYFD TDRLKSFGYG WTHVSADAKN LIDGSKKIIQ   540
```

```
IPAVKGKALY GEASVVRGPG STGGDLVSLR PGGELVVTVT LPPPDQPGDF KSYVLGIRFA    600
NDLTTRLKVS YSDGYGESRS VIGTFGATSN PGPDGRLRFQ SFAYRDFDTM WITQKEGLNE    660
FDFTFENLGA VDGDGISNFQ IDKLEFIPIE RSLAEYQANQ DIEKARKAVN ALFTSDAKNA    720
LKLNVTDYAV DQAANLVECV SEEFHAQEKM ILLDQVKYGK RLSQARNLLN YGDFESSDWS    780
GENGWRTSHH VHVASDNPIF KGRYLHIPGA MSPQFSNKTY PTYAYQKVDE SKLKSYTRYL    840
VRGFVGNSKD LELLVERYGK DVHVEMDVPN DITYSLPINE CGGSDRCKPA SYQASPPHTC    900
TCKDKENRNL TNRYTTEPTG SAVYLNRPDH KSCGCKNDDM YQNGTHLHKS CGCKDPHVFT    960
YHIDTGYVDQ EENLGLFFAL KIASENGIAN IDNLEIIEAQ PLTGEALARV KKREQKWKQD   1020
MVQKRAQTEK AVQAAQGAIQ TLFTNVQYNY LKFETLFPQI VHAEKLVQQI PYAYHPFLGE   1080
ALPTVPGMNF EIIQQLLAVI GNAHALYEQR NLVRNGTFSS GTGNWHVTEG VKVQLLQDTS   1140
VLVLSEWSHG ASQQLHIDPD RGYVLRVTAR KEGGGKGTVT MSDCAAYTET VTFTSCDYNT   1200
VGSQMMTSGT LSGFVTKTLE IFPDTDRIQI DIGETEGTFQ VESVELLCMK QMENAGNFED   1260
EM                                                                 1262

SEQ ID NO: 96          moltype = AA  length = 349
FEATURE                Location/Qualifiers
source                 1..349
                       mol_type = protein
                       organism = Bacillus sp.
SEQUENCE: 96
MINNQFFLDT TYTIANKKSN FLFDIQKEST SNGTPIVLNT PDSKKNQQFI FFKLDGELYT     60
IANLSSGKII DLTGSNHSHI LVQNTWNGES SQIWYINHSD ISESDYKIIN HQNGKVVQSI   120
SDPNDMKNLI TLTSWNNQDT QQWNFISKES IELPNISESK PLPLPPDYFS NIYEVLPLQT   180
NPVIISSILL PCILIHDNEW DYPTKIQNSP YYKFVKEQYW ERVQSITLEP GQTNTFQYKT   240
GIKASDQKSM INTLGMSIGT DLGFQFNKSS TKISTQFTTT LKTLKSITSE QLSEITINDS   300
ITNIKSTKIG ITKYQLVTLY SLFRTDNSLV TEPWKIRDHL TTKDRSISN               349

SEQ ID NO: 97          moltype = AA  length = 560
FEATURE                Location/Qualifiers
source                 1..560
                       mol_type = protein
                       organism = Bacillus sp.
SEQUENCE: 97
MVQNNLEIKA LPSFIDNFNG VFGFVENIVG IFDKIFGTNT GNENLELEEI LRNQELLNEL     60
RDKLTGISGD LDSIIKNGEM NTELLNQLIQ LSNKQGDMLQ NIQSQIDSLQ SMIAGYMAEI   120
TGMLKQIQIQ NNILSAQMVY ITEILLAISQ KLDTINVNLL VNATITEITP SYQRMKYINK   180
KYDELSASHI ENYSKFTQDN SNGISLDTED LRKLNELIEL ATSITHNSQN SFEFYLETFQ   240
DIMVGQTLFE RSALQSIGEL IRSDQTPKGY GSEVAKAYTF LTSLTSIQAK SYATLAACRK   300
ILGLSDIDYT PILTDYIQKQ INIFKLEELP RFSDEFVGFN HIDTEGGGDL SKDYSFSVEA   360
NPGYALVGFE IIKNNTDYDL ISYQAKLKQN YEVDAETISK ITVSQINKVF GSRYDAKHEM   420
FADQVGFMPG DLQFPKDYVI TKLDFLAPVN TVGFLYEVTA NHYDPVTGKI DVTTSLTKNP   480
EDEEGTQFID VKANANHGVY LPSKIIDTFL SPMYSFKIDA DPDTSKFDIS CKNYLSHYLE   540
ASDLNNKETS LPYIIDDTKK                                               560

SEQ ID NO: 98          moltype = AA  length = 651
FEATURE                Location/Qualifiers
REGION                 1..651
                       note = Unknown organism from environmental sample
source                 1..651
                       mol_type = protein
                       organism = unidentified
SEQUENCE: 98
MNNKSNKNEI INSRFPVNFP NRNNRDLAYF VVNNQNSTLL DKNSKGWLVN CDKNTLVNID     60
PTGAATALSI ATVAVGTVLI LGFPVVGTIL VLFGTILPIF WSDPSDNQSV WEDFIKMTEE   120
STQYSITGSI RITALSHLRG LQTNLYEFYN TFVTWESNQT DPSALSRLLR AFDDLNTTFR   180
SAMPHFSPKD PEINQIENQI ILLPTYAVYA FMHLITLSTA SIYGKSWGMS DNVIADYERE   240
QSKLLNEYTS YCTDTYFLGL FRLSIRGNTD WNKYNTYRRN MTISVLDIVA QFPQYCDKRKY   300
PMQVKPELTR EIYTDALSFD GSLIEYYNLG LADEKLTRKP HLFTWLTGLD FYQLNTNAPN   360
NFFTSHRNVI ETTYGQRDYS PVFGNQNSDD LLLESGRAII PYDEFIYSLT TLNFLSTHPD   420
EYNNINEIKF SVTNGETTRP INIKPVTQVT RNLITNTWSL PPRDQSYILG PTNYSHTLSF   480
VKAFNSSNVR RSIVYSFAWN HFSVNDINQI YLDSITTVPA VKAFSLGNSS IVFEGPGHTG   540
GDMINLRDSM EFRCRSASNS KSYFIRLRYA ANTPMVVSIT LPGISGQSMR LNQTFSGNNY   600
TALKYNELNY LQFPNEVIIP SNRLFNIILQ KIYFQTDEVL IIDKIEFLPI S            651

SEQ ID NO: 99          moltype = AA  length = 1165
FEATURE                Location/Qualifiers
REGION                 1..1165
                       note = Unknown organism from environmental sample
source                 1..1165
                       mol_type = protein
                       organism = unidentified
SEQUENCE: 99
MDGNYQSQCG PYNCFSNSEA IILDEERLEV GNTVADFSLG LINFLYSNFA PGGGFVVGLL     60
ELIWGILGPS QWGIFLNQIE QMINQRIEEF ARNQAISRME GLGNLYNVYT EAFKAWEADP   120
DNPALKEEMR IQFNDMNSAL ITAIPLLRVQ NYEVALLSVY TQAANLHLSV LRDVSVFGQN   180
WGFDMATINS RYSELTRLIH VYTDHCVDTY NEGLKNLEGP RLGSWVVYNR FRRRLTISVL   240
DIIAFFPNYD IKAYPIQTTT QLTREIYLDL PFVNENVSDS RYFPSFSTVE NAIIRRPHLV   300
DFLGRLTVFT DRWSARLFWG GHRVRFSRTG TTAFIDSPIY GVEASVERPI IFSPSKDVPK   360
IRTLSYSSQL EDRVPDVVVE GVEFQDTQQI SEIYRKSGPI DSLSELPPEN TSVPLALGYS   420
```

```
HRLCHANFLR QDGAPRIGGL VFSWTHRSAS PTNEISSSRI TQIPLVKAHT LGVNASVLKG    480
PGFTGGDILY QNRLGSLGTI RMNFTGRFPQ IYYIRIRYAS PRNTSGFIVN SEMPYDSYPI    540
SFLKTMEIDR PLTSRSFALA SIDIPITIRR YQVDFELTLQ SGVYIDRIEF VPADATFEAE    600
YDLERVQKAV NALFTSTNQK GLQTDVTDYH IDQVSNLVDC LFDEFCLDEK RELSEKVKQA    660
KRLSDERNLL QDSNFRGINR EQDRGWRGST DITIQGGRDV FKENYVTLPG AFDECYPTYL    720
YQKIDESKLK AYTRYQLRGY LEDSQDLEIY LIRYNAKHET LNVPGTGSLW PLAVENPIGR    780
CGEPNRCAPH IEWNPDLDCS CGDGEKCAHH SHQFSLDIDV GCTDLNEDLG VWVIFKIKTQ    840
DGYARLGNLE FLEEKPLVGE ALSRVKRAEK KWRDKREKLQ LETNIVYKEA KESVDALFVN    900
SRYDRLQADT NIAMIHAADK RVHRIRGAYL PELSVIPVVN AGIFEELEGL IPNAFSLYDA    960
RNVIKNGDFN NGLSYWNVKG HVDVQQNNHR SVLVLPEWKA EVSQEVRVCP GRGYILRVTA   1020
YKEGYGEGCI TIHEIENHTD KLKFRNCEEE EIYPTNTVTC HDYTVSQGAE GCADTCNSRH   1080
RGYDEANGNN PSVSANYTPV FEEEVYTDGR RDNPCEMERG YTPLPVGYVT KELEYFPETD   1140
TVWIEIGETE GTFIVDSVEL LLMEE                                         1165

SEQ ID NO: 100          moltype = AA   length = 593
FEATURE                 Location/Qualifiers
REGION                  1..593
                        note = variant of native sequence
source                  1..593
                        mol_type = protein
                        organism = synthetic construct
SEQUENCE: 100
MDGNYQSQCG PYNCFSNSEA IILDEERLEV GNTVADFSLG LINFLYSNFA PGGGFVVGLL     60
ELIWGILGPS QWGIFLNQIE QMINQRIEEF ARNQAISRME GLGNLYNVYT EAFKAWEADP    120
DNPALKEEMR IQFNDMNSAL ITAIPLLRVQ NYEVALLSVY TQAANLHLSV LRDVSVFGQN    180
WGFDMATINS RYSELTRLIH VYTDHCVDTY NEGLKNLEGP RLGSWVVYNR FRRRLTISVL    240
DIIAFFPNYD IKAYPIQTTT QLTREIYLDL PFVNENVSDS RYFPSFSTVE NAIIRRPHLV    300
DPLGRLTVFT DRWSARLFWG GHRVRFSRTG TTAFIDSPIY GVEASVERPI IFSPSKDVPK    360
IRTLSYSSQL EDRVPDVVVE GVEFQDTQQI SEIYRKSGPI DSLSELPPEN TSVPLALGYS    420
HRLCHANFLR QDGAPRIGGL VFSWTHRSAS PTNEISSSRI TQIPLVKAHT LGVNASVLKG    480
PGFTGGDILY QNRLGSLGTI RMNFTGRFPQ IYYIRIRYAS PRNTSGFIVN SEMPYDSYPI    540
SFLKTMEIDR PLTSRSFALA SIDIPITIRR YQVDFELTLQ SGVYIDRIEF VPA           593

SEQ ID NO: 101          moltype = AA   length = 1280
FEATURE                 Location/Qualifiers
REGION                  1..1280
                        note = Unknown organism from environmental sample
source                  1..1280
                        mol_type = protein
                        organism = unidentified
SEQUENCE: 101
MNQNYNNNEY EIKDVGVMDY QPRYPLAQAP SAELQQMSYK DWMDRCERGS LAITFKSVIT     60
TALDITSAIL GAAKSPKAKV ARAAVQVLNS VIKLLWPEPE KPSEPAYDID FIWKELIKRV    120
EILIEEKIDR EAYNAAIGRL SGLKRALNLY QIAFWDWLKD ENDPELQAEL RTRFTAALFE    180
LVTTIETFKY NGQELNLLTI FVQAADFHLM LLQQGIMYGV RWGFDQRTVD SLYQNDSGEG    240
LKNLLPKYSD YATYWYGQGL NRAKNLKANL SDTVRYPWAA NLEDTSVLQE LEDWNLYNDY    300
RRDMTILVLD LVAVWPTYDL HYYDNGNYGV QSELTRSIYS QAVGNVMGTV FTKEQYEVSF    360
VRPPHLVTWL EKMFVHIRDK EQGAPNDAEM AGISLDYSYS GWDNTVYDIL QGYPATGGSQ    420
IRVLAKSNVI VQDQEKNRAI YNTDLQHDKL VDRFVFYQNS GEVNYAGRDN PSSYKTFAWD    480
TDVTNYSSQM TWINGPVNEG HFGYIQAYAP EWIPASCEPF NTIVDAEDVI TQIPAVKARE    540
LKYGARVIKG LGYTGDLVS IAPNGLCELY VSFPNVARRY QVRVHYACQD STKIKLRIGD    600
SSHDIKLQST YSGGALTYDS FGYATSEYSY LFYPDFYDEK QIVRLGNDFD ITQQDIIIDK    660
IEFIPVDIFY AEEQALKQAR KAVNALFTGD AKDVLKLNVT DYAVDQAANL VECVSDEFHA    720
QEKMILLDQV KFAKRLSQAR NLLHYGDFES LDWSGENGWR TSHHVSVRSD NPIFKGRYLH    780
MPGATSSQFS NNVYPTYVYQ KVDESKLKSY TRYLVRGRVG NSKDLELLVE RYGKDVHVEM    840
DVPNDIRYSL PMNECGGFDR CKSASDQTRP PHTCTCKNTA VAHTDCQCQD KGNRISTGVY    900
TNGPTGSAVY TNGFHTHQSC GCKNKNSDRY QSGTHPQKSC GCKDPHVFSY HIDTGCVDQE    960
ENLGLWFALK VASENGVANI DNLEIIEAQP LTGEALARVK KREQKWKQEM AQKRFQTDKA   1020
VQAAQGAIQP LFTNAQYNRL QFETLFPQIV NAEMLVQQIP YMYHPFLSGA LPTVPGMNFE   1080
IIQRLLAVTG NARGLYEQRN LVRNGTFSSG TGNWHVTEGV KVQPLQNTSV LVLSEWNQEA   1140
SQQLHIDPDR GYVLRVTARK EGGGKGTVTM SDCAAYTETL TFTSCDFNTS GSQTMTSGTL   1200
SGFVTKTLEI FPDTDRIRID MGETEGTFQI ESVELICMEQ MEDDLYDMAG NLEEEMLDLG   1260
IENINAVTNK MCFSWDIQCP                                               1280

SEQ ID NO: 102          moltype = AA   length = 666
FEATURE                 Location/Qualifiers
REGION                  1..666
                        note = variant of native sequence
source                  1..666
                        mol_type = protein
                        organism = synthetic construct
SEQUENCE: 102
MNQNYNNNEY EIKDVGVMDY QPRYPLAQAP SAELQQMSYK DWMDRCERGS LAITFKSVIT     60
TALDITSAIL GAAKSPKAKV ARAAVQVLNS VIKLLWPEPE KPSEPAYDID FIWKELIKRV    120
EILIEEKIDR EAYNAAIGRL SGLKRALNLY QIAFWDWLKD ENDPELQAEL RTRFTAALFE    180
LVTTIETFKY NGQELNLLTI FVQAADFHLM LLQQGIMYGV RWGFDQRTVD SLYQNDSGEG    240
LKNLLPKYSD YATYWYGQGL NRAKNLKANL SDTVRYPWAA NLEDTSVLQE LEDWNLYNDY    300
RRDMTILVLD LVAVWPTYDL HYYDNGNYGV QSELTRSIYS QAVGNVMGTV FTKEQYEVSF    360
VRPPHLVTWL EKMFVHIRDK EQGAPNDAEM AGISLDYSYS GWDNTVYDIL QGYPATGGSQ    420
```

```
IRVLAKSNVI VQDQEKNRAI YNTDLQHDKL VDRFVFYQNS GEVNYAGRDN PSSYKTFAWD      480
TDVTNYSSQM TWINGPVNEG HFGYIQAYAP EWIPASCEPF NTIVDAEDVI TQIPAVKARE      540
LKYGARVIKG LGYTGGDLVS IAPNGLCELY VSFPNVARRY QVRVHYACQD STKIKLRIGD      600
SSHDIKLQST YSGGALTYDS FGYATSEYSY LFYPDFYDEK QIVRLGNDFD ITQQDIIIDK      660
IEFIPV                                                                 666

SEQ ID NO: 103            moltype = AA  length = 123
FEATURE                   Location/Qualifiers
REGION                    1..123
                          note = Unknown organism from environmental sample
source                    1..123
                          mol_type = protein
                          organism = unidentified
SEQUENCE: 103
MEKKQECCEE VNTKALFCCR VQVPHSFPYM PNSASKIAYN LDCLSVVEES CRKTIQVEDC       60
GAVEVKLNLL KVVGFIPYIA NATVEGEHGK ECDYDANGRH QVSVCCNGSI FIVYKSEHKC      120
KKT                                                                    123

SEQ ID NO: 104            moltype = AA  length = 811
FEATURE                   Location/Qualifiers
REGION                    1..811
                          note = Unknown organism from environmental sample
source                    1..811
                          mol_type = protein
                          organism = unidentified
SEQUENCE: 104
MNLNDNKNEF EIMGNGSMAY QPRYPLAQAP GSAFQGMDYK DWLNLCASGE FGELFVDSDA       60
VKNGVVAGLA ITSYILSIPF PFQSAALGII SILLPILWPE QAGNPGTTEA QFTWDQWMKA      120
AENMADQKIA DSVKTSAINT TKTLQSRIDD YTQAICNLKT DPNNEAYKEE VRRQFNDADD      180
WAKATVIEFG NSAYAIPLLA DYAQAANLHL LLLQEGIKFG ESWGFSALKV QQLYSNTSVG      240
NPGMKELLAI YTDHCVRYYN EGLKKRYETG NWYTFNDYRK NMTLMVMDIV SFWPTYDPIL      300
YPVPTKSQLT RTVYTDFLRD TISPPAISDV ENSVTVPLGL FRWMIGLGYH GVTVNSSNVW      360
MGLEQLYHYT LRGDRYEERQ GEFPHDSKLL GYLATANDDV WSIIPNYIPI EDGSEVGYIP      420
NTASFFHDFR FQLLKSEEQR VHLAYEEGIS RKFGLPCKSN TGTDCDPCQP CTALPNASDP      480
CDDKSLYSHR FSYMGIYNPY IEFTLSPCFG WTHVSADANN LIDAEKITQI PAVKAYAIAT      540
NSRVVKGPGS TGGDVVQLSS GTERGIISMW ITTPPGALAY RVRIRYASSM QTNVEIYMLG      600
ANGQFDVPAT TTDLTNLTYN KFKYLDTVVY SYSEVEENRE HIRIGATGSG SGSFILDKIE      660
FIPIRGSVEE FEANQALEKA RKEVNALFTG DAKSALKLNI TDYAVDQASN LVECVSDEFH      720
AQEKMILVDQ VKYAKRLSHA RNLLNYGDFE SSDWSGENGW KTSHHVHVTA NNPIFKGRYL      780
HMPGATSSQF SKNLFRIYGI ICTKKDVSYD T                                     811

SEQ ID NO: 105            moltype = AA  length = 664
FEATURE                   Location/Qualifiers
REGION                    1..664
                          note = variant of native sequence
source                    1..664
                          mol_type = protein
                          organism = synthetic construct
SEQUENCE: 105
MNLNDNKNEF EIMGNGSMAY QPRYPLAQAP GSAFQGMDYK DWLNLCASGE FGELFVDSDA       60
VKNGVVAGLA ITSYILSIPF PFQSAALGII SILLPILWPE QAGNPGTTEA QFTWDQWMKA      120
AENMADQKIA DSVKTSAINT TKTLQSRIDD YTQAICNLKT DPNNEAYKEE VRRQFNDADD      180
WAKATVIEFG NSAYAIPLLA DYAQAANLHL LLLQEGIKFG ESWGFSALKV QQLYSNTSVG      240
NPGMKELLAI YTDHCVRYYN EGLKKRYETG NWYTFNDYRK NMTLMVMDIV SFWPTYDPIL      300
YPVPTKSQLT RTVYTDFLRD TISPPAISDV ENSVTVPLGL FRWMIGLGYH GVTVNSSNVW      360
MGLEQLYHYT LRGDRYEERQ GEFPHDSKLL GYLATANDDV WSIIPNYIPI EDGSEVGYIP      420
NTASFFHDFR FQLLKSEEQR VHLAYEEGIS RKFGLPCKSN TGTDCDPCQP CTALPNASDP      480
CDDKSLYSHR FSYMGIYNPY IEFTLSPCFG WTHVSADANN LIDAEKITQI PAVKAYAIAT      540
NSRVVKGPGS TGGDVVQLSS GTERGIISMW ITTPPGALAY RVRIRYASSM QTNVEIYMLG      600
ANGQFDVPAT TTDLTNLTYN KFKYLDTVVY SYSEVEENRE HIRIGATGSG SGSFILDKIE      660
FIPI                                                                   664

SEQ ID NO: 106            moltype = AA  length = 325
FEATURE                   Location/Qualifiers
REGION                    1..325
                          note = Unknown organism from environmental sample
source                    1..325
                          mol_type = protein
                          organism = unidentified
SEQUENCE: 106
MVFLYNFVTL GTLISNLFLG SDVKMNRKVI LCGVLASTLL GGGTLSTNVS AAEIEENKNS       60
IINTPASKSQ KVMNDINQEA IQDIDQKVNK MIDSIPPIFG SKYTRTDRFY GESLTYSGIN      120
LEENNSTHVE PMYFGSNTFY NDSELEQSYN TTSFSEAVTK STTTQTQNGF KSGTLTGGEV      180
GIPFVAKGEV KINLEYNFTH TNSNTTSKTT TLTAPPQPVK VPAGKVYKTD VYFEKKSTSG      240
TVELYADFLT GVVAEGRVAP IGSVLYKAND KQGLIQSPND PSKVRAIGKG TFNVEHGSNF      300
IVKTYDVTSK GKTAKLVDTK VIPIK                                            325

SEQ ID NO: 107            moltype = AA  length = 275
FEATURE                   Location/Qualifiers
```

| | | | |
|---|---|---|---|
| REGION | 1..275<br>note = variant of native sequence | | |
| source | 1..275<br>mol_type = protein<br>organism = synthetic construct | | |

SEQUENCE: 107
```
MAEIEENKNS IINTPASKSQ KVMNDINQEA IQDIDQKVNK MIDSIPPIFG SKYTRTDRFY    60
GESLTYSGIN LEENNSTHVE PMYFGSNTFY NDSELEQSYN TTSFSEAVTK STTTQTQNGF   120
KSGVTTGGEV GIPFVAKGEV KINLEYNFTH TNSNTTSKTT TLTAPPQPVK VPAGKVYKTD   180
VYFEKKSTSG TVELYADFLT GVVAEGRVAP IGSVLYKAND KQGLIQSPND PSKVRAIGKG   240
TFNVEHGSNF IVKTYDVTSK GKTAKLVDTK VIPIK                             275
```

| | | | |
|---|---|---|---|
| SEQ ID NO: 108 | moltype = AA length = 301 | | |
| FEATURE | Location/Qualifiers | | |
| REGION | 1..301<br>note = variant of native sequence | | |
| source | 1..301<br>mol_type = protein<br>organism = synthetic construct | | |

SEQUENCE: 108
```
MNRKVILCGV LASTLLGGGT LSTNVSAAEI EENKNSIINT PASKSQKVMN DINQEAIQDI    60
DQKVNKMIDS IPPIFGSKYT RTDRFYGESL TYSGINLEEN NSTHVEPMYF GSNTFYNDSE   120
LEQSYNTTSF SEAVTKSTTT QTQNGFKSGV TTGGEVGIPF VAKGEVKINL EYNFTHTNSN   180
TTSKTTTLTA PPQPVKVPAG KVYKTDVYFE KKSTSGTVEL YADFLTGVVA EGRVAPIGSV   240
LYKANDKQGL IQSPNDPSKV RAIGKGTFNV EHGSNFIVKT YDVTSKGKTA KLVDTKVIPI   300
K                                                                  301
```

| | | | |
|---|---|---|---|
| SEQ ID NO: 109 | moltype = AA length = 656 | | |
| FEATURE | Location/Qualifiers | | |
| REGION | 1..656<br>note = Unknown organism from environmental sample | | |
| source | 1..656<br>mol_type = protein<br>organism = unidentified | | |

SEQUENCE: 109
```
VENMNSYENK SEYEILNASP NNTNMPNRYP FANDPNIFPI NLNDCQGKPW QNTWKSVSDI    60
LSAAFTLWRF LQAPSPALGA TALLGVINIL IPPAGPSVAS LSICDLLSII RKEVDQSVLD   120
DGVADFNGKL TNYKEYYLSS LQEWLSAGKP NDKRLSNVVE YFKKSEEGFN EILAGSLSRE   180
NARILLLPTF AQAANFQLLL LRDAVQYKKE WGALLSAEKV GSELISPTID YGQRLKDKIA   240
QYTKYCVTWY QEGLNQIKEG GARTETWLKF NKFRREMTLA VLDIIALFPT YDFAKYPLGT   300
SVELTREIYT DPVGYSGGTY GWEQFFSFNS LEANGTRGPG LVTWLLAIDI YSHSVLSLTG   360
WGGTRHYEDY TKGNGAFQRM SGTTSNDPHP ISFGTTDIFK ISSLARYVLQ QFPGFIVPRH   420
LVSRAEFFPT TPNTLLYERN SSGNSQTIES VLPGIDNDLP PSRTNYSHRL SNAACVQYET   480
SVVTVFGWTH TSMTRNNPIH PDKITQIPAV KAFALENNAY VSAGPGDTGG DVVTLRYHGR   540
LKIRLTPAPT NKDYLVRIRY SALAYGAVYV ERWSPSGSVY DVPPLPYTSV STYGYVDTLV   600
TTFNQSSVEI IIENRHISDI IIDKVEFIPQ DSTALEYEGK QSLEKAQNVV NDLFIN       656
```

| | | | |
|---|---|---|---|
| SEQ ID NO: 110 | moltype = AA length = 627 | | |
| FEATURE | Location/Qualifiers | | |
| REGION | 1..627<br>note = variant of native sequence | | |
| source | 1..627<br>mol_type = protein<br>organism = synthetic construct | | |

SEQUENCE: 110
```
MNSYENKSEY EILNASPNNT NMPNRYPFAN DPNIFPINLN DCQGKPWQNT WKSVSDILSA    60
AFTLWRFLQA PSPALGATAL LGVINILIPP AGPSVASLSI CDLLSIIRKE VDQSVLDDGV   120
ADFNGKLTNY KEYYLSSLQE WLSAGKPNDK RLSNVVEYFK KSEEGFNEIL AGSLSRENAR   180
ILLLPTFAQA ANFQLLLLRD AVQYKKEWGA LLSAEKVGSE LISPTIDYGQ RLKDKIAQYT   240
KYCVTWYQEG LNQIKEGGAR TETWLKFNKF RREMTLAVLD IIALFPTYDF AKYPLGTSVE   300
LTREIYTDPV GYSGGTYGWE QFFSFNSLEA NGTRGPGLVT WLLAIDIYSH SVLSLTGWGG   360
TRHYEDYTKG NGAFQRMSGT TSNDPHPISF GTTDIFKISS LARYVLQQFP GFIVPRHLVS   420
RAEFFPTTPN TLLYERNSSG NSQTIESVLP GIDNDLPPSR TNYSHRLSNA ACVQYETSVV   480
TVFGWTHTSM TRNNPIHPDK ITQIPAVKAF ALENNAYVSA GPGDTGGDVV TLRYHGRLKI   540
RLTPAPTNKD YLVRIRYSAL AYGAVYVERW SPSGSVYDVF PLPYTSVSTY GYVDTLVTTF   600
NQSSVEIIIE NRHISDIIID KVEFIPQ                                      627
```

| | | | |
|---|---|---|---|
| SEQ ID NO: 111 | moltype = AA length = 653 | | |
| FEATURE | Location/Qualifiers | | |
| REGION | 1..653<br>note = variant of native sequence | | |
| source | 1..653<br>mol_type = protein<br>organism = synthetic construct | | |

SEQUENCE: 111
```
MNSYENKSEY EILNASPNNT NMPNRYPFAN DPNIFPINLN DCQGKPWQNT WKSVSDILSA    60
AFTLWRFLQA PSPALGATAL LGVINILIPP AGPSVASLSI CDLLSIIRKE VDQSVLDDGV   120
ADFNGKLTNY KEYYLSSLQE WLSAGKPNDK RLSNVVEYFK KSEEGFNEIL AGSLSRENAR   180
ILLLPTFAQA ANFQLLLLRD AVQYKKEWGA LLSAEKVGSE LISPTIDYGQ RLKDKIAQYT   240
```

```
KYCVTWYQEG LNQIKEGGAR TETWLKFNKF RREMTLAVLD IIALFPTYDF AKYPLGTSVE  300
LTREIYTDPV GYSGGTYGWE QFFSFNSLEA NGTRGPGLVT WLLAIDIYSH SVLSLTGWGG  360
TRHYEDYTKG NGAFQRMSGT TSNDPHPISF GTTDIFKISS LARYVLQQFP GFIVPRHLVS  420
RAEFFPTTPN TLLYERNSSG NSQTIESVLP GIDNDLPPSR TNYSHRLSNA ACVQYETSVV  480
TVFGWTHTSM TRNNPIHPDK ITQIPAVKAF ALENNAYVSA GPGDTGGDVV TLRYHGRLKI  540
RLTPAPTNKD YLVRIRYSAL AYGAVYVERW SPSGSVYDVF PLPYTSVSTY GYVDTLVTTF  600
NQSSVEIIIE NRHISDIIID KVEFIPQDST ALEYEGKQSL EKAQNVVNDL FIN         653

SEQ ID NO: 112           moltype = AA   length = 564
FEATURE                  Location/Qualifiers
REGION                   1..564
                         note = Unknown organism from environmental sample
source                   1..564
                         mol_type = protein
                         organism = unidentified
SEQUENCE: 112
VNPMFPSGTK NTLSIETTDY EIDQAAISIE CMSDEQNSQE KMVLWDEVKR AKQLSQSRNL   60
LQNGDFGEFS GNDWTFSNDI IIGSNNSIFK GNFLQMRGAR DIYGTIFPTY IYQKIDESKL  120
KPYTRYRVRG FVGSSKDLKL MVTRYGKEID AIMNVSNDLA YMQPNPSCGD YRCEPSSQYV  180
SQGGYPTPTD GYALDMYACP SSSDKKHVMC HDRHPFDFHI DTGEVDANTN VGIDVLFKIS  240
NPDGYATVGN LEVIEEGPLT SEALSHVKQK EMKWHQHMEK KRWETQQAYD RAKQAVDALF  300
TNAQGEALHY HTTLDQIQNA DRLVQSIPYV NHAWLPNAPG INYDVYQGLN ARIMQARYLY  360
DARNVITNGD FTQGLTGWHA TGKAAVQQMD GSSVLVLSNW SAGVSQNLHA QNHRGYMLRV  420
IAKKEGPGKG YVTMMDCNGK QETLKFTSCE EGYMTKTVEV FPESDRIRIE MGETEGTFYI  480
DSIELLCMKG YNNPHTGNMY EQSYNGNYHQ NTSDVYHQGY TNNYNQDSSS MYNQNYTNND  540
DLHSGCTCNQ GHNSGCTCGQ EYNR                                        564

SEQ ID NO: 113           moltype = AA   length = 384
FEATURE                  Location/Qualifiers
source                   1..384
                         mol_type = protein
                         organism = Bacillus sp.
SEQUENCE: 113
MKSISKKVVT GLFAGAMGLS IFAPASQAAP ANNEYTYIAL KADQHQLWDV YEGATYDNAG   60
IRLYADAGTP DNRKFLLVPL DGGTYAIVNK NSGKPSVSGS GWVGPGIQKN DILTQQSWTG  120
SATQQWYLRD KGNDYYEIVN QGYGKVASWG WNGVTGAASI QYVDLDDSDP SDSNRVFKIP  180
RSWDTFSLPT LPATGTRPDA PNYTGGIDQQ LPQTSNSVVV GASLIPSIMV KDSQASDYTK  240
IHNSPYYTLV KEEYWDKTFS AVIPAGLTRS YTFKSGMTST DQQKMTDTLS ISVGADFGFK  300
FKDATAAIKT SLTKTLQTEI SSTSTEASEE TVSSTVTSEP GKTTGFTEYQ LVTKYSLKRA  360
DGSTVSDPWI VKNNKITVAR KNSI                                        384

SEQ ID NO: 114           moltype = AA   length = 355
FEATURE                  Location/Qualifiers
REGION                   1..355
                         note = variant of native sequence
source                   1..355
                         mol_type = protein
                         organism = synthetic construct
SEQUENCE: 114
MANNEYTYIA LKADQHQLWD VYEGATYDNA GIRLYADAGT PDNRKFLLVP LDGGTYAIVN   60
KNSGKPSVSG SGWVGPGIQK NDILTQQSWT GSATQQWYLR DKGNDYYEIV NQGYGKVASW  120
GWNGVTGAAS IQYVDLDDSD PSDSNRVFKI PRSWDTFSLP TLPATGTRPD APNYTGGIDQ  180
QLPQTSNSVV VGASLIPSIM VKDSQASDYT KIHNSPYYTL VKEEYWDKTF SAVIPAGLTR  240
SYTFKSGMTS TDQQKMTDTL SISVGADFGF KFKDATAAIK TSLTKTLQTE ISSTSTEASE  300
ETVSSTVTSE PGKTTGFTEY QLVTKYSLKR ADGSTVSDPW IVKNNKITVA RKNSI       355

SEQ ID NO: 115           moltype = AA   length = 592
FEATURE                  Location/Qualifiers
source                   1..592
                         mol_type = protein
                         organism = Bacillus sp.
SEQUENCE: 115
MKYKDRKHAK CYKPALLAT VATMTLGVST FGSTASVFAA ENSINSQQAT STPATNDDVF    60
KVEKDGTIKI LKDKLFTTDN LKAIGSLGGS VLKQAYTDAH TNNGNFNNTF RTLTMGTTAL  120
IPYGGVVISP LIGLLWPENV DAQKNQIKKM MEELATMMDQ KIEDYDLGTL KQQTKALMND  180
LQSFEDSING RPLAKSPTAG SIEETRRTQA LIINAKFKEI IQLCQKEDQK IAELPIFTII  240
ATAHLEFLHF MEKNGQGSKI KFDDESLKTQ FTNDIPKITE DYIHHVQQTY KLGKQQFNKK  300
MYDVAANTPG GNANANSTSE EEIIGKMQKY ILDLHPLANG YGEKRRQMQD ALTNYGKLRD  360
TRNQYYKNTS NNEAFQLVAL GDWKKENNGW YFIDTKGKKK IGWIQLGEKH YYLSPSDGKM  420
VTGSVAIKTS DGRTGTYQFN SSGECTNYDT ASPNGTYKIV YSKANKVVDF GYDGKEHPVI  480
WDYHDGKNQQ WEFKYDAEKN AYQIINKDDE RVLAYNTSGA SDTALVTRND HKPEHYWTLE  540
DAGDGNVLLV NYADKNKVLD VYGEKTAGGS RLFVRDKLNN SAAQKFKLVK IS          592

SEQ ID NO: 116           moltype = AA   length = 554
FEATURE                  Location/Qualifiers
REGION                   1..554
                         note = variant of native sequence
source                   1..554
                         mol_type = protein
```

```
                        organism = synthetic construct
SEQUENCE: 116
MAENSINSQQ ATSTPATNDD VFKVEKDGTI KILKDKLFTT DNLKAIGSLG GSVLKQAYTD    60
AHTNNGNFNN TFRTLTMGTT ALIPYGGVVI SPLIGLLWPE NVDAQKNQIK KMMEELATMM   120
DQKIEDYDLG TLKQQTKALM NDLQSFEDSI NGRPLAKSPT AGSIEETRRT QALIINAKFK   180
EIIQLCQKED QKIAELPIFT IIATAHLEFL HFMEKNGQGS KIKFDDESLK TQFTNDIPKI   240
TEDYIHHVQQ TYKLGKQQFN KKMYDVAANT PGGNANANST SEEEIIGKMQ KYILDLHPLA   300
NGYGEKRRQM QDALTNYGKL RDTRNQYYKN TSNNEAFQLV ALGDWKKENN GWYFIDTKGK   360
KKIGWIQLGE KHYYLSPSDG KMVTGSVAIK TSDGRTGTYQ FNSSGECTNY DTASPNGTYK   420
IVYSKANKVV DFGYDGKEHP VIWDYHDGKN QQWEFKYDAE KNAYQIINKD DERVLAYNTS   480
GASDTALVTR NDHKPEHYWT LEDAGDGNVL LVNYADKNKV LDVYGEKTAG GSRLFVRDKL   540
NNSAAQKFKL VKIS                                                    554

SEQ ID NO: 117          moltype = AA  length = 1326
FEATURE                 Location/Qualifiers
REGION                  1..1326
                        note = Unknown organism from environmental sample
source                  1..1326
                        mol_type = protein
                        organism = unidentified
SEQUENCE: 117
LKGEISMTTL SYYNVLAYPP LILDEKSPYD QYKEWQKKID KTWKEYDEDF LPKPVMDLGK    60
NLAEVFKGDP QAYLHLANTA IRLAFLIIPG GQTAAWGVNL VLNKVVGIFF PPQNKSLFDQ   120
IKDAVSNLVD QKLIDQEING LMIKLNSLNQ PLSRFGNSIQ RAIGKPQDFE TTSSNAIILD   180
ATQDCSKDSA CSCSNDTNRP PNAPLCTPCD CRMKEVQTIF GESSGDVNRA LSDMKTTLNN   240
VVGADQLRSY MQIYLPLYVA AATMELQMYK TYIDFAQKFD FDVTGTTKEH VNELRQKIKT   300
HSEYIMNLFK NSLPEVSSNT KNQLHAYIRY TRNITLNALD MVSTWKFLDP VDYPTTATFN   360
PTRIIFNDLA GPVECLTSNQ NSNQLHFNFY DMNGQGLPNN DIFNYFYRGM QVKGLQIQTY   420
TSSDTKSPQH FPVGFLSSYY GSNGDFQFDK RVDPSNFVGG SNSVKLGDDV YKSHPALSVI   480
NAVSNQLQVF LNYIDTEDLY FDQTVSPGGT ACGSGNSTIW PDQKIQAIYP ITPDNTKKYE   540
QYFATSKIGF VTTLVPSDTT PWITFTDNGD NSIYTFSAEN TRTLTGSAGP VREFITGSAP   600
LGLSPGGGAQ YSINTNDAPS GDYQVRVRVA TPGSGGSLAI SVDGKTQTLQ LPDTNVNDTN   660
HIAGFAGTYT LAPATQIDAA TLKPKAPTEN IFPVRQTSSL PVSITNNSST VINIDRIEFV   720
PVSVSPTTSI HRDIPTTTTQ PNRTQEIWSG SKYATGLSVT GTASNDASIV FQLYDGNNVV   780
QEIPAQGPGH GSSSMIGCYD RDGSIDKQNP TTQKYNKLVL KELSNSAYSC SRGKTGNNTY   840
AVGIDILFST SQSNFSSAAD LEQITQQVYA LFTSSSHTEL ASTISNYQIN QVAMKVSALS   900
DEVFGKEKAL LRKLVNKAKQ FMKTRNLLIG GDFETLDKWL LGTQATIADD SALFKGRYLS   960
LQPTNGIASS YAFQKLDESK LKPYTRYKVS GFIGQSKQVE LVVSRYGKEI DTILNVPYGA  1020
ALPITSGPNP TCCAPEACQC PTCDGSQPDS HFFSYSIDVG KLYPDLNPGI EFGLRLAHPS  1080
GNAKVSNLEI VEERLLTEKE IKKLQRKEQK WKKAWDKERA EISAILQPVI NQINAFYKNE  1140
DWSSDILPHI TYQDLYNVVL PALPKLRHWF MKDREGEHYG SIQQFKQAIE RVFTQLEERN  1200
LIHNGSFTNE LTDWLVDGDA QITTLENGNL ALQLSTWYAS ASQSIDISDF DEDKEYKLRV  1260
RGKGKGTITI QHGEETETMS FDKNGFYFQE QPFYFEEPSF YLQIQSEGNE FIADSVEIIE  1320
IPEEDE                                                            1326

SEQ ID NO: 118          moltype = AA  length = 1320
FEATURE                 Location/Qualifiers
REGION                  1..1320
                        note = variant of native sequence
source                  1..1320
                        mol_type = protein
                        organism = synthetic construct
SEQUENCE: 118
MTTLSYYNVL AYPPLILDEK SPYDQYKEWQ KKIDKTWKEY DEDFLPKPVM DLGKNLAEVF    60
KGDPQAYLHL ANTAIRLAFL IIPGGQTAAW GVNLVLNKVV GIFFPPQNKS LFDQIKDAVS   120
NLVDQKLIDQ EINGLMIKLN SLNQPLSRFG NSIQRAIGKP QDFETTSSNA IILDATQDCS   180
KDSACSCSND TNRPPNAPLC TPCDCRMKEV QTIFGESSGD VNRALSDMKT TLNNVVGADQ   240
LRSYMQIYLP LYVAAATMEL QMYKTYIDFA QKFDFDVTGT TKEHVNELRQ KIKTHSEYIM   300
NLFKNSLPEV SSNTKNQLHA YIRYTRNITL NALDMVSTWK FLDPVDYPTT ATFNPTRIIF   360
NDLAGPVECL TSNQNSNQLH FNFYDMNGQG LPNNDIFNYF YRGMQVKGLQ IQTYTSSDTK   420
SPQHFPVGFL SSYYGSNGDF QFDKRVDPSN FVGGSNSVKL GDDVYKSHPA LSVINAVSNQ   480
LQVFLNYIDT EDLYFDQTVS PGGTACGSGN STIWPDQKIQ AIYPITPDNT KKYEQYFATS   540
KIGFVTTLVP SDTTPWITFT DNGDNSIYTF SAENTRTLTG SAGPVREFIT GSAPLGLSPG   600
GGAQYSINTN DAPSGDYQVR VRVATPGSGG SLAISVDGKT QTLQLPDTNV NDTNHIAGFA   660
GTYTLAPATQ IDAATLKPKA PTENIFPVRQ TSSLPVSITN NSSTVINIDR IEFVPVSVSP   720
TTSIHRDIPT TTTQPNRTQE IWSGSKYATG LSVTGTASND ASIVFQLYDG NNVVQEIPAQ   780
GPGHGSSSMI GCYRDGSID KQNPTTQKYN KLVLKELSNS AYSCSRGKTG NNTYAVGIDI   840
LFSTSQSNFS SAADLEQITQ QVYALFTSSS HTELASTISN YQINQVAMKV SALSDEVFGK   900
EKALLRKLVN KAKQFMKTRN LLIGGDFETL DKWLLGTQAT IADDSALFKG RYLSLQPTNG   960
IASSYAFQKL DESKLKPYTR YKVSGFIGQS KQVELVVSRY GKEIDTILNV PYGAALPITS  1020
GPNPTCCAPE ACQCPTCDGS QPDSHFFSYS IDVGKLYPDL NPGIEFGLRL AHPSGNAKVS  1080
NLEIVEERLL TEKEIKKLQR KEQKWKKAWD KERAEISAIL QPVINQINAF YKNEDWSSDI  1140
LPHITYQDLY NVVLPALPKL RHWFMKDREG EHYGSIQQFK QAIERVFTQL EERNLIHNGS  1200
FTNELTDWLV DGDAQITTLE NGNLALQLST WYASASQSID ISDFDEDKEY KLRVRGKGKG  1260
TITIQHGEET ETMSFDKNGF YFQEQPFYFE EPSFYLQIQS EGNEFIADSV EIIEIPEEDE  1320

SEQ ID NO: 119          moltype = AA  length = 716
FEATURE                 Location/Qualifiers
REGION                  1..716
```

```
                        note = variant of native sequence
source                  1..716
                        mol_type = protein
                        organism = synthetic construct
SEQUENCE: 119
MTTLSYYNVL AYPPLILDEK SPYDQYKEWQ KKIDKTWKEY DEDFLPKPVM DLGKNLAEVF    60
KGDPQAYLHL ANTAIRLAFL IIPGGQTAAW GVNLVLNKVV GIFFPPQNKS LFDQIKDAVS   120
NLVDQKLIDQ EINGLMIKLN SLNQPLSRFG NSIQRAIGKP QDFETTSSNA IILDATQDCS   180
KDSACSCSND TNRPPNAPLC TPCDCRMKEV QTIFGESSGD VNRALSDMKT TLNNVVGADQ   240
LRSYMQIYLP LYVAAATMEL QMYKTYIDFA QKFDFDVTGT TKEHVNELRQ KIKTHSEYIM   300
NLFKNSLPEV SSNTKNQLHA YIRYTRNITL NALDMVSTWK FLDPVDYPTT ATFNPTRIIF   360
NDLAGPVECL TSNQNSNQLH FNFYDMNGQG LPNNDIFNYF YRGMQVKGLQ IQTYTSSDTK   420
SPQHFPVGFL SSYYGSNGDF QFDKRVDPSN FVGGSNSVKL GDDVYKSHPA LSVINAVSNQ   480
LQVFLNYIDT EDLYFDQTVS PGGTACGSGN STIWPDQKIQ AIYPITPDNT KKYEQYFATS   540
KIGFVTTLVP SDTTPWITFT DNGDNSIYTF SAENTRTLTG SAGPVREFIT GSAPLGLSPG   600
GGAQYSINTN DAPSGDYQVR VRVATPGSGG SLAISVDGKT QTLQLPDTNV NDTNHIAGFA   660
GTYTLAPATQ IDAATLKPKA PTENIFPVRQ TSSLPVSITN NSSTVINIDR IEFVPV       716

SEQ ID NO: 120          moltype = AA   length = 812
FEATURE                 Location/Qualifiers
REGION                  1..812
                        note = Unknown organism from environmental sample
source                  1..812
                        mol_type = protein
                        organism = unidentified
SEQUENCE: 120
MRAGDFMTKK QKKILSMTLA TGVFAGTYIP TAYTAFAENE QKENQSKNIS QNNLQIEPYG    60
WFENPYKGVT FSQFIDAFNN NQWKPLLVNI KNKGDAGAGT ISFLKGMLTT GISLLPPPAS   120
LLGSMWSVFM PTNDANGTDM WRQLETYIDE KIDSKINDYH KYLMGAEFNG AMSAIQEYQR   180
VLQIYNDSKN SLKRVEEPGT PVIEAVRAAD RKLKEFIAVI QTPEKSTDSV YQQITAPIFV   240
QAANAHLLLQ RDMILYGEEW GMDKNQWQGY KDNQKKLIQD YTNYAMKVYN EGLEKRKKEA   300
EEINTQQPNR NTDRWNHIND YVREYTLSVL DFVALFPATN PETYSKGAMQ ENSRQIYSSI   360
KGAVISQGGT GEGTTWENIQ KTLDSQEYKG DLHKLDIRSY DRIDAIQPWY SDKLNGGSNW   420
TTPGWTGNTT GGTLKPPLIN SLDNPITRVK AQSSRTPNYI DFKFDSGGDN PSFGTYRSAV   480
GYKEDVFEYP NQKLSQIHAF NRSTYPGFEG IDAVVFGFVD KNLNQSSTYL MTNMITTIPA   540
AKYNRGMSNF QPQVESIHAK QKAMKTSTTN SYLAYNVEVS KEQEYKIRYK VAANENSKIS   600
LSHRKPGGNY AKLADTTIPI TGNAADTVKG EYGSYKIVEG PTIKLTKGAH DLKLENSQGK   660
FSLDQIELEP VEQDQVIVQD NFDNQRLNWI NLGGIVNGGI TGNAGMIGTN GDTWTYIQDK   720
VLPFSKYTLS IKVKLDSNDG NERQKVTVFT DNLKHERITK TVELKGKAGY QEIQLDFITS   780
RDLANTHVGI LTSNGTSNVL FDDVQVIGAK KS                                 812

SEQ ID NO: 121          moltype = AA   length = 806
FEATURE                 Location/Qualifiers
REGION                  1..806
                        note = variant of native sequence
source                  1..806
                        mol_type = protein
                        organism = synthetic construct
SEQUENCE: 121
MTKKQKKILS MTLATGVFAG TYIPTAYTAF AENEQKENQS KNISQNNLQI EPYGWFENPY    60
KGVTFSQFID AFNNNQWKPL LVNIKNKGDA GAGTISFLKG MLTTGISLLP PPASLLGSMW   120
SVFMPTNDAN GTDMWRQLET YIDEKIDSKI NDYHKYLMGA EFNGAMSAIQ EYQRVLQIYN   180
DSKNSLKRVE EPGTPVIEAV RAADRKLKEF IAVIQTPEKS TDSVYQQITA PIFVQAANAH   240
LLLQRDMILY GEEWGMDKNQ WQGYKDNQKK LIQDYTNYAM KVYNEGLEKR KKEAEEINTQ   300
QPNRNTDRWN HINDYVREYT LSVLDFVALF PATNPETYSK GAMQENSRQI YSSIKGAVIS   360
QGGTGEGTTW ENIQKTLDSQ EYKGDLHKLD IRSYDRIDAI QPWYSDKLNG GSNWTTPGWT   420
GNTTGGTLKP PLINSLDNPI TRVKAQSSRT PNYIDFKFDS GGDNPSFGTY RSAVGYKEDV   480
FEYPNQKLSQ IHAFNRSTYP GFEGIDAVVF GFVDKNLNQS STYLMTNMIT TIPAAKYNRG   540
MSNFQPQVES IHAKQKAMKT STTNSYLAYN VEVSKEQEYK IRYKVAANEN SKISLSHRKP   600
GGNYAKLADT TIPITGNAAD TVKGEYGSYK IVEGPTIKLT KGAHDLKLEN SQGKFSLDQI   660
ELEPVEQDQV IVQDNFDNQR LNWINLGGIV NGGITGNAGM IGTNGDTWTY IQDKVLPFSK   720
YTLSIKVKLD SNDGNERQKV TVFTDNLKHE RITKTVELKG KAGYQEIQLD FITSRDLANT   780
HVGILTSNGT SNVLFDDVQV IGAKKS                                        806

SEQ ID NO: 122          moltype = AA   length = 636
FEATURE                 Location/Qualifiers
REGION                  1..636
                        note = variant of native sequence
source                  1..636
                        mol_type = protein
                        organism = synthetic construct
SEQUENCE: 122
MAENEQKENQ SKNISQNNLQ IEPYGWFENP YKGVTFSQFI DAFNNNQWKP LLVNIKNKGD    60
AGAGTISFLK GMLTTGISLL PPPASLLGSM WSVFMPTNDA NGTDMWRQLE TYIDEKIDSK   120
INDYHKYLMG AEFNGAMSAI QEYQRVLQIY NDSKNSLKRV EEPGTPVIEA VRAADRKLKE   180
FIAVIQTPEK STDSVYQQIT APIFVQAANA HLLLQRDMIL YGEEWGMDKN QWQGYKDNQK   240
KLIQDYTNYA MKVYNEGLEK RKKEAEEINT QQPNRNTDRW NHINDYVREY TLSVLDFVAL   300
FPATNPETYS KGAMQENSRQ IYSSIKGAVI SQGGTGEGTT WENIQKTLDS QEYKGDLHKL   360
DIRSYDRIDA IQPWYSDKLN GGSNWTTPGW TGNTTGGTLK PPLINSLDNP ITRVKAQSSR   420
```

```
TPNYIDFKFD SGGDNPSFGT YRSAVGYKED VFEYPNQKLS QIHAFNRSTY PGFEGIDAVV    480
FGFVDKNLNQ SSTYLMTNMI TTIPAAKYNR GMSNFQPQVE SIHAKQKAMK TSTTNSYLAY    540
NVEVSKEQEY KIRYKVAANE NSKISLSHRK PGGNYAKLAD TTIPITGNAA DTVKGEYGSY    600
KIVEGPTIKL TKGAHDLKLE NSQGKFSLDQ IELEPV                              636

SEQ ID NO: 123             moltype = AA   length = 777
FEATURE                    Location/Qualifiers
REGION                     1..777
                           note = variant of native sequence
source                     1..777
                           mol_type = protein
                           organism = synthetic construct
SEQUENCE: 123
MAENEQKENQ SKNISQNNLQ IEPYGWFENP YKGVTFSQFI DAFNNQWKP LLVNIKNKGD      60
AGAGTISFLK GMLTTGISLL PPPASLLGSM WSVFMPTNDA NGTDMWRQLE TYIDEKIDSK    120
INDYHKYLMG AEFNGAMSAI QEYQRVLQIY NDSKNSLKRV EEPGTPVIEA VRAADRKLKE    180
FIAVIQTPEK STDSVYQQIT APIFVQAANA HLLLQRDMIL YGEEWGMDKN QWQGYKDNQK    240
KLIQDYTNYA MKVYNEGLEK RKKEAEEINT QQPNRNTDRW NHINDYVREY TLSVLDFVAL    300
FPATNPETYS KGAMQENSRQ IYSSIKGAVI SQGGTGEGTT WENIQKTLDS QEYKGDLHKL    360
DIRSYDRIDA IQPWYSDKLN GGSNWTTPGW TGNTTGGTLK PPLINSLDNP ITRVKAQSSR    420
TPNYIDFKFD SGGDNPSFGT YRSAVGYKED VFEYPNQKLS QIHAFNRSTY PGFEGIDAVV    480
FGFVDKNLNQ SSTYLMTNMI TTIPAAKYNR GMSNFQPQVE SIHAKQKAMK TSTTNSYLAY    540
NVEVSKEQEY KIRYKVAANE NSKISLSHRK PGGNYAKLAD TTIPITGNAA DTVKGEYGSY    600
KIVEGPTIKL TKGAHDLKLE NSQGKFSLDQ IELEPVEQDQ VIVQDNFDNQ RLNWINLGGI    660
VNGGITGNAG MIGTNGDTWT YIQDKVLPFS KYTLSIKVKL DSNDGNERQK VTVFTDNLKH    720
ERITKTVELK GKAGYQEIQL DFITSRDLAN THVGILTSNG TSNVLFDDVQ VIGAKKS      777

SEQ ID NO: 124             moltype = AA   length = 665
FEATURE                    Location/Qualifiers
REGION                     1..665
                           note = variant of native sequence
source                     1..665
                           mol_type = protein
                           organism = synthetic construct
SEQUENCE: 124
MTKKQKKILS MTLATGVFAG TYIPTAYTAF AENEQKENQS KNISQNNLQI EPYGWFENPY     60
KGVTFSQFID AFNNQWKPL LVNIKNKGDA GAGTISFLKG MLTTGISLLP PPASLLGSMW    120
SVFMPTNDAN GTDMWRQLET YIDEKIDSKI NDYHKYLMGA EFNGAMSAIQ EYQRVLQIYN    180
DSKNSLKRVE EPGTPVIEAV RAADRKLKEF IAVIQTPEKS TDSVYQQITA PIFVQAANAH    240
LLLQRDMILY GEEWGMDKNQ WQGYKDNQKK LIQDYTNYAM KVYNEGLEKR KKEAEEINTQ    300
QPNRNTDRWN HINDYVREYT LSVLDFVALF PATNPETYSK GAMQENSRQI YSSIKGAVIS    360
QGGTGEGTTW ENIQKTLDSQ EYKGDLHKLD IRSYDRIDAI QPWYSDKLNG GSNWTTPGWT    420
GNTTGGTLKP PLINSLDNPI TRVKAQSSRT PNYIDFKFDS GGDNPSFGTY RSAVGYKEDV    480
FEYPNQKLSQ IHAFNRSTYP GFEGIDAVVF GFVDKNLNQS STYLMTNMIT TIPAAKYNRG    540
MSNFQPQVES IHAKQKAMKT STTNSYLAYN VEVSKEQEYK IRYKVAANEN SKISLSHRKP    600
GGNYAKLADT TIPITGNAAD TVKGEYGSYK IVEGPTIKLT KGAHDLKLEN SQGKFSLDQI    660
ELEPV                                                                665

SEQ ID NO: 125             moltype = AA   length = 671
FEATURE                    Location/Qualifiers
REGION                     1..671
                           note = variant of native sequence
source                     1..671
                           mol_type = protein
                           organism = synthetic construct
SEQUENCE: 125
MRAGDFMTKK QKKILSMTLA TGVFAGTYIP TAYTAFAENE QKENQSKNIS QNNLQIEPYG     60
WFENPYKGVT FSQFIDAFNN NQWKPLLVNI KNKGDAGAGT ISFLKGMLTT GISLPPPAS    120
LLGSMWSVFM PTNDANGTDM WRQLETYIDE KIDSKINDYH KYLMGAEFNG AMSAIQEYQR    180
VLQIYNDSKN SLKRVEEPGT PVIEAVRAAD RKLKEFIAVI QTPEKSTDSV YQQITAPIFV    240
QAANAHLLLQ RDMILYGEEW GMDKNQWQGY KDNQKKLIQD YTNYAMKVYN EGLEKRKKEA    300
EEINTQQPNR NTDRWNHIND YVREYTLSVL DFVALFPATN PETYSKGAMQ ENSRQIYSSI    360
KGAVISQGGT GEGTTWENIQ KTLDSQEYKG DLHKLDIRSY DRIDAIQPWY SDKLNGGSNW    420
TTPGWTGNTT GGTLKPPLIN SLDNPITRVK AQSSRTPNYI DFKFDSGGDN PSFGTYRSAV    480
GYKEDVFEYP NQKLSQIHAF NRSTYPGFEG IDAVVFGFVD KNLNQSSTYL MTNMITTIPA    540
AKYNRGMSNF QPQVESIHAK QKAMKTSTTN SYLAYNVEVS KEQEYKIRYK VAANENSKIS    600
LSHRKPGGNY AKLADTTIPI TGNAADTVKG EYGSYKIVEG PTIKLTKGAH DLKLENSQGK    660
FSLDQIELEP V                                                         671

SEQ ID NO: 126             moltype = AA   length = 484
FEATURE                    Location/Qualifiers
source                     1..484
                           mol_type = protein
                           organism = Bacillus sp.
SEQUENCE: 126
MKPYQEHDEQ NYTENKINEN CGCNSSVQNK SFKENEEWNN SYSFQGHKGN EKDWNGQRER     60
RYYDCNPIRS QSPNLPDESK RFQAIMLNNN IHTCVTESNH PLGEIAPLQP RECRQIITDY    120
QTLVGSLELG TDIYFIFYQ TDGDYVIAN RENGRVLEYM DNASELFRVL TSRLYTGGAN    180
QIFNMNRATN NDFRLLTQTQ PSGARYVLRP CNDSNQSLLS LVFTPASSGL GNPNTLLRFR    240
```

```
ESERIPPVPI PSLPSPTRLD PVPDLLNLND EGTPPRYAPR ATIGSALIPC IFVNDVIPLD  300
QRIKQSPYYV LEYRQYWHQL WSYIIPSGGL REPEEITGIR PEAQEDMRDS LDIVIGADWN  360
LRFGDKSHAF RQQISHGLNT LISRTPDNLG LRREETKYYN VHPQQVRFAK YAKAHEYRLT  420
RPNGTEVSSP WVALDYNTML LKSYPNNLEI VMQNSKIINS SNSYDLSVWK TPLMIRDGKI  480
ITRK                                                               484

SEQ ID NO: 127          moltype = AA  length = 302
FEATURE                 Location/Qualifiers
REGION                  1..302
                        note = Unknown organism from environmental sample
source                  1..302
                        mol_type = protein
                        organism = unidentified
SEQUENCE: 127
MLATMGTSLV ITYPNSVSAD QINPIKSTTQ TQQKPSISNW SEPIQQIYKA RKQNSPNTHI   60
SKEARISGFN IIQSSVEADG PTFTNKKTMY IGRAILNNPS NKERTLSTAE FSKTIENSVT  120
NSTTNGFNLG VSTSASFGIP LIGQTSVELS TEYNFSNTAA KTKTESYTYT APKQEIVVPA  180
YSSVEVIVQL DMVKVSGNVK LLSHVDGSVY WQYDKNKPNN LRGFPLKHFV RDSGTNVPSN  240
IKAHPQNGAY LIGTGNYSAE YGTEFTVTVK DTSPIRPGSI RPTRGTNDEY TYKVKPQVKK  300
VK                                                                 302

SEQ ID NO: 128          moltype = AA  length = 284
FEATURE                 Location/Qualifiers
REGION                  1..284
                        note = variant of native sequence
source                  1..284
                        mol_type = protein
                        organism = synthetic construct
SEQUENCE: 128
MDQINPIKST TQTQQKPSIS NWSEPIQQIY KARKQNSPNT HISKEARISG FNIIQSSVEA   60
DGPTFTNKKT MYIGRAILNN PSNKERTLST AEFSKTIENS VTNSTTNGFN LGVSTSASFG  120
IPLIGQTSVE LSTEYNFSNT AAKTKTESYT YTAPKQEIVV PAYSSVEVIV QLDMVKVSGN  180
VKLLSHVDGS VYWQYDKNKP NNLRGFPLKH FVRDSGTNVP SNIKAHPQNG AYLIGTGNYS  240
AEYGTEFTVT VKDTSPIRPG SIRPTRGTND EYTYKVKPQV KKVK                   284

SEQ ID NO: 129          moltype = AA  length = 1302
FEATURE                 Location/Qualifiers
REGION                  1..1302
                        note = Unknown organism from environmental sample
source                  1..1302
                        mol_type = protein
                        organism = unidentified
SEQUENCE: 129
LRNLIDVPVF LDQVIKKIRG GLYMNINDNK NEYEILDSGN LSYQPRYPLA RAPGSECQKP   60
NAKDGIYTPV GRVDTALQNI DIGLSIRTAL SILQMLLSVS FPALGRAAGL INIIFGFLWG  120
TLAGQSVWEK FMRAVESLVN QKITDAVRVK ALSELEGVQN ALELYQEAAD DWNENPTDAS  180
NKERVRRQFT STNTTIEYAM PSFRVPTFEV PLLTVYAQAA NLHLQLLRDA VKFGNEWGMP  240
SEEVEDMYNR LTRRTAEYTD HCVATYDKGL KEAYDLAPNP TDYNKYPYLN PYSKDPIYGK  300
YYTAPVDWNL FNDYRRDMTL MVLDIVAVWP TYNPRIYTNP NGVQVELSRE VYSTVYGRGG  360
SNNSSFDAIE SQIVRPPHLV TELTNLKIEQ GATLDMEQIQ YPKYMKVTNT LHYVGSSSTW  420
EQSSSAIPIR PITQIHTIPA NNIGNLSLSQ LDVPYRFSFY NKDDALIAAV GAEFPPNTVT  480
WNGIPKAEDS NQNSHHLSYV GALGTQSSAG FPWTYPTELL GEWGFGWLHN SLTPTNRLDP  540
DKSTQLPAVK AYWYYASSGV PVIKGPGSTG GDLVLLTFYQ EIALSITSNI SRSYRLRFRY  600
ASTSDIRIVV YWRLENTGVV YGHNVNLPAT YSGGSLTYNT FSVFDTGLII QNAHWFTFNI  660
RNDSGGTLIL DKLEFIPIEE PLEVYQAKQD LEKAKKAVNT LFTSDAKNVL KVNVTDYEVD  720
QVANLVECVS DESHAQEKMI LLDQVKFAKR LSQARNLLNY GDFESSDWSG ENGWRTSHHV  780
SVRSDNPTFK GHYLHMPGAM SPQFSNNIYP TYAYQKVDES KLKSYTRYLV RGFVGNSKDL  840
ELLVERYGKD VHVEMDVPND IRYTLPMNEC GGFDRCKPAS HQTGSPHTYT CKDTAVAHTD  900
CQCKDKENRT STNMYTNVPT DSAVYMNGSH THQSCGCKIN NSDRYQSGTH PQKSCGCKDP  960
HVFSYHIDTG CVDQEENLGL WFALKIASEN GVANIDNLEI IEAQPLTGEA LARVKKREQK 1020
WKQEMAQKRF QTDKAVQAAQ TAMQALFTNA QYNRLKFETL FPQIVNAEML VQQIPYMYHP 1080
FLSGALPTVP GMNFEIIQRL LAVTGNARGL YEQRNLVRNG TFSSGTGSWH VTEGVEVQPL 1140
QNTSVLVLSE WSHEASQQVR IDPDRGYVLR VTARKEGAGL GTVTMSDCAD YTETLTFTSC 1200
DYNTVGTQTM TGGTLSGFVT KTLEIFPETD RIRIDIGETE GTFKIESVEL ICMEQMEDHL 1260
YDMAGNLEEE MLDLQSARSG SGTKLIPPLT FSDCYTNNEY CY                   1302

SEQ ID NO: 130          moltype = AA  length = 1279
FEATURE                 Location/Qualifiers
REGION                  1..1279
                        note = variant of native sequence
source                  1..1279
                        mol_type = protein
                        organism = synthetic construct
SEQUENCE: 130
MNINDNKNEY EILDSGNLSY QPRYPLARAP GSECQKPNAK DGIYTPVGRV DTALQNIDIG   60
LSIRTALSIL QMLLSVSFPA LGRAAGLINI IFGFLWGTLA GQSVWEKFMR AVESLVNQKI  120
TDAVRVKALS ELEGVQNALE LYQEAADDWN ENPTDASNKE RVRRQFTSTN TTIEYAMPSF  180
RVPTFEVPLL TVYAQAANLH LQLLRDAVKF GNEWGMPSEE VEDMYNRLTR RTAEYTDHCV  240
ATYDKGLKEA YDLAPNPTDY NKYPYLNPYS KDPIYGKYYT APVDWNLFND YRRDMTLMVL  300
```

```
DIVAVWPTYN PRIYTNPNGV QVELSREVYS TVYGRGGSNN SSFDAIESQI VRPPHLVTEL    360
TNLKIEQGAT LDMEQIQYPK YMKVTNTLHY VGSSSTWEQS SSAIPIRPIT QIHTIPANNI    420
GNLSLSQLDV PYRFSFYNKD DALIAAVGAE FPPNTVTWNG IPKAEDSNQN SHHLSYVGAL    480
GTQSSAGFPW TYPTELLGEW GFGWLHNSLT PTNRLDPDKS TQLPAVKAYW YYASSGVPVI    540
KGPGSTGGDL VLLTFYQEIA LSITSNISRS YRLRFRYAST SDIRIVVYWR LENTGVVYGH    600
NVNLPATYSG GSLTYNTFSV FDTGLIIQNA HWFTFNIRND SGGTLILDKL EFIPIEEPLE    660
VYQAKQDLEK AKKAVNTLFT SDAKNVLKVN VTDYEVDQVA NLVECVSDES HAQEKMILLD    720
QVKFAKRLSQ ARNLLNYGDF ESSDWSGENG WRTSHHVSVR SDNPTFKGHY LHMPGAMSPQ    780
FSNNIYPTYA YQKVDESKLK SYTRYLVRGF VGNSKDLELL VERYGKDVHV EMDVPNDIRY    840
TLPMNECGGF DRCKPASHQT GSPHTYTCKD TAVAHTDCQC KDKENRTSTN MYTNVPTDSA    900
VYMNGSHTHQ SCGCKNKNSD RYQSGTHPQK SCGCKDPHVF SYHIDTGCVD QEENLGLWFA    960
LKIASENGVA NIDNLEIIEA QPLTGEALAR VKKREQKWKQ EMAQKRFQTD KAVQAAQTAM   1020
QALFTNAQYN RLKFETLFPQ IVNAEMLVQQ IPYMYHPFLS GALPTVPGMN FEIIQRLLAV   1080
TGNARGLYEQ RNLVRNGTFS SGTGSWHVTE GVEVQPLQNT SVLVLSEWSH EASQQVRIDP   1140
DRGYVLRVTA RKEGAGKGTV TMSDCADYTE TLTFTSCDYN TVGTQTMTGG TLSGFVTKTL   1200
EIFPETDRIR IDIGETEGTF KIESVELICM EQMEDHLYDM AGNLEEEMLD LQSARSGSGT   1260
KLIPPLTFSD CYTNNEYCY                                                1279

SEQ ID NO: 131          moltype = AA  length = 655
FEATURE                 Location/Qualifiers
REGION                  1..655
                        note = variant of native sequence
source                  1..655
                        mol_type = protein
                        organism = synthetic construct
SEQUENCE: 131
MNINDNKNEY EILDSGNLSY QPRYPLARAP GSECQKPNAK DGIYTPVGRV DTALQNIDIG     60
LSIRTALSIL QMLLSVSFPA LGRAAGLINI IFGFLWGTLA GQSVWEKFMR AVESLVNQKI    120
TDAVRVKALS ELEGVQNALE LYQEAADDWN ENPTDASNKE RVRRQFTSTN TTIEYAMPSF    180
RVPTFEVPLL TVYAQAANLH LQLLRDAVKF GNEWGMPSEE VEDMYNRLTR RTAEYTDHCV    240
ATYDKGLKEA YDLAPNPTDY NKYPYLNPYS KDPIYGKYYT APVDWNLFND YRRDMTLMVL    300
DIVAVWPTYN PRIYTNPNGV QVELSREVYS TVYGRGGSNN SSFDAIESQI VRPPHLVTEL    360
TNLKIEQGAT LDMEQIQYPK YMKVTNTLHY VGSSSTWEQS SSAIPIRPIT QIHTIPANNI    420
GNLSLSQLDV PYRFSFYNKD DALIAAVGAE FPPNTVTWNG IPKAEDSNQN SHHLSYVGAL    480
GTQSSAGFPW TYPTELLGEW GFGWLHNSLT PTNRLDPDKS TQLPAVKAYW YYASSGVPVI    540
KGPGSTGGDL VLLTFYQEIA LSITSNISRS YRLRFRYAST SDIRIVVYWR LENTGVVYGH    600
NVNLPATYSG GSLTYNTFSV FDTGLIIQNA HWFTFNIRND SGGTLILDKL EFIPI         655

SEQ ID NO: 132          moltype = AA  length = 303
FEATURE                 Location/Qualifiers
source                  1..303
                        mol_type = protein
                        organism = Bacillus sp.
SEQUENCE: 132
MAELDLAKIL QPISLRGLHN LIGCDMELYR RWNFDTEFYP MPVSPKITPS CGMDMPYEGK     60
DCSLQGLKLH GVGVEIDPLD LIANSVPWFI SVGTFQNASD LTQTFQTTEF TEKITDTTTV    120
TKTKTLKVGN TTSTKTTLDV FLIDAEVSTS ITVEGTWSTA ETQTHTVEKT LRVPPMSVIV    180
PPRKGMRVKA EYFKGELNSK DIKINAQLSG KYKINNGHHW YDQDLYPIIK SLQLGSPNIW    240
KGIEGNGIKL NDATQTVTCY GLGTLNANFT TSTYNVLYEE FNLSTGRVEK VTKVAVYPHF    300
PKN                                                                  303

SEQ ID NO: 133          moltype = AA  length = 1054
FEATURE                 Location/Qualifiers
source                  1..1054
                        mol_type = protein
                        organism = Bacillus sp.
SEQUENCE: 133
MPISKEPILY PLVSSTSNIP TSESFTFDWN WGLHQALSIG TGLMKFIPGL GVVAGPYGAL     60
LNYVGGVID ELFPKKDAEG QDTVDPTVLF QTFMAAAEQM INEKLNDTVK STAVTKLAGL    120
KNNLTDLKTK LDTLKDNSDP KDTDELKKQV RDKFEAVHGL FRSDMPQFRV AGYESILLPV    180
YAQAANLHLI FLREAIIKGA SEWGFPQVTI DKFYDNPTDH NGFKQLMEEY TTNCMSAYQQ    240
GLDKLATQSI DLCASDQSYW NPAYYNQYVF LDDLYSYATC QHSLGDMSYG CGGGKLKPIC    300
KNYNSRIYSK YMQSIANWNQ YNEYVMSMQV TALDLVAMWP YWDPKVYPNG AKKELTREIY    360
TDILGSPDGQ TKGVTTISQE LLPQPRLFTQ LTQLDLNTES HTIEQDTFNP VSGKVNASYK    420
YLDGEIIVGI TQHLQTTLGD SKLHAQGSGG SKTKSYDNSH TNDFTMPLKV ASWFEPRTIG    480
FAKSSGEIYP VGTIGDETPF VEISKSIGHN SGTITAIAHH AVKISESTQS GYYEEYQGDT    540
AYSIDEHRLS WMNYTPTSAS SFVVTGKQIG SLTLGWTSST VDPTNKVQKG TTTSIPAVKS    600
HSITDWGTGT VVKGPGHTGG DLVKLPPNTR AKMIVTIEDT STSYDVRIRY AAPSGGHIQF    660
SYWNGGSDVK VADTQLQNTG GNTNFEHFQY AMLTTDNAKF KAPFSPVEIL IENIGDSDVY    720
LDKVEFLVLS QLPPETTPLT SQYMNPYGYN ILWQSKNGEA ANQGMVTFSQ NDSAIKTFYL    780
YNTEVVHQTT GSPSSWNGKF DTLYVQSPTS INLTQGFIVI DTTKNNPEPP IALPNQDILR    840
PFTNEHEIWN GRYSTKALNL SLLTSSGAEG KIRFYNNTNL VHESPALSGS PSEPYTWEGS    900
FNRITVYQSN SSDSNYFNLF GGFLKLDPNS NDNGNNGGPH NNCENIAHPD QPIYYESNNL    960
IWTAAPNKLA YSTTEMQFVL SGGLGFTPED IGAKVKLNFW KNDSIQYVAY GAVANLDFIS   1020
APAQSIPGGF DKITMDDVDS FSTSFRMTLG SVCY                               1054

SEQ ID NO: 134          moltype = AA  length = 729
FEATURE                 Location/Qualifiers
REGION                  1..729
```

```
                        note = variant of native sequence
source                  1..729
                        mol_type = protein
                        organism = synthetic construct
SEQUENCE: 134
MPISKEPILY PLVSSTSNIP TSESFTFDWN WGLHQALSIG TGLMKFIPGL GVVAGPYGAL    60
LNYVYGGVID ELFPKKDAEG QDTVDPTVLF QTFMAAAEQM INEKLNDTVK STAVTKLAGL   120
KNNLTDLKTK LDTLKDNSDP KDTDELKKQV RDKFEAVHGL FRSDMPQFRV AGYESILLPV   180
YAQAANLHLI FLREAIIKGA SEWGFPQVTI DKFYDNPTDH NGFKQLMEEY TTNCMSAYQQ   240
GLDKLATQSI DLCASDQSYW NPAYYNQYVF LDDLYSYATC QHSLGDMSYG CGGGKLKPIC   300
KNYNSRIYSK YMQSIANWNQ YNEYVMSMQV TALDDLVAMWP YWDPKVYPNG AKKELTREIY   360
TDILGSPDGQ TKGVTTISQE LLPQPRLFTQ LTQLDLNTES HTIEQDTFNP VSGKVNASYK   420
YLDGEIIVGI TQHLQTTLGD SKLHAQGSGG SKTKSYDNSH TNDFTMPLKV ASWFEPRTIG   480
FAKSSGEIYP VGTIGDETPF VEISKSIGHN SGTITAIAHH AVKISESTQS GYYEEYQGDT   540
AYSIDEHRLS WMNYTPTSAS SFVVTGKQIG SLTLGWTSST VDPTNKVQKG TTTSIPAVKS   600
HSITDWGTGT VVKGPGHTGG DLVKLPPNTR AKMIVTIEDT STSYDVRIRY AAPSGGHIQF   660
SYWNGGSDVK VADTQLQNTG GNTNFEHFQY AMLTTDNAKF KAPFSPVEIL IENIGDSDVY   720
LDKVEFLVL                                                          729

SEQ ID NO: 135          moltype = AA  length = 522
FEATURE                 Location/Qualifiers
source                  1..522
                        mol_type = protein
                        organism = Bacillus sp.
SEQUENCE: 135
MLLTQKGGHV MAISRIINPI FTKQEHLNQL STLVNNLFSS GSSSLSQGVS DYWIDQVLLK    60
VNALSDTVFP TQKEQLRQRL AQAKQISKAR NLLVGGNFET LNKWKLSRNA FLVAGHELFQ   120
GYHLELPPAI DSVKYPSYAY QKIDESKLKT NTRYYVSAFI AQGSQLEIMV SRYGQEYSQI   180
LYVPAEMAKP ISPDGGPNCC SPHPCNCAAC NEEEVDSHFF QVPIDVGNLQ SSQNLGIEIG   240
FKVASTDGFA KLSNIEVFEG RPLTTAEQRK ASRLENEWKE EQQTKETERT QLLQQIQQRF   300
NMLYTTPEHH TLRTETSYQH LLETMLPSLH HVYHWFMPDV PDSDYALYYE LQQKLERGWD   360
QYFSRNLLEN GDFLEPLDDS WYTQGNVSLH TINNNTMLRL HHWDSLIRKN VSLPVVNEDA   420
EYVIRVIGKG TGSVLIQNGT TTNKLVFTNS RQMETKEFHL QPEKEQLSLT IRSDANEFLV   480
DAIEVILITD GAEEEEQLPG MFPPINSSMG STPNSNMMNN NQ                     522

SEQ ID NO: 136          moltype = AA  length = 924
FEATURE                 Location/Qualifiers
source                  1..924
                        mol_type = protein
                        organism = Bacillus sp.
SEQUENCE: 136
MIFVIPKKNE FYKMTAKHSG KVAEVYAGYT SDNTNIEQWS WLGGNNQQWM FVPLDNNYYA    60
VVNKNSGKVM EVYGGYTSDN TNIEQWSWLG GNNQQWFLHD LGSGYNKIQV KHSGKVMEVY   120
AGYTENNRNI EQWSWNGGNN QQWQISTTGN FTLPSIQTYP VPLPPAYDNI DEILPPTTPS   180
VVTQYTLAPG IAVADPYYND QQKMQTGNEY YRYVREQYWE KIFSQTLAPG ETFTYSQTTG   240
MTQTDQQTVT NTVSHSIGAD VGFQFMGVSA GLSYQYTQEL SVTKSSTTTE LTETTQTYEI   300
RNPHNQTAAY SKYLLVSKYY VLRADTDYMIG EDWTVKDINE TRTVSFPPNL LPTERELNEP   360
FVSAQQAVYD LFADAYSTL KIETTDYMID QAALQLEQVS DEIDALEKMM LFNLVRCAKQ   420
LSTKRNLLHY GDFESPNWRN PEDGWQASSN VTVLSDNPIF KGNYANMPGA NARNGSVTPT   480
YLYQKVGESK LKPYTRYLVR GFVGSSKELE LFVTRYGKEV RDNMNIPTSP MNICNQTDGM   540
GYGSHYTMSS DPCQYVYPTN PKGLCEDKQH FVFHIDVGEI YPRTDLGIGV GFKISSPSGM   600
AQLSNIEVIE ANPLTGEALA RVKKREQKWK REMEQKCAQT ERAVSLATQA VDHLFTDTQK   660
NRLRATTTMQ DIRNVEAKVK AIPYVYNLYF EEIPGMNYAI SQALQSDVYT ASSLYSIRNI   720
IRNGDFSSGL SNWHTTAGAD VQERDGNPHV LVISQWDTNV SQEVCVQPEH GYVLRVTARK   780
EGSGKGYVTL TDCTAENTET VTFKSDERVA TSMPPVRPER PVEPGICDMT RYSESFGIVP   840
EMSPMRNEQP ANYGTESCSC GCGCASTTYQ TQAYEPQPSM NRPSSAYITK TIEIFPETNR   900
LRIEIGETEG TFLVESIELI CMED                                         924

SEQ ID NO: 137          moltype = AA  length = 403
FEATURE                 Location/Qualifiers
source                  1..403
                        mol_type = protein
                        organism = Bacillus sp.
SEQUENCE: 137
MKSISKKVMA GLLVGATSLS IWAPTSDAAS LEKNRYYSVH LKKDFFLTWD VYRSKDYDNA    60
GILLYKTNGQ DNQQFVFFPL DGGSYAIVNK NSGKPVGIGD PIANDDGVRR MTLFDNDGLL   120
QKSWTGASAE QWYLRDQGNN NYEFVNQGYG KVASYAWTGT LAQNWTYVDL DDANPSDNNR   180
VPFTISKSALP GSGFEIPGFN LDHGTFSLQQ LPATGTRPDA PNYTGGIDQQ LPQTSNSVVV   240
GASLVPCIMV KDSQASDYTK IHNSPYYTLV KEEYWDKTFS KVIQPGLSES YQYKTGVSSV   300
DQQKMTDTLS MKIGADLGLK FGQESASLKS EISRTIQTEI STTNTEATEE TRSYTATGEP   360
GKATGYTQYQ LATKYTLKRA DGSIVSDPWV VKNDRITVTR KTS                    403

SEQ ID NO: 138          moltype = AA  length = 376
FEATURE                 Location/Qualifiers
REGION                  1..376
                        note = variant of native sequence
source                  1..376
                        mol_type = protein
                        organism = synthetic construct
```

```
SEQUENCE: 138
MASLEKNRYY  SVHLKKDFFL  TWDVYRSKDY  DNAGILLYKT  NGQDNQQFVF  FPLDGGSYAI   60
VNKNSGKPVG  IGDPIANDDG  VRRMTLFDND  GLLQKSWTGA  SAEQWYLRDQ  GNNNYEFVNQ  120
GYGKVASYAW  TGTLAQNWTY  VDLDDANPSD  NNRVFTISKS  ALPGSGFEIP  GFNLDHGTFS  180
LQQLPATGTR  PDAPNYTGGI  DQQLPQTSNS  VVVGASLVPC  IMVKDSQASD  YTKIHNSPYY  240
TLVKEEYWDK  TFSKVIQPGL  SESYQYKTGV  SSVDQQKMTD  TLSMKIGADL  GLKFGQESAS  300
LKSEISRTIQ  TEISTTNTEA  TEETRSYTAT  GEPGKATGYT  QYQLATKYTL  KRADGSIVSD  360
PWVVKNDRIT  VTRKTS                                                      376

SEQ ID NO: 139          moltype = AA  length = 752
FEATURE                 Location/Qualifiers
REGION                  1..752
                        note = Unknown organism from environmental sample
source                  1..752
                        mol_type = protein
                        organism = unidentified
SEQUENCE: 139
MYNIEIQIRT  GGISMNHNNE  YEIIDSHTLP  YSSNKNSNDS  RYPYTNDPNQ  PLQNTNYKDW   60
LNMCQGNTQY  GDNFETFASA  DTIAAISAGT  IVSGTLLAGF  GGLTAISGPI  GLIGAIIISF  120
GTLLPIFWHA  GDPNQTVWTQ  FIKIGEKFAS  QELTKNEFDK  AMRSLDGTKN  VLDLYEDALN  180
SWIRLKKQQS  PGLPPSTALQ  HAADQVKHLF  NIAHAHFVDD  LPDFKGGDLA  TLYLPIFAQL  240
ANYYLNLLQQ  GVEFADTWIK  DAYPSLMEPG  SGTSDYYYKL  LKESIPKYSN  YCANTYREGL  300
DNLRNQPNIR  WSTFNDYRRY  MTITVLDTIA  QFPLYDIKRY  RDSIGGIQGI  NYELTREIYT  360
TEINFDRLTS  TTLPAQPNLT  TMEYNLTRSG  RLFSFLDQLV  FYTENTNSGN  RLVGIINRSK  420
PTYGQGTEYL  YGQKTGSPDT  KTLIPFESYK  VSIITDRQFY  PLTYFIINQI  ELYLNGSPSN  480
IPKYSAGGSL  SDDKKTNDYQ  FPVKKECKQI  TDPNCSPYNS  SYSHILSHFS  LYSYSYLFSF  540
TIYHIVYTGA  LGWTHSSVSR  NNEISDKVIT  IIPAVKGSYL  DTNSKVIEGP  GHTGGNLVYL  600
QSLDRLEITC  RTPNSTQSYY  IRLRYATNGT  GNIIPAIFLI  IPGVISTPPQ  RLNNTFSGTN  660
YNNLQYENFG  YFEFPSTVTL  PSNRTITCTL  TREDISNSIL  IIDKIEFIPI  TSSMHQNREK  720
QKLETVQTKI  NTFFTNHTKN  TLNIETTNYD  ID                                  752

SEQ ID NO: 140          moltype = AA  length = 738
FEATURE                 Location/Qualifiers
REGION                  1..738
                        note = variant of native sequence
source                  1..738
                        mol_type = protein
                        organism = synthetic construct
SEQUENCE: 140
MNHNNEYEII  DSHTLPYSSN  KNSNDSRYPY  TNDPNQPLQN  TNYKDWLNMC  QGNTQYGDNF   60
ETFASADTIA  AISAGTIVSG  TLLAGFGGLT  AISGPIGLIG  AIIISFGTLL  PIFWHAGDPN  120
QTVWTQFIKI  GEKFASQELT  KNEFDKAMRS  LDGTKNVLDL  YEDALNSWIR  LKKQQSPGLP  180
PSTALQHAAD  QVKHLFNIAH  AHFVDDLPDF  KGGDLATLYL  PIFAQLANYY  LNLLQQGVEF  240
ADTWIKDAYP  SLMEPGSGTS  DYYYKLLKES  IPKYSNYCAN  TYREGLDNLR  NQPNIRWSTF  300
NDYRRYMTIT  VLDTIAQFPL  YDIKRYRDSI  GGIQGINYEL  TREIYTTEIN  FDRLTSTTLP  360
AQPNLTTMEY  NLTRSGRLFS  FLDQLVFYTE  NTNSGNRLVG  IINRSKPTYG  QGTEYLYGQK  420
TGSPDTKTLI  PFESYKVSII  TDRQFYPLTY  FIINQIELYL  NGSPSNIFKY  SAGGSLSDDK  480
KTNDYQFPVK  KECKQITDPN  CSPNYNSYSH  ILSHFSLYSY  SYLFSFTIYH  IVYTGALGWT  540
HSSVSRNNEI  SDKVITIIPA  VKGSYLDTNS  KVIEGPGHTG  GNLVYLQSLD  RLEITCRTPN  600
STQSYYIRLR  YATNGTGNII  PAIFLIIPGV  ISTPPQRLNN  TFSGTNYNNL  QYENFGYFEF  660
PSTVTLPSNR  TITCTLTRED  ISNSILIIDK  IEFIPITSSM  HQNREKQKLE  TVQTKINTFF  720
TNHTKNTLNI  ETTNYDID                                                    738

SEQ ID NO: 141          moltype = AA  length = 696
FEATURE                 Location/Qualifiers
REGION                  1..696
                        note = variant of native sequence
source                  1..696
                        mol_type = protein
                        organism = synthetic construct
SEQUENCE: 141
MNHNNEYEII  DSHTLPYSSN  KNSNDSRYPY  TNDPNQPLQN  TNYKDWLNMC  QGNTQYGDNF   60
ETFASADTIA  AISAGTIVSG  TLLAGFGGLT  AISGPIGLIG  AIIISFGTLL  PIFWHAGDPN  120
QTVWTQFIKI  GEKFASQELT  KNEFDKAMRS  LDGTKNVLDL  YEDALNSWIR  LKKQQSPGLP  180
PSTALQHAAD  QVKHLFNIAH  AHFVDDLPDF  KGGDLATLYL  PIFAQLANYY  LNLLQQGVEF  240
ADTWIKDAYP  SLMEPGSGTS  DYYYKLLKES  IPKYSNYCAN  TYREGLDNLR  NQPNIRWSTF  300
NDYRRYMTIT  VLDTIAQFPL  YDIKRYRDSI  GGIQGINYEL  TREIYTTEIN  FDRLTSTTLP  360
AQPNLTTMEY  NLTRSGRLFS  FLDQLVFYTE  NTNSGNRLVG  IINRSKPTYG  QGTEYLYGQK  420
TGSPDTKTLI  PFESYKVSII  TDRQFYPLTY  FIINQIELYL  NGSPSNIFKY  SAGGSLSDDK  480
KTNDYQFPVK  KECKQITDPN  CSPNYNSYSH  ILSHFSLYSY  SYLFSFTIYH  IVYTGALGWT  540
HSSVSRNNEI  SDKVITIIPA  VKGSYLDTNS  KVIEGPGHTG  GNLVYLQSLD  RLEITCRTPN  600
STQSYYIRLR  YATNGTGNII  PAIFLIIPGV  ISTPPQRLNN  TFSGTNYNNL  QYENFGYFEF  660
PSTVTLPSNR  TITCTLTRED  ISNSILIIDK  IEFIPI                              696

SEQ ID NO: 142          moltype = AA  length = 400
FEATURE                 Location/Qualifiers
source                  1..400
                        mol_type = protein
                        organism = Bacillus sp.
```

```
SEQUENCE: 142
MKLKVLSTVG LALSLGLTSL GSGGTAFAEK PDDSYFYQIK NKQYNDKAMF ASSIMMPLMI     60
NTPTFLVPDS QVQKYIFYAL DNGYYAIANK DTGNVLTNAE NNGWDKTDGA RPYLQMGWSN    120
TNDISRKTFR LENEYNGSFV LRNQFDGTIV NGHAKGIVLQ RDFANILYNY WEPTNKEHIN    180
GNMPQLLPNQ SLPDVPKYTG YGQNLPDQTV PVVTGSTIMP AIMVTDSNWS DATKIQNSPY    240
YRLVKKQYWK RLYSRNFTPG SSETVTTKTG MSRVDVDSMV DKTGIEIKAD LGASFGGEKA    300
SKKGTASLEA KFTKELTITR STTTTDINET TVEQVVKNPS DTKDFAWAKY ALATEYSLER    360
MDGSKVSSPW TVIDGTSTRE TSWPSGQQPT VQSTKTISVN                          400

SEQ ID NO: 143          moltype = AA  length = 373
FEATURE                 Location/Qualifiers
REGION                  1..373
                        note = variant of native sequence
source                  1..373
                        mol_type = protein
                        organism = synthetic construct
SEQUENCE: 143
MEKPDDSYFY QIKNKQYNDK AMFASSIMMP LMINTPTFLV PDSQVQKYIF YALDNGYYAI     60
ANKDTGNVLT NAENNGWDKT DGARPYLQMG WSNTNDISRK TFRLENEYNG SFVLRNQFDG    120
TIVNGHAKGI VLQRDFANIL YNYWEPTNKE HINGNMPQLL PNQSLPDVPK YTGYGQNLPD    180
QTVPVVTGST IMPAIMVTDS NWSDATKIQN SPYYRLVKKQ YWKRLYSRNF TPGSSETVTT    240
KTGMSRVDVD SMVDKTGIEI KADLGASFGG EKASKKGTAS LEAKFTKELT ITRSTTTTDI    300
NETTVEQVVK NPSDTKDFAW AKYALATEYS LERMDGSKVS SPWTVIDGTS TRETSWPSGQ    360
QPTVQSTKTI SVN                                                       373

SEQ ID NO: 144          moltype = AA  length = 395
FEATURE                 Location/Qualifiers
REGION                  1..395
                        note = Unknown organism from environmental sample
source                  1..395
                        mol_type = protein
                        organism = unidentified
SEQUENCE: 144
MFYIFCYYQV AISDFKYFDY RGVGKSMAFK VGTKYMFRNK NSRKYLDISG NETGNNANVQ     60
QYEYVKDALS ERFFLHPLDN NYYAMINLNS GKVIDISGNE TGNNANIQQY EWLGNSPSEY    120
WYFHREADGY YVIESKHSGK VLDISGNETG NNANVQYEY IKDAPSERFA VEEDESVLLP     180
SIITQPLSPV PQYETINDQL PNETDHVVTA FTIVPAISVK DPKYGGDTAK QIKENPYYMV    240
VKRQWWKKQE SYVLAPGETY KYTSKTGMKV MDQETATKTV SWSIGADMGL SFKGFSVGMS    300
TQYSTELQTT ISHTTEQLKE ETWDHEIKNP FSNRMAYSRY ILTTEYSVQR KDETTVSPSW    360
TMTDKTSTHS VTYPNAEEKP LNENTKQLSK AESVN                               395

SEQ ID NO: 145          moltype = AA  length = 369
FEATURE                 Location/Qualifiers
REGION                  1..369
                        note = variant of native sequence)
source                  1..369
                        mol_type = protein
                        organism = synthetic construct
SEQUENCE: 145
MAFKVGTKYM FRNKNSRKYL DISGNETGNN ANVQQYEYVK DALSERFFLH PLDNNYYAMI     60
NLNSGKVIDI SGNETGNNAN IQQYEWLGNS PSEYWYFHRE ADGYYVIESK HSGKVLDISG    120
NETGNNANVQ QYEYIKDAPS ERFAVEEDES VLLPSIITQP LSPVPQYETI NDQLPNETDH    180
VVTAFTIVPA ISVKDPKYGG DTAKQIKENP YYMVVKRQWW KKQESYVLAP GETYKYTSKT    240
GMKVMDQETA TKTVSWSIGA DMGLSFKGFS VGMSTQYSTE LQTTISHTTE QLKEETWDHE    300
IKNPFSNRMA YSRYILTTEY SVQRKDETTV SPSWTMTDKT STHSVTYPNA EEKPLNENTK    360
QLSKAESVN                                                            369

SEQ ID NO: 146          moltype = AA  length = 804
FEATURE                 Location/Qualifiers
REGION                  1..804
                        note = Unknown organism from environmental sample
source                  1..804
                        mol_type = protein
                        organism = unidentified
SEQUENCE: 146
MNTNQNRNEY EISGASSNDE HISNRYPFAK NPNVMKNTNY KDWFNECQDV APSSIVSTIG     60
IMFNIFRQFL AFMENPDLSL GVGILRGIIG TIGGRQVINL TINDVQRLIN QALENEIRNQ    120
ANQRFNSIQS NYNQYLSNKS NYINNPSPQT RNLFVTSLTL NERDLRTALD VTFSLANREL    180
LLLPSFTQIA MLHLAVLRDA VIYSGPDLIA PTISEAPGTS SLNRPPSNSY ESAILTSIRM    240
YSNYCVRHYN EGLIRIRNRG NSSRNWLDFN EYRLEMTAII LDFVSLFSLF DTTKYPVSRN    300
FTRSVVPQLS RVIYTDPVGA ITTDRGWFD PPTGTDRLRV NFTSIENEIP APTTSRHLSE     360
LTISSGPLGF GINPTRTHSW QGNRVNISA PTDVSGVISN RTRTIPARNI FRVNSRVYTL     420
DWRLFGVYRA EFFQDAHPQV FTENPPTGTG AQSANNFRFL PGENSDIPTP QDYTHVLSRV    480
VNATVGLTPA TGNQRNSVLI FGWTHKSLTS ENRYDINKIT QVAAVNTRSN SGIRVISGPG    540
FTGGDLVRMD PNGRVSYNFT PANQQALQSN VAIRLRYACQ GEASLRITFG NSSSQIIPLV    600
STTSSINNLQ YESFHSVNIP NNVSFQTVGT SMDIQNISTN SNVVLDRIEL FSNIPIPSET    660
PPIPVVPPLP SGTYQILTAL NNNFVIDLNP NNNVTMWTNN VSPNQRWIFT YDQSRSAYVI    720
RSASNQNLVL AGNVLPFNV FATPLVPGRE EHFWTLERFQ NGFVIKNLRD ANLVLDVAGG     780
RVGNGTNLIV YPRHSGTGQI FNIR                                           804
```

```
SEQ ID NO: 147           moltype = AA  length = 655
FEATURE                  Location/Qualifiers
REGION                   1..655
                         note = variant of native sequence
source                   1..655
                         mol_type = protein
                         organism = synthetic construct
SEQUENCE: 147
MNTNQNRNEY EISGASSNDE HISNRYPFAK NPNVMKNTNY KDWFNECQDV APSSIVSTIG    60
IMFNIFRQFL AFMENPDLSL GVGILRGIIG TIGGRQVINL TINDVQRLIN QALENEIRNQ   120
ANQRFNSIQS NYNQYLSNKS NYINNPSPQT RNLFVTSLTL NERDLRTALD VTFSLANREL   180
LLLPSFTQIA MLHLAVLRDA VIYSGPDLIA PTISEAPGTS SLNRPPSNSY ESAILTSIRM   240
YSNYCVRHYN EGLIRIRNRG NSSRNWLDFN EYRLEMTAII LDFVSLFSLF DTTKYPVSRN   300
FTRSVVPQLS RVIYTDPVGA ITTDGRGWFD PPTGTDRLRV NFTSIENEIP APTTSRHLSE   360
LTISSGPLGF GINPTRTHSW QGNRNVNISA PTDVSGVISN RTRTIPARNI FRVNSRVYTL   420
DWRLFGVYRA EFFQDAHPQV FTENPPTGTG AQSANNFRRL PGENSDIPTP QDYTHVLSRV   480
VNATVGLTPA TGNQRNSVLI FGWTHKSLTS ENRYDINKIT QVAAVNTRSN SGIRVISGPG   540
FTGGDLVRMD PNGRVSYNFT PANQQALQSN VAIRLRYACQ GEASLRITFG NSSSQIIPLV   600
STTSSINNLQ YESFHSVNIP NNVSFQTVGT SMDIQNISTN SNVVLDRIEL FSNIP        655

SEQ ID NO: 148           moltype = AA  length = 890
FEATURE                  Location/Qualifiers
REGION                   1..890
                         note = Unknown organism from environmental sample
source                   1..890
                         mol_type = protein
                         organism = unidentified
SEQUENCE: 148
MATVSELYPV PYNVLAISPS RLSSNWDEFQ DIFNGVKEAF GEFQKTGQLQ KEAIKQGWNA    60
YREGKIDYLA LVKASLSIVG LIVPGGEAAV PFIGMFLDFV WPKLFGGASN DETTLLNVIN   120
DVVNQILDKR LSEQQLQTVN NVLNGFQTQM LDLNQKILSA TFDATTQKPR TPSASDMINV   180
YNEFNLEQGL IHNDLYEFIL KDYEDITLPM YVMAITLKLL SYQAFIQFAN QWIDTVYPDT   240
TSGEGYTFKT NLDAAKTKMQ DDIDTASQHV LTVFQDHMVP AGVNKLQHNL HNQYVNTMVL   300
QCFDFVAMWP TLHPDVYPAN TSLDLTRVLF SDIVGPDEVH DGKVTLYNIF DNDNPKGYDH   360
GSINMEDILY LRKELEQVSI FSHEDGTYCW PYGIGLKYAG DPNTYMYSPR SFDPSHTVPS   420
STVQAPIILV NASTQYMKGL LDKESIDIHA DSGESGGGAY CPLPGHDGVE GYGRSHNSPL   480
ANQKINAFYP VTAEHVAGDQ TKLGLIATHV SFDLVPQNII GQTDTDETIS VRGFPAEKGT   540
IDNIGSLQLV PEHINGANAV KLNFQQILAI PITSVTSGYY SIRIRYASSS DITGYFHVQT   600
PAGDLNRGAI TFPNTQNMEN TIDKMYVTGA NGKYTLLTVT QAIKIPSGNS TIYIQNNSNA   660
DFFLDRIEVI PITASQLPAP SSANQFTFVG PYTVLPEPVG KDFVIWQTSQ TCAYTPNSTL   720
SFTILGGSEF QALDKNNNII ARKVENQNNQ TTETWNLPQN VEKIRFVAND YVVLRNIIGK   780
INCQEPIKPC TLGGQTLVDI DYNANGEQVL WSSTEPMGNC TVDIVLDSDF ISSIATLQFQ   840
DNTGTVVRSI DFGPGEQNQT VSVASTTKIV LKPTTFGPIS GHLKIQVVTN              890

SEQ ID NO: 149           moltype = AA  length = 672
FEATURE                  Location/Qualifiers
REGION                   1..672
                         note = variant of native sequence
source                   1..672
                         mol_type = protein
                         organism = synthetic construct
SEQUENCE: 149
MATVSELYPV PYNVLAISPS RLSSNWDEFQ DIFNGVKEAF GEFQKTGQLQ KEAIKQGWNA    60
YREGKIDYLA LVKASLSIVG LIVPGGEAAV PFIGMFLDFV WPKLFGGASN DETTLLNVIN   120
DVVNQILDKR LSEQQLQTVN NVLNGFQTQM LDLNQKILSA TFDATTQKPR TPSASDMINV   180
YNEFNLEQGL IHNDLYEFIL KDYEDITLPM YVMAITLKLL SYQAFIQFAN QWIDTVYPDT   240
TSGEGYTFKT NLDAAKTKMQ DDIDTASQHV LTVFQDHMVP AGVNKLQHNL HNQYVNTMVL   300
QCFDFVAMWP TLHPDVYPAN TSLDLTRVLF SDIVGPDEVH DGKVTLYNIF DNDNPKGYDH   360
GSINMEDILY LRKELEQVSI FSHEDGTYCW PYGIGLKYAG DPNTYMYSPR SFDPSHTVPS   420
STVQAPIILV NASTQYMKGL LDKESIDIHA DSGESGGGAY CPLPGHDGVE GYGRSHNSPL   480
ANQKINAFYP VTAEHVAGDQ TKLGLIATHV SFDLVPQNII GQTDTDETIS VRGFPAEKGT   540
IDNIGSLQLV PEHINGANAV KLNFQQILAI PITSVTSGYY SIRIRYASSS DITGYFHVQT   600
PAGDLNRGAI TFPNTQNMEN TIDKMYVTGA NGKYTLLTVT QAIKIPSGNS TIYIQNNSNA   660
DFFLDRIEVI PI                                                      672

SEQ ID NO: 150           moltype = AA  length = 695
FEATURE                  Location/Qualifiers
REGION                   1..695
                         note = Unknown organism from environmental sample
source                   1..695
                         mol_type = protein
                         organism = unidentified
SEQUENCE: 150
VKSMNSYQEK NESEILDASQ NNSNMSNRYP RYPLANNPQD SIKHTNYKDW LAMCESNQQY    60
DVNPAAINSS SVSTALKLVG KLLKFIEPTA GTAFTVLGSI LPVLWPPETA PTPERVWNDF   120
MTNTGSLIDL TVTDFVRRDA NARMAVVKDN LNRYTTAFNN WNGNQNNPLF ITAVRDQFNA   180
ANGVLRDAAI YFSNLAGYEL LLLPIYTQVA NFHLLLLRDG IINARYWSLA RNTGAQPGDQ   240
LHVDLVKYTA QYIRHCITWY TNGLNTLRNR NVQWGTFNDY RREMIIQVLD IISLFSSYDP   300
```

```
RLYPAYTTDT TILPKTELTR EIYSALLDSP PNRPIATLEE SLTRDVHLFT WLKNVDFWTS  360
TLYPDVRFLS ANRIGFSYTN SSAIQDSAIY GNSSFGTAQT HQFSLNSNVY RTSITATTAV  420
PDQVTRMDLD LINGTSAIYN SNITPVPGGL RTSNFGFSSN ESRPNQPTLQ DYTHILSYIK  480
TDIIGGHRSR VSFAWTHRTV DSNNQILTDN ITQVPAVKSS VLNAQARVIK GPGHTGGDLV  540
AITSNGTQNG RMEIQCRASN FSGTERRYRL RIRFAANSNI LVNVTYTSNG IPRQTPFTTN  600
LIPSNNEIFF PGNTIPADLR YEYFYYREPF DTILPMRVTP GELINVAIQP TNMLSNQILI  660
IDRIEFIPIT QSVLDYTEEQ NLETAQEVVN NLFIN                            695

SEQ ID NO: 151            moltype = AA   length = 692
FEATURE                   Location/Qualifiers
REGION                    1..692
                          note = variant of native sequence
source                    1..692
                          mol_type = protein
                          organism = synthetic construct
SEQUENCE: 151
MNSYQEKNES EILDASQNNS NMSNRYPRYP LANNPQDSIK HTNYKDWLAM CESNQQYDVN   60
PAAINSSSVS TALKLVGKLL KFIEPTAGTA FTVLGSILPV LWPPETAPTP ERVWNDFMTN  120
TGSLIDLTVT DFVRRDANAR MAVVKDNLNR YTTAFNNWNG NQNNPLFITA VRDQFNAANG  180
VLRDAAIYFS NLAGYELLLL PIYTQVANFH LLLLRDGIIN ARYWSLARNT GAQPGDQLHV  240
DLVKYTAQYI RHCITWYTNG LNTLRNRNVQ WGTFNDYRRE MIIQVLDIIS LFSSYDPRLY  300
PAYTTDTTIL PKTELTREIY SALLDSPPNR PIATLEESLT RDVHLFTWLK NVDFWTSTLY  360
PDVRFLSANR IGFSYTNSSA IQDSAIYGNS SFGTAQTHQF SLNSNVYRTS ITATTAVPDQ  420
VTRMDLDLIN GTSAIYNSNI TPVPGGLRTS NFGFSSNESR PNQPTLQDYT HILSYIKTDI  480
IGGHRSRVSF AWTHRTVDSN NQILTDNITQ VPAVKSSVLN AQARVIKGPG HTGGDLVAIT  540
SNGTQNGRME IQCRASNFSG TERRYRLRIR FAANSNILVN VTYTSNGIPR QTPFTTNLIP  600
SNNEIFFPGN TIPADLRYEY FYYREPFDTI LPMRVTPGEL INVAIQPTNM LSNQILIIDR  660
IEFIPITQSV LDYTEEQNLE TAQEVVNNLF IN                               692

SEQ ID NO: 152            moltype = AA   length = 666
FEATURE                   Location/Qualifiers
REGION                    1..666
                          note = variant of native sequence
source                    1..666
                          mol_type = protein
                          organism = synthetic construct
SEQUENCE: 152
MNSYQEKNES EILDASQNNS NMSNRYPRYP LANNPQDSIK HTNYKDWLAM CESNQQYDVN   60
PAAINSSSVS TALKLVGKLL KFIEPTAGTA FTVLGSILPV LWPPETAPTP ERVWNDFMTN  120
TGSLIDLTVT DFVRRDANAR MAVVKDNLNR YTTAFNNWNG NQNNPLFITA VRDQFNAANG  180
VLRDAAIYFS NLAGYELLLL PIYTQVANFH LLLLRDGIIN ARYWSLARNT GAQPGDQLHV  240
DLVKYTAQYI RHCITWYTNG LNTLRNRNVQ WGTFNDYRRE MIIQVLDIIS LFSSYDPRLY  300
PAYTTDTTIL PKTELTREIY SALLDSPPNR PIATLEESLT RDVHLFTWLK NVDFWTSTLY  360
PDVRFLSANR IGFSYTNSSA IQDSAIYGNS SFGTAQTHQF SLNSNVYRTS ITATTAVPDQ  420
VTRMDLDLIN GTSAIYNSNI TPVPGGLRTS NFGFSSNESR PNQPTLQDYT HILSYIKTDI  480
IGGHRSRVSF AWTHRTVDSN NQILTDNITQ VPAVKSSVLN AQARVIKGPG HTGGDLVAIT  540
SNGTQNGRME IQCRASNFSG TERRYRLRIR FAANSNILVN VTYTSNGIPR QTPFTTNLIP  600
SNNEIFFPGN TIPADLRYEY FYYREPFDTI LPMRVTPGEL INVAIQPTNM LSNQILIIDR  660
IEFIPI                                                            666

SEQ ID NO: 153            moltype = AA   length = 1297
FEATURE                   Location/Qualifiers
REGION                    1..1297
                          note = Unknown organism from environmental sample
source                    1..1297
                          mol_type = protein
                          organism = unidentified
SEQUENCE: 153
MNGGENMNQN NQNEMQIIDS SSNDFSQSNR YPRYPLAKES NYKEWLASCD ESNLDRLSTP   60
SSVQDAVVTS LNIASYLFSF LDFGAIGTGL GILGVLFGQF WPSNNNAVWE TFLRSVEELI  120
AREIDIVERN RIMAQPDGLR NVMSNYNGAL RDWNGNRDNT ALQSEVSRSF DNADDAFALR  180
IPEFRIKDFE IQSLAVYAQA ATLHLLLLRD AVVNGQLWGV DPVTTQRRYE KLVCLSGAYA  240
DHCTFFYRQG LEELRGKGNW TAFNNYRRNM TIQVLDVISL FSNYDPRIYG NNTNTQLTRE  300
IFTEPLATPG WLDRYSNPDQ FQQIEYNLNP SPSLSSTLLN LAADTGLGYY GAGAVTPRPI  360
IQRTSMRRLN TGATVPFTTA WQGAPNPLIS QQKQLSFEGF DVFNINSVVS REVSSQTSSL  420
FGVQQAVFHT VIAGGNIPPT MKIIDLQPRG NYSTSVTSNI PGKRSATPTA SDYTHRLSSI  480
TSTSVGTAYR DRTNIMAYGW THVSSEKTNR ILPNRITQIP FVKGIITWSG THVRSGPDHT  540
GGSLVSMGGD AQFGMVVTSS ARQRYRVRLR YAASNSVDFR LRISPLGVDY NPTLPGGGTS  600
FNPDLRYSSF RYITLPIEFE TPNSLLNFSF DLDTLTLMNG TCFFDRVEFL PVNSIALEYE  660
GKQKLEKAKQ AVDNLFTNTG KNALKVDTTD YDVDQAANLV ECVTEELYAK EKMILLDEVK  720
HAKQLNASRN LIQNGHFAFY TDEWMTSNNV SIQADNLIFK GNYLKMPGAS ETEGGTTSFP  780
TYVLQKIDES KLKPYTRYKV RGFVGSSHDV KLIVERYGKE VDALLNVRND LALNTVAPSR  840
IEASQCPSKT YPIIHDGCLT NVIDTNYYEE AQSGHANFKK EHGMCHQSHQ FDFHIDTGEV  900
HINKNPGIWV LFKISSPEGH ATLDNIELIE EGPLVGESLA LVKKREKKWK HEMGTRWLQT  960
KEVYEKAKGE IDALFTDAQD QALKFDTNIS HIISAEHLVQ SMPYVYNKWI SDVPGMNYDI 1020
YTELERRIMQ AYSLYERRNI IKNGDFDHGL NHWHATPHAK VQQMDGTAVL VIPNWSSNVS 1080
QNLCVEHNHG YVLRVTAKKE DMGKGYVTIS DCNGNQETLK FTSCDNYVSN EITNDQSEYP 1140
FSQEMNEQRS YNPNETINEQ LDYSLGQVRN EQRCYTRNEI TNDQSEYHSS QEMNEQRSYN 1200
PNETINEQLD YSLGQVRNEQ RCYTRNEITS DQSEYHSSQE MNEQRNYNSN EAINEQRNYV 1260
```

```
TRTIDFFPDT DQVRIDIGET EGIFKVESIE LICMKSQ                      1297

SEQ ID NO: 154           moltype = AA   length = 646
FEATURE                  Location/Qualifiers
REGION                   1..646
                         note = variant of native sequence
source                   1..646
                         mol_type = protein
                         organism = synthetic construct
SEQUENCE: 154
MNQNNQNEMQ IIDSSSNDFS QSNRYPRYPL AKESNYKEWL ASCDESNLDR LSTPSSVQDA   60
VVTSLNIASY LFSFLDFGAI GTGLGILGVL FGQFWPSNNN AVWETFLRSV EELIAREIDI  120
VERNRIMAQF DGLRNVMSNY NGALRDWNGN RDNTALQSEV RSRFDNADDA FALRIPEFRI  180
KDFEIQSLAV YAQAATLHLL LLRDAVVNGQ LWGVDPVTTQ RRYEKLVCLS GAYADHCTFF  240
YRQGLEELRG KGNWTAFNNY RRNMTIQVLD VISLFSNYDP RIYGNNTNTQ LTREIFTEPL  300
ATPGWLDRYS NPDQFQQIEY NLNPSPSLSS TLLNLAADTG LGYYGAGAVT PRPIIQRTSM  360
RRLNTGATVP FTTAWQGAPN PLISQQKQLS FEGFDVFNIN SVVSREVSSQ TSSLFGVQQA  420
VPHTVIAGGN IPPTMKIIDL QPRGNYSTSV TSNIPGKRSA TPTASDYTHR LSSITSTSVG  480
TAYRDRTNIM AYGWTHVSSE KTNRILPNRI TQIPFVKGII TWSGTHVRSG PDHTGGSLVS  540
MGGDAQFGMV VTSSARQRYR VRLRYAASNS VDFRLRISPL GVDYNFTLPG GGTSFNPDLR  600
YSSFRYITLP IEFETPNSLL NFSFDLDTLT LMNGTCFFDR VEFLPV              646

SEQ ID NO: 155           moltype = AA   length = 1291
FEATURE                  Location/Qualifiers
REGION                   1..1291
                         note = variant of native sequence
source                   1..1291
                         mol_type = protein
                         organism = synthetic construct
SEQUENCE: 155
MNQNNQNEMQ IIDSSSNDFS QSNRYPRYPL AKESNYKEWL ASCDESNLDR LSTPSSVQDA   60
VVTSLNIASY LFSFLDFGAI GTGLGILGVL FGQFWPSNNN AVWETFLRSV EELIAREIDI  120
VERNRIMAQF DGLRNVMSNY NGALRDWNGN RDNTALQSEV RSRFDNADDA FALRIPEFRI  180
KDFEIQSLAV YAQAATLHLL LLRDAVVNGQ LWGVDPVTTQ RRYEKLVCLS GAYADHCTFF  240
YRQGLEELRG KGNWTAFNNY RRNMTIQVLD VISLFSNYDP RIYGNNTNTQ LTREIFTEPL  300
ATPGWLDRYS NPDQFQQIEY NLNPSPSLSS TLLNLAADTG LGYYGAGAVT PRPIIQRTSM  360
RRLNTGATVP FTTAWQGAPN PLISQQKQLS FEGFDVFNIN SVVSREVSSQ TSSLFGVQQA  420
VPHTVIAGGN IPPTMKIIDL QPRGNYSTSV TSNIPGKRSA TPTASDYTHR LSSITSTSVG  480
TAYRDRTNIM AYGWTHVSSE KTNRILPNRI TQIPFVKGII TWSGTHVRSG PDHTGGSLVS  540
MGGDAQFGMV VTSSARQRYR VRLRYAASNS VDFRLRISPL GVDYNFTLPG GGTSFNPDLR  600
YSSFRYITLP IEFETPNSLL NFSFDLDTLT LMNGTCFFDR VEFLPVNSIA LEYEGKQKLE  660
KAKQAVDNLF TNTGKNALKV DTTDYDVDQA ANLVECVTEE LYAKEKMILL DEVKHAKQLN  720
ASRNLIQNGH FAFYTDEWMT SNNVSIQADN LIFKGNYLKM PGASETEGGT TSFPTYVLQK  780
IDESKLKPYT RYKVRGFVGS SHDVKLIVER YGKEVDALLN VRNDLALNTV APSRIEASQC  840
PSKTYPIIHD GCLTNVIDTN YYEEAQSGHA NFKKEHGMCH QSHQFDFHID TGEVHINKNP  900
GIWVLFKISS PEGHATLDNI ELIEEGPLVG ESLALVKKRE KKWKHEMGTR WLQTKEVYEK  960
AKGEIDALFT DAQDQALKFD TNISHIISAE HLVQSMPYVY NKWISDVPGM NYDIYTELER 1020
RIMQAYSLYE RRNIIKNGDF DHGLNHWHAT PHAKVQQMDG TAVLVIPNWS SNVSQNLCVE 1080
HNHGYVLRVT AKKEDMGKGY VTISDCNGNQ ETLKFTSCDN YVSNEITNDQ SEYPFSQEMN 1140
EQRSYNPNET INEQLDYSLG QVRNEQRCYT RNEITNDQSE YHSSQEMNEQ RSYNPNETIN 1200
EQLDYSLGQV RNEQRCYTRN EITSDQSEYH SSQEMNEQRN YNSNEAINEQ RNYVTRTIDF 1260
FPDTDQVRID IGETEGIFKV ESIELICMKS Q                              1291

SEQ ID NO: 156           moltype = AA   length = 590
FEATURE                  Location/Qualifiers
source                   1..590
                         mol_type = protein
                         organism = Bacillus sp.
SEQUENCE: 156
MKYKDRAHAK RKYEQALLVT VATMTLVVST FGSTAPTFAA ENTANVQQAP TVPATDEPVF   60
KRESNGTITV LKDKLFNMET LKAIGSLGGD TLKQAWADSK VEGGNFNNTF RTLTMGSAAL  120
IPYGGVVISP LIGLLWPEDT TDAKKRLENL MKDISKQTHA QIESYDLETL GQKLDKLYKD  180
LKEFEEIINP NGRQLAKAPS VGDEAAAIRS KAEFIHNDFK ELISESQKPS YKEAELPIFM  240
VAATAHLNFL HYMELHGKDP KINYNDTGLK LTFLDPQKQA RKDYLDYATS FAKKDVDNAD  300
QFVQKSIPEY LYKISRSDQW GASLLKSAME LTIKGMSEHL ENTLNNSINN IAFKQILGIQ  360
SEWTMNQNGR TLYYDLQGQM QTGWKEISTS FATKYDRGSS SYPLSHESLK KLLPYSWYYF  420
SPEKTDKFEK GEMYRDTTQT IDGKTYQFDS DGKCLNPDGG KPTGWSHQGD VWHYLSPTDG  480
FQNYDGQSFK KGEMVTGWIT LDGQYFYLSP VDGTTNDNND TGVNVSFKKG DMMTGWVKVK  540
GTWYYLNDKS EYGTVGHALT GDNFGKGFNL KNKEGKINNH KFNTNGTWIH            590

SEQ ID NO: 157           moltype = AA   length = 552
FEATURE                  Location/Qualifiers
REGION                   1..552
                         note = variant of native sequence
source                   1..552
                         mol_type = protein
                         organism = synthetic construct
SEQUENCE: 157
MAENTANVQQ APTVPATDEP VFKRESNGTI TVLKDKLFNM ETLKAIGSLG GDTLKQAWAD   60
```

```
SKVEGGNFNN TFRTLTMGSA ALIPYGGVVI SPLIGLLWPE DTTDAKKRLE NLMKDISKQT    120
HAQIESYDLE TLGQKLDKLY KDLKEFEEII NPNGRQLAKA PSVGDEAAAI RSKAEFIHND    180
FKELISESQK PSYKEAELPI FMVAATAHLN FLHYMELHGK DPKINYNDTG LKLTFLDPQK    240
QARKDYLDYA TSFAKKDVDN ADQFVQKSIP EYLYKISRSD QWGASLLKSA MELTIKGMSE    300
HLENTLNNSI NNIAFKQILG IQSEWTMNQN GRTLYYDLQG QMQTGWKEIS TSFATKYDRG    360
SSSYPLSHES LKKLLPYSWY YFSPEKTDKF EKGEMYRDTT QTIDGKTYQF DSDGKCLNPD    420
GGKPTGWSHQ GDVWHYLSPT DGFQNYDGQS FKKGEMVTGW ITLDGQYFYL SPVDGTTNDN    480
NDTGVNVSFK KGDMMTGWVK VKGTWYYLND KSEYGTVGHA LTGDNFGKGF NLKNKEGKIN    540
NHKFNTNGTW IH                                                       552

SEQ ID NO: 158         moltype = AA  length = 734
FEATURE                Location/Qualifiers
source                 1..734
                       mol_type = protein
                       organism = Bacillus sp.
SEQUENCE: 158
MVVLKDIYKG PYNVLAIPPL QNAAIPVSNY DELIEDLQTE LFLGRSERAI ASILENIADN     60
NINYQTIVMM SLGLASFAVP ALGLLTPFVG LFFSLLNPGP EPPTVEDIFK AMQPAIQDMI    120
DRSLTQTELN QMNNHSDALQ KQLGIYKDAM EHFHSLTNPT DIQVNDLHNQ IDYTNNILQT    180
GLSFFKTKDY EVLGLPYYTM FATISLLLLS DKVKHGLAWR YSSNDISFFE GQFNAATQEY    240
SSQIVKIIQT MERKQVESID FYQNVTGFMS TWPGISPINY KMKNNLDNTQ TFKYKIYNPN    300
PGDPPITEYK MFDRTPIAQL KSVPCTNNKT SVTAIDTINN SYSLGMVDFD TYAFYLRPSD    360
PSDCAQTYTI DPMLPLLAEW ARYNAGQPPI GRAFAFWTNP PVIPNGIVFF PYIDDLMFIG    420
ETGFGNNVIH NGMKISQITG FFNFNFVNIL TVPENISNDA HSILSIPAEK YSLINGWKSV    480
LEANLNYPNE AVTGSTPLIS TAVNQDLAFN VINLLPPNGS WTQYKLRVHY ATDADGAELS    540
LINYGYNTQY YPTQSSIKLT NTVTLSNQQP SDVQENILLS YPSTKGLLGT YMISTDTIPI    600
NLGQGQCQFT LRNTGGKKII LDRIELIPIL PGPIVDIIPQ KFFPATPEPP VIWENTTVRA    660
VRAELRLEPQ QSLYEMVVDF LLEGVVQSTQ QARIGTFLYD YVPQGFDEII IHFRNVPWLF    720
QLDVTVSGTL YGPN                                                     734

SEQ ID NO: 159         moltype = AA  length = 629
FEATURE                Location/Qualifiers
REGION                 1..629
                       note = variant of native sequence
source                 1..629
                       mol_type = protein
                       organism = synthetic construct
SEQUENCE: 159
MVVLKDIYKG PYNVLAIPPL QNAAIPVSNY DELIEDLQTE LFLGRSERAI ASILENIADN     60
NINYQTIVMM SLGLASFAVP ALGLLTPFVG LFFSLLNPGP EPPTVEDIFK AMQPAIQDMI    120
DRSLTQTELN QMNNHSDALQ KQLGIYKDAM EHFHSLTNPT DIQVNDLHNQ IDYTNNILQT    180
GLSFFKTKDY EVLGLPYYTM FATISLLLLS DKVKHGLAWR YSSNDISFFE GQFNAATQEY    240
SSQIVKIIQT MERKQVESID FYQNVTGFMS TWPGISPINY KMKNNLDNTQ TFKYKIYNPN    300
PGDPPITEYK MFDRTPIAQL KSVPCTNNKT SVTAIDTINN SYSLGMVDFD TYAFYLRPSD    360
PSDCAQTYTI DPMLPLLAEW ARYNAGQPPI GRAFAFWTNP PVIPNGIVFF PYIDDLMFIG    420
ETGFGNNVIH NGMKISQITG FFNFNFVNIL TVPENISNDA HSILSIPAEK YSLINGWKSV    480
LEANLNYPNE AVTGSTPLIS TAVNQDLAFN VINLLPPNGS WTQYKLRVHY ATDADGAELS    540
LINYGYNTQY YPTQSSIKLT NTVTLSNQQP SDVQENILLS YPSTKGLLGT YMISTDTIPI    600
NLGQGQCQFT LRNTGGKKII LDRIELIPI                                     629

SEQ ID NO: 160         moltype = AA  length = 883
FEATURE                Location/Qualifiers
source                 1..883
                       mol_type = protein
                       organism = Bacillus sp.
SEQUENCE: 160
MATVSELYPV PYNVLAISPS RLSSNWDEFQ EIFNGVKEAF GEFQKTGQLQ KEAIQQGWNA     60
YQGGKIDYLA LVKASLSIVG LIVPGGEAAV PFIGMFLDFV WPKLFGGTSN DNTTLLNIIN    120
DAVNKILDKR LSDQQLHTVN NILNGFQAQM IDLNQKILSA TFDATTQKPR TPNASDLNSV    180
YNEFNLEQGL IHNNLYEFIL EDYEDITLPM YVIAITIKLL TYQAFIQFAN RWIDTVFPDT    240
TSGEGYTFKT NLDLAKTNMQ NDINEASQHV LTVFKNHMVP AGVNKLQHNL HNQYVNTMVL    300
QCFDFVAMWP TLYPDLYPAN TSLDLTRVLF SDIVGPDEAH DGNVTLYNIL ESPQDYKHNP    360
INMEDIFYSR KELEQVQFAT ESSTNKCWPY GIGLKYAGDG SIQYQGTRDP SNNFTYTITV    420
PTTVVNAHTQ YVSATHLDME DIFIDNAEGY SGGLHCPIPG QDGSEGFARS NNSPLSNQKI    480
NAFYPVTAER VAGDQGKLGL IAAHVPFDLV PQNIIGQRDT DETISGRGFP AEKGTINNNT    540
GSLQIVPEHI NGANAVKLNY QQILAIPIIS VTNGYYSIRI RYASSSDITG YFHVQTPAGD    600
SNRGSITFPN TQNTIDKMYV TGENGNYTLL TVAQAIKFSS GKSTIYIQNN SNADLFLDRI    660
EVVPITASQL PAPSSANQFT LVGPYTMLPE PVGEEFVVWQ TSQTCAYTPN STLSFTILGS    720
GEFQVLDKNN NIIARRSENQ NNQTTETWNL PQNVEKIRFV ANDYVVLRNI IGKINCQEPI    780
KPCTLGGQTL VDINYNANGE QVLWSSTEPM GNCTVDIVID SDFISSIATL QFQDNTGTVV    840
RSIDFGPGEQ NQTVSVASTT KIVLKPTTFG PISGHLKIQV VTN                     883

SEQ ID NO: 161         moltype = AA  length = 665
FEATURE                Location/Qualifiers
REGION                 1..665
                       note = variant of native sequence
source                 1..665
                       mol_type = protein
                       organism = synthetic construct
```

-continued

```
SEQUENCE: 161
MATVSELYPV PYNVLAISPS RLSSNWDEFQ EIFNGVKEAF GEFQKTGQLQ KEAIQQGWNA  60
YQGGKIDYLA LVKASLSIVG LIVPGGEAAV PFIGMFLDFV WPKLFGGTSN DNTTLLNIIN  120
DAVNKILDKR LSDQQLHTVN NILNGFQAQM IDLNQKILSA TFDATTQKPR TPNASDLNSV  180
YNEFNLEQGL IHNNLYEFIL EDYEDITLPM YVIAITIKLL TYQAFIQFAN RWIDTVFPDT  240
TSGEGYTFKT NLDLAKTNMQ NDINEASQHV LTVFKNHMVP AGVNKLQHNL HNQYVNTMVL  300
QCFDFVAMWP TLYPDLYPAN TSLDLTRVLF SDIVGPDEAH DGNVTLYNIL ESPQDYKHNP  360
INMEDIFYSR KELEQVQFAT ESSTNKCWPY GIGLKYAGDQ SIYQYGTRDP SNNFTYTITV  420
PTTVVNAHTQ YVSATHLDME DIFIDNAEGY SGGLHCPIPG QDGSEGFARS NNSPLSNQKI  480
NAFYPVTAER VAGDQGKLGL IAAHVPFDLV PQNIIGQRDT DETISGRGFP AEKGTINNNT  540
GSLQIVPEHI NGANAVKLNY QQILAIPIIS VTNGYYSIRI RYASSSDITG YFHVQTPAGD  600
SNRGSITFPN TQNTIDKMYV TGENGNYTLL TVAQAIKFSS GKSTIYIQNN SNADLFLDRI  660
EVVPI                                                             665

SEQ ID NO: 162          moltype = AA  length = 687
FEATURE                 Location/Qualifiers
source                  1..687
                        mol_type = protein
                        organism = Bacillus sp.
SEQUENCE: 162
MYSYQNKNKR EILDTPKNKC EMSNHYSKYP LTNVPNQQLK NTNYKDWVST CEGIFEQSLT  60
FPTLMRVIGS ITSKVLGLLP IPGASYLSFL VSTFWPTISG PPNTIWEDMM KYVSNLIQQE  120
LEGEIIDHVT RNLVGLNETL DIYNRALDGW KQNNHSYASA ETVRQLISSL HLIFTDHIQV  180
DFSLKKYETI LLPSYASAAT LHLLLLRDVA IYGEELGYKK EDLEFYYGEL RYFTEKYTNY  240
CMYTYNTGLM VEKEKGWPAF NQYRREMTMA VLDVIALFPI YDARLYPSKD SMINVKSELT  300
REIYSDVINS DVPGIISPNF EYNDLGYTRS PHLFTWLRGL RLVRNTISNS RYNWYILSGV  360
TNKYSYTNGF DINLGPFMGQ DTDYGGASYN IEIPSGSYIY NLWTRHFDWI YPYTDPINIS  420
DIHFFVTDNY SSKEVTFGHT GSTVLPVTRT DFDFLFNKEG TAPATYNDYS HILSYISLIS  480
SGQKRHGYSF SFTHSSVDPY NTIVPDKITQ IPAVKANGLY NGATVIKGPG HTGGDVLFLP  540
GNTSEDPNFG IYMTNSISQP MSFKIRIRYA SNINNVTLHM IDTFEGTQDS FFELKSTFLG  600
NQIENLSYNN FQYTETPIIR SISGMKPNAF LRFFNTNPNA QILIDKIEFI PINLFTTQYL  660
KQTQRYNNTY KESCDCTCNQ HNNYYSK                                     687

SEQ ID NO: 163          moltype = AA  length = 652
FEATURE                 Location/Qualifiers
REGION                  1..652
                        note = variant of native sequence
source                  1..652
                        mol_type = protein
                        organism = synthetic construct
SEQUENCE: 163
MYSYQNKNKR EILDTPKNKC EMSNHYSKYP LTNVPNQQLK NTNYKDWVST CEGIFEQSLT  60
FPTLMRVIGS ITSKVLGLLP IPGASYLSFL VSTFWPTISG PPNTIWEDMM KYVSNLIQQE  120
LEGEIIDHVT RNLVGLNETL DIYNRALDGW KQNNHSYASA ETVRQLISSL HLIFTDHIQV  180
DFSLKKYETI LLPSYASAAT LHLLLLRDVA IYGEELGYKK EDLEFYYGEL RYFTEKYTNY  240
CMYTYNTGLM VEKEKGWPAF NQYRREMTMA VLDVIALFPI YDARLYPSKD SMINVKSELT  300
REIYSDVINS DVPGIISPNF EYNDLGYTRS PHLFTWLRGL RLVRNTISNS RYNWYILSGV  360
TNKYSYTNGF DINLGPFMGQ DTDYGGASYN IEIPSGSYIY NLWTRHFDWI YPYTDPINIS  420
DIHFFVTDNY SSKEVTFGHT GSTVLPVTRT DFDFLFNKEG TAPATYNDYS HILSYISLIS  480
SGQKRHGYSF SFTHSSVDPY NTIVPDKITQ IPAVKANGLY NGATVIKGPG HTGGDVLFLP  540
GNTSEDPNFG IYMTNSISQP MSFKIRIRYA SNINNVTLHM IDTFEGTQDS FFELKSTFLG  600
NQIENLSYNN FQYTETPIIR SISGMKPNAF LRFFNTNPNA QILIDKIEFI PI          652

SEQ ID NO: 164          moltype = AA  length = 680
FEATURE                 Location/Qualifiers
REGION                  1..680
                        note = Unknown organism from environmental sample
source                  1..680
                        mol_type = protein
                        organism = unidentified
SEQUENCE: 164
VKSMDSYQNK NEYEILDASQ KNSNMSNRYP RYPHAHNPKI PMRNTNYKDW LNGCEGTTNG  60
DCSPISPSNI GFDTLQTSMN LMITLIGALG GPVTSIIYTL GNTFINLLWG AVGNKWDSSR  120
DMVEEIINQR LEGNLRERAA AESKGLETTF TLYLTRLQTW QRTLDPRDLE ELKRQFTATD  180
NVLMYNLDLF TQGNARPILL PSYVYAATLH LNLLRDSTIY GEQWGYSREQ IECNYARLRV  240
EIAQRSDYCA RTYHEGLNNL RGSTSSQWIK FNRYRTNLTI SALDLAMLFP FYDPRSYPSA  300
VKTELTREIY TDPVGYLDWE LNLSSFNTLE ATGTRGPGLV TWLKKIDIFT DELLSYSGWT  360
PVVYLRGWGG TRHYESYTSG DNFQRISGTT SNEVRSLDPL ANDVFKITSL SRYALAGGGA  420
PGSPRYRVSR AELFRNLNVY DLVYEVPSPG LGSMTIESML PGIKNQSPNR TDYSHRLSNA  480
ACVPFGDSRI NVFGWTHQGM LNRNLVYKDK ITQIAAVKAW EIRGNSSVVA GPGNTGGNLV  540
KMSNHSVWSM RIHCEQLKNY RVRIRYASDG NSQLEMRRWT AAGYVQSANH HVQRTFSGTM  600
TYDSFKFLDV FTMVAEASYF DLTIDVFGAG ALFIDKIEFI PVEIPIIKCT DCQYSTSICE  660
CKCGGVQSSE KEIVNSLFVK                                             680

SEQ ID NO: 165          moltype = AA  length = 639
FEATURE                 Location/Qualifiers
REGION                  1..639
                        note = variant of native sequence
source                  1..639
```

```
                            mol_type = protein
                            organism = synthetic construct
SEQUENCE: 165
MDSYQNKNEY EILDASQKNS NMSNRYPRYP HAHNPKIPMR NTNYKDWLNG CEGTTNGDCS    60
PISPSNIGFD TLQTSMNLMI TLIGALGGPV TSIIYTLGNT FINLLWGAVG NKWDSSRDMV   120
EEIINQRLEG NLRERAAAES KGLETTFTLY LTRLQTWQRT LDPRDLEELK RQFTATDNVL   180
MYNLDLFTQG NARPILLPSY VYAATLHLNL LRDSTIYGEQ WGYSREQIEC NYARLRVEIA   240
QRSDYCARTY HEGLNNLRGS TSSQWIKFNR YRTNLTISAL DLAMLFPFYD PRSYPSAVKT   300
ELTREIYTDP VGYLDWELNL SSFNTLEATG TRGPGLVTWL KKIDIFTDEL LSYSGWTPVV   360
YLRGWGGTRH YESYTSGDNF QRISGTTSNE VRSLDFLAND VFKITSLSRY ALAGGGAPGS   420
PRYRVSRAEL FRNLNVYDLV YEVPSPGLGS MTIESMLPGI KNQSPNRTDY SHRLSNAACV   480
PFGDSRINVF GWTHQGMLNR NLVYKDKITQ IAAVKAWEIR GNSSVVAGPG NTGGNLVKMS   540
NHSVWSMRIH CEQLKNYRVR IRYASDGNSQ LEMRRWTAAG YVQSANHHVQ RTFSGTMTYD   600
SFKFLDVFTM VAEASYFDLT IDVFGAGALF IDKIEFIPV                          639

SEQ ID NO: 166              moltype = AA  length = 677
FEATURE                     Location/Qualifiers
REGION                      1..677
                            note = variant of native sequence
source                      1..677
                            mol_type = protein
                            organism = synthetic construct
SEQUENCE: 166
MDSYQNKNEY EILDASQKNS NMSNRYPRYP HAHNPKIPMR NTNYKDWLNG CEGTTNGDCS    60
PISPSNIGFD TLQTSMNLMI TLIGALGGPV TSIIYTLGNT FINLLWGAVG NKWDSSRDMV   120
EEIINQRLEG NLRERAAAES KGLETTFTLY LTRLQTWQRT LDPRDLEELK RQFTATDNVL   180
MYNLDLFTQG NARPILLPSY VYAATLHLNL LRDSTIYGEQ WGYSREQIEC NYARLRVEIA   240
QRSDYCARTY HEGLNNLRGS TSSQWIKFNR YRTNLTISAL DLAMLFPFYD PRSYPSAVKT   300
ELTREIYTDP VGYLDWELNL SSFNTLEATG TRGPGLVTWL KKIDIFTDEL LSYSGWTPVV   360
YLRGWGGTRH YESYTSGDNF QRISGTTSNE VRSLDFLAND VFKITSLSRY ALAGGGAPGS   420
PRYRVSRAEL FRNLNVYDLV YEVPSPGLGS MTIESMLPGI KNQSPNRTDY SHRLSNAACV   480
PFGDSRINVF GWTHQGMLNR NLVYKDKITQ IAAVKAWEIR GNSSVVAGPG NTGGNLVKMS   540
NHSVWSMRIH CEQLKNYRVR IRYASDGNSQ LEMRRWTAAG YVQSANHHVQ RTFSGTMTYD   600
SFKFLDVFTM VAEASYFDLT IDVFGAGALF IDKIEFIPVE IPIIKCTDCQ YSTSICECKC   660
GGVQSSEKEI VNSLFVK                                                  677

SEQ ID NO: 167              moltype = AA  length = 398
FEATURE                     Location/Qualifiers
source                      1..398
                            mol_type = protein
                            organism = Bacillus sp.
SEQUENCE: 167
MKSISKKVMA GLLVGATSLS IWAPISEAAA PENNRYYNIK LKSNQNKVWN VSQASNDNDR    60
AIVLWQGGSA DNEKFAFFQL DGGAYAIVNK NSGKVVTFGD LSYFGDKNII PDNDGLQQQS   120
WNGEAKQKWN LRDLGDNNYE IMNQGNGKVA SYAWQGTLAD NVEYVDLDNS NPSDADRVFT   180
LFNGTVNFLG QNITFFNDTI LVPSLPATGT RPDAPNYTGG VDQQLPQTSN SVVVGASLIP   240
CFMVNDNQAS DYTKIHNSPY YTLVKEEYWD KTFSAVIPAG LTRNYSFKTG MTSVDQQKMT   300
DTLSMKIGAD LGLKFGQQSA SIKTEVSRTL QTEISTTNTE ASEETVTSTV ASEPGKTTGY   360
TEYQLATKYT LKRADGSIVS DPWVVKNNKI TIARKNAQ                           398

SEQ ID NO: 168              moltype = AA  length = 369
FEATURE                     Location/Qualifiers
REGION                      1..369
                            note = variant of native sequence
source                      1..369
                            mol_type = protein
                            organism = synthetic construct
SEQUENCE: 168
MPENNRYYNI KLKSNQNKVW NVSQASNDND RAIVLWQGGS ADNEKFAFFQ LDGGAYAIVN    60
KNSGKVVTFG DLSYFGDKNI IPDNDGLQQQ SWNGEAKQKW NLRDLGDNNY EIMNQGNGKV   120
ASYAWQGTLA DNVEYVDLDN SNPSDADRVF TLFNGTVNFL GQNITFFNDT ILVPSLPATG   180
TRPDAPNYTG GVDQQLPQTS NSVVVGASLI PCFMVNDNQA SDYTKIHNSP YYTLVKEEYW   240
DKTFSAVIPA GLTRNYSFKT GMTSVDQQKM TDTLSMKIGA DLGLKFGQQS ASIKTEVSRT   300
LQTEISTTNT EASEETVTST VASEPGKTTG YTEYQLATKY TLKRADGSIV SDPWVVKNNK   360
ITIARKNAQ                                                           369

SEQ ID NO: 169              moltype = AA  length = 286
FEATURE                     Location/Qualifiers
source                      1..286
                            mol_type = protein
                            organism = Bacillus sp.
SEQUENCE: 169
LKMAISDMRV LAEQYARWSL ERDSNVVPGS PKNFNMFDSV VYDDVATPTQ TNFKVTPALA    60
RTAVQTLKNG TDVPQNQTVK FSETKTLTTK TTTTEGVKNT QSTKTSTKFS TGFKIDWFNA   120
GMDFTIEVTS TGEYSYTTST EQSFSNSSLW EVTQPVTVPP HSTVRAVLYI YEATFNVDYD   180
LNAKVRGTAT SPIPTYYDYF NMQYTKKSGG TATRWFYASN LYNTSWPGKP SSFVGYDSDS   240
YHPLRFKGKG TSTVATGLFT EVEFIQSPLP GYAGETKTWK TGPILV                  286

SEQ ID NO: 170              moltype = AA  length = 284
```

```
FEATURE                 Location/Qualifiers
REGION                  1..284
                        note = variant of native sequence
source                  1..284
                        mol_type = protein
                        organism = synthetic construct
SEQUENCE: 170
MAISDMRVLA EQYARWSLER DSNVVPGSPK NFNMFDSVVY DDVATPTQTN FKVTPALART   60
AVQTLKNGTD VPQNQTVKFS ETKTLTTKTT TTEGVKNTQS TKTSTKFSTG FKIDWFNAGM  120
DFTIEVTSTG EYSYTTSTEQ SFSNSSLWEV TQPVTPPHS TVRAVLYIYE ATFNVDYDLN  180
AKVRGTATSP IPTYYDYFNM QYTKKSGGTA TRWFYASNLY NTSWPGKPSS FVGYDSDSYH  240
PLRFKGKGTS TVATGLFTEV EFIQSPLPGY AGETKTWKTG PILV                   284

SEQ ID NO: 171          moltype = AA   length = 673
FEATURE                 Location/Qualifiers
source                  1..673
                        mol_type = protein
                        organism = Bacillus sp.
SEQUENCE: 171
VGNMDSYQNK NECEVLDPSG NNVNMSNRYP YANDSNMEMR NMNYTDWMAN SEEITSSSIS   60
LILSSIGIIN KLITLTGVLG KTPAIINIVG EIIGLIRPNT GNDLLVRVEQ LIQQTLANQY  120
RNDATGAIYG ISRAYNNYLL FFSRWERDRT FQNGQQVESA FTTVNTLCIS ALATQAILAR  180
RGFETLLLPN YAIAANFHLL LLRDAAIYRR QWLQINNFTE NENLIILRQA IDEYINHCTR  240
WYNDGLQRFT RTGTLNNWDA FNSYRRDMTL SVLDFATIFP TYDPGRFPVG TNVQLTRRVY  300
TDLVHDVPVH LNRGPHFAMI EPLTHINGPA DFLNELRIYT TYYHRPNNVY RDYWVGNRNT  360
FRNGNLTSSG GTSPWPTNLN MNNIDIFRVN STTHFINQTG ARYTGVHRAD FIGVNRLNNQ  420
NTTLRYNQNN STGSFRHRNI SSFLPGETTL EPNAQNYTHR LFDANTTFRS QHNERDAVYL  480
YGWTHRSLTS GNTFKVNQIT QIPAVKTTST NNDCVIISNT GENMIKLDNL TTDIYYELTT  540
ADSEAMNTCF IVRIRYASMN NNRLKLILDG TEIASLNVES TIQSNKPLTD LQYKDFKYAT  600
FAGNFKMGSQ STLGILKETS NTEFVLDKIE LIPIEIFRNQ LLEERQSYTN NYDEDFGYTC  660
NQGYNGDCNQ RLH                                                     673

SEQ ID NO: 172          moltype = AA   length = 631
FEATURE                 Location/Qualifiers
REGION                  1..631
                        note = variant of native sequence
source                  1..631
                        mol_type = protein
                        organism = synthetic construct
SEQUENCE: 172
MDSYQNKNEC EVLDPSGNNV NMSNRYPYAN DSNMEMRNMN YTDWMANSEE ITSSSISLIL   60
SSIGIINKLI TLTGVLGKTP AIINIVGEII GLIRPNTGND LLVRVEQLIQ QTLANQYRND  120
ATGAIYGISR AYNNYLLFFS RWERDRTFQN GQQVESAFTT VNTLCISALA TQAILARRGF  180
ETLLLPNYAI AANFHLLLLR DAAIYRRQWL QINNFTENEN LIILRQAIDE YINHCTRWYN  240
DGLQRFTRTG TLNNWDAFNS YRRDMTLSVL DFATIFPTYD PGRFPVGTNV QLTRRVYTDL  300
VHDVPVHLNR GPHFAMIEPL THINGPADFL NELRIYTTYY HRPNNVYRDY WVGNRNTFRN  360
GNLTSSGGTS PWPTNLMNN IDIFRVNSTT HFINQTGARY TGVHRADFIG VNRLNNQNTT  420
LRYNQNNSTG SFRHRNISSF LPGETTLEPN AQNYTHRLFD ANTTFRSQHN ERDAVYLYGW  480
THRSLTSGNT FKVNQITQIP AVKTTSTNND CVIISNTGEN MIKLDNLTTD IYYELTTADS  540
EAMNTCFIVR IRYASMNNNR LKLILDGTEI ASLNVESTIQ SNKPLTDLQY KDFKYATFAG  600
NFKMGSQSTL GILKETSNTE FVLDKIELIP I                                 631

SEQ ID NO: 173          moltype = AA   length = 670
FEATURE                 Location/Qualifiers
REGION                  1..670
                        note = variant of native sequence
source                  1..670
                        mol_type = protein
                        organism = synthetic construct
SEQUENCE: 173
MDSYQNKNEC EVLDPSGNNV NMSNRYPYAN DSNMEMRNMN YTDWMANSEE ITSSSISLIL   60
SSIGIINKLI TLTGVLGKTP AIINIVGEII GLIRPNTGND LLVRVEQLIQ QTLANQYRND  120
ATGAIYGISR AYNNYLLFFS RWERDRTFQN GQQVESAFTT VNTLCISALA TQAILARRGF  180
ETLLLPNYAI AANFHLLLLR DAAIYRRQWL QINNFTENEN LIILRQAIDE YINHCTRWYN  240
DGLQRFTRTG TLNNWDAFNS YRRDMTLSVL DFATIFPTYD PGRFPVGTNV QLTRRVYTDL  300
VHDVPVHLNR GPHFAMIEPL THINGPADFL NELRIYTTYY HRPNNVYRDY WVGNRNTFRN  360
GNLTSSGGTS PWPTNLNMNN IDIFRVNSTT HFINQTGARY TGVHRADFIG VNRLNNQNTT  420
LRYNQNNSTG SFRHRNISSF LPGETTLEPN AQNYTHRLFD ANTTFRSQHN ERDAVYLYGW  480
THRSLTSGNT FKVNQITQIP AVKTTSTNND CVIISNTGEN MIKLDNLTTD IYYELTTADS  540
EAMNTCFIVR IRYASMNNNR LKLILDGTEI ASLNVESTIQ SNKPLTDLQY KDFKYATFAG  600
NFKMGSQSTL GILKETSNTE FVLDKIELIP IEIFRNQLLE ERQSYTNNYD EDFGYTCNQG  660
YNGDCNQRLH                                                         670

SEQ ID NO: 174          moltype = AA   length = 684
FEATURE                 Location/Qualifiers
REGION                  1..684
                        note = Unknown organism from environmental sample
source                  1..684
                        mol_type = protein
```

```
                           organism   = unidentified
SEQUENCE: 174
MNQNNNNEYE  IIDSKNLPCP  SNRNIDYSRY  PFTNNPNQPL  QNTNYKDWIN  MYQKNQQYGE    60
NLETFASADT  IAAVSAGVIV  VGTMLGAFAA  PVTAGLIISF  GTLLPIFWKP  SEDPKTVWKA   120
FLTIGNRPFG  SPVDQAIIDL  LYTKVNGLRL  QFEDFQRYFD  IWKNNKTPGN  AGEVLRRFSS   180
LDADVIRELE  QLKGTYYITL  LPGYTQVANW  HLNLLRQAAY  YDEWAPSSN   LLIQSIYPQD   240
YTSDLQTCLK  NCAGESNNKV  TSAYYKCILK  CRINEYINYC  SKTYQDGLNI  LKNSSGIQWN   300
IYNMYRREMT  LTVLDLIASF  PNYDLEKYPM  RTKSQLTREI  YTDALIDAYA  NAHFNINDIE   360
NSLTRPPGLV  TWINRLDFYT  GNFPGDVPGL  TANSINYSFT  NGNSNDSPIY  GYRLNNDSRN   420
PIQIPLNEYV  YNMLITYLRD  SQSVIQKIDF  NLTNQQTRTY  NTGLTLSPIY  QSTITLSLLG   480
QDGSIPPKFD  KYTHFLSYVK  TAPGDARPSS  SRARNVCFGW  MHYSVNDYST  ILGGYNTIFD   540
TITTQIPAVK  ARHLSTPSFV  MPGPGHTGGN  LVVLSTEIEF  QCIVLNPAFY  KMRIRYVAYS   600
PNRSISLRVN  IRGEAVNYQH  PIPNIGSTVQ  SPGDTANPKY  DHFQYLDIPI  SLGLLGITNI   660
AITRLDSISN  NTLIIDKIEF  IPDV                                             684

SEQ ID NO: 175              moltype = AA  length = 1275
FEATURE                     Location/Qualifiers
source                      1..1275
                            mol_type  = protein
                            organism  = Bacillus sp.
SEQUENCE: 175
LIGGHLMNQN  YGSYDNNEME  IIDYGMRNAR  YPYASPPGAH  LQNMNHTEWI  NMCAGVETSD    60
TTSAVRDGLI  IGTGVAWALL  GLIPGIGPAA  SAIAGLFNVL  IPYWWPEAAG  DPGTPQAQYS   120
WDQLMTAVED  MINVKIADLN  RANAIARLEG  IQLLAIDFYQ  ARCDWLQDPG  NPTKQAKVRD   180
TFDDVEDYIK  VSMPFFRASG  YEVQMLAMYA  HAANMHLLFL  RDVVLNGLAW  GFEQYDVDRY   240
YSNVNTQANR  GLRELLAVYT  DYCVSIYNTG  LQSQYGKGDW  TLKYNDFRKNM  TLMVLDIVAI   300
WPTFDTKNYS  LPTKSQLTRL  VYTRRVRGYD  FHLAPSIGML  ENTIVAVPKL  FSWLVRLYYY   360
VYDNYNQTGG  YGYIKGLQFD  YKNTLFNEIL  TTPLLGGTTN  ILQSVIVNDE  ANKSIYLTER   420
KGKEGDGFFQ  LRYRYIDGTK  SGVVGQTVDT  TETFTPLGMP  CRRDEIPSTN  CDPCDPNNPC   480
RVGTTDTNDP  CMDNQLYSHR  LAHVGGGADT  TNSLTYAYL   GYGWSHFSAD  TNNLVDPDRI   540
TQIPAVKAHL  LSGGAKVIKS  PGSTGGDLVE  LTTGSDYEFM  QIYTSMIAGQ  GAYRVRIRYA   600
CNMQTTVDIF  MTGVTGKFIA  PTTTTDMTNL  TYDMFSYLDT  VVYSYSAAAD  FQDIIRMYAT   660
GSGSGSFVID  KIEFIPITGS  LTEYEAKQSL  EKAWKAVNAL  FTNDTKSTLR  LDVTDYDVDQ   720
AANKVDCMSD  DMFPKEKMML  RDQVKHAKRL  SQARNLLNYG  DFESPNWSNA  NGWKVSNSVT   780
VQASHPIARG  RYLNMPGARS  IEFSNTLYPT  YAYQKVDESK  LKPYTRYWVR  GFVGNSRDLE   840
LFVTRYGEEV  HTTMNIPTYS  VNTRAPIERG  STQFGTMQVD  YMMSSDPCQM  NAYLPSSSDM   900
PLASPTMGCE  ERAHFVFPID  VGEIDQRTNL  GIEIGFKISS  PEGMAQLDNI  EIIEAQPLTG   960
EALALVKKRE  QKWKKERERQ  CMETEKALAS  ATQAVKSLFT  SAEYNRLKPT  TMMQDILSAE  1020
AKVNAIPYVR  HPEFEDISGM  NALIFQQLQS  VIMTAINLYS  RRNVIRNGDF  SEGLSNWHAT  1080
AGADVQERDG  GSHVLVISQW  DANVSQDVCV  QPERGYVLRV  TARKEGSGKG  YVTISDCTEE  1140
NTKTVTFTSD  EMVNMPRSSV  SPQRSRESSV  CDNLDRYSES  FGIVPDMNRM  NYTTENAHME  1200
ACSCGCNNTI  HKPATGYQEM  AYQSQPSMPN  MTSPSSRYIT  KTIEIFPETN  RMRIEMGETE  1260
GTFVVESIEL  MCMED                                                      1275

SEQ ID NO: 176              moltype = AA  length = 1269
FEATURE                     Location/Qualifiers
REGION                      1..1269
                            note  = variant of native sequence
source                      1..1269
                            mol_type  = protein
                            organism  = synthetic construct
SEQUENCE: 176
MNQNYGSYDN  NEMEIIDYGM  RNARYPYASP  PGAHLQNMNH  TEWINMCAGV  ETSDTTSAVR    60
DGLIIGTGVA  WALLGLIPGI  GPAASAIAGL  FNVLIPYWWP  EAAGDPGTPQ  AQYSWDQLMT   120
AVEDMINVKI  ADLNRANAIA  RLEGIQLLAI  DFYQARCDWL  QDPGNPTKQA  KVRDTFDDVE   180
DYIKVSMPFF  RASGYEVQML  AMYAHAANMH  LLFLRDVVLN  GLAWGFEQYD  VDRYYSNVNT   240
QANRGLRELL  AVYTDYCVSI  YNTGLQSQYG  KGDWDKYNDF  RKNMTLMVLD  IVAIWPTFDT   300
KNYSLPTKSQ  LTRLVYTRRV  RGYDFHLAPS  IGMLENTIVA  VPKLFSWLVR  LYYYVYDNYN   360
QTGGYGYIKG  LQFDYKNTLF  NEILTTPLLG  GTTNILQSVI  VNDEANKSIY  LTERKGKEGD   420
GFFQLRYRYI  DGTKSGVVGQ  TVDTTETFTP  LGMPCRRDEI  PSTNCDPCDP  NNPCRVGTTD   480
TNDPCMDNQL  YSHRLAHVGG  GADTTNSLTY  LAYLGYGWSH  FSADTNNLVD  PDRITQIPAV   540
KAHLLSGGAK  VIKSPGSTGG  DLVELTTGSD  YEFMQIYTSM  IAGQGAYRVR  IRYACNMQTT   600
VDIFMTGVTG  KFIAPTTTTD  MTNLTYDMFS  YLDTVVYSYS  AAADFQDIIR  MYATGSGSGS   660
FVIDKIEFIP  ITGSLTEYEA  KQSLEKAWKA  VNALFTNDTK  STLRLDVTDY  DVDQAANKVD   720
CMSDDMFPKE  KMMLRDQVKH  AKRLSQARNL  LNYGDFESPN  WSNANGWKVS  NSVTVQASHP   780
IARGRYLNMP  GARSIEFSNT  LYPTYAYQKV  DESKLKPYTR  YWVRGFVGNS  RDLELFVTRY   840
GEEVHTTMNI  PTYSVNTRAP  IERGSTQFGT  MQVDYMMSSD  PCQMNAYLPS  SSDMPLASPT   900
MGCEERAHFV  FPIDVGEIDQ  RTNLGIEIGF  KISSPEGMAQ  LDNIEIIEAQ  PLTGEALALV   960
KKREQKWKKE  RERQCMETEK  ALASATQAVK  SLFTSAEYNR  LKPTTMMQDI  LSAEAKVNAI  1020
PYVRHPEFED  ISGMNALIFQ  QLQSVIMTAI  NLYSRRNVIR  NGDFSEGLSN  WHATAGADVQ  1080
ERDGGSHVLV  ISQWDANVSQ  DVCVQPERGY  VLRVTARKEG  SGKGYVTISD  CTEENTKTVT  1140
FTSDEMVNMP  RSSVSPQRSR  ESSVCDNLDR  YSESFGIVPD  MNRMNYTTEN  AHMEACSCGC  1200
NNTIHKPATG  YQEMAYQSQP  SMPNMTSPSS  RYITKTIEIF  PETNRMRIEM  GETGTFVVE  1260
SIELMCMED                                                              1269

SEQ ID NO: 177              moltype = AA  length = 671
FEATURE                     Location/Qualifiers
REGION                      1..671
                            note  = variant of native sequence
```

```
source                   1..671
                         mol_type = protein
                         organism = synthetic construct
SEQUENCE: 177
MNQNYGSYDN NEMEIIDYGM RNARYPYASP PGAHLQNMNH TEWINMCAGV ETSDTTSAVR    60
DGLIIGTGVA WALLGLIPGI GPAASAIAGL FNVLIPYWWP EAAGDPGTPQ AQYSWDQLMT   120
AVEDMINVKI ADLNRANAIA RLEGIQLLAI DFYQARCDWL QDPGNPTKQA KVRDTFDDVE   180
DYIKVSMPFF RASGYEVQML AMYAHAANMH LLFLRDVVLN GLAWGFEQYD VDRYYSNVNT   240
QANRGLRELL AVYTDYCVSI YNTGLQSQYG KGDWDKYNDF RKNMTLMVLD IVAIWPTFDT   300
KNYSLPTKSQ LTRLVYTRRV RGYDFHLAPS IGMLENTIVA VPKLFSWLVR LYYYVYDNYN   360
QTGGYGYIKG LQFDYKNTLF NEILTTPLLG GTTNILQSVI VNDEANKSIY LTERKGKEGD   420
GFFQLRYRYI DGTKSGVVGQ TVDTTETFTP LGMPCRRDEI PSTNCDPCDP NNPCRVGTTD   480
TNDPCMDNQL YSHRLAHVGG GADTTNSLTY LAYLGYGWSH FSADTNNLVD PDRITQIPAV   540
KAHLLSGGAK VIKSPGSTGG DLVELTTGSD YEFMQIYTSM IAGQGAYRVR IRYACNMQTT   600
VDIFMTGVTG KFIAPTTTTD MTNLTYDMFS YLDTVVYSYS AAADFQDIIR MYATGSGSGS   660
FVIDKIEFIP I                                                        671

SEQ ID NO: 178           moltype = AA   length = 197
FEATURE                  Location/Qualifiers
source                   1..197
                         mol_type = protein
                         organism = Bacillus sp.
SEQUENCE: 178
VEVISLHPKN YGKDNEWRHI GSSNDILLEG KAQSAATIEY AESVHANLSF CGMLHIPHGF    60
VYIPNSTRQL TYSLADLFVM KETSQRTIVV EDCGPVDVTL NVLKLVGNIP YIATAMVQGD   120
NGKTYDSSPK EENQIHLSYT DYIQVDTVLK LSVASLPEYS IQEDIVKISD FQVTPVQDQG   180
SNLLRFTGTF SFQNIPQ                                                  197

SEQ ID NO: 179           moltype = AA   length = 1146
FEATURE                  Location/Qualifiers
REGION                   1..1146
                         note = Unknown organism from environmental sample
source                   1..1146
                         mol_type = protein
                         organism = unidentified
SEQUENCE: 179
MKKIKFKYCI QGDLNMNQKN YDIIGASTNG TNKLLEGYNI IISPYEAPTS VTTTIEITGT    60
ILSDLGVPGA SSVSLLLNKL LNILWPNDAN TVWGTFAKET ADLLNEVLSA DDPVVIQANE   120
NLEGLKNTLD LYLQALKEWK NDPQNPASQE RVRTRFRNVD DDFTHDMPSF AKVGYETKLL   180
TVYAQAANLH LLLLLRDASMF GEGWGMTQTN INDNYNRQLR LTAHHTDYSV KWYNAGLEKL   240
KGNLTGENWY TYNRFRREMT LMVLDIVALF PNYDARMYPI ATSSELTRMI YTDPIAYTQS   300
DPWYKMTNLS FSSIENSAIP IPSFFRWLKS VSINSQWWGS GSNQTYYWVG HELVYSNSNY   360
NQSLKVKYGD PNSYIEPPDS ISFSSTDVYR TISVVRNSIS NYIVSEVQFN SISNTNQVSE   420
EIYKHQSNWS RRETKDSITE LSLAANPPTT FGNVAEYSHR LAYISEAYQS HNPSKYPAYI   480
PVFGWTHTSV RYDNKIFPDK ITQIPAVKSS SSEGGTWQNI AKGPGFTGGD VTTAVSPAVI   540
TDVIKIHVTL DTNSLSQKYR ARLRYASNAN VNATLYTNSS SNYNFELTKG TTETFTTYYS   600
YQYVDIPGSI QFNTTSDTVS VYLHMDSTTN ANVHVDRIEF IPVDENYDER VTLEKAQKAV   660
NALFTAGRHA LQTDVTDYKV DQVSILVDCV SGELYQSEKR ELLSLVKYAK RLSYSRNLLL   720
DPTFDSINSS EENGWYGSNG IAIGNGNFVF KGNYLIFSGT NDTQYPTYLY QKIDESKLKE   780
YTRYKLRGFI ESSQDLEAYV IRYDAKHETL DVSNNLFPDI SPVNACGEPN RCAVLPYLDE   840
NPRLECSSIQ DGILSDSHSF SLNIDTGSID SNENVGIVTK FKISTPEGYA KFGNLEVIEN   900
GPVIGEALAR VKRQETKWRN QLIQLRTETQ AIYTRAKQAL DNLFANAQDS HLKIGATFAS   960
IVAARKIVQS IREAYMSWLS IVPDVNYPIF TELNERVQQA FQLYDVRNVV RNGRFLSGLS  1020
DWIVTSDVKV QEDNGNNVLV LSNWDAQVLQ CLKLYQDRGY ILRVTARKEG LGEGYVTITD  1080
EEGHTDQLTF GTCEEIDASN TFVSTGYITK ELEFFPDTEK VRIEIGETEG TFQVESVELF  1140
LMEDLC                                                             1146

SEQ ID NO: 180           moltype = AA   length = 628
FEATURE                  Location/Qualifiers
REGION                   1..628
                         note = variant of native sequence
source                   1..628
                         mol_type = protein
                         organism = synthetic construct
SEQUENCE: 180
MNQKNYDIIG ASTNGTNKLL EGYNIIISPY EAPTSVTTTI EITGTILSDL GVPGASSVSL    60
LLNKLLNILW PNDANTVWGT FAKETADLLN EVLSADDPVV IQANENLEGL KNTLDLYLQA   120
LKEWKNDPQN PASQERVRTR FRNVDDDFTH DMPSFAKVGY ETKLLTVYAQ AANLHLLLLR   180
DASMFGEGWG MTQTNINDNY NRQLRLTAHH TDYSVKWYNA GLEKLKGNLT GENWYTYNRF   240
RREMTLMVLD IVALFPNYDA RMYPIATSSE LTRMIYTDPI AYTQSDPWYK MTNLSFSSIE   300
NSAIPIPSFF RWLKSVSINS QWWGSGSNQT YYWVGHELVY SNSNYNQSLK VKYGDPNSYI   360
EPPDSISFSS TDVYRTISVV RNSISNYIVS EVQFNSISNT NQVSEEIYKH QSNWSRRETK   420
DSITELSLAA NPPTTFGNVA EYSHRLAYIS EAYQSHNPSK YPAYIPVFGW THTSVRYDNK   480
IFPDKITQIP AVKSSSSEGG TWQNIAKGPG FTGGDVTTAV SPAVITDVIK IHVTLDTNSL   540
SQKYRARLRY ASNANVNATL YTNSSSNYNF ELTKGTTETF TTYYSYQYVD IPGSIQFNTT   600
SDTVSVYLHM DSTTNANVHV DRIEFIPV                                      628

SEQ ID NO: 181           moltype = AA   length = 1131
FEATURE                  Location/Qualifiers
```

| REGION | 1..1131 |
| | note = variant of native sequence |
| source | 1..1131 |
| | mol_type = protein |
| | organism = synthetic construct |

SEQUENCE: 181

```
MNQKNYDIIG ASTNGTNKLL EGYNIIISPY EAPTSVTTTI EITGTILSDL GVPGASSVSL   60
LLNKLLNILW PNDANTVWGT FAKETADLLN EVLSADDPVV IQANENLEGL KNTLDLYLQA  120
LKEWKNDPQN PASQERVRTR FRNVDDDFTH DMPSFAKVGY ETKLLTVYAQ AANLHLLLLR  180
DASMFGEGWG MTQTNINDNY NRQLRLTAHH TDYSVKWYNA GLEKLKGNLT GENWYTYNRF  240
RREMTLMVLD IVALFPNYDA RMYPIATSSE LTRMIYTDPI AYTQSDPWYK MTNLSFSSIE  300
NSAIPIPSFF RWLKSVSINS QWWGSGSNQT YYWVGHELVY SNSNYNQSLK VKYGDPNSYI  360
EPPDSISFSS TDVYRTISVV RNSISNYIVS EVQFNSISNT NQVSEEIYKH QSNWSRRETK  420
DSITELSLAA NPPTTFGNVA EYSHRLAYIS EAYQSHNPSK YPAYIPVFGW THTSVRYDNK  480
IFPDKITQIP AVKSSSSEGG TWQNIAKGPG FTGGDVTTAV SPAVITDVIK IHVTLDTNSL  540
SQKYRARLRY ASNANVNATL YTNSSSNYNF ELTKGTTETF TTYYSYQYVD IPGSIQFNTT  600
SDTVSVYLHM DSTTNANVHV DRIEFIPVDE NYDERVTLEK AQKAVNALFT AGRHALQTDV  660
TDYKVDQVSI LVDCVSGELY QSEKRELLSL VKYAKRLSYS RNLLLDPTFD SINSSEENGW  720
YGSNGIAIGN GNFVFKGNYL IFSGTNDTQY PTYLYQKIDE SKLKEYTRYK LRGFIESSQD  780
LEAYVIRYDA KHETLDVSNN LFPDISPVNA CGEPNRCAVL PYLDENPRLE CSSIQDGILS  840
DSHSFSLNID TGSIDSNENV GIWVLFKIST PEGYAKFGNL EVIENGPVIG EALARVKRQE  900
TKWRNQLIQL RTETQAIYTR AKQALDNLFA NAQDSHLKIG ATFASIVAAR KIVQSIREAY  960
MSWLSIVPDV NYPIFTELNE RVQQAFQLYD VRNVVRNGRF LSGLSDWIVT SDVKVQEDNG 1020
NNVVLVLSNWD AQVLQCLKLY QDRGYILRVT ARKEGLGEGY VTITDEEGHT DQLTFGTCEE 1080
IDASNTFVST GYITKELEFF PDTEKVRIEI GETEGTFQVE SVELFLMEDL C          1131
```

| SEQ ID NO: 182 | moltype = AA  length = 713 |
| FEATURE | Location/Qualifiers |
| REGION | 1..713 |
| | note = Unknown organism from environmental sample |
| source | 1..713 |
| | mol_type = protein |
| | organism = unidentified |

SEQUENCE: 182

```
MESIICMFRV LYIRNYEHTG GIKMKPYQNE NEYEILDAFP KYSNIVNVYS RYPLANNPQV   60
PLKNTNYKDW LNMCQTITPL CTPIDVDSNL VKVAIGVLGA IFKAMPGPGT AVGLVLKSFS  120
TIIIPILWPND TTPIWKEFTK QGLQLFRPEL GRDAIEIIGN DVQAEYNSLK IMMQDFETKF  180
AIWEPNRTRA NAIAVTTAFS SVNNQIIRLK ERFLIAAENR PAFLNLYAQT ANIDLILYQR  240
GSVNGDKWVA DINNRSISPF SSKDYYQSLK SKIQEYTNYC AETYRNSLDI LKNKPNIHWD  300
IYNRYRREAT LGALDLVALF PNYDICIYPI QTKTELTRKV YMPSFFLQAL EQSGNLESLE  360
NQLTHPPSLF TWLNELNLYT ISENFNPALR VFSLSGLQAK YRYTQNSTIL PNPPAQGITN  420
GTPIPIIGLN NLFIYKLSMS QYHDPNGCYP IAGISDMTFY KSDYNGNASA TQTYQAGRNS  480
NNVIDTFMNG PQNATTSNNI SIKDTNHVLS DIKMNYSRVG GIYPSYTFGY SFAWTHTSVD  540
PDNLIVPNRI TQIPAVKAYS LTSPARVIAG PGHTGGDLVA LLNSGTQAGR MQIQCKTGSF  600
TEATRRYGIR IRYAANNEFI VSLSYTLQGG NIMGTTFGTE RTFSRLNNII PTDLKYAEFK  660
YKEYNQIIITI NSPQNTIVTI AIQQQNPISN DQLIIDRIEF YPIDQGVVAC TVN        713
```

| SEQ ID NO: 183 | moltype = AA  length = 680 |
| FEATURE | Location/Qualifiers |
| REGION | 1..680 |
| | note = variant of native sequence |
| source | 1..680 |
| | mol_type = protein |
| | organism = synthetic construct |

SEQUENCE: 183

```
MKPYQNENEY EILDAFPKYS NIVNVYSRYP LANNPQVPLK NTNYKDWLNM CQTITPLCTP   60
IDVDSNLVKV AIGVLGAIFK AMPGPGTAVG LVLKSFSTII PILWPNDTTP IWKEFTKQGL  120
QLFRPELGRD AIEIIGNDVQ AEYNSLKIMM QDFETKFAIW EPNRTRANAI AVTTAFSSVN  180
NQIIRLKERF LIAAENRPAF LNLYAQTANI DLILYQRGSV NGDKWVADIN NRSISPFSSK  240
DYYQSLKSKI QEYTNYCAET YRNSLDILKN KPNIHWDIYN RYRREATLGA LDLVALFPNY  300
DICIYPIQTK TELTRKVYMP SFFLQALEQS GNLESLENQL THPPSLFTWL NELNLYTISE  360
NFNPALRVFS LSGLQAKYRY TQNSTILPNP PAQGITNGTP IPIIGLNNLF IYKLSMSQYH  420
DPNGCYPIAG ISDMTFYKSD YNGNASATQT YQAGRNSNNV IDTFMNGPQN ATTSNNISIK  480
DTNHVLSDIK MNYSRVGGIY PSYTFGYSFA WTHTSVDPDN LIVPNRITQI PAVKAYSLTS  540
PARVIAGPGH TGGDLVALLN SGTQAGRMQI QCKTGSFTEA TRRYGIRIRY AANNEFIVSL  600
SYTLQGGNIM GTTFGTERTF SRLNNIIPTD LKYAEFKYKE YNQIITINSP QNTIVTIAIQ  660
QQNPISNDQL IIDRIEFYPI                                              680
```

| SEQ ID NO: 184 | moltype = AA  length = 690 |
| FEATURE | Location/Qualifiers |
| REGION | 1..690 |
| | note = variant of native sequence |
| source | 1..690 |
| | mol_type = protein |
| | organism = synthetic construct |

SEQUENCE: 184

```
MKPYQNENEY EILDAFPKYS NIVNVYSRYP LANNPQVPLK NTNYKDWLNM CQTITPLCTP   60
IDVDSNLVKV AIGVLGAIFK AMPGPGTAVG LVLKSFSTII PILWPNDTTP IWKEFTKQGL  120
QLFRPELGRD AIEIIGNDVQ AEYNSLKIMM QDFETKFAIW EPNRTRANAI AVTTAFSSVN  180
```

```
NQIIRLKERF LIAAENRPAF LNLYAQTANI DLILYQRGSV NGDKWVADIN NRSISPFSSK 240
DYYQSLKSKI QEYTNYCAET YRNSLDILKN KPNIHWDIYN RYRREATLGA LDLVALFPNY 300
DICIYPIQTK TELTRKVYMP SFFLQALEQS GNLESLENQL THPPSLFTWL NELNLYTISE 360
NFNPALRVFS LSGLQAKYRY TQNSTILPNP PAQGITNGTP IPIIGLNNLF IYKLSMSQYH 420
DPNGCYPIAG ISDMTFYKSD YNGNASATQT YQAGRNSNNV IDTFMNGPQN ATTSNNISIK 480
DTNHVLSDIK MNYSRVGGIY PSYTFGYSFA WTHTSVDPDN LIVPNRITQI PAVKAYSLTS 540
PARVIAGPGH TGGDLVALLN SGTQAGRMQI QCKTGSFTEA TRRYGIRIRY AANNEFIVSL 600
SYTLQGGNIM GTTFGTERTF SRLNNIIPTD LKYAEFKYKE YNQIITINSP QNTIVTIAIQ 660
QQNPISNDQL IIDRIEFYPI DQGVVACTVN               690

SEQ ID NO: 185        moltype = AA  length = 334
FEATURE               Location/Qualifiers
REGION                1..334
                      note = Unknown organism from environmental sample
source                1..334
                      mol_type = protein
                      organism = unidentified
SEQUENCE: 185
LHIKKTENYN HNKGGKNMKK PSKKTKQILS LAMIGAIGTS VAFASPDSVS AAQINPTQVN 60
AQTPGSVSIS DWKAPIQQTY QTYKKRQPAL FLSKDVIIKN TKIYNSYVEA DGSPTITDSK 120
SLFVGRSILT NISNQEQTLT TNQFSKTFES SVTNSTTQGF NFGVSTSASF GIPLIGATNV 180
QISTEYNFSN TVEKRKAESY TYTAIPQNIV VPANSSVEVL VSLNTSKISG NVNLLTHVDG 240
TLYFNTNPNN PGSMRVMGLK PFLSSFGSID KNIKPHPQNG AYVIGKGKYS AEYGSDFSVT 300
VRPINKPNVA STKLSESANE GYTYTVKPEV KKEQ         334

SEQ ID NO: 186        moltype = AA  length = 284
FEATURE               Location/Qualifiers
REGION                1..284
                      note = variant of native sequence
source                1..284
                      mol_type = protein
                      organism = synthetic construct
SEQUENCE: 186
MAQINPTQVN AQTPGSVSIS DWKAPIQQTY QTYKKRQPAL FLSKDVIIKN TKIYNSYVEA 60
DGSPTITDSK SLFVGRSILT NISNQEQTLT TNQFSKTFES SVTNSTTQGF NFGVSTSASF 120
GIPLIGATNV QISTEYNFSN TVEKRKAESY TYTAIPQNIV VPANSSVEVL VSLNTSKISG 180
NVNLLTHVDG TLYFNTNPNN PGSMRVMGLK PFLSSFGSID KNIKPHPQNG AYVIGKGKYS 240
AEYGSDFSVT VRPINKPNVA STKLSESANE GYTYTVKPEV KKEQ 284

SEQ ID NO: 187        moltype = AA  length = 317
FEATURE               Location/Qualifiers
REGION                1..317
                      note = variant of native sequence
source                1..317
                      mol_type = protein
                      organism = synthetic construct
SEQUENCE: 187
MKKPSKKTKQ ILSLAMIGAI GTSVAFASPD SVSAAQINPT QVNAQTPGSV SISDWKAPIQ 60
QTYQTYKKRQ PALFLSKDVI IKNTKIYNSY VEADGSPTIT DSKSLFVGRS ILTNISNQEQ 120
TLTTNQFSKT FESSVTNSTT QGFNFGVSTS ASFGIPLIGA TNVQISTEYN FSNTVEKRKA 180
ESYTYTAIPQ NIVVPANSSV EVLVSLNTSK ISGNVNLLTH VDGTLYFNTN PNNPGSMRVM 240
GLKPFLSSFG SIDKNIKPHP QNGAYVIGKG KYSAEYGSDF SVTVRPINKP NVASTKLSES 300
ANEGYTYTVK PEVKKEQ                            317

SEQ ID NO: 188        moltype = AA  length = 713
FEATURE               Location/Qualifiers
REGION                1..713
                      note = Unknown organism from environmental sample
source                1..713
                      mol_type = protein
                      organism = unidentified
SEQUENCE: 188
MNQNNNEYEI TDVNTPSYPS NRINNYSRYP FANDPNQLLQ QTNYKDWLNI CQGNNQNSGN 60
LKALTDAGAG VSAGIIVTGT MIAAFAALAV APFPIVGAIV GGIVISFGTL LPLVWPGGSG 120
DRTVWTQFFA LGETLLGKSL TDEAKKTAGE TVDGFEKVLT NYEDALNKWM DLKKEQIPGS 180
PPTPELKEAA ENVKNRLDSI HLQFDGNMAH LGNPQSTYKE VLLSSYAHAA NLHLNLLQQG 240
VRFADQWNQD IYSSQIVPAA GTSVAYLKLL QERIQEYVNY CTKTYRSGLN ILENSNDITW 300
DIYNTYRRDL TLAVLDLVAA FPNYDPTYYP IDTKIQLTRT LYSDLLGITQ SGRKNLEALE 360
NALTMRPNLY RILRGFTFNT TFGSGVNYLS GISNTRGLIK TDPSNKDKQP FYGQSNGKQD 420
PLDFANGLNI FRVNLLRNKR YIPSPVPPSL FSADQITDLK LYYGNATEYH HYQPANQGLT 480
TENTDLSFPP KNDEYLNAIL MTSPGTIYDN PTNIYSFAWT KKDIDQQNNI IINAITQIPA 540
VKGNELGSKS RVIQGPGHTS GDLVDLKDSI VLKCQYTGPQ QSYFVRIRYA SNGILNNRAT 600
IGLTIPGVTG QSITLSETFS GTDYNVLEFQ NFKSYQFNGQ IQLNPSQNIF IYLNRLDQNA 660
NTTLLIDKIE FIPAPLPRIL SEQKLKKVKQ KVNDLFIDSE NGCFCPSHEK DLR 713

SEQ ID NO: 189        moltype = AA  length = 674
FEATURE               Location/Qualifiers
REGION                1..674
                      note = variant of native sequence
```

```
source                      1..674
                            mol_type = protein
                            organism = synthetic construct
SEQUENCE: 189
MNQNNNEYEI TDVNTPSYPS NRINNYSRYP FANDPNQLLQ QTNYKDWLNI CQGNNQNSGN   60
LKALTDAGAG VSAGIIVTGT MIAAFAALAV APFPIVGAIV GGIVISFGTL LPLVWPGGSG  120
DRTVWTQFFA LGETLLGKSL TDEAKKTAGE TVDGFEKVLT NYEDALNKWM DLKKEQIPGS  180
PPTPELKEAA ENVKNRLDSI HLQFDGNMAH LGNPQSTYKE VLLSSYAHAA NLHLNLLQQG  240
VRFADQWNQD IYSSQIVPAA GTSVAYLKLL QERIQEYVNY CTKTYRSGLN ILENSNDITV  300
DIYNTYRRDL TLAVLDLVAA FPNYDPTYYP IDTKIQLTRT IYSDLLGITQ SGRKNLEALE  360
NALTMRPNLY RILRGFTFNT TFGSGVNYLS GISNTRGLIK TDPSNKDQP FYGQSNGKQD  420
PLDFANGLNI FRVNLLRNKR YIPSPVPPSL FSADQITDLK LYYGNATEYH HYQPANQGLT  480
TENTDLSFPP KNDEYLNAIL MTSPGTIYDN PTNIYSFAWT KKDIDQQNNI IINAITQIPA  540
VKGNELGSKS RVIQGPGHTS GDLVDLKDSI VLKCQYTGPQ QSYFVRIRYA SNGILNNRAT  600
IGLTIPGVTG QSITLSETFS GTDYNVLEFQ NFKSYQFNGQ IQLNPSQNIF IYLNRLDQNA  660
NTTLLIDKIE FIPA                                                   674

SEQ ID NO: 190              moltype = AA   length = 660
FEATURE                     Location/Qualifiers
REGION                      1..660
                            note = Unknown organism from environmental sample
source                      1..660
                            mol_type = protein
                            organism = unidentified
SEQUENCE: 190
VKNMNSYQNK NEYELLDTSP NSSTMSTRYP SYPLAKNPQI SMQNTNYKDW INMCTNNTLI   60
PIEPLDLTWQ NALVSVFGIA SAVAGLLASP ITGGTSIAAG AAIIANILPL TFPANAESVP  120
NKLMDATQEL LGPLEEYTRN RANSELLSLS SQLEAFKGLF DYWLANRQNP SATNSVSARF  180
TAIHNNFIGA MALFKIPGYE ALLLPVYAQA ARLHLLHLRD GITYADEWQL ADPTNATYAG  240
DYHYSEFKKY SAQYADHCEV VVNNQLNKIK NTTGKTWKEY NEYRRKMILS VPDIVAEFST  300
FDPILYKGAI NREILTRKIY TDPVNFTPGS SIANDENKYT IYPTPVKELV AIRLYTNVAS  360
EQYAGFIGNK NRYLSLSGGE PLDGPLIGKS VYENVVAGVP TTESIYEGVG NGYPNDYPRN  420
IGLRWGSLTG FQNYYAGGST NLGSLTSVSV PPKNNAPINN TNFTHRLSDV ILPGNSGSSF  480
AWTHVEINPT GNYLSTNQIN LISATKTSSY SNFNFIEGPR FTGGYLIRNA SGTSCQSSYP  540
LKLKPGGSST SFRVRIRYGS NIAGKVYFRF NGKDSSPTSF PSTNFSAAYK YDTFRVVELL  600
STLQNFTGGE LIIIIELDSF ISFFVLERLE LIPMTGMPTE YTEPQKLETA QKAVNDLFTN  660

SEQ ID NO: 191              moltype = AA   length = 657
FEATURE                     Location/Qualifiers
REGION                      1..657
                            note = variant of native sequence
source                      1..657
                            mol_type = protein
                            organism = synthetic construct
SEQUENCE: 191
MNSYQNKNEY ELLDTSPNSS TMSTRYPSYP LAKNPQISMQ NTNYKDWINM CTNNTLIPIE   60
PLDLTWQNAL VSVFGIASAV AGLLASPITG GTSIAAGAAI IANILPLTFP ANAESVPNKL  120
MDATQELLGP LEEYTRNRAN SELLSLSSQL EAFKGLFDYW LANRQNPSAT NSVSARFTAI  180
HNNFIGAMAL FKIPGYEALL LPVYAQAARL HLLHLRDGIT YADEWQLADP TNATYAGDYH  240
YSEFKKYSAQ YADHCEVVVN NQLNKIKNTT GKTWKEYNEY RRKMILSVFD IVAEFSTFDP  300
ILYKGAINRE ILTRKIYTDP VNFTPGSSIA NDENKYTIYP TPVKELVAIR LYTNVASEQY  360
AGFIGNKNRY LSLSGGEPLD GPLIGKSVYE NVVAGVPTTE SIYEGVGNGY PNDYPRNIGL  420
RWGSLTGFQN YYAGGSTNLG SLTSVSVPPK NNAPINNTNF THRLSDVILP GNSGSSFAWT  480
HVEINPTGNY LSTNQINLIS ATKTSSYSNF NFIEGPRFTG GYLIRNASGT SCQSSYPLKL  540
KPGGSSTSFR VRIRYGSNIA GKVYFRFNGK DSSPTSFPST NFSAAYKYDT FRVVELLSTL  600
QNFTGGELII IIELDSFISF FVLERLELIP MTGMPTEYTE PQKLETAQKA VNDLFTN    657

SEQ ID NO: 192              moltype = AA   length = 631
FEATURE                     Location/Qualifiers
REGION                      1..631
                            note = variant of native sequence
source                      1..631
                            mol_type = protein
                            organism = synthetic construct
SEQUENCE: 192
MNSYQNKNEY ELLDTSPNSS TMSTRYPSYP LAKNPQISMQ NTNYKDWINM CTNNTLIPIE   60
PLDLTWQNAL VSVFGIASAV AGLLASPITG GTSIAAGAAI IANILPLTFP ANAESVPNKL  120
MDATQELLGP LEEYTRNRAN SELLSLSSQL EAFKGLFDYW LANRQNPSAT NSVSARFTAI  180
HNNFIGAMAL FKIPGYEALL LPVYAQAARL HLLHLRDGIT YADEWQLADP TNATYAGDYH  240
YSEFKKYSAQ YADHCEVVVN NQLNKIKNTT GKTWKEYNEY RRKMILSVFD IVAEFSTFDP  300
ILYKGAINRE ILTRKIYTDP VNFTPGSSIA NDENKYTIYP TPVKELVAIR LYTNVASEQY  360
AGFIGNKNRY LSLSGGEPLD GPLIGKSVYE NVVAGVPTTE SIYEGVGNGY PNDYPRNIGL  420
RWGSLTGFQN YYAGGSTNLG SLTSVSVPPK NNAPINNTNF THRLSDVILP GNSGSSFAWT  480
HVEINPTGNY LSTNQINLIS ATKTSSYSNF NFIEGPRFTG GYLIRNASGT SCQSSYPLKL  540
KPGGSSTSFR VRIRYGSNIA GKVYFRFNGK DSSPTSFPST NFSAAYKYDT FRVVELLSTL  600
QNFTGGELII IIELDSFISF FVLERLELIP M                                631

SEQ ID NO: 193              moltype = AA   length = 575
FEATURE                     Location/Qualifiers
```

```
REGION                  1..575
                        note = Unknown organism from environmental sample
source                  1..575
                        mol_type = protein
                        organism = unidentified
SEQUENCE: 193
LFKKYEEKVV NPMYTNAMKN TLKIETTDYE IDQAASSIEC MSHEKYPQEK MILWDEVKQA    60
KQLSQSRNLL YNGDFKDASN GWKTSYTIEI RNNSPIFKGN YLHMFGAREV LDEVFPTYIY   120
QKIDESKLKP YTRYRVRGFV GSSQDLELVV ARYGKEIDAI MSVPHEGLAY MQANPSCGDY   180
RCDSSSHSMM SQGYPTPVTD GYASDMYACP SDRVKKHVKC HDRHPFDFHI DTGELDTNTN   240
LGILVLFKIS HPNGYATLGN LEVIEEGPLT DEALEHVNHK EKKWNRHIEK ARMETQQAYD   300
PAKQAVDALF TSAQELHYHT TLNHIKNANQ LVQSIPYVNH AWLPDAPGMN YDLYQGLNAR   360
IMQAYNVYDA RNVITNGDFT QGLQGWHATG NAVVQQMDGA SVLVLSNWSA GVSQNLHAQD   420
HHGYVLRVIA KKEGTGKGYV TMMDCNGKQE TLTFTSCEEG YMTKTVEVFP ESDRVRIEIG   480
ETEGTFYIDS IELLCMKGYT SNYNQNTGNM YEQSYNGNYN QNTSDVYHQG YTNNYNKDSS   540
SMYNQNYTNN DDQHSGCTCN QGHNPGCTCN QRYNR                              575

SEQ ID NO: 194          moltype = AA  length = 387
FEATURE                 Location/Qualifiers
source                  1..387
                        mol_type = protein
                        organism = Bacillus sp.
SEQUENCE: 194
MKSISKKVMA GLLVGATSLS IWAPSSQAAP ANNAYHSIHL AANTWLKWDV IWDSTNDDAG    60
IVLYNGGISD NEQFVFFPLD GGAYAIVNKN SGKPVATGSG WIAGNTLSHN SEGVKQANWT   120
GAATEKWYLR DQGNNNYEIV NQGYGKVASY AKAGIGPLEY EYVDLDNSNP SDNDRLFHIP   180
AAARSTFSLP TLPAIGTRPN APDYNPNGSI DQQLPQASNS VVVGASLIPC IMVKDNGASD   240
YTKIHNSPYY VLEKEEYWEK VRSEIIPAGS TSKYTVKTGV STVDQQKMTD TLAMNFGADL   300
GFKFGDQSAS LKYGISKTLQ TEVSKTSTDS KEETEEKNLT SINNKNTGFT VYQLVTKYTL   360
KRTDGSVVSD PWTVRDKEQT IVRPITN                                       387

SEQ ID NO: 195          moltype = AA  length = 360
FEATURE                 Location/Qualifiers
REGION                  1..360
                        note = variant of native sequence
source                  1..360
                        mol_type = protein
                        organism = synthetic construct
SEQUENCE: 195
MAPANNAYHS IHLAANTWLK WDVIWDSTND DAGIVLYNGG ISDNEQFVFF PLDGGAYAIV    60
NKNSGKPVAT GSGWIAGNTL SHNSEGVKQA NWTGAATEKW YLRDQGNNNY EIVNQGYGKV   120
ASYAKAGIGP LGPEYVDLDN SNPSDNDRLF HIPAAARSTF SLPTLPAIGT RPNAPDYNPN   180
GSIDQQLPQA SNSVVVGASL IPCIMVKDNG ASDYTKIHNS PYYVLEKEEY WEKVRSEIIP   240
AGSTSKYTVK TGVSTVDQQK MTDTLAMNFG ADLGFKFGDQ SASLKYGISK TLQTEVSKTS   300
TDSKEETEEK NLTSINNKNT GFTVYQLVTK YTLKRTDGSV VSDPWTVRDK EQTIVRPITN   360

SEQ ID NO: 196          moltype = AA  length = 264
FEATURE                 Location/Qualifiers
REGION                  1..264
                        note = Unknown organism from environmental sample
source                  1..264
                        mol_type = protein
                        organism = unidentified
SEQUENCE: 196
LPSFIAYFYA DCLGTAHTMM EVFKAEEYPE RGTPVHATEK QPVDRQIFVS NRIETFSLPE    60
YRLGKLGDIP HYQGYDTNLP ETTPSVIVAI TTLPAMMVND TWEGKQKMQT SPYYQLIKKQ   120
YWKKQDAHIL SPGREHVITE THGMTQTDVK SMTEKSGLTM QGDAGFTQA ITASLSSTIT   180
RELDISRSTT IQEMKEHKVE DTIRNTSTEK LAWARYVLVS EYHIERVDGT FVSTPWTYIH   240
ETDTRETVWP TGEKQKIMAV PVKK                                          264

SEQ ID NO: 197          moltype = AA  length = 246
FEATURE                 Location/Qualifiers
REGION                  1..246
                        note = variant of native sequence
source                  1..246
                        mol_type = protein
                        organism = synthetic construct
SEQUENCE: 197
MMEVFKAEEY PERGTPVHAT EKQPVDRQIF VSNRIETFSL PEYRLGKLGD IPHYQGYDTN    60
LPETTPSVIV AITTLPAMMV NDTWEGKQKM QTSPYYQLIK KQYWKKQDAH ILSPGREHVI   120
TETHGMTQTD VKSMTEKSGL TMQGDAGFTF QAITASLSST ITRELDISRS TTIQEMKEHK   180
VEDTIRNTST EKLAWARYVL VSEYHIERVD GTFVSTPWTY IHETDTRETV WPTGEKQKIM   240
AVPVKK                                                              246

SEQ ID NO: 198          moltype = AA  length = 951
FEATURE                 Location/Qualifiers
source                  1..951
                        mol_type = protein
                        organism = Bacillus sp.
```

```
SEQUENCE: 198
MIMQMVTKAM TPKLGALPDF IDDFNGIFGF MDNITGVMST IFGIDTGDSS IDNVLNNQEL    60
LQEMLDQMST MQSSIQDILE QQGISADIEK QILALTTDLA TSINAELGKI EGILNTYLPA   120
ISNMLSNIYE QTSMIDQKVD KLLALMTFAL KELDYIKDNV VLNSSIVEIT PHVQKLVYVN   180
KKFLSLTRGF LQGEDVSIDS MQEIQEWAKS ILATEMNSFE FSVDTLHNII IGDNLYKRSA   240
LKTFSDVLLD DADQYGDFGT PLAKFYTFFS SLATLQINAY LCLTFARKVL GLSEIDYQVT   300
MQDRIEQQNQ MFVNLIQDKN YSNVLEIEGI YPMPQQSGDC NSLDLQAKSG YALIGLEFFM   360
DNGIYKAKAY QAKIDKNFSI HADTVEEIIS DDLSKVFLNT MNQSEYFRYP LFGELKGVPN   420
TIITRIGFGT KYDESRKVKA FAYIDADFSP YDPKSGYIST EGTQTFQIEG TEDKNWCYSA   480
WPIGLIGDLY MTPLKSLSLN VDVDLHGGNT LNMSGESYFS TILSREYNAN FILFPYTNNS   540
GLIDNNLIQN GNLEDQDKYW EGTEPSFFAE GEGTFGSNAL KVQAQGAFDQ IVKLEPNTTY   600
RLTAFTKVKD SNYSKGKIGI RDMYDYRVEK SFLHTRYNQT KVEFTTGADT SKLSVFIQGG   660
GDQESIAWAD NIELYKVHQQ DNMISDFDFD TYIIYSNMCW KLSGGGDFVEK EGLFNSKALK   720
ITNSGGAEQE VKLKANTNYI FTAYVKVDNT TAQIGCGSNQ VTCNSTSYTP VKLKFRTGED   780
PSTTEGSIYC SNPNDSGTVW ADDFVLYEVP NLIINGDFEQ MDLSSWNPSP TDVGKIYLRS   840
GAGMSHSTAI VLAGEGQISQ KVPLKPYTKY RLTAYVRVPN GVTALLGYGN GGNDDYRVHC   900
TSTEFKQESL VFTTGANPLQ SEDAIYLSTP DDGFKIATGD NFELYELDQI E           951

SEQ ID NO: 199          moltype = AA  length = 949
FEATURE                 Location/Qualifiers
REGION                  1..949
                        note = variant of native sequence
source                  1..949
                        mol_type = protein
                        organism = synthetic construct
SEQUENCE: 199
MQMVTKAMTP KLGALPDFID DFNGIFGFMD NITGVMSTIF GIDTGDSSID NVLNNQELLQ    60
EMLDQMSTMQ SSIQDILEQQ GISADIEKQI LALTTDLATS INAELGKIEG ILNTYLPAIS   120
NMLSNIYEQT SMIDQKVDKL LALMTFALKE LDYIKDNVVL NSSIVEITPH VQKLVYVNKK   180
FLSLTRGFLQ GEDVSIDSMQ EIQEWAKSIL ATEMNSFEFS VDTLHNIIIG DNLYKRSALK   240
TFSDVLLDDA DQYGDFGTPL AKFYTFFSSL ATLQINAYLC LTFARKVLGL SEIDYQVTMQ   300
DRIEQQNQMF VNLIQDKNYS NVLEIEGIYP MPQQSGDCNS LDLQAKSGYA LIGLEFFMDN   360
GIYKAKAYQA KIDKNFSIHA DTVEEIISDD LSKVFLNTMN QSEYFRYPLF GELKGVPNTI   420
ITRIGFGTKY DESRKVKAFA YIDADFSPYD PKSGYISTEG TQTFQIEGTE DKNWCYSAWP   480
IGLIGDLYMT PLKSLSLNVD VDLHGGNTLN MSGESYFSTI LSREYNANFI LFPYTNNSGL   540
IDNNLIQNGN LEDQDKYWEG TEPSFFAEGE GTFGSNALKV QAQGAFDQIV KLEPNTTYRL   600
TAFTKVKDSN YSKGKIGIRD MYDYRVEKSF LHTRYNQTKV EFTTGADTSK LSVFIQGGGD   660
QESIAWADNI ELYKVHQQDN MISDFDFDTY IYSNMCWKLS GGGDFVEKEG LFNSKALKIT   720
NSGGAEQEVK LKANTNYIFT AYVKVDNTTA QIGCGSNQVT CNSTSYTPVK LKFRTGEDPS   780
TTEGSIYCSN PNDSGTVWAD DFVLYEVPNL IINGDFEQMD LSSWNPSPTD VGKIYLRSGA   840
GMSHSTAIVL AGEGQISQKV PLKPYTKYRL TAYVRVPNGV TALLGYGNGG NDDYRVHCTS   900
TEFKQESLVF TTGANPLQSE DAIYLSTPDD GFKIATGDNF ELYELDQIE              949

SEQ ID NO: 200          moltype = AA  length = 691
FEATURE                 Location/Qualifiers
REGION                  1..691
                        note = Unknown organism from environmental sample
source                  1..691
                        mol_type = protein
                        organism = unidentified
SEQUENCE: 200
VKKMNSYQNK NEYEILDASQ NNSTMSNRYP RYPLANDPQA SMQNTSYKEW LNMCDSNTQF    60
VGDISTYSSP EAALSARDAV FTGINVANSI LSHFGYFGVP FAGFSFQLIG ALLGILWPGP   120
DPFAALMVLV EELINDRIKD EIREHALLEL AGLKDIMDLY RTRWLAWDLN KDNPDTEIRE   180
RAKEAVRLQY RIADNFFIQN MPKFGRADHG VLLLAVYAQA ANLHLILLRD ADVYGEKWGL   240
GPDEIRDNYI RLQKKIREYK DHCVTFYNQG LNRFNHSNAQ DWVSFNRFRT DMTITVLDLA   300
TLFPNYDPRI YPSAVKTELT REIYTDPVGY TEQGRPWYNP NNTTFATMEN NARRRPSFTT   360
WLNGVRIFTG HLSNFSAARN VWGGHELFER QNNDSEIMRK FGNTDTSTVP VRNWDFTDQN   420
RTVFSIVSNA SVFVVGPQPE RGSQYGVSKI NMHTAIHGNS KGGEFIYDVP NVLRPQAIVS   480
ELPAEDQQRP DARNHSHILS YISNFDAHRG GSGGNVSLLT YGWTHTSMDR NNRLERDRIT   540
QIDAVKGWGG LTGSVIPGPT GGNLVTIPGS PFDVFLRVQA PQIQTDYRIR LRFACVWPGT   600
HSMWVNYGGI SHPVQLLCNN TSGRPSNNLL ESDFGYVVVP GIFSPSINPE IRFSAISGTP   660
VLDKIEFIPL DMFNELFPGD REKTVNDLFI N                                 691

SEQ ID NO: 201          moltype = AA  length = 688
FEATURE                 Location/Qualifiers
REGION                  1..688
                        note = variant of native sequence
source                  1..688
                        mol_type = protein
                        organism = synthetic construct
SEQUENCE: 201
MNSYQNKNEY EILDASQNNS TMSNRYPRYP LANDPQASMQ NTSYKEWLNM CDSNTQFVGD    60
ISTYSSPEAA LSARDAVFTG INVANSILSH FGYFGVPFAG FSFQLIGALL GILWPGPDPF   120
AALMVLVEEL INDRIKDEIR EHALLELAGL KDIMDLYRTR WLAWDLNKDN PDTEIRERAK   180
EAVRLQYRIA DNFFIQNMPK FGRADHGVLL LAVYAQAANL HLILLRDADV YGEKWGLGPD   240
EIRDNYIRLQ KKIREYKDHC VTFYNQGLNR FNHSNAQDWV SFNRFRTDMT ITVLDLATLF   300
PNYDPRIYPS AVKTELTREI YTDPVGYTEQ GRPWYNPNNT TFATMENNAR RRPSFTTWLN   360
GVRIFTGHLS NFSAARNVWG GHELFERQNN DSEIMRKFGN TDTSTVPVRN WDFTDQNRTV   420
```

```
FSIVSNASVF VVGPQPERGS QYGVSKINMH TAIHGNSFGG EFIYDVPNVL RPQAIVSELP   480
AEDQQRPDAR NHSHILSYIS NFDAHRGGSG GNVSLLTYGW THTSMDRNNR LERDRITQID   540
AVKGWGGLTG SVIPGPTGGN LVTIPGSPFD VFLRVQAPQI QTDYRIRLRF ACVWPGTHSM   600
WVNYGGISHP VQLLCNNTSG RPSNNLLESD FGYVVVPGIF SPSINPEIRF SAISGTPVLD   660
KIEFIPLDMF NELFPGDREK TVNDLFIN                                      688

SEQ ID NO: 202         moltype = AA   length = 667
FEATURE                Location/Qualifiers
REGION                 1..667
                       note = variant of native sequence
source                 1..667
                       mol_type = protein
                       organism = synthetic construct
SEQUENCE: 202
MNSYQNKNEY EILDASQNNS TMSNRYPRYP LANDPQASMQ NTSYKEWLNM CDSNTQFVGD    60
ISTYSSPEAA LSARDAVFTG INVANSILSH FGYFGVPFAG FSFQLIGALL GILWPGDPF    120
AALMVLVEEL INDRIKDEIR EHALLELAGL KDIMDLYRTR WLAWDLNKDN PDTEIRERAK   180
EAVRLQYRIA DNFFIQNMPK FGRADHGVLL LAVYAQAANL HLILLRDADV YGEKWGLGPD   240
EIRDNYIRLQ KKIREYKDHC VTFYNQGLNR FNHSNAQDWV SFNRFRTDMT ITVLDLATLF   300
PNYDPRIYPS AVKTELTREI YTDPVGYTEQ GRPWYNPNNT TFATMENNAR RRPSFTTWLN   360
GVRIFTGHLS NFSAARNVWG GHELFERQNN DSEIMRKFGN TDTSTVPVRN WDFTDQNRTV   420
FSIVSNASVF VVGPQPERGS QYGVSKINMH TAIHGNSFGG EFIYDVPNVL RPQAIVSELP   480
AEDQQRPDAR NHSHILSYIS NFDAHRGGSG GNVSLLTYGW THTSMDRNNR LERDRITQID   540
AVKGWGGLTG SVIPGPTGGN LVTIPGSPFD VFLRVQAPQI QTDYRIRLRF ACVWPGTHSM   600
WVNYGGISHP VQLLCNNTSG RPSNNLLESD FGYVVVPGIF SPSINPEIRF SAISGTPVLD   660
KIEFIPL                                                             667

SEQ ID NO: 203         moltype = AA   length = 559
FEATURE                Location/Qualifiers
REGION                 1..559
                       note = Unknown organism from environmental sample
source                 1..559
                       mol_type = protein
                       organism = unidentified
SEQUENCE: 203
VKKVVNPMFT SGAKNTLKIE TTDYQIDQVA HSIECMSEEQ NPQKKMMLWD EIKQAKQLSR    60
SRNLLHNGDF EDLFGGWTTS THITIQVDNP IFKGNHLNIP GAGDIDGTLF PSYIYQKIDE   120
SKLKPNTRYR VRGFVGSSKN LKLVVTRYGK EIDASMQNDN DLAYMQPNLS CGGYRCDSSS   180
QSVMSQGSPT PVTEGYASDM YSCPSNLGKK HVKCHDRHPF DFHIDTGELD INTNVGIWVL   240
FKISNPDGYA TLGNLEVIEE GPLTDESLAH VKQKEQKWHQ QMEKKRMETQ QAYAPAKQAV   300
DALFANAQEL QYHITLDHIQ NADQLVQSIP YVHHAWLPDA PGMNYDGYQG LNASIMQARY   360
LYDARNVITN GDFTQGLTGW HATGKVDVQQ MAGAFVLVLS NWSAGVSQNI HVQHHCGYVL   420
RVIAKKEGPG KGYVTMMDCN GKQETLTFTS CEEGYMTKTV EVFPPESDRVR IEIGETEGTF   480
YIDSIELICM KGYNSNYNQN TSNMYDQSYN RNYSQNTSDM YNQSYTNNYD QHSGCTCNQG   540
HNNNDNQSSG CTCNQGYNS                                                559

SEQ ID NO: 204         moltype = AA   length = 408
FEATURE                Location/Qualifiers
source                 1..408
                       mol_type = protein
                       organism = Bacillus sp.
SEQUENCE: 204
MIIVALIPNG EAFISQILGA VCPNNVEDNQ LKYVQSQINR LDKKVEDLSA AILKSHYDIL    60
LKEIQLFENC VNILDSSDVY YSTGNVYENR RWHARHINQK FKELIRDCNK EILQAKELPM   120
YTTVATAYLL FLKFIEKNGK GPKIKFDNAS FNEEFMHDIQ TAAKEYKIHI EYTYNAEAHR   180
LREEMIAIAQ KARSVTHAYL TGNESSFDDA VVRALKKMED KYNELLKNFM RDGAASVLSG   240
QNTIMNNLGK DIDNYRNKLN EQNKYYNRTW GNQAFRVIAR IDTWVQESGK WYYYDHDMLL   300
VNHIFYSGGK WYYLSPEKTD KLEKGQMATG WLSLPSNKMG VVMMFMYSKN VGGKYSNELP   360
KIMELMKKSA NTKFWLYFSP NGELVHNTKK TIGGKEYEFD KYGICLNP                 408

SEQ ID NO: 205         moltype = AA   length = 272
FEATURE                Location/Qualifiers
source                 1..272
                       mol_type = protein
                       organism = Bacillus sp.
SEQUENCE: 205
MLFLVLSFRG IFLLKNQRSV LMPIQEKFSF SELSAVGSNP NSVREKFKER FGTLPDGIAV    60
NSETYYDAVK PAITEQYGHP CYKTLGEFTY QVGNGKPPSE AILGSNYAVN HGDEEASISL   120
SVQGNWTETK TWSSETTTGL TISSKFTLEG VFESGAEFSV STTVGESSST SVSRSASSTV   180
TVTVPPRSKK KVSMVGTMKQ ETMNFQAPLS VQGSFGANFP RKVEDHYFWF LGADNVLNST   240
TGTLTGKIKN TAVFNVQTEV GAAEPLDAKT PV                                 272

SEQ ID NO: 206         moltype = AA   length = 251
FEATURE                Location/Qualifiers
REGION                 1..251
                       note = variant of native sequence
source                 1..251
                       mol_type = protein
                       organism = synthetic construct
```

```
SEQUENCE: 206
MPIQEKFSFS ELSAVGSNPN SVREKFKERF GTLPDGIAVN SETYYDAVKP AITEQYGHPC    60
YKTLGEFTYQ VGNGKPPSEA ILGSNYAVNH GDEEASISLS VQGNWTETKT WSSETTTGLT   120
ISSKFTLEGV FESGAEFSVS TTVGESSSTS VSRSASSTVT VTVPPRSKKK VSMVGTMKQE   180
TMNFQAPLSV QGSFGANFPR KVEDHYFWFL GADNVLNSTT GTLTGKIKNT AVFNVQTEVG   240
AAEPLDAKTP V                                                      251

SEQ ID NO: 207           moltype = AA  length = 251
FEATURE                  Location/Qualifiers
source                   1..251
                         mol_type = protein
                         organism = Bacillus sp.
SEQUENCE: 207
MPIQEKFSFS ELSAVGSNPN SIREKFKERF GVLPDGIAVN SETYYDAAKP AITEQYGHPC    60
YKTLGEFTYQ IGNGKPPSEA ILGSNYAVNH GDEEASISLS VQGNWTETKT WSSQTTTGLT   120
ISSKFTLEGV FESGAEFSVS TTVGESSSTS ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                      251

SEQ ID NO: 208           moltype = AA  length = 252
FEATURE                  Location/Qualifiers
source                   1..252
                         mol_type = protein
                         organism = Bacillus sp.
SEQUENCE: 208
LMPIQEKFSF SELSAVGSNP NSVREKFKER FGVLPDGIAV NSETYYNAEK PAITEQYGHP    60
CYKTLGEFTY QIGNGQPPSE AILGSNYAVN HGDEEASISL SVQGNWTETK TWSSQTTTGL   120
TISSKFTLEG VFESGAEFSV STTVGESSST SISRSASSTV TVNVPPRSKK KISMVGTMKQ   180
ETMNFQAPLS VQGSFGANFP RKVEDHYFWF LGADNVLNST TGTLTGKIKN TAVFDVQTEV   240
GAAEPLDAKT PV                                                     252

SEQ ID NO: 209           moltype = AA  length = 251
FEATURE                  Location/Qualifiers
REGION                   1..251
                         note = variant of native sequence
source                   1..251
                         mol_type = protein
                         organism = synthetic construct
SEQUENCE: 209
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGESSSTS ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                      251

SEQ ID NO: 210           moltype = AA  length = 251
FEATURE                  Location/Qualifiers
REGION                   1..251
                         note = variant of native sequence
source                   1..251
                         mol_type = protein
                         organism = synthetic construct
SEQUENCE: 210
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGESSTTS ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                      251

SEQ ID NO: 211           moltype = AA  length = 251
FEATURE                  Location/Qualifiers
REGION                   1..251
                         note = variant of native sequence
source                   1..251
                         mol_type = protein
                         organism = synthetic construct
SEQUENCE: 211
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGETSSTS ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                      251

SEQ ID NO: 212           moltype = AA  length = 251
FEATURE                  Location/Qualifiers
REGION                   1..251
                         note = variant of native sequence
source                   1..251
                         mol_type = protein
```

```
                        organism = synthetic construct
SEQUENCE: 212
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGESKSTS ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                       251

SEQ ID NO: 213          moltype = AA   length = 251
FEATURE                 Location/Qualifiers
REGION                  1..251
                        note = variant of native sequence
source                  1..251
                        mol_type = protein
                        organism = synthetic construct
SEQUENCE: 213
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGESSSES ISRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                       251

SEQ ID NO: 214          moltype = AA   length = 251
FEATURE                 Location/Qualifiers
REGION                  1..251
                        note = variant of native sequence
source                  1..251
                        mol_type = protein
                        organism = synthetic construct
SEQUENCE: 214
MPIQEKFSFS ELSAVGSNPN SVREKFKERF GVLPDGIAVN SETYYNAEKP AITEQYGHPC    60
YKTLGEFTYQ IGNGQPPSEA ILGSNYAVNH GDEEASISLS VQGNWTETKT WSSQTTTGLT   120
ISSKFTLEGV FESGAEFSVS TTVGESSSTS ESRSASSTVT VNVPPRSKKK ISMVGTMKQE   180
TMNFQAPLSV QGSFGANFPR KVEDHYFWFL GADNVLNSTT GTLTGKIKNT AVFDVQTEVG   240
AAEPLDAKTP V                                                       251

SEQ ID NO: 215          moltype = AA   length = 306
FEATURE                 Location/Qualifiers
source                  1..306
                        mol_type = protein
                        organism = Bacillus sp.
SEQUENCE: 215
VERRLKFMAI FDLDVYLMEL AKKHFPPPFN QYISRIDTTS LLKVKNAESY GFEIKNSKPQ    60
GTMFMGESVL KNDTNETQTI KSDSFTKTIT DSITLSVTNG IKTGIEINVG GKVFGIGVET   120
SMSFEVSTST TREQTSTEGV AYTVPSQDVV VPAKKIYYVY TALQRSQLEG TIRLRADLFN   180
GFGIYMNIGG KEIPLGSYWI YDFIKENQSL HPLPSGISLN HNDRSVHFEG VAEYLYGTGT   240
KFNVTITDTP SSQGTQEHKP FDAKTGLGTY ELRLDGKKLG FDLNDLKEHM DPKDFEKLKE   300
MQNEIV                                                             306

SEQ ID NO: 216          moltype = AA   length = 299
FEATURE                 Location/Qualifiers
REGION                  1..299
                        note = variant of native sequence
source                  1..299
                        mol_type = protein
                        organism = synthetic construct
SEQUENCE: 216
MAIFDLDVYL MELAKKHFPP PFNQYISRID TTSLLKVKNA ESYGFEIKNS KPQGTMFMGE    60
SVLKNDTNET QTIKSDSFTK TITDSITLSV TNGIKTGIEI NVGGKVFGIG VETSMSFEVS   120
TSTTREQTST EGVAYTVPSQ DVVVPAKKIY YVYTALQRSQ LEGTIRLRAD LFNGFGIYMN   180
IGGKEIPLGS YWIYDFIKEN QSLHPLPSGI SLNHNDRSVH FEGVAEYLYG TGTKFNVTIT   240
DTPSSQGTQE HKPFDAKTGL GTYELRLDGK KLGFDLNDLK EHMDPKDFEK LKEMQNEIV    299

SEQ ID NO: 217          moltype = AA   length = 331
FEATURE                 Location/Qualifiers
source                  1..331
                        mol_type = protein
                        organism = Bacillus sp.
SEQUENCE: 217
MVRAYPDFDE MIREAAQKWS EANGLLFQNV SYSDPLTNTD TISLSVKFKD IGSLEECVEL    60
EKIRVSQAFT NNTGQQQKET FETITYVEDE YTWENDYHLV LPGQNFLTMP RLPRSAHKDI   120
NPGFLVNFFG ENQQFHTKMR ERRPIRGEVF LEPSSSATIQ LQVEKHHISQ PYEIELSILG   180
SIIVTAQDRG QEQGTDRYVG LTDLIPFLCP HKNFFSKGRA LIFLEQGTFT GILSRAIRAY   240
ATQTLHCDGK TLEYEIPLNN PLPESALQPK PMTTNATSCG CSSDRPSVVS TYSHPANPTA   300
YSQQPMTTDS TSCGCSSCMS ARSNKTLYTN Q                                 331

SEQ ID NO: 218          moltype = AA   length = 331
FEATURE                 Location/Qualifiers
source                  1..331
```

```
                    mol_type = protein
                    organism = Bacillus sp.
SEQUENCE: 218
MVRVYPDFDE  MIREAAQKWS  EANGLLFQNV  SYSDPLTNTD  TFSLNVKFKD  IGCPEECVEL   60
EKINVSQAFT  NNTGQQQKET  FETITYVEDE  YTWENDYHFV  LPGQNFLTMP  RLPRSAHKDI  120
NPGFLVNFFG  ENQQFHTKMR  ERRPIRGEVF  LEPSSSATIQ  LQVEKHHISQ  PYEIELSILG  180
SIIVTARDRG  QEQGTDRYVG  LTDLIPFLCP  YKNFFSKGRA  LIFLAQGTFT  GILSRAIHAY  240
ATQTLHCDGK  TLEYEIPLNN  TLPESALQPQ  PMKTNATSCG  CSSDRPSVVS  TYSPPANPTA  300
YSQQPMTTDS  TSCGCSSCMS  ARSNKTLYTN  Q                                   331
```

PESTICIDAL GENES AND METHODS OF USE

CROSS REFERENCE TO RELATED APPLICATION

This application is a divisional of U.S. Nonprovisional application Ser. No. 17/398,575, filed on Aug. 10, 2021, which is a divisional of U.S. Nonprovisional application Ser. No. 16/426,332, filed on May 30, 2019, now U.S. Pat. No. 11,118,190, issued Sep. 14, 2021, which is a divisional of U.S. Nonprovisional application Ser. No. 15/530,267, filed on Dec. 16, 2016, now U.S. Pat. No. 10,358,654, issued Jul. 23, 2019, which claims the benefit of U.S. Provisional Application Ser. No. 62/412,619 filed Oct. 25, 2016 and U.S. Provisional Application Ser. No. 62/270,742 filed Dec. 22, 2015, the contents of each of these applications are herein incorporated by reference in their entirety.

REFERENCE TO A SEQUENCE LISTING

The official copy of the sequence listing is submitted electronically concurrently with the specification as an XML formatted sequence listing with a file name of AgB024USDIV3_SeqList.xml, created on Sep. 11, 2023, and having a size of 398,435 bytes. The sequence listing contained in this XML formatted document is part of the specification and is herein incorporated by reference in its entirety.

BACKGROUND

Field

The invention is drawn to methods and compositions for controlling pests, particularly plant pests.

Pests, plant diseases, and weeds can be serious threats to crops. Losses due to pests and diseases have been estimated at 37% of the agricultural production worldwide, with 13% due to insects, bacteria and other organisms.

Toxins are virulence determinants that play an important role in microbial pathogenicity and/or evasion of the host immune response. Toxins from the gram-positive bacterium *Bacillus*, particularly *Bacillus thuringiensis*, have been used as insecticidal proteins. Current strategies use the genes expressing these toxins to produce transgenic crops. Transgenic crops expressing insecticidal protein toxins are used to combat crop damage from insects.

While the use of *Bacillus* toxins has been successful in controlling insects, resistance to Bt toxins has developed in some target pests in many parts of the world where such toxins have been used intensively. One way of solving this problem is sowing Bt crops with alternating rows of regular non Bt crops (refuge). An alternative method to avoid or slow down development of insect resistance is stacking insecticidal genes with different modes of action against insects in transgenic plants. The current strategy of using transgenic crops expressing insecticidal protein toxins is placing increasing emphasis on the discovery of novel toxins, beyond those already derived from the bacterium *Bacillus thuringiensis*. These toxins may prove useful as alternatives to those derived from *B. thuringiensis* for deployment in insect- and pest-resistant transgenic plants. Thus, new toxin proteins are needed.

BRIEF DESCRIPTION OF THE FIGURES

Figure 1:
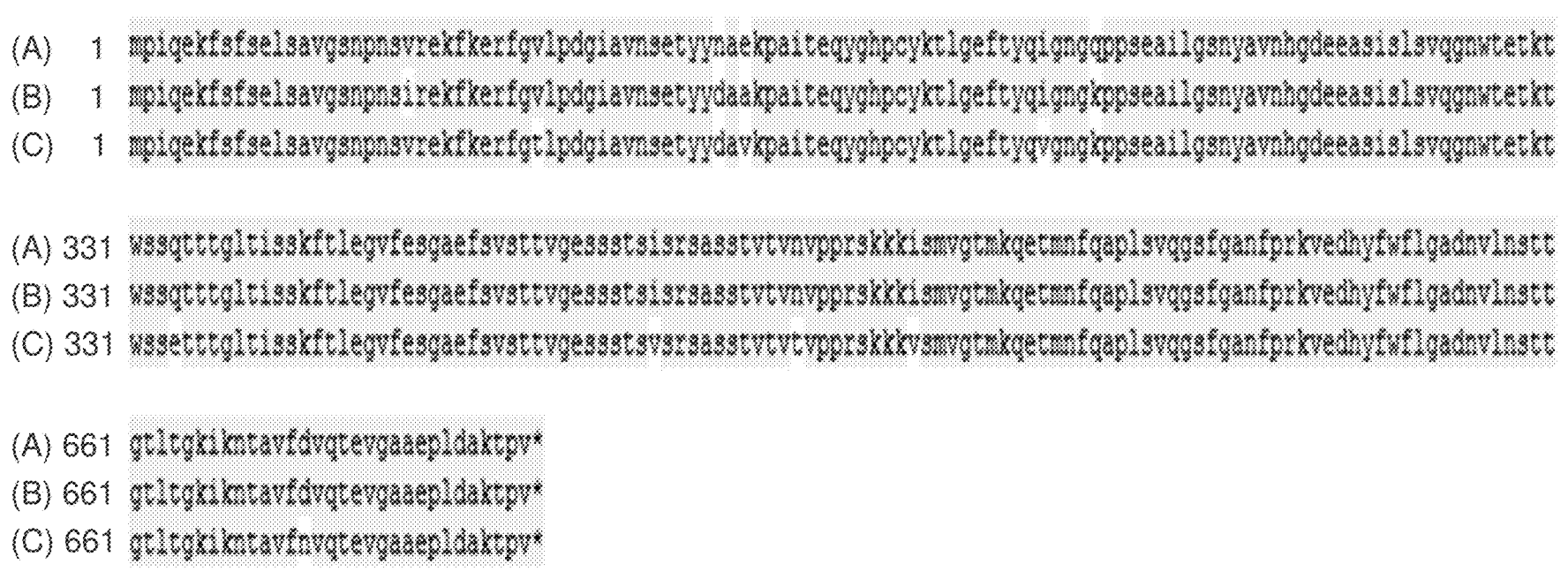

FIG. 1 provides an amino acid alignment of SEQ ID NO: 209, 207, and 206. Highlighted regions denote regions where the amino acids are the same between the three polypeptides.

FIG. 2 provides the assay scoring guidelines (size x mortality matrix) employed in the western corn rootworm bioassay. "S" indicates small in size, "m" indicates medium in size, and "b" indicated big in size.

FIG. 8 provides an alignment of SEQ ID NO: 209 against various active variants. The sequences present in the alignment are as follows: APG01037.1 (SEQ ID NO: 209); APG01037.0 (SEQ ID NO: 208); APG01037.4 (SEQ ID NO: 210); APG01037.5 (SEQ ID NO: 211); APG01037.6 (SEQ ID NO: 212); APG01037.7 (SEQ ID NO: 213); APG01037.8 (SEQ ID NO: 214); APG00556.0 (SEQ ID NO: 205); APG00556.1 (SEQ ID NO: 206); and APG00623.0 (SEQ ID NO: 207).

FIG. 9 provides the sequences identity relationships of various active variants of SEQ ID NO: 209.

SUMMARY

Figure 3:
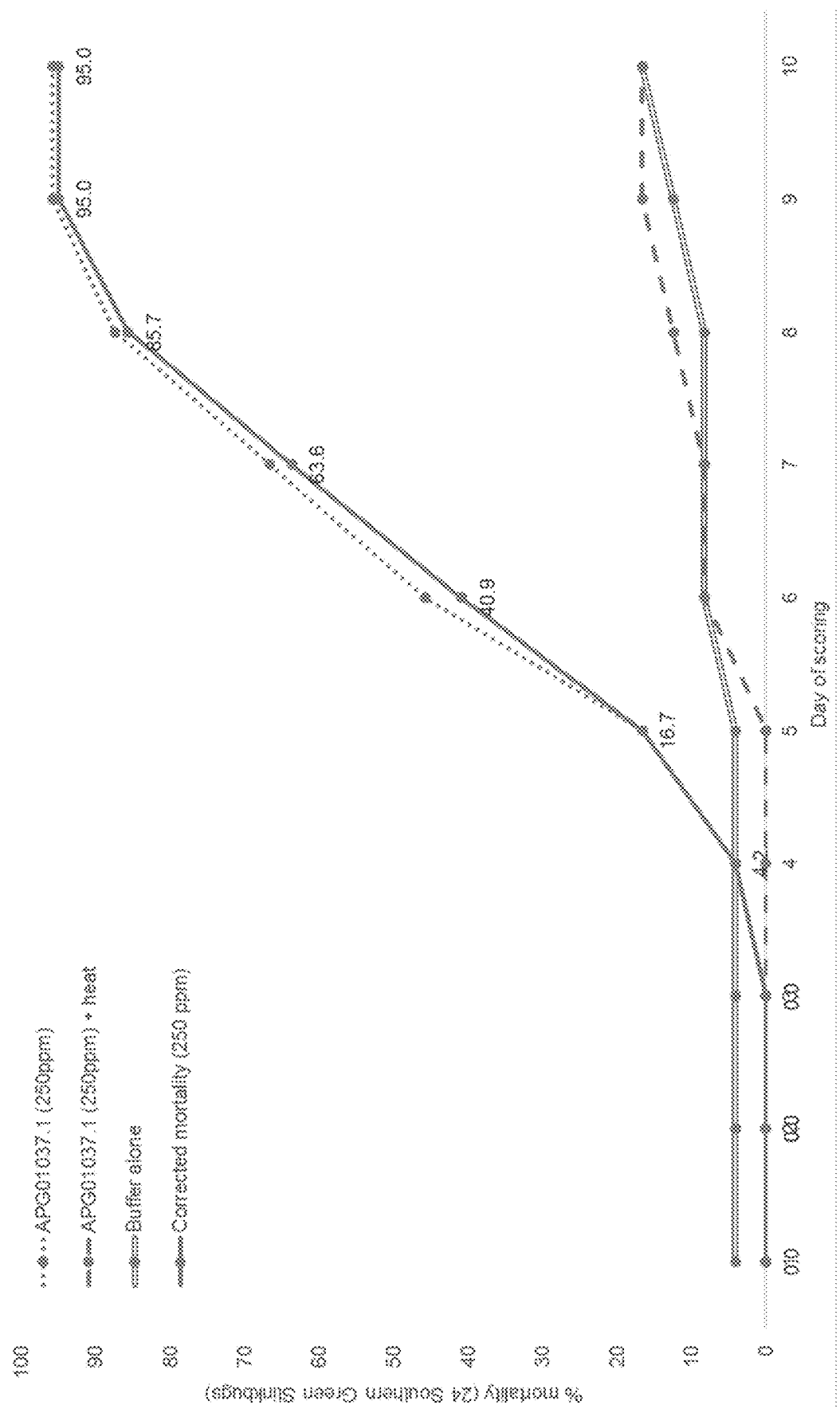
FIG. 3 provides the results of the time course assay of APG01037.1 (SEQ ID NO: 209) against SGSB.

Compositions having pesticidal activity and methods for their use are provided. Compositions include isolated and recombinant polypeptide sequences having pesticidal activity, recombinant and synthetic nucleic acid molecules encoding the pesticidal polypeptides, DNA constructs comprising the nucleic acid molecules, vectors comprising the nucleic acid molecules, host cells comprising the vectors, and antibodies to the pesticidal polypeptides. Nucleotide sequences encoding the polypeptides provided herein can be used in DNA constructs or expression cassettes for transformation and expression in organisms of interest, including microorganisms and plants.

The compositions and methods provided herein are useful for the production of organisms with enhanced pest resistance or tolerance. These organisms and compositions comprising the organisms are desirable for agricultural purposes. Transgenic plants and seeds comprising a nucleotide sequence that encodes a pesticidal protein of the invention are also provided. Such plants are resistant to insects and other pests.

Methods are provided for producing the various polypeptides disclosed herein, and for using those polypeptides for controlling or killing a pest. Methods and kits for detecting polypeptides of the invention in a sample are also included.

DETAILED DESCRIPTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Polynucleotides and Polypeptides

Compositions and method for conferring pesticidal activity to an organism are provided. The modified organism exhibits pesticidal resistance or tolerance. Recombinant pesticidal proteins, or polypeptides and fragments and variants thereof that retain pesticidal activity, are provided and include those set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218. The pesticidal proteins are biologically active (e.g., pesticidal) against pests including insects, fungi, nematodes, and the like. Nucleotides encoding the pesticidal polypeptides, including for example, SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218 or active fragments or variants thereof, can be used to produce transgenic organisms, such as plants and microorganisms. The pesticidal proteins are biologically active (for example, are pesticidal) against pests including insects, fungi, nematodes, and the like. Polynucleotides encoding the pesticidal polypeptides, including for example, SEQ ID NOS: 1-218 or active fragments or variants thereof, can be used to produce transgenic organisms, such as plants and microorganisms. The transformed organisms are characterized by genomes that comprise at least one stably incorporated DNA construct comprising a coding sequence for a pesticidal protein disclosed herein. In some embodiments, the coding sequence is operably linked to a promoter that drives expression of the encoded pesticidal polypeptide. Accordingly, transformed microorganisms, plant cells, plant tissues, plants, seeds, and plant parts are provided. A summary of various polypeptides, active variants and fragments thereof, and polynucleotides encoding the same are set forth below in Table 1. As noted in Table 1, various forms of polypeptides are provided. Full length pesticidal polypeptides, as well as, modified versions of the original full-length sequence (i.e., variants) are provided. Table 1 further denotes "CryBP1" sequences. Such sequences (SEQ ID NOS: 103 and 178) comprise accessory polypeptides that can be associated with some of the toxin genes. In such instances, the CryBP1 sequences can be used alone or in combination with any of the pesticidal polypeptides provided herein. Table 1 further provides Split-Cry C-terminus polypeptides (SEQ ID NO: 30, 112, 135, 193, or 203). Such sequence comprises the sequence of a downstream protein that has homology to the C-terminal end of the Cry class of toxin genes and are usually found after a Cry gene that is not full-length and is missing the expected C-terminal region.

TABLE 1

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00326 | 1 | 2, 3 | | | Cry4A | 85, 90, 95, 96, 97, 98, 99 | 90, 95, 96, 97, 98, 99 | Cry4Aa2 (80.48% identity, 86.85% similarity) ABM97547.1 (79.57% identity, 86.35% similarity) ABR12216.1 (79.24% identity, 86.02% similarity) A9XI31_BACTU (79.16% identity, 85.94% similarity) |
| APG00343 | 4 | 5 | | | Cry | 60, 65, 70, 75, 80, 85, 90, 95, 96, 97, 98, 99 | 75, 80, 85, 90, 95, 96, 97, 98, 99 | APG00514 (89.36% identity, 94.53% similarity) |

TABLE 1-continued Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | APG00654 (80.12% identity, 87.72% similarity) APG00164 (77.19% identity, 84.36% similarity) CBL59393.1 (56.49% identity, 72.61% similarity) CBL59396.1 (56.49% identity, 72.47% similarity) D5H3I8_BACTG (56.35% identity, 72.47% similarity) APG00084 (52.79% identity, 69.81% similarity) Cry8Aa1 (35.34% identity, 43.05% similarity) |
| APG00383 | 6 | 7 | | | Cry | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00101 (96.93% identity, 97.16% similarity) APG00034 (61.93% identity, 74.85% similarity) APG00048 (52.09% identity, 63.77% similarity) US_2011_0231963_A1-9 (37.27% identity, 51.39% similarity) Cry13Aa1 (36.96% identity, 53.97% similarity) |
| APG00493 | 8 | 9 | | | Mtx | 90, 95, 96, 97, 98, 99 | 90, 95, 96, 97, 98, 99 | WP_020294695.1 (85.08% identity, 89.15% similarity) US20140007292A1_4 (84.41% identity, 88.81% similarity) US20140007292A1_2 (82.71% identity, 88.14% similarity) US20140007292A1_332 (76.61% identity, 83.39% similarity) APG00659 (72.26% identity, 80.0% similarity) |
| APG00494 | 10 | 11 | | | Bin | 90, 95, 96, 97, 98, 99 | 95, 96, 97, 98, 99 | APG00731 (89.01% identity, 93.03% similarity) APG00669 (88.2% identity, 92.49% similarity) APG00035 (87.67% identity, 92.76% similarity) APG00568 (86.86% identity, 91.96% similarity) WP_000143307.1 (86.6% identity, 91.69% similarity) APG00356 (86.6% identity, 91.96% similarity) APG00284 (86.06% identity, 92.23% similarity) WP_000143308.1 |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | (85.79% identity, 91.69% similarity) WP_050845516.1 (84.18% identity, 90.35% similarity) APG00735 (75.19% identity, 82.78% similarity) Cry35Ac2 (22.22% identity, 41.06% similarity) |
| APG00495 | 12 | 13 | | | Mtx | 80, 85, 90, 95, 96, 97, 98, 99 | 85, 90, 95, 96, 97, 98, 99 | WP_016099228.1 (75.77% identity, 82.52% similarity) APG00693 (70.06% identity, 79.64% similarity) AGP17978.1 (68.77% identity, 78.98% similarity) APG00049 (50.76% identity, 62.69% similarity) EEM56710.1 (50.46% identity, 64.74% similarity) WP_008180054.1 (50.3% identity, 63.94% similarity) |
| APG00513 | 14 | | | | Mtx | 65, 70, 75, 80, 85, 90, 95, 96, 97, 98, 99 | 80, 85, 90, 95, 96, 97, 98, 99 | APG00846 (85.63% identity, 91.38% similarity) AGA40030.1 (62.71% identity, 77.12% similarity) APG00609 (53.44% identity, 69.15% similarity) APG00224 (53.33% identity, 69.44% similarity) CAA67205.1 (43.06% identity, 60.06% similarity) AGA40032.1 (40.93% identity, 53.85% similarity) R8R7A7_BACCE (20.75% identity, 31.6% similarity) |
| APG00514 | 15 | 16 | | | Cry | 60, 65, 70, 75, 80, 85, 90, 95, 96, 97, 98, 99 | 75, 80, 85, 90, 95, 96, 97, 98, 99 | APG00343 (89.36% identity, 94.53% similarity) APG00654 (81.47% identity, 88.38% similarity) APG00164 (78.09% identity, 85.29% similarity) CBL59393.1 (56.7% identity, 72.36% similarity) CBL59396.1 (56.55% identity, 72.36% similarity) D5H3I8_BACTG (56.55% identity, 72.22% similarity) APG00084 (52.7% identity, 69.18% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | similarity) Cry8Aa1 (36.45% identity, 43.86% similarity) |
| APG00524 | 17 | 18, 19 | | | Cry14 | 55, 60, 65, 70, 75, 80, 85, 90, 95, 96, 97, 98, 99 | 70, 75, 80, 85, 90, 95, 96, 97, 98, 99 | APG00651 (77.43% identity, 84.21% similarity) Cry14Aa1 (54.15% identity, 67.51% similarity) APG00052 (52.77% identity, 65.77% similarity) Cry21Ba1 (45.51% identity, 61.62% similarity) Cry21Ca2 (43.99% identity, 60.21% similarity) |
| APG00528 | 20 | | | | Mtx | 55, 60, 65, 70, 75, 80, 85, 90, 95, 96, 97, 98, 99 | 65, 70, 75, 80, 85, 90, 95, 96, 97, 98, 99 | APG00661 (57.14% identity, 66.98% similarity) US_2008_0070829_A1-25 (54.57% identity, 64.87% similarity) AGA40029.1 (53.41% identity, 62.82% similarity) CAA63374.1 (41.55% identity, 51.37% similarity) AGA40031.1 (41.41% identity, 54.12% similarity) |
| APG00533 | 21 | | | | Cry11B | 80, 85, 90, 95, 96, 97, 98, 99 | 85, 90, 95, 96, 97, 98, 99 | APG00607 (97.89% identity, 97.89% similarity) Cry11Bb1 (77.26% identity, 84.18% similarity) ADI59541.1 (74.56% identity, 80.60% similarity) Cry11Ba1 (74.13% identity, 82.44% similarity) AEK06469.1 (67.07% identity, 73.79% similarity) |
| APG00534 | 22 | 23 | | | Cry | 50, 55, 60, 65, 70, 75, 80, 85, 90, 95, 96, 97, 98, 99 | 65, 70, 75, 80, 85, 90, 95, 96, 97, 98, 99 | APG00120 (82.82% identity, 88.17% similarity) WP_001070417.1 (45.9% identity, 60.78% similarity) Cry41Ba2 (44.35% identity, 59.13% similarity) Cry41Aa1 (41.39% identity, 56.51% similarity) Cry41Ab1 (38.61% identity, 54.79% similarity) |
| APG00536 | 24 | 25, 26 | | | Cry | 85, 90, 95, 96, 97, 98, 99 | 90, 95, 96, 97, 98, 99 | WO_2014_138339-52 (83.47% identity, 88.74% similarity) APG00046 (83.47% identity, 88.74% similarity) WO_2014_138339-53 (83.35% identity, 88.5% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00537 | 27 | 28, 29 | | 30 | Cry53A | 85, 90, 95, 96, 97, 98, 99 | 90, 95, 96, 97, 98, 99 | WO_2014_138339-54 (76.65% identity, 80.24% similarity) Cry68Aa1 (33.02% identity, 46.38% similarity) AGP17986.1 (83.11% identity, 87.81% similarity) WP_014990538.1 (80.7% identity, 86.26% similarity) ACP43734.1 (80.26% identity, 85.96% similarity) APG00606 (77.73% identity, 82.82% similarity) Cry53Aa1 (77.29% identity, 83.41% similarity) |
| APG00543 | 31 | 32 | | | Cry27A | 90, 95, 96, 97, 98, 99 | 95, 96, 97, 98, 99 | WP_016098322.1 (89.92% identity, 94.26% similarity) AGV55018.1 (86.13% identity, 89.02% similarity) Cry27Aa1 (75.99% identity, 83.43% similarity) WO_2014_102697-1 (40.07% identity, 53.93% similarity) WO_2014_102697-2 (39.83% identity, 53.39% similarity) |
| APG00555 | 33 | 34, 35 | | | Cry | 75, 80, 85, 90, 95, 96, 97, 98, 99 | 85, 90, 95, 96, 97, 98, 99 | CA_2843744-20 (71.12% identity, 80.7% similarity) CA_2843744-22 (69.81% identity, 79.1% similarity) APG01028 (66.91% identity, 76.83% similarity) US20130227743A1_26 (59.91% identity, 73.13% similarity) APG00039 (50.93% identity, 63.04% similarity) Cry53Aa1 (39.83% identity, 55.76% similarity) |
| APG00557 | 36 | 37 | | | Bin | 30, 35, 40, 45, 50, 55, 60, 65, 70, 75, 80, 85, 90, 95, 96, 97, 98, 99 | 45, 50, 55, 60, 65, 70, 75, 80, 85, 90, 95, 96, 97, 98, 99 | APG00050 (60.99% identity, 71.39% similarity) APG00461 (46.58% identity, 59.62% similarity) APG00474 (43.05% identity, 53.67% similarity) APG00629 (42.52% identity, 56.78% similarity) Cry49Aa1 (29.92% identity, 42.37% similarity) |
| APG00558 | 38 | 39, 40 | | | Cry | 45, 50, 55, 60, 65, 70, 75, 80, 85, 90, 95, 96, 97, 98, 99 | 60, 65, 70, 75, 80, 85, 90, 95, 96, 97, 98, 99 | AGV55021.1 (42.52% identity, 56.5% similarity) APG00153 (36.59% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | identity, 50.49% similarity) Cry53Aa1 (33.51% identity, 50.0% similarity) |
| APG00565 | 41 | 42, 43 | | | Cry30D | 90, 95, 96, 97, 98, 99 | 95, 96, 97, 98, 99 | Cry30Db1 (88.73% identity, 90.87% similarity) Cry30Da1 (86.31% identity, 89.87% similarity) Cry30Ga2 (70.54% identity, 78.19% similarity) Cry30Ga1 (69.97% identity, 77.76% similarity) ADK47393.1 (69.96% identity, 77.86% similarity) APG00972 (63.5% identity, 75.94% similarity) |
| APG00566 | 44 | 45 | | | Mtx | 75, 80, 85, 90, 95, 96, 97, 98, 99 | 85, 90, 95, 96, 97, 98, 99 | APG01086 (97.39% identity, 99.02% similarity) APG00201 (82.03% identity, 91.5% similarity) APG00006 (80.07% identity, 90.52% similarity) APG00260 (78.43% identity, 88.24% similarity) APG00036 (75.24% identity, 84.04% similarity) APG00022 (75.16% identity, 83.33% similarity) WP_000963933.1 (73.62% identity, 84.04% similarity) US20130227743A1_100 (72.22% identity, 83.33% similarity) US20130227743A1_60 (45.1% identity, 50.33% similarity) ABV97497.1 (24.15% identity, 39.49% similarity) |
| APG00572 | 46 | | | | PI-PLC | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | WP_016084067.1 (38.65% identity, 50.15% similarity) WP_000836979.1 (38.12% identity, 49.85% similarity) EEM93103.1 (37.91% identity, 49.05% similarity) Cry73Aa (17.75% identity, 29.44% similarity) |
| APG00587 | 47 | 48 | | | Cry | 50, 55, 60, 65, 70, 75, 80, 85, 90, 95, 96, 97, 98, 99 | 65, 70, 75, 80, 85, 90, 95, 96, 97, 98, 99 | WP_048536363.1 (45.21% identity, 60.54% similarity) WP_048536362.1 (31.16% identity, 46.29% similarity) US20130227743A1_200 (27.52% identity, |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | 44.36% similarity) Cry42Aa1 (14.96% identity, 24.9% similarity) |
| APG00939 | 49 | 50 | | | Vip3 | 95, 96, 97, 98, 99 | 97, 98, 99 | WP_048517127.1 (94.07% identity, 96.88% similarity) APG00077 (81.86% identity, 88.35% similarity) APG00278 (81.14% identity, 86.94% similarity) APG00875 (80.82% identity, 86.19% similarity) APG00173 (80.0% identity, 86.19% similarity) APG00175 (80.0% identity, 86.6% similarity) APG00657 (73.63% identity, 82.73% similarity) APG01003 (72.64% identity, 80.23% similarity) WP_050001316.1 (67.11% identity, 78.07% similarity) CA_2866166-1528 (23.27% identity, 39.55% similarity) Vip3Aa18 (23.21% identity, 40.48% similarity) |
| APG00606 | 51 | 52, 53 | | | Cry53 | 80, 85, 90, 95, 96, 97, 98, 99 | 85, 90, 95, 96, 97, 98, 99 | APG00537 (77.73% identity, 82.82% similarity) WP_014990538.1 (76.17% identity, 82.6% similarity) ACP43734.1 (76.02% identity, 82.6% similarity) AGP17986.1 (75.98% identity, 82.53% similarity) Cry53Aa1 (71.93% identity, 79.68% similarity) APG01028 (54.05% identity, 66.71% similarity) |
| APG00607 | 54 | | | | Cry11B | 80, 85, 90, 95, 96, 97, 98, 99 | 85, 90, 95, 96, 97, 98, 99 | APG00533 (97.89% identity, 97.89% similarity) Cry11Bb1 (77.49% identity, 83.77% similarity) |
| APG00608 | 55 | 56 | | | Cry | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00034 (49.72% identity, 62.43% similarity) APG00002 (44.42% identity, 56.00% similarity) APG00383 (43.43% identity, 58.13% similarity) APG00101 (42.70% identity, 56.97% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00609 | 57 | | | | Mtx | 65, 70, 75, 80, 85, 90, 95, 96, 97, 98, 99 | 75, 80, 85, 90, 95, 96, 97, 98, 99 | APG00048 (40.55% identity, 54.86% similarity) Cry13Aa1 (38.05% identity, 53.68% similarity) APG00224 (63.1% identity, 73.52% similarity) AGA40030.1 (60.72% identity, 71.87% similarity) APG00513 (53.44% identity, 69.15% similarity) APG00846 (52.62% identity, 67.49% similarity) AGA40032.1 (39.61% identity, 54.21% similarity) CAA67205.1 (39.6% identity, 57.83% similarity) C4B693_CLOBO (20.11% identity, 35.92% similarity) |
| APG00622 | 58 | 59 | | | Cry5 | 60, 65, 70, 75, 80, 85, 90, 95, 96, 97, 98, 99 | 70, 75, 80, 85, 90, 95, 96, 97, 98, 99 | Cry5Ba1 (56.24% identity, 65.33% similarity) Cry5Ba2 (56.24% identity, 65.27% similarity) Cry5Ba3 (56.03% identity, 65.13% similarity) APG00217 (53.75% identity, 62.25% similarity) |
| APG00624 | 60 | 61 | | | Cyt | 45, 50, 55, 60, 65, 70, 75, 80, 85, 90, 95, 96, 97, 98, 99 | 60, 65, 70, 75, 80, 85, 90, 95, 96, 97, 98, 99 | Cyt1Da1 (43.72% identity, 58.52% similarity) WP_000079177.1 (42.96% identity, 60.14% similarity) WP_043939324.1 (42.42% identity, 59.28% similarity) |
| APG00637 | 62 | 63, 64 | | | Cry | 60, 65, 70, 75, 80, 85, 90, 95, 96, 97, 98, 99 | 70, 75, 80, 85, 90, 95, 96, 97, 98, 99 | APG00115 (92.62% identity, 94.99% similarity) US_2015_0218583_A1-3 (57.11% identity, 65.14% similarity) EJR93120.1 (56.83% identity, 67.66% similarity) AGP18037.1 (54.79% identity, 64.79% similarity) Cry32Ea1 (36.19% identity, 48.14% similarity) |
| APG00638 | 65 | | | | PI-PLC | 80, 85, 90, 95, 96, 97, 98, 99 | 90, 95, 96, 97, 98, 99 | WP_050845433.1 (79.88% identity, 86.65% similarity) AGA40046.1 (68.23% identity, 79.34% similarity) WP_000513490.1 (67.84% identity, 78.36% similarity) Cyt1Da1 (22.69% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | identity, 34.85% similarity) |
| APG00641 | 66 | 67 | | | Mtx | 35, 40, 45, 50, 55, 60, 65, 70, 75, 80, 85, 90, 95, 96, 97, 98, 99 | 50, 55, 60, 65, 70, 75, 80, 85, 90, 95, 96, 97, 98, 99 | APG00807 (73.68% identity, 82.57% similarity) APG00434 (49.68% identity, 66.77% similarity) WP_054770413.1 (31.91% identity, 47.42% similarity) Cry64Aa1 (31.68% identity, 47.2% similarity) |
| APG00643 | 68 | 69 | | | Cry | 85, 90, 95, 96, 97, 98, 99 | 90, 95, 96, 97, 98, 99 | APG00800 (87.98% identity, 93.99% similarity) WP_012259841.1 (80.77% identity, 88.77% similarity) US20130227743A1_24 (78.12% identity, 84.75% similarity) APG00088 (64.81% identity, 75.19% similarity) WP_025988975.1 (62.92% identity, 67.17% similarity) Cry8Ca1 (24.72% identity, 34.83% similarity) |
| APG00644 | 70 | 71, 72 | | | Cry | 60, 65, 70, 75, 80, 85, 90, 95, 96, 97, 98, 99 | 65, 70, 75, 80, 85, 90, 95, 96, 97, 98, 99 | US20130227743A1_202 (58.97% identity, 63.99% similarity) WP_048536362.1 (20.86% identity, 34.16% similarity) AFU11621.1 (19.84% identity, 32.76% similarity) US20130227743A1_204 (19.27% identity, 32.47% similarity) |
| APG00648 | 73 | 74 | | | Bin | 70, 75, 80, 85, 90, 95, 96, 97, 98, 99 | 80, 85, 90, 95, 96, 97, 98, 99 | APG00261 (69.58% identity, 79.05% similarity) APG00988 (67.83% identity, 77.06% similarity) WP_001258160.1 (66.17% identity, 78.7% similarity) WP_001258161.1 (66.17% identity, 78.7% similarity) US20130227743A1_10 (66.0% identity, 78.5% similarity) APG00223 (61.22% identity, 71.43% similarity) APG00454 (61.22% identity, 71.43% similarity) APG00242 (61.0% identity, 71.2% similarity) APG00335 (60.77% identity, 71.2% similarity) APG00724 (55.9% identity, 68.19% |

TABLE 1-continued

| Summary of SEQ ID NOs, Gene Class, and Variants thereof | | | | | | | | |
|---|---|---|---|---|---|---|---|---|
| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
| | | | | | | | | similarity)<br>APG00716 (55.09% identity, 69.23% similarity)<br>APG00806 (52.8% identity, 64.96% similarity)<br>Cry35Ab4 (22.58% identity, 38.02% similarity) |
| APG00649 | 75 | 76 | | | Bin | 70, 75, 80, 85, 90, 95, 96, 97, 98, 99 | 85, 90, 95, 96, 97, 98, 99 | APG00413 (69.63% identity, 81.68% similarity)<br>APG00230 (68.23% identity, 81.25% similarity)<br>WP_017154552.1 (67.72% identity, 80.31% similarity)<br>WP_050001305.1 (67.62% identity, 79.9% similarity)<br>US_2014_0033363_A1-2 (66.06% identity, 78.76% similarity)<br>APG00596 (65.28% identity, 77.98% similarity)<br>APG00373 (65.27% identity, 77.02% similarity)<br>APG00090 (63.45% identity, 78.85% similarity)<br>Cry35Ab2 (22.78% identity, 34.17% similarity) |
| APG00651 | 77 | 78 | | | Cry14 | 60, 65, 70, 75, 80, 85, 90, 95, 96, 97, 98, 99 | 75, 80, 85, 90, 95, 96, 97, 98, 99 | APG00524 (77.43% identity, 84.21% similarity)<br>Cry14Aa1 (57.4% identity, 70.63% similarity)<br>APG00052 (54.52% identity, 68.23% similarity) |
| APG00657 | 79 | 80 | | | Vip3 | 75, 80, 85, 90, 95, 96, 97, 98, 99 | 85, 90, 95, 96, 97, 98, 99 | APG00175 (74.79% identity, 82.85% similarity)<br>APG00939 (73.63% identity, 82.73% similarity)<br>APG00077 (73.33% identity, 81.8% similarity)<br>WP_048517127.1 (73.21% identity, 82.55% similarity)<br>APG00273 (72.12% identity, 81.66% similarity)<br>APG00278 (71.29% identity, 80.48% similarity)<br>APG00173 (71.03% identity, 80.48% similarity)<br>APG01003 (67.97% identity, 78.06% similarity)<br>WP_050001316.1 (66.7% identity, 78.35% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00659 | 81 | 82 | | | Mtx | 80, 85, 90, 95, 96, 97, 98, 99 | 85, 90, 95, 96, 97 98, 99 | Vip3Aa13 (23.92% identity, 39.9% similarity) US20140007292A1_332 (79.39% identity, 84.46% similarity) CA_2878263-105 (78.04% identity, 84.8% similarity) US20140007292A1_2 (76.01% identity, 83.11% similarity) WP_020294695.1 (75.68% identity, 83.78% similarity) APG00493 (72.26% identity, 80.0% similarity) |
| APG00661 | 83 | | | | Mtx | 85, 90, 95, 96, 97, 98, 99 | 95, 96, 97, 98, 99 | APG06508 (96.41% identity, 97.31% similarity) APG09801 (94.91% identity, 97.01% similarity) US_2008_0070829_A1-25 (83.63% identity, 90.48% similarity) AGA40029.1 (74.63% identity, 84.78% similarity) CAA63374.1 (58.4% identity, 68.09% similarity) APG00528 (57.14% identity, 66.98% similarity) AGA40031.1 (46.57% identity, 63.58% similarity) |
| APG00662 | 84 | 85, 86 | | | Cry69 | 75, 80, 85, 90, 95, 96, 97, 98, 99 | 85, 90, 95, 96, 97, 98, 99 | APG00079 (77.58% identity, 85.14% similarity) CA_2753918-13 (72.5% identity, 80.38% similarity) US_2011_0197314_A1-13 (72.5% identity, 80.3% similarity) APG00786 (70.46% identity, 77.45% similarity) AFU17214.1 (66.67% identity, 76.58% similarity) APG00059 (65.69% identity, 75.59% similarity) Cry69Aa1 (63.54% identity, 73.38% similarity) |
| APG00663 | 87 | 88 | | | Cry5 | 50, 55, 60, 65, 70, 75, 80, 85, 90, 95, 96, 97, 98, 99 | 65, 70, 75, 80, 85, 90, 95, 96, 97, 98, 99 | APG00217 (51.48% identity, 62.91% similarity) Cry5Ca2 (49.46% identity, 61.2% similarity) Cry5Ba1 (49.27% identity, 60.66% similarity) Cry5Ba3 (49.16% identity, 60.75% similarity) Cry5Ba2 (49.12% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | identity, 60.58% similarity) |
| APG00664 | 89 | 90 | | | Cry54 | 65, 70, 75, 80, 85, 90, 95, 96, 97, 98, 99 | 75, 80, 85, 90, 95, 96, 97, 98, 99 | AGA40050.1 (60.55% identity, 72.55% similarity) Cry54Aa2 (59.72% identity, 71.59% similarity) APG00864 (58.9% identity, 70.48% similarity) Cry54Aa1 (56.40% identity, 68.39% similarity) AFU17297.1 (55.65% identity, 66.80% similarity) |
| APG00672 | 91 | 92 | | | Cry | 95, 96, 97, 98, 99 | 96, 97, 98, 99 | AGA40064.1 (91.5% identity, 95.46% similarity) APG00045 (83.92% identity, 90.26% similarity) APG00110 (61.34% identity, 73.07% similarity) WP_016110336.1 (49.54% identity, 63.7% similarity) AGP18054.1 (31.23% identity, 47.85% similarity) Cry70Ba1 (23.84% identity, 40.99% similarity) |
| APG00673 | 93 | 94, 95 | | | Cry32 | 70, 75, 80, 85, 90, 95, 96, 97, 98, 99 | 80, 85, 90, 95, 96, 97, 98, 99 | Cry32Ea1 (66.69% identity, 75.3% similarity) AGU13851.1 (66.69% identity, 75.19% similarity) APG00054 (59.06% identity, 69.02% similarity) APG00310 (57.34% identity, 67.43% similarity) APG00068 (56.63% identity, 68.54% similarity) APG00469 (54.97% identity, 66.89% similarity) APG00710 (51.05% identity, 61.25% similarity) APG00687 (50.5% identity, 61.08% similarity) |
| APG00674 | 96 | | | | Bin | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00472 (71.06% identity, 83.67% similarity) APG00642 (69.71% identity, 80.86% similarity) WP_029439068.1 (35.26% identity, 50.96% similarity) WP_002187944.1 (31.71% identity, 47.56% similarity) WP_028595059.1 (31.41% identity, |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00675 | 97 | | | | Vip3 | 35, 40, 45, 50, 55, 60, 65, 70, 75, 80, 85, 90, 95, 96, 97, 98, 99 | 45, 50, 55, 60, 65, 70, 75, 80, 85, 90, 95, 96, 97, 98, 99 | 47.49% similarity) Cry35Aa2 (24.76% identity, 40.0% similarity) APG00131 (62.46% identity, 78.65% similarity) APG00181 (60.35% identity, 74.87% similarity) APG00038 (60.35% identity, 74.26% similarity) Vip3Ba1 (30.77% identity, 44.23% similarity) |
| APG00677 | 98 | | | | Cry | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00003 (65.55% identity, 77.44% similarity) BAE79727.1 (35.46% identity, 51.52% similarity) KIQ78015.1 (34.63% identity, 50.13% similarity) US20130227743A1_74 (34.18% identity, 49.67% similarity) Cry4Aa1 (21.23% identity, 30.85% similarity) |
| APG00679 | 99 | 100 | | | Cry1D | 80, 85, 90, 95, 96, 97, 98, 99 | 90, 95, 96, 97, 98, 99 | Cry1Db1 (77.55% identity, 85.86% similarity) Cry1Da1 (77.52% identity, 84.87% similarity) Cry1Db2 (77.46% identity, 85.78% similarity) AEH31432.1 (77.35% identity, 85.04% similarity) WP_000405159.1 (77.35% identity, 85.13% similarity) |
| APG00687 | 101 | 102 | | 103 | Cry32C | 90, 95, 96, 97, 98, 99 | 95, 96, 97, 98, 99 | AGU13873.1 (85.7% identity, 90.23% similarity) Cry32Ca1 (84.22% identity, 89.92% similarity) APG00710 (55.17% identity, 65.22% similarity) APG00430 (54.82% identity, 64.77% similarity) APG00469 (53.5% identity, 64.89% similarity) APG00056 (52.93% identity, 65.09% similarity) APG00058 (50.85% identity, 63.43% similarity) APG00105 (50.75% identity, 62.69% similarity) APG00673 (50.5% identity, 61.08% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00688 | 104 | 105 | | | Cry | 40, 45, 50, 55, 60, 65, 70, 75, 80, 85, 90, 95, 96, 97, 98, 99 | 45, 50, 55, 60, 65, 70, 75, 80, 85, 90, 95, 96, 97, 98, 99 | AGU13850.1 (36.79% identity, 44.66% similarity) AGU13871.1 (34.44% identity, 43.46% similarity) AGU13875.1 (32.76% identity, 40.49% similarity) Cry32Ea1 (29.64% identity, 40.09% similarity) |
| APG00693 | 106 | 107, 108 | | | Mtx | 85, 90, 95, 96, 97, 98, 99 | 90, 95, 96, 97, 98, 99 | AGP17978.1 (81.23% identity, 88.0% similarity) WP_016099228.1 (80.62% identity, 86.46% similarity) APG00495 (70.06% identity, 79.64% similarity) EEM56710.1 (50.46% identity, 66.57% similarity) WP_008180054.1 (50.0% identity, 65.85% similarity) |
| APG00695 | 109 | 110, 111 | | 112 | Cry40D | 80, 85, 90, 95, 96, 97, 98, 99 | 90, 95, 96, 97, 98, 99 | Cry40Da1 (79.91% identity, 86.06% similarity) APG00204 (61.61% identity, 74.7% similarity) APG00111 (52.52% identity, 61.84% similarity) |
| APG00701 | 113 | 114 | | | Bin | 70, 75, 80, 85, 90, 95, 96, 97, 98, 99 | 85, 90, 95, 96, 97, 98, 99 | WP_002191947.1 (69.07% identity, 81.44% similarity) APG00243 (68.99% identity, 80.36% similarity) WP_000839920.1 (68.86% identity, 80.51% similarity) WP_002166959.1 (68.81% identity, 81.44% similarity) APG00065 (66.91% identity, 77.94% similarity) APG00459 (66.1% identity, 77.8% similarity) APG00412 (65.83% identity, 77.64% similarity) APG00132 (65.6% identity, 78.87% similarity) APG00806 (64.75% identity, 77.75% similarity) APG00716 (63.5% identity, 77.89% similarity) APG00724 (63.05% identity, 74.88% similarity) APG00988 (61.32% identity, 75.06% similarity) Cry35Ab3 (23.53% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00702 | 115 | 116 | | | Cry | 65, 70, 75, 80, 85, 90, 95, 96, 97, 98, 99 | 75, 80, 85, 90, 95, 96, 97, 98, 99 | identity, 38.82% similarity), WP_048536362.1 (62.74% identity, 70.16% similarity) APG00401 (60.03% identity, 71.78% similarity) APG00255 (59.87% identity, 71.62% similarity) WP_048536324.1 (43.52% identity, 56.17% similarity) WP_048536363.1 (33.39% identity, 49.37% similarity) Cry73Aa (19.2% identity, 29.02% similarity) |
| APG00703 | 117 | 118, 119 | | | Cry | 80, 85, 90, 95, 96, 97, 98, 99 | 85, 90, 95, 96, 97, 98, 99 | AGP18005.1 (77.0% identity, 84.57% similarity) AGA40033.1 (51.02% identity, 64.04% similarity) AEH76823.1 (49.6% identity, 61.56% similarity) Cry21Ca2 (40.2% identity, 55.84% similarity) |
| APG00705 | 120 | 121, 122, 123, 124, 125 | | | Cry70B | 95, 96, 97, 98, 99 | 96, 97, 98, 99 | ETT82181.1 (91.91% identity, 95.59% similarity) Cry70Bb1 (91.67% identity, 95.71% similarity) WP_016093954.1 (91.67% identity, 95.34% similarity) APG00526 (86.9% identity, 92.53% similarity) APG00025 (84.82% identity, 91.55% similarity) APG00728 (84.09% identity, 90.94% similarity) APG00595 (65.25% identity, 77.64% similarity) APG00027 (57.19% identity, 72.54% similarity) |
| APG00706 | 126 | | | | Bin | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00063 (39.49% identity, 51.87% similarity) Cry49Ab1 (39.13% identity, 52.96% similarity) |
| APG00707 | 127 | 128 | | | Mtx | 60, 65, 70, 75, 80, 85, 90, 95, 96, 97, 98, 99 | 75, 80, 85, 90, 95, 96, 97, 98, 99 | APG00939 (55.76% identity, 68.48% similarity) AGA40045.1 (55.49% identity, 71.04% similarity) APG00146 (50.47% identity, 66.36% similarity) APG00351 (50.14% identity, 65.13% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | similarity) WP_000794514.1 (49.84% identity, 67.29% similarity) US20130227743A1_102 (46.27% identity, 62.11% similarity) ETK27180.1 (41.61% identity, 56.52% similarity) |
| APG00710 | 129 | 130, 131 | | | Cry32 | 95, 96, 97, 98, 99 | 95, 96, 97, 98, 99 | AGU13855.1 (91.28% identity, 94.34% similarity) US20110203014_23 (89.51% identity, 92.47% similarity) AGU13869.1 (89.43% identity, 92.47% similarity) APG00430 (78.11% identity, 83.98% similarity) APG00056 (69.24% identity, 79.31% similarity) APG00058 (66.26% identity, 75.28% similarity) APG00687 (55.17% identity, 65.22% similarity) Cry32Ab1 (53.65% identity, 64.62% similarity) APG00469 (53.09% identity, 64.73% similarity) APG00504 (52.35% identity, 64.28% similarity) APG00673 (51.24% identity, 61.54% similarity) |
| APG00718 | 132 | | | | Cry | 40, 45, 50, 55, 60, 65, 70, 75, 80, 85, 90, 95, 96, 97, 98, 99 | 60, 65, 70, 75, 80, 85, 90, 95, 96, 97, 98, 99 | APG00860 (54.49% identity, 73.08% similarity) AGA40044.1 (38.97% identity, 55.59% similarity) |
| APG00721 | 133 | 134 | | 135 | Cry65 | 55, 60, 65, 70, 75, 80, 85, 90, 95, 96, 97, 98, 99 | 65, 70, 75, 80, 85, 90, 95, 96, 97, 98, 99 | APG00136 (95.85% identity, 97.36% similarity) Cry65Aa2 (51.84% identity, 60.91% similarity) APG00123 (38.24% identity, 51.05% similarity) |
| APG00722 | 136 | | | | Bin | 70, 75, 80, 85, 90, 95, 96, 97, 98, 99 | 80, 85, 90, 95, 96, 97, 98, 99 | AGP18023.1 (67.35% identity, 78.52% similarity) APG00340 (65.84% identity, 76.4% similarity) APG00151 (65.25% identity, 76.01% similarity) US20130227743A1_40 (65.12% identity, 72.03% similarity) US20130227743A1_48 (36.16% identity, 45.72% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | identity, 88.1% similarity) APG00157 (83.04% identity, 88.1% similarity) APG00377 (82.78% identity, 88.35% similarity) APG00231 (82.53% identity, 87.85% similarity) WP_050845516.1 (80.76% identity, 86.84% similarity) AEX56523.1 (80.51% identity, 86.33% similarity) APG00494 (75.19% identity, 82.78% similarity) WP_000143307.1 (75.19% identity, 83.29% similarity) Cry35Ac2 (21.33% identity, 37.61% similarity) |
| APG00781 | 146 | 147 | | | Cry68 | 75, 80, 85, 90, 95, 96, 97, 98, 99 | 85, 90, 95, 96, 97, 98, 99 | WP_016083794.1 (71.85% identity, 82.25% similarity) APG00026 (71.2% identity, 80.64% similarity) CA_2753918-14 (70.55% identity, 79.88% similarity) APG00109 (68.01% identity, 77.56% similarity) AFU17323.1 (66.24% identity, 74.1% similarity) Cry68Aa1 (66.13% identity, 73.99% similarity) |
| APG00784 | 148 | 149 | | | Cry | 35, 40, 45, 50, 55, 60, 65, 70, 75, 80, 85, 90, 95, 96, 97, 98, 99 | 50, 55, 60, 65, 70, 75, 80, 85, 90, 95, 96, 97, 98, 99 | APG00099 (95.29% identity, 96.86% similarity) APG00801 (84.55% identity, 90.37% similarity) Cry13Aa1 (30.61% identity, 45.66% similarity) |
| APG00785 | 150 | 151, 152 | | | Cry50 | 80, 85, 90, 95, 96, 97, 98, 99 | 90, 95, 96, 97, 98, 99 | AGA40023.1 (77.24% identity, 85.06% similarity) US20130227743A1_78 (61.79% identity, 74.2% similarity) KIQ78153.1 (61.54% identity, 73.57% similarity) Cry50Ba1 (50.9% identity, 63.25% similarity) |
| APG00786 | 153 | 154, 155 | | | Cry69 | 95, 96, 97, 98, 99 | 95, 96, 97, 98, 99 | US_2011_0197314_A1-13 (91.13% identity, 92.98% similarity) CA_2753918-13 (90.92% identity, 92.77% similarity) APG00662 (70.46% identity, 77.45% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | similarity) APG00079 (68.76% identity, 76.11% similarity) WP_016084057.1 (64.86% identity, 74.7% similarity) APG00059 (64.27% identity, 74.75% similarity) Cry69Aa1 (59.64% identity, 69.36% similarity) |
| APG00787 | 156 | 157 | | | Cry | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00723 (50.82% identity, 62.48% similarity) WP_048536362.1 (38.59% identity, 52.5% similarity) AGA40057.1 (33.33% identity, 46.48% similarity) WP_017762581.1 (29.66% identity, 40.4% similarity) AGA40058.1 (28.99% identity, 42.17% similarity) |
| APG00799 | 158 | 159 | | | Cry | 25, 30, 35, 40, 45, 50, 55, 60, 65, 70, 75, 80, 85, 90, 95, 96, 97, 98, 99 | 40, 45, 50, 55, 60, 65, 70, 75, 80, 85, 90, 95, 96, 97, 98, 99 | C0ZKJ5_BREBN (23.19% identity, 37.57% similarity) Cry5Ad1 (21.24% identity, 32.24% similarity) |
| APG00801 | 160 | 161 | | | Cry | 30, 35, 40, 45, 50, 55, 60, 65, 70, 75, 80, 85, 90, 95, 96, 97, 98, 99 | 50, 55, 60, 65, 70, 75, 80, 85, 90, 95, 96, 97, 98, 99 | APG00099 (85.30% identity, 90.68% similarity) APG00784 (84.55% identity, 90.37% similarity) Cry13Aa1 (29.5% identity, 45.1% similarity) |
| APG00802 | 162 | 163 | | | Cry19 | 55, 60, 65, 70, 75, 80, 85, 90, 95, 96, 97, 98, 99 | 70, 75, 80, 85, 90, 95, 96, 97, 98, 99 | Cry19Ba1 (51.48% identity, 67.28% similarity) AGV55021.1 (48.09% identity, 61.10% similarity) Cry52Aa1 (42.10% identity, 57.08% similarity) Cry19Aa1 (40.17% identity, 55.23% similarity) ACP43735.1 (40.03% identity, 54.79% similarity) |
| APG00805 | 164 | 165, 166 | | | Cry40 | 60, 65, 70, 75, 80, 85, 90, 95, 96, 97, 98, 99 | 70, 75, 80, 85, 90, 95, 96, 97, 98, 99 | WP_050845421.1 (56.11% identity, 69.03% similarity) WO_2015_039599-9 (53.89% identity, 66.25% similarity) Cry40Ba1 (48.4% identity, 60.89% similarity) |
| APG00806 | 167 | 168 | | | Bin | 85, 90, 95, 96, 97, 98, 99 | 95, 96, 97, 98, 99 | US20130227743A1_146 (84.73% identity, 90.39% similarity) APG00212 (84.71% identity, 88.59% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | APG00592 (80.34% identity, 85.92% similarity) APG00619 (80.2% identity, 87.38% similarity) APG00600 (79.65% identity, 87.1% similarity) APG00798 (79.42% identity, 85.47% similarity) WP_002166959.1 (74.0% identity, 83.0% similarity) WP_002191947.1 (73.75% identity, 83.0% similarity) APG00724 (67.08% identity, 79.7% similarity) APG00716 (66.83% identity, 76.66% similarity) APG00701 (64.75% identity, 77.75% similarity) APG00988 (59.25% identity, 71.25% similarity) Cry35Ac2 (21.85% identity, 35.32% similarity) |
| APG00807 | 169 | 170 | | | Mtx | 35, 40, 45, 50, 55, 60, 65, 70, 75, 80, 85, 90, 95, 96, 97, 98, 99 | 50, 55, 60, 65, 70, 75, 80, 85, 90, 95, 96, 97, 98, 99 | APG00641 (73.68% identity, 82.57% similarity) APG00434 (52.88% identity, 68.59% similarity) Cry64Aa1 (32.69% identity, 48.08% similarity) |
| APG00810 | 171 | 172, 173 | | | Cry20 | 60, 65, 70, 75, 80, 85, 90, 95, 96, 97, 98, 99 | 70, 75, 80, 85, 90, 95, 96, 97, 98, 99 | AGV55017.1 (57.12% identity, 68.39% similarity) WP_016098327.1 (53.01% identity, 64.12% similarity) Cry20Ba2 (52.47% identity, 62.58% similarity) |
| APG00864 | 174 | | | | Cry54A | 85, 90, 95, 96, 97, 98, 99 | 95, 96, 97, 98, 99 | AGA40050.1 (84.65% identity, 90.2% similarity) Cry54Aa2 (83.63% identity, 89.18% similarity) APG00664 (58.9% identity, 70.48% similarity) |
| APG00912 | 175 | 176, 177 | | 178 | Cry | 70, 75, 80, 85, 90, 95, 96, 97, 98, 99 | 80, 85, 90, 95, 96, 97, 98, 99 | AEH76820.1 (69.56% identity, 78.62% similarity) US20100298211A1_8 (65.27% identity, 73.73% similarity) US20130227743A1_48 (55.33% identity, 70.45% similarity) Cry32Ea1 (44.82% identity, 57.88% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| APG00960 | 179 | 180, 181 | | | Cry7 | 95, 96, 97, 98, 99 | 95, 96, 97, 98, 99 | AGU13819.1 (90.49% identity, 94.42% similarity) AGM39662.1 (88.66% identity, 93.37% similarity) AGU13834.1 (87.78% identity, 93.28% similarity) Cry7Ab3 (58.23% identity, 69.62% similarity) |
| APG00972 | 182 | 183, 184 | | | Cry30F | 90, 95, 96, 97, 98, 99 | 95, 96, 97, 98, 99 | CA__2753918-15 (85.29% identity, 90.76% similarity) AFU17333.1 (84.87% identity, 90.48% similarity) WP__000806152.1 (81.65% identity, 87.25% similarity) Cry30Fa1 (80.81% identity, 86.69% similarity) APG00565 (63.5% identity, 75.94% similarity) |
| APG00980 | 185 | 186, 187 | | | Mtx | 65, 70, 75, 80, 85, 90, 95, 96, 97, 98, 99 | 75, 80, 85, 90, 95, 96, 97, 98, 99 | AGA40045.1 (61.81% identity, 71.14% similarity) APG00351 (58.84% identity, 72.46% similarity) APG00939 (58.52% identity, 69.32% similarity) US20130227743A1__102 (56.65% identity, 69.08% similarity) APG00146 (55.46% identity, 69.32% similarity) APG00387 (55.3% identity, 67.91% similarity) WP__000794514.1 (54.28% identity, 69.32% similarity) APG00938 (51.83% identity, 65.07% similarity) WP__036654376.1 (41.38% identity, 56.32% similarity) |
| APG00981 | 188 | 189 | | | Cry | 40, 45, 50, 55, 60, 65, 70, 75, 80, 85, 90, 95, 96, 97, 98, 99 | 55, 60, 65, 70, 75, 80, 85, 90, 95, 96, 97, 98, 99 | APG00076 (85.87% identity, 91.14% similarity) CA__2843744-7 (39.07% identity, 54.08% similarity) CA__2843744-9 (38.92% identity, 54.29% similarity) US20130227743A1__74 (34.23% identity, 50.19% similarity) Cry4Cc1 (21.66% identity, 32.04% similarity) |
| APG00986 | 190 | 191, 192 | | 193 | Cry56 | 85, 90, 95, 96, 97, 98, 99 | 90, 95, 96, 97, 98, 99 | AGV55019.1 (81.41% identity, 86.81% similarity) ACR88315.1 (63.53% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | identity, 75.44% similarity) WP_050845711.1 (54.32% identity, 69.79% similarity) Cry56Aa2 (54.3% identity, 69.73% similarity) |
| APG00988 | 194 | 195 | | | Bin | 75, 80, 85, 90, 95, 96, 97, 98, 99 | 90, 95, 96, 97, 98, 99 | WP_002114997.1 (73.67% identity, 81.01% similarity) WP_002187944.1 (73.67% identity, 85.06% similarity) WP_001258160.1 (72.91% identity, 84.56% similarity) APG00213 (72.49% identity, 82.26% similarity) APG00243 (72.35% identity, 82.43% similarity) APG00412 (71.21% identity, 80.56% similarity) APG00844 (70.28% identity, 81.65% similarity) APG00118 (67.96% identity, 76.43% similarity) APG00648 (67.83% identity, 77.06% similarity) APG00716 (65.9% identity, 76.41% similarity) APG00724 (60.78% identity, 71.32% similarity) APG00806 (59.25% identity, 71.25% similarity) Cry35Ab4 (23.15% identity, 40.33% similarity) |
| APG01000 | 196 | 197 | | | Bin | 30, 35, 40, 45, 50, 55, 60, 65, 70, 75, 80, 85, 90, 95, 96, 97, 98, 99 | 45, 50, 55, 60, 65, 70, 75, 80, 85, 90, 95, 96, 97, 98, 99 | WP_002090518.1 (26.42% identity, 40.16% similarity) WP_048517129.1 (26.3% identity, 40.55% similarity) WP_016093722.1 (26.22% identity, 41.35% similarity) Cry49Ab1 (16.28% identity, 24.74% similarity) |
| APG01003 | 198 | 199 | | | Vip3 | 80, 85, 90, 95, 96, 97, 98, 99 | 90, 95, 96, 97, 98, 99 | APG00875 (87.19% identity, 90.21% similarity) APG00278 (85.25% identity, 90.06% similarity) APG00173 (85.18% identity, 89.77% similarity) APG00358 (81.35% identity, 87.4% similarity) APG00273 (78.16% identity, 85.2% |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | similarity) WP_050001316.1 (75.08% identity, 85.24% similarity) APG00939 (72.64% identity, 80.23% similarity) WP_048517127.1 (72.11% identity, 79.78% similarity) APG00657 (67.97% identity, 78.06% similarity) AIT93175.1 (23.47% identity, 39.55% similarity) Vip3Ad2 (23.32% identity, 39.53% similarity) |
| APG01028 | 200 | 201, 202 | | 203 | Cry | 85, 90, 95, 96, 97, 98, 99 | 90, 95, 96, 97, 98, 99 | CA_2753918-17 (81.0% identity, 87.71% similarity) APG00555 (66.91% identity, 76.83% similarity) US20130227743A1_26 (61.01% identity, 72.81% similarity) APG00606 (54.05% identity, 66.71% similarity) ACP43734.1 (41.05% identity, 55.06% similarity) Cry53Aa1 (40.14% identity, 54.69% similarity) |
| APG01112 | 204 | | | | Cry | 30, 35, 40, 45, 50, 55, 60, 65, 70, 75, 80, 85, 90, 95, 96, 97, 98, 99 | 45, 50, 55, 60, 65, 70, 75, 80, 85, 90, 95, 96, 97, 98, 99 | APG00603 (79.84% identity, 81.48% similarity) WP_017762616.1 (26.86% identity, 41.34% similarity) WP_044306756.1 (26.77% identity, 40.34% similarity) US20130227743A1_206 (23.74% identity, 37.77% similarity) AGA40058.1 (22.9% identity, 35.14% similarity) |
| APG00556 | 205 | 206 | | | Mtx | 65, 70, 75, 80, 85, 90, 95, 96, 97, 98, 99 | 80, 85, 90, 95, 96, 97, 98, 99 | APG00623 (88.97% identity, 91.18% similarity) APG01037 (88.97% identity, 91.54% similarity) US_2014_0283208_A1-2 (61.29% identity, 76.34% similarity) WO_2014_159836-52 (60.93% identity, 76.34% similarity) WO_2014_159836-61 (60.93% identity, 76.34% similarity) Cry46Ab (38.31% identity, 56.17% similarity) |
| APG00623 | 207 | | | | Mtx | 65, 70, 75, 80, 85, 90, 95, 96, 97, 98, 99 | 85, 90, 95, 96, 97, 98, 99 | APG01037 (98.02% identity, 99.21% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Similarity from nearest non-APG | Homologs |
|---|---|---|---|---|---|---|---|---|
| | | | | | | | | APG00556 (88.97% identity, 91.18% similarity) US_2014_0283208_A1-2 (64.34% identity, 81.4% similarity) WO_2014_159836-52 (63.95% identity, 81.4% similarity) WO_2014_159836-61 (63.95% identity, 81.4% similarity) Cry46Ab (35.83% identity, 52.77% similarity) |
| APG01037 | 208 | 209, 210, 211, 212, 213, 214 | | | Mtx | 65, 70, 75, 80, 85, 90, 95, 96, 97, 98, 99 | 85, 90, 95, 96, 97, 98, 99 | APG00623 (98.02% identity, 99.21% similarity) APG00556 (88.97% identity, 91.54% similarity) US_2014_0283208_A1-2 (64.48% identity, 81.08% similarity) WO_2014_159836-52 (64.09% identity, 81.08% similarity) WO_2014_159836-61 (64.09% identity, 81.08% similarity) Cry46Ab (36.51% identity, 53.29% similarity) |
| APG01086 | 215 | 216 | | | Mtx | 75, 80, 85, 90, 95, 96, 97, 98, 99 | 85, 90, 95, 96, 97, 98, 99 | APG00566 (97.39% identity, 99.02% similarity) APG00201 (81.05% identity, 90.85% similarity) APG00006 (78.76% identity, 90.20% similarity) APG00260 (78.10% identity, 87.58% similarity) APG00036 (75.24% identity, 83.71% similarity) APG00022 (75.16% identity, 83.01% similarity) WP_000963933.1 (74.18% identity, 84.31% similarity) US_2013_0227743_A1-100 (72.88% identity, 83.66% similarity) US_2013_0227743_A1-99 (72.64% identity, 83.39% similarity) APG00345 (68.08% identity, 80.46% similarity) |
| APG06508 | 217 | | | | Mtx | 85, 90, 95, 96, 97, 98, 99 | 95, 96, 97, 98, 99 | APG00661 (96.41% identity, 97.31% similarity) APG09801 (95.47% identity, 96.68% similarity) US_8829279_B2-24 (84.13% identity, 90.12% similarity) |

TABLE 1-continued

Summary of SEQ ID NOs, Gene Class, and Variants thereof

| Gene Name | Full-length SEQ ID No. | Modified SEQ ID No.(s) | CryBP1 SEQ ID No. | Split-Cry C-terminus SEQ ID No. | Gene Class | Identity from nearest non-APG | Simil obvious sequence similarity to a known Cyt protein. These toxins are highly specific to their target organism, are innocuous to humans, vertebrates, and plants.

The structure of the Cry toxins reveals five conserved amino acid blocks, concentrated mainly in the center of the domain or at the junction between the domains. The Cry toxin consists of three domains, each with a specific function. Domain I is a seven α-helix bundle in which a central helix is completely surrounded by six outer helices. This domain is implicated in channel formation in the membrane. Domain II appears as a triangular column of three antiparallel β-sheets, which are similar to antigen-binding regions of immunoglobulins. Domain III contains antiparallel β-strands in a β sandwich form. The N-terminal part of the toxin protein is responsible for its toxicity and specificity and contains five conserved regions. The C-terminal part is usually highly conserved and probably responsible for crystal formation. See, for example, U.S. Pat. No. 8,878,007.

Strains of *B. thuringiensis* show a wide range of specificity against different insect orders (Lepidoptera, Diptera, Coleoptera, Hymenoptera, Homoptera, Phthiraptera or Mallophaga, and Acari) and other invertebrates (Nemathelminthes, Platyhelminthes, and Sarocomastebrates). The cry proteins have been classified into groups based on toxicity to various insect and invertebrate groups. Generally, Cry I demonstrates toxicity to lepidopterans, Cry II to lepidopterans and dipterans, CryIII to coleopterans, Cry IV to dipterans, and Cry V and Cry VI to nematodes. New Cry proteins can be identified and assigned to a Cry group based on amino acid identity. See, for example, Bravo, A. (1997) *J. of Bacteriol.* 179:2793-2801; Bravo et al. (2013) *Microb. Biotechnol.* 6:17-26, herein incorporated by reference.

Over 750 different cry gene sequences have been classified into 73 groups (Cry1-Cry73), with new members of this gene family continuing to be discovered (Crickmore et al. (2014) www.btnomenclature.info/). The cry gene family consists of several phylogenetically non-related protein families that may have different modes of action: the family of three-domain Cry toxins, the family of mosquitocidal Cry toxins, the family of the binary-like toxins, and the Cyt family of toxins (Bravo et al., 2005). Some Bt strains produce additional insecticidal toxins, the VIP toxins. See, also, Cohen et al. (2011) *J. Mol. Biol.* 413:4-814; Crickmore et al. (2014) *Bacillus thuringiensis* toxin nomenclature, found on the world wide web at lifesci.sussex.ac.uk/home/Neil_Crickmore/Bt/; Crickmore et al. (1988) *Microbiol. Mol. Biol. Rev.* 62: 807-813; Gill et al. (1992) *Ann. Rev. Entomol.* 37: 807-636; Goldbert et al. (1997) *Appl. Environ. Microbiol.* 63:2716-2712; Knowles et al. (1992) *Proc. R Soc. Ser. B.* 248: 1-7; Koni et al. (1994) Microbiology 140: 1869-1880; Lailak et al. (2013) *Biochem. Biophys. Res. Commun.* 435: 216-221; Lopez-Diaz et al. (2013) *Environ. Microbiol.* 15: 3030-3039; Perez et al. (2007) *Cell. Microbiol.* 9: 2931-2937; Promdonkoy et al. (2003) *Biochem. J.* 374: 255-259; Rigden (2009) *FEBS Lett.* 583: 1555-1560; Schnepf et al. (1998)*Microbiol. Mol. Biol. Rev.* 62: 775-806; Soberon et al. (2013) *Peptides* 41: 87-93; Thiery et al. (1998) *J. Am. Mosq. Control Assoc.* 14: 472-476; Thomas et al. (1983) *FEBS Lett.* 154: 362-368; Wirth et al. (1997) *Proc. Natl. Acad. Sci. U.S.A.* 94: 10536-10540; Wirth et al (2005) *Appl. Environ. Microbiol.* 71: 185-189; and, Zhang et al. (2006) *Biosci. Biotechnol. Biochem.* 70: 2199-2204; each of which is herein incorporated by reference in their entirety.

Cyt designates a parasporal crystal inclusion protein from *Bacillus thuringiensis* with cytolytic activity, or a protein with sequence similarity to a known Cyt protein. (Crickmore et al. (1998)*Microbiol. Mol. Biol. Rev.* 62: 807-813). The gene is denoted by cyt. These proteins are different in structure and activity from Cry proteins (Gill et al. (1992) *Annu. Rev. Entomol.* 37: 615-636). The Cyt toxins were first discovered in *B. thuringiensis* subspecies *israelensis* (Goldberg et al. (1977) Mosq. News. 37: 355-358). There are 3 Cyt toxin families including 11 holotype toxins in the current nomenclature (Crickmore et al. (2014) *Bacillus thuringiensis* toxin nomenclature found on the world wide web at lifesci.sussex.ac.uk/home/Neil_Crickmore/Bt/). The majority of the *B. thuringiensis* isolates with cyt genes show activity against dipteran insects (particularly mosquitoes and black flies), but there are also cyt genes that have been described in *B. thuringiensis* strains targeting lepidopteran or coleopteran insects (Guerchicoff et al. (1997) *Appl. Environ. Microbiol.* 63: 2716-2721).

The structure of Cyt2A, solved by X-ray crystallography, shows a single domain where two outer layers of α-helix wrap around a mixed β-sheet. Further available crystal structures of Cyt toxins support a conserved α-β structural model with two α-helix hairpins flanking a β-sheet core containing seven to eight β-strands. (Cohen et al. (2011) *J. Mol. Biol.* 413: 80 4-814) Mutagenic studies identified β-sheet residues as critical for toxicity, while mutations in the helical domains did not affect toxicity (Adang et al.; Diversity of *Bacillus thuringiensis* Crystal Toxins and Mechanism of Action. In: T. S. Dhadialla and S. S. Gill, eds, *Advances in Insect Physiology*, Vol. 47, Oxford: Academic Press, 2014, pp. 39-87.) The representative domain of the Cyt toxin is a δ-endotoxin, Bac_thur_toxin (Pfam PF01338).

There are multiple proposed models for the mode of action of Cyt toxins, and it is still an area of active investigation. Some Cyt proteins (Cyt1A) have been shown to require the presence of accessory proteins for crystallization. Cyt1A and Cyt2A protoxins are processed by digestive proteases at the same sites in the N- and C-termini to a stable toxin core. Cyt toxins then interact with non-saturated membrane lipids, such as phosphatidylcholine, phosphatidylethanolamine, and sphingomyelin. For Cyt toxins, pore-formation and detergent-like membrane disruption have been proposed as non-exclusive mechanisms; and it is generally accepted that both may occur depending on toxin concentration, with lower concentrations favoring oligomeric pores and higher concentrations leading to membrane breaks. (Butko (2003) *Appl. Environ. Microbiol.* 69: 2415-2422) In the pore-formation model, the Cyt toxin binds to the cell membrane, inducing the formation of cation-selective channels in the membrane vesicles leading to colloid-osmotic lysis of the cell. (Knowles et al. (1989) FEBS Lett. 244: 259-262; Knowles et al. (1992) *Proc. R Soc. Ser. B.* 248: 1-7 and Promdonkoy et al. (2003) *Biochem. J.* 374: 255-259). In the detergent model, there is a nonspecific aggregation of the toxin on the surface of the lipid bilayer leading to membrane disassembly and cell death. (Butko (2003) supra; Manceva et al. (2005) *Biochem.* 44: 589-597).

Multiple studies have shown synergistic activity between Cyt toxins and other *B. thuringiensis* toxins, particularly the Cry, Bin, and Mtx toxins. This synergism has even been shown to overcome an insect's resistance to the other toxin. (Wirth 1997, Wirth 2005, Thiery 1998, Zhang 2006) The Cyt synergistic effect for Cry toxins is proposed to involve Cyt1A binding to domain II of Cry toxins in solution or on the membrane plane to promote formation of a Cry toxin pre-pore oligomer. Formation of this oligomer is independent of the Cyt oligomerization, binding or insertion. (Lailak 2013, Perez 2007, Lopez-Diaz 2013)

A number of pesticidal proteins unrelated to the Cry proteins are produced by some strains of *B. thuringiensis* and *B. cereus* during vegetative growth (Estruch et al. (1996) *Proc Natl Acad Sci USA* 93:5389-5394; Warren et al. (1994) WO 94/21795). These vegetative insecticidal proteins, or Vips, do not form parasporal crystal proteins and are apparently secreted from the cell. The Vips are presently excluded from the Cry protein nomenclature because they are not crystal-forming proteins. The term VIP is a misnomer in the sense that some *R. thuringiensis* Cry proteins are also produced during vegetative growth as well as during the stationary and sporulation phases, most notably Cry3Aa. The location of the Vip genes in the *B. thuringiensis* genome has been reported to reside on large plasmids that also encode cry genes (Mesrati et al. (2005) *FEMS Microbiol. Lett.* 244(2):353-8). A web-site for the nomenclature of Bt toxins can be found on the world wide web at lifesci.sussex.ac.uk with the path "/home/Neil_Crickmore/Bt/" and at: "btnomenclature.info/". See also, Schnepf et al. (1998) *Microbiol. Mol. Biol. Rev.* 62(3):775-806. Such references are herein incorporated by reference.

To date four categories of Vips have been identified. Some Vip genes form binary two-component protein complexes; an "A" component is usually the "active" portion, and a "B" component is usually the "binding" portion. (Pfam_p-fam.xfam.org/family/PF03495). The Vip1 and Vip4 proteins generally contain binary toxin B protein domains. Vip2 proteins generally contain binary toxin A protein domains.

The Vip1 and Vip2 proteins are the two components of a binary toxin that exhibits toxicity to coleopterans. Vip1Aa1 and Vip2Aa1 are very active against corn rootworms, particularly *Diabrotica virgifera* and *Diabrotica longicornis* (Han et al. (1999) *Nat. Struct. Biol.* 6:932-936; Warren GW (1997) "Vegetative insecticidal proteins: novel proteins for control of corn pests" In: Carozzi NB, Koziel M (eds) *Advances in insect control, the role of transgenic plants*; Taylor & Francis Ltd, London, pp 109-21). The membrane-binding 95 kDa Vip1 multimer provides a pathway for the 52 kDa vip2 ADP-ribosylase to enter the cytoplasm of target western corn rootworm cells (Warren (1997) supra). The NAD-dependent ADP-ribosyltransferase Vip2 likely modifies monomeric actin at Arg177 to block polymerization, leading to loss of the actin cytoskeleton and eventual cell death due to the rapid subunit ex-change within actin filaments in vivo (Carlier M. F. (1990) *Adv. Biophys.* 26:51-73).

Like Cry toxins, activated Vip3A toxins are pore-forming proteins capable of making stable ion channels in the membrane (Lee et al. (2003) *Appl. Environ. Microbiol.* 69:4648-4657). Vip3 proteins are active against several major lepidopteran pests (Rang et al. (2005) *Appl. Environ. Microbiol.* 71(10):6276-6281; Bhalla et al. (2005) *FEMS Microbiol. Lett.* 243:467-472; Estruch et al. (1998) WO 9844137; Estruch et al. (1996) *Proc Natl Acad Sci USA* 93:5389-5394; Selvapandiyan et al. (2001) *Appl. Environ Microbiol.* 67:5855-5858; Yu et al. (1997) *Appl. Environ Microbiol.* 63:532-536). Vip3A is active against *Agrotis ipsilon*, *Spodoptera frugiperda*, *Spodoptera exigua*, *Heliothis virescens*, and *Helicoverpa zea* (Warren et al. (1996) WO 96/10083; Estruch et al. (1996) *Proc Natl Acad Sci USA* 93:5389-5394). Like Cry toxins, Vip3A proteins must be activated by proteases prior to recognition at the surface of the midgut epithelium of specific membrane proteins different from those recognized by Cry toxins.

The MTX family of toxin proteins is characterized by the presence of a conserved domain, ETX_MTX2 (pfam 03318). Members of this family share sequence homology with the mosquitocidal toxins Mtx2 and Mtx3 from *Bacillus sphaericus*, as well as with the epsilon toxin ETX from *Clostridium perfringens* (Cole et al. (2004) *Nat. Struct. Mol. Biol.* 11: 797-8; Thanabalu et al. (1996) *Gene* 170:85-9). The MTX-like proteins are structurally distinct from the three-domain Cry toxins, as they have an elongated and predominately β-sheet-based structure. However, similar to the three-domain toxins, the MTX-like proteins are thought to form pores in the membranes of target cells (Adang et al. (2014) supra). Unlike the three-domain Cry proteins, the MTX-like proteins are much smaller in length, ranging from 267 amino acids (Cry23) to 340 amino acids (Cry15A.

To date, only 15 proteins belonging to the family of MTX-like toxins have been assigned Cry names, making this a relatively small class compared to the three-domain Cry family (Crickmore et al. (2014) supra; Adang et al. (2014) supra). The members of the MTX-like toxin family include Cry15, Cry23, Cry33, Cry38, Cry45, Cry46, Cry51, Cry60A, Cry60B, and Cry64. This family exhibits a range of insecticidal activity, including activity against insect pests of the Lepidopteran and Coleopteran orders. Some members of this family may form binary partnerships with other proteins, which may or may not be required for insecticidal activity.

Cry15 is a 34 kDA protein that was identified in *Bacillus thuringiensis* serovar thompsoni HD542; it occurs naturally in a crystal together with an unrelated protein of approximately 40 kDa. The gene encoding Cry15 and its partner protein are arranged together in an operon. Cry15 alone has been shown to have activity against lepidopteran insect pests including *Manduca sexta, Cydia pomonella*, and *Pieris rapae*, with the presence of the 40 kDA protein having been shown to increase activity of Cry15 only against *C. pomonella* (Brown K. and Whiteley H. (1992) *J. Bacteriol.* 174:549-557; Naimov et al. (2008) *Appl. Environ. Microbiol.* 74:7145-7151). Further studies are needed to elucidate the function of the partner protein of Cry15. Similarly, Cry23 is a 29 kDA protein that has been shown to have activity against the coleopteran pests Tribolium castaneum and *Popillia japonica* together with its partner protein Cry37 (Donovan et al. (2000) U.S. Pat. No. 6,063,756).

New members of the MTX-like family are continuing to be identified. An ETX_MTX toxin gene was recently identified in the genome of *Bacillus thuringiensis* serovar tolworthi strain Na205-3. This strain was found to be toxic against the lepidpoteran pest *Helicoverpa armigera*, and it also contained homologs of Cry1, Cry11, Vip1, Vip2, and Vip3 (Palma et al. (2014) *Genome Announc.* 2(2): e00187-14. Published online Mar. 13, 2014 at doi: 10.1128/genomeA.00187-14; PMCID: PMC3953196). Because the MTX-like proteins have a unique domain structure relative to the three-domain Cry proteins, they are believed to possess a unique mode of action, thereby making them a valuable tool in insect control and the fight against insect resistance.

Bacterial cells produce large numbers of toxins with diverse specificity against host and non-host organisms. Large families of binary toxins have been identified in numerous bacterial families, including toxins that have activity against insect pests. (Poopathi and Abidha (2010) *J. Physiol. Path.* 1(3): 22-38). Lysinibacillus *sphaericus* (Ls), formerly *Bacillus sphaericus*, (Ahmed et al. (2007) *Int. J. Syst. Evol. Microbiol.* 57:1117-1125) is well-known as an insect biocontrol strain. Ls produces several insecticidal proteins, including the highly potent binary complex BinA/BinB. This binary complex forms a parasporal crystal in Ls cells and has strong and specific activity against dipteran insects, specifically mosquitos. In some areas, insect resistance to existing Ls mosquitocidal strains has been reported. The discovery of new binary toxins with different target specificity or the ability to overcome insect resistance is of significant interest.

The Ls binary insecticidal protein complex contains two major polypeptides, a 42 kDa polypeptide and a 51 kDa polypepdide, designated BinA and BinB, respectively (Ahmed et al. (2007) supra). The two polypeptides act synergistically to confer toxicity to their targets. Mode of action involves binding of the proteins to receptors in the larval midgut. In some cases, the proteins are modified by protease digestion in the larval gut to produce activated forms. The BinB component is thought to be involved in binding, while the BinA component confers toxicity (Nielsen-LeRoux et al. (2001) Appl. Environ. Microbiol. 67(11):5049-5054). When cloned and expressed separately, the BinA component is toxic to mosquito larvae, while the BinB component is not. However, co-administration of the proteins markedly increases toxicity (Nielsen-LeRoux et al. (2001) supra).

A small number of Bin protein homologs have been described from bacterial sources. Priest et al. (1997) Appl. Environ. Microbiol. 63(4):1195-1198 describe a hybridization effort to identify new Ls strains, although most of the genes they identified encoded proteins identical to the known BinA/BinB proteins. The BinA protein contains a defined conserved domain known as the Toxin 10 superfamily domain. This toxin domain was originally defined by its presence in BinA and BinB. The two proteins both have the domain, although the sequence similarity between BinA and BinB is limited in this region (<40%). The Cry49Aa protein, which also has insecticidal activity, also has this domain (described below).

The Cry48Aa/Cry49Aa binary toxin of Ls has the ability to kill Culex quinquefasciatus mosquito larvae. These proteins are in a protein structural class that has some similarity to the Cry protein complex of Bacillus thuringiensis (Bt), a well-known insecticidal protein family. The Cry34/Cry35 binary toxin of Bt is also known to kill insects, including Western corn rootworm, a significant pest of corn. Cry34, of which several variants have been identified, is a small (14 kDa) polypeptide, while Cry35 (also encoded by several variants) is a 44 kDa polypeptide. These proteins have some sequence homology with the BinA/BinB protein group and are thought to be evolutionarily related (Ellis et al. (2002) Appl. Environ. Microbiol. 68(3):1137-1145).

Phosphoinositide phospholipase C proteins (PI-PLC; also phosphotidylinositol phospholipase C) are members of the broader group of phospholipase C proteins. Many of these proteins play important roles in signal transduction as part of normal cell physiology. Several important bacterial toxins also contain domains with similarity to these proteins (Titball, R. W. (1993)Microbiological Reviews. 57(2):347-366). Importantly, these proteins are implicated in signal amplification during intoxication of insect cells by Bt Cry proteins (Valaitis, A. P. (2008) Insect Biochemistry and Molecular Biology. 38: 611-618).

The PI-PLC toxin class occurs in Bacillus isolates, commonly seen in co-occurrence with homologs to other described toxin classes, such as Binary Toxins. This class of sequences has homology to phosphatidylinositol phosphodiesterases (also referred to as phosphatidylinositol-specific phospholipase C—PI-PLC). The crystal structure and its active site were solved for B. cereus PI-PLC by Heinz et al (Heinz, et. al., (1995) The EAMBO Journal. 14(16): 3855-3863). The roles of the B. cereus PI-PLC active site amino acid residues in catalysis and substrate binding were investigated by Gässler et al using site-directed mutagenesis, kinetics, and crystal structure analysis (Gässler, et. al., (1997) Biochemistry. 36(42):12802-13).

These PI-PLC toxin proteins contain a PLC-like phosphodiesterase, TIM beta/alpha-barrel domain (IPR017946) and/or a Phospholipase C, phosphatidylinositol-specific, X domain (IPR000909) (also referred to as the PI-PLC X-box domain). We have also seen proteins with these domains in combination with other typical Bacillus protein toxin domains. This list includes most commonly a lectin domain (IPR000772), a sugar-binding domain that can be present in one or more copies and is thought to bind cell membranes, as well as the Insecticidal crystal toxin (IPR008872) (also referred to as Toxin10 or P42), which is the defining domain of the Binary Toxin.

Previously, toxins of this PI-PLC class were defined in U.S. Pat. No. 8,318,900 B2 SEQ ID NOs 30 (DNA) and 79 (amino acid), in U.S. Patent Publication No. 20110263488A1 SEQ ID NOs 8 (DNA) and 9 (amino acid), and in U.S. Pat. No. 8,461,421B2 SEQ ID NOs 3 (DNA) and 63 (amino acid).

Provided herein are pesticidal proteins from these classes of toxins. The pesticidal proteins are classified by their structure, homology to known toxins and/or their pesticidal specificity. Table 2 provides the PFAM domains present in some of the recited SEQ ID NOS.

Further provided are APG01037.1 is set forth in SEQ ID NO:209 and it is a fragment of SEQ ID NO: 208 (APG01037); shares 98% sequence identity to SEQ ID NO: 207 (APG00623); shares 96% sequence identity to SEQ ID NO: 206 (APG00556.1); and shares 96% sequence identity to SEQ ID NO: 205 (APG00556).

TABLE 2

PFAM domains

| APG ID | Seq ID | Modification Type | PFAM domain | Domain Description | Domain positions Start | Stop |
|---|---|---|---|---|---|---|
| APG00326 | Seq ID 1 | | PF03945 | Endotoxin N | 87 | 332 |
| | | | PF00555 | Endotoxin M | 337 | 543 |
| | | | PF03944 | Endotoxin C | 553 | 697 |
| APG00326 modified | Seq ID 2 | Alternate start | PF03945 | Endotoxin N | 70 | 315 |
| | | | PF00555 | Endotoxin M | 320 | 526 |
| | | | PF03944 | Endotoxin C | 536 | 680 |
| APG00326 modified | Seq ID 3 | Alternate start and 3' Truncation | PF03945 | Endotoxin N | 70 | 315 |
| | | | PF00555 | Endotoxin M | 320 | 526 |
| | | | PF03944 | Endotoxin C | 536 | 679 |

TABLE 2-continued

PFAM domains

| APG ID | Seq ID | Modification Type | PFAM domain | Domain Description | Domain positions Start | Stop |
|---|---|---|---|---|---|---|
| APG00343 | Seq ID 4 | | PF03945 | Endotoxin N | 84 | 307 |
| | | | PF00555 | Endotoxin M | 312 | 530 |
| | | | PF03944 | Endotoxin C | 540 | 677 |
| APG00343 modified | Seq ID 5 | Alternate start | PF03945 | Endotoxin N | 72 | 295 |
| | | | PF00555 | Endotoxin M | 300 | 518 |
| | | | PF03944 | Endotoxin C | 528 | 665 |
| APG00383 | Seq ID 6 | | PF03945 | Endotoxin N | 78 | 329 |
| | | | PF03944 | Endotoxin C | 557 | 717 |
| APG00383 modified | Seq ID 7 | 3' Truncation | PF03945 | Endotoxin N | 78 | 329 |
| | | | PF03944 | Endotoxin C | 557 | 716 |
| APG00493 | Seq ID 8 | | no PFAM domains | | | |
| APG00493 modified | Seq ID 9 | Alternate start | no PFAM domains | | | |
| APG00494 | Seq ID 10 | | PF14200 | Ricin B Lectin 2 | 48 | 150 |
| | | | PF05431 | Toxin 10 | 156 | 353 |
| APG00494 modified | Seq ID 11 | Alternate start | PF14200 | Ricin B Lectin 2 | 44 | 145 |
| | | | PF05431 | Toxin 10 | 152 | 349 |
| APG00495 | Seq ID 12 | | PF03318 | ETX MTX2 | 50 | 310 |
| APG00495 modified | Seq ID 13 | Signal peptide removed | PF03318 | ETX MTX2 | 8 | 267 |
| APG00513 | Seq ID 14 | | PF03318 | ETX MTX2 | 80 | 326 |
| APG00514 | Seq ID 15 | | PF03945 | Endotoxin N | 84 | 307 |
| | | | PF00555 | Endotoxin M | 312 | 530 |
| | | | PF03944 | Endotoxin C | 540 | 677 |
| APG00514 modified | Seq ID 16 | Alternate start | PF03945 | Endotoxin N | 72 | 295 |
| | | | PF00555 | Endotoxin M | 300 | 518 |
| | | | PF03944 | Endotoxin C | 528 | 665 |
| APG00524 | Seq ID 17 | | PF03945 | Endotoxin N | 66 | 316 |
| | | | PF00555 | Endotoxin M | 321 | 523 |
| | | | PF03944 | Endotoxin C | 541 | 681 |
| APG00524 modified | Seq ID 18 | Alternate start and 3' Truncation | PF03945 | Endotoxin N | 66 | 316 |
| | | | PF00555 | Endotoxin M | 321 | 523 |
| | | | PF03944 | Endotoxin C | 541 | 680 |
| APG00524 modified | Seq ID 19 | Alternate start | PF03945 | Endotoxin N | 66 | 316 |
| | | | PF00555 | Endotoxin M | 321 | 523 |
| | | | PF03944 | Endotoxin C | 541 | 681 |
| APG00528 | Seq ID 20 | | no PFAM domains | | | |
| APG00533 | Seq ID 21 | | PF03945 | Endotoxin N | 37 | 232 |
| APG00534 | Seq ID 22 | | PF03945 | Endotoxin N | 53 | 259 |
| | | | PF03945 | Endotoxin N | 290 | 331 |
| | | | PF00555 | Endotoxin M | 338 | 544 |
| | | | PF03944 | Endotoxin C | 554 | 693 |
| APG00534 modified | Seq ID 23 | 3' Truncation | PF03945 | Endotoxin N | 53 | 259 |
| | | | PF03945 | Endotoxin N | 290 | 331 |
| | | | PF00555 | Endotoxin M | 338 | 544 |
| | | | PF03944 | Endotoxin C | 554 | 692 |
| APG00536 | Seq ID 24 | | PF03945 | Endotoxin N | 103 | 336 |
| | | | PF00555 | Endotoxin M | 341 | 552 |
| | | | PF03944 | Endotoxin C | 562 | 691 |
| | | | PF14200 | Ricin B Lectin 2 | 731 | 833 |
| APG00536 modified | Seq ID 25 | Alternate start and 3' Truncation | PF03945 | Endotoxin N | 56 | 289 |
| | | | PF00555 | Endotoxin M | 294 | 505 |
| | | | PF03944 | Endotoxin C | 515 | 644 |
| APG00536 modified | Seq ID 26 | Alternate start | PF03945 | Endotoxin N | 56 | 289 |
| | | | PF00555 | Endotoxin M | 294 | 505 |
| | | | PF03944 | Endotoxin C | 515 | 644 |
| | | | PF14200 | Ricin B Lectin 2 | 684 | 786 |
| APG00537 | Seq ID 27 | | PF03945 | Endotoxin N | 72 | 296 |
| | | | PF00555 | Endotoxin M | 301 | 507 |
| | | | PF03944 | Endotoxin C | 517 | 655 |
| APG00537 modified | Seq ID 28 | Alternate start | PF03945 | Endotoxin N | 69 | 293 |
| | | | PF00555 | Endotoxin M | 298 | 504 |
| | | | PF03944 | Endotoxin C | 514 | 652 |
| APG00537 modified | Seq ID 29 | Alternate start and 3' Truncation | PF03945 | Endotoxin N | 69 | 293 |
| | | | PF00555 | Endotoxin M | 298 | 504 |
| | | | PF03944 | Endotoxin C | 514 | 651 |

TABLE 2-continued

| | | | PFAM domains | | | |
|---|---|---|---|---|---|---|
| | | Modification | | Domain | Domain positions | |
| APG ID | Seq ID | Type | PFAM domain | Description | Start | Stop |
| APG00537 Split-Cry C-term | Seq ID 30 | | no PFAM domains | | | |
| APG00543 | Seq ID 31 | | PF03945 | Endotoxin N | 76 | 304 |
| | | | PF03944 | Endotoxin C | 523 | 682 |
| APG00543 modified | Seq ID 32 | 3' Truncation | PF03945 | Endotoxin N | 76 | 304 |
| | | | PF03944 | Endotoxin C | 523 | 681 |
| APG00555 | Seq ID 33 | | PF03945 | Endotoxin N | 80 | 300 |
| | | | PF00555 | Endotoxin M | 305 | 515 |
| | | | PF03944 | Endotoxin C | 525 | 659 |
| APG00555 modified | Seq ID 34 | Alternate start | PF03945 | Endotoxin N | 77 | 297 |
| | | | PF00555 | Endotoxin M | 302 | 512 |
| | | | PF03944 | Endotoxin C | 522 | 656 |
| APG00555 modified | Seq ID 35 | Alternate start and 3' Truncation | PF03945 | Endotoxin N | 77 | 297 |
| | | | PF00555 | Endotoxin M | 302 | 512 |
| | | | PF03944 | Endotoxin C | 522 | 655 |
| APG00557 | Seq ID 36 | | PF05431 | Toxin 10 | 210 | 404 |
| APG00557 modified | Seq ID 37 | Alternate start | PF05431 | Toxin 10 | 201 | 395 |
| APG00558 | Seq ID 38 | | PF03945 | Endotoxin N | 75 | 297 |
| | | | PF00555 | Endotoxin M | 302 | 521 |
| | | | PF03944 | Endotoxin C | 531 | 664 |
| APG00558 modified | Seq ID 39 | Alternate start | PF03945 | Endotoxin N | 75 | 297 |
| | | | PF00555 | Endotoxin M | 302 | 521 |
| | | | PF03944 | Endotoxin C | 531 | 664 |
| APG00558 modified | Seq ID 40 | Alternate start and 3' Truncation | PF03945 | Endotoxin N | 75 | 297 |
| | | | PF00555 | Endotoxin M | 302 | 521 |
| | | | PF03944 | Endotoxin C | 531 | 663 |
| APG00565 | Seq ID 41 | | PF03945 | Endotoxin N | 85 | 321 |
| | | | PF00555 | Endotoxin M | 326 | 532 |
| | | | PF03944 | Endotoxin C | 542 | 691 |
| APG00565 modified | Seq ID 42 | Alternate start and 3' Truncation | PF03945 | Endotoxin N | 68 | 304 |
| | | | PF00555 | Endotoxin M | 309 | 515 |
| | | | PF03944 | Endotoxin C | 525 | 673 |
| APG00565 modified | Seq ID 43 | Alternate start | PF03945 | Endotoxin N | 68 | 304 |
| | | | PF00555 | Endotoxin M | 309 | 515 |
| | | | PF03944 | Endotoxin C | 525 | 674 |
| APG00566 | Seq ID 44 | | PF03318 | ETX MTX2 | 36 | 260 |
| APG00566 modified | Seq ID 45 | Alternate start | PF03318 | ETX MTX2 | 29 | 253 |
| APG00572 | Seq ID 46 | | PF00388 | PI-PLC-X | 334 | 472 |
| | | | PF14200 | Ricin B Lectin 2 | 760 | 866 |
| APG00587 | Seq ID 47 | | PF03945 | Endotoxin N | 111 | 312 |
| | | | PF14200 | Ricin B Lectin 2 | 433 | 540 |
| | | | PF02839 | CBM 5 12 | 557 | 593 |
| APG00587 modified | Seq ID 48 | Signal peptide removed | PF03945 | Endotoxin N | 73 | 274 |
| | | | PF14200 | Ricin B Lectin 2 | 395 | 502 |
| | | | PF02839 | CBM 5 12 | 519 | 555 |
| APG00939 | Seq ID 49 | | PF12495 | Vip3A N | 16 | 188 |
| | | | PF02018 | CBM 4 9 | 546 | 670 |
| | | | PF02018 | CBM 4 9 | 825 | 910 |
| APG00939 modified | Seq ID 50 | Alternate start | PF12495 | Vip3A N | 14 | 186 |
| | | | PF02018 | CBM 4 9 | 544 | 668 |
| | | | PF02018 | CBM 4 9 | 823 | 908 |
| APG00606 | Seq ID 51 | | PF03945 | Endotoxin N | 72 | 296 |
| | | | PF00555 | Endotoxin M | 301 | 507 |
| | | | PF03944 | Endotoxin C | 517 | 649 |
| APG00606 modified | Seq ID 52 | Alternate start and 3' Truncation | PF03945 | Endotoxin N | 69 | 293 |
| | | | PF00555 | Endotoxin M | 298 | 504 |
| | | | PF03944 | Endotoxin C | 514 | 645 |
| APG00606 modified | Seq ID 53 | Alternate start | PF03945 | Endotoxin N | 69 | 293 |
| | | | PF00555 | Endotoxin M | 298 | 504 |
| | | | PF03944 | Endotoxin C | 514 | 646 |
| APG00607 | Seq ID 54 | | PF03945 | Endotoxin N | 37 | 232 |
| APG00608 | Seq ID 55 | | PF03945 | Endotoxin N | 76 | 341 |
| | | | PF03944 | Endotoxin C | 572 | 727 |
| APG00608 modified | Seq ID 56 | 3' Truncation | PF03945 | Endotoxin N | 76 | 341 |
| | | | PF03944 | Endotoxin C | 572 | 726 |
| APG00609 | Seq ID 57 | | PF03318 | ETX MTX2 | 66 | 327 |
| APG00622 | Seq ID 58 | | PF03945 | Endotoxin N | 69 | 161 |

TABLE 2-continued

| | | | PFAM domains | | | |
|---|---|---|---|---|---|---|
| APG ID | Seq ID | Modification Type | PFAM domain | Domain Description | Domain positions Start | Stop |
| | | | PF03945 | Endotoxin N | 188 | 335 |
| | | | PF03944 | Endotoxin C | 556 | 694 |
| APG00622 modified | Seq ID 59 | 3' Truncation | PF03945 | Endotoxin N | 69 | 161 |
| | | | PF03945 | Endotoxin N | 188 | 335 |
| | | | PF03944 | Endotoxin C | 556 | 693 |
| APG00624 | Seq ID 60 | | PF01338 | Bac thur toxin | 65 | 297 |
| | | | PF14200 | Ricin B Lectin 2 | 325 | 427 |
| | | | PF14200 | Ricin B Lectin 2 | 467 | 570 |
| APG00624 modified | Seq ID 61 | Alternate start | PF01338 | Bac thur toxin | 12 | 244 |
| | | | PF14200 | Ricin B Lectin 2 | 272 | 374 |
| | | | PF14200 | Ricin B Lectin 2 | 414 | 517 |
| APG00637 | Seq ID 62 | | PF03945 | Endotoxin N | 71 | 284 |
| | | | PF03945 | Endotoxin N | 290 | 360 |
| | | | PF00555 | Endotoxin M | 365 | 583 |
| | | | PF03944 | Endotoxin C | 593 | 725 |
| APG00637 modified | Seq ID 63 | Alternate start and 3' Truncation | PF03945 | Endotoxin N | 66 | 280 |
| | | | PF03945 | Endotoxin N | 284 | 355 |
| | | | PF00555 | Endotoxin M | 360 | 578 |
| | | | PF03944 | Endotoxin C | 588 | 719 |
| | Seq ID 64 | Alternate start | PF03945 | Endotoxin N | 66 | 279 |
| APG00637 modified | | | PF03945 | Endotoxin N | 285 | 355 |
| | | | PF00555 | Endotoxin M | 360 | 578 |
| | | | PF03944 | Endotoxin C | 588 | 720 |
| APG00638 | Seq ID 65 | | PF00388 | PI-PLC-X | 78 | 204 |
| | | | PF14200 | Ricin B Lectin 2 | 391 | 493 |
| APG00641 | Seq ID 66 | | PF03318 | ETX MTX2 | 30 | 280 |
| APG00641 modified | Seq ID 67 | Alternate start | PF03318 | ETX MTX2 | 25 | 275 |
| APG00643 | Seq ID 68 | | PF03945 | Endotoxin N | 68 | 294 |
| | | | PF00555 | Endotoxin M | 299 | 506 |
| | | | PF03944 | Endotoxin C | 516 | 647 |
| APG00643 modified | Seq ID 69 | 3' Truncation | PF03945 | Endotoxin N | 68 | 294 |
| | | | PF00555 | Endotoxin M | 299 | 506 |
| | | | PF03944 | Endotoxin C | 516 | 646 |
| APG00644 | Seq ID 70 | | PF03945 | Endotoxin N | 98 | 294 |
| | | | PF01473 | CW binding 1 | 588 | 607 |
| | | | PF01473 | CW binding 1 | 612 | 627 |
| | | | PF01473 | CW binding 1 | 655 | 670 |
| | | | PF01473 | CW binding 1 | 816 | 831 |
| APG00644 modified | Seq ID 71 | Alternate start | PF03945 | Endotoxin N | 93 | 289 |
| | | | PF01473 | CW binding 1 | 583 | 602 |
| | | | PF01473 | CW binding 1 | 607 | 622 |
| | | | PF01473 | CW binding 1 | 650 | 665 |
| | | | PF01473 | CW binding 1 | 811 | 826 |
| APG00644 modified | Seq ID 72 | Signal peptide removed | PF03945 | Endotoxin N | 55 | 251 |
| | | | PF01473 | CW binding 1 | 545 | 564 |
| | | | PF01473 | CW binding 1 | 569 | 584 |
| | | | PF01473 | CW binding 1 | 612 | 627 |
| | | | PF01473 | CW binding 1 | 773 | 788 |
| APG00648 | Seq ID 73 | | PF05431 | Toxin 10 | 202 | 398 |
| APG00648 modified | Seq ID 74 | Signal peptide removed | PF05431 | Toxin 10 | 168 | 364 |
| APG00649 | Seq ID 75 | | PF00652 | Ricin B Lectin | 40 | 170 |
| | | | PF05431 | Toxin 10 | 181 | 380 |
| APG00649 modified | Seq ID 76 | Alternate start | PF00652 | Ricin B Lectin | 38 | 168 |
| | | | PF05431 | Toxin 10 | 179 | 378 |
| APG00651 | Seq ID 77 | | PF03945 | Endotoxin N | 65 | 315 |
| | | | PF00555 | Endotoxin M | 320 | 515 |
| | | | PF03944 | Endotoxin C | 533 | 673 |
| | Seq ID 78 | 3' Truncation | PF03945 | Endotoxin N | 65 | 315 |
| APG00651 modified | | | PF00555 | Endotoxin M | 320 | 515 |
| | | | PF03944 | Endotoxin C | 533 | 672 |
| APG00657 | Seq ID 79 | | PF12495 | Vip3A N | 16 | 188 |
| | | | PF02018 | CBM 4 9 | 814 | 914 |

TABLE 2-continued

| | | | PFAM domains | | | |
|---|---|---|---|---|---|---|
| | | Modification | | Domain | Domain positions | |
| APG ID | Seq ID | Type | PFAM domain | Description | Start | Stop |
| APG00657 modified | Seq ID 80 | Alternate start | PF12495 PF02018 | Vip3A N CBM 4 9 | 14 812 | 186 912 |
| APG00659 | Seq ID 81 | | no PFAM domains | | | |
| APG00659 modified | Seq ID 82 | Alternate start | no PFAM domains | | | |
| APG00661 | Seq ID 83 | | no PFAM domains | | | |
| APG00662 | Seq ID 84 | | PF03945 PF00555 PF03944 | Endotoxin N Endotoxin M Endotoxin C | 70 298 515 | 293 504 651 |
| APG00662 modified | Seq ID 85 | Alternate start | PF03945 PF00555 PF03944 | Endotoxin N Endotoxin M Endotoxin C | 61 289 506 | 284 495 642 |
| APG00662 modified | Seq ID 86 | Alternate start and 3' Truncation | PF03945 PF00555 PF03944 | Endotoxin N Endotoxin M Endotoxin C | 61 289 506 | 284 495 641 |
| APG00663 | Seq ID 87 | | PF03945 PF03944 | Endotoxin N Endotoxin C | 70 537 | 318 687 |
| APG00663 modified | Seq ID 88 | 3' Truncation | PF03945 PF03944 | Endotoxin N Endotoxin C | 70 537 | 318 686 |
| APG00664 | Seq ID 89 | | PF03945 PF00555 PF03944 | Endotoxin N Endotoxin M Endotoxin C | 74 332 541 | 325 531 687 |
| APG00664 modified | Seq ID 90 | 3' Truncation | PF03945 PF00555 PF03944 | Endotoxin N Endotoxin M Endotoxin C | 74 332 541 | 325 531 686 |
| APG00672 | Seq ID 91 | | PF03945 PF03944 PF01473 PF01473 PF01473 PF01473 PF01473 | Endotoxin N Endotoxin C CW binding 1 CW binding 1 CW binding 1 CW binding 1 CW binding 1 | 98 526 685 714 743 772 801 | 335 661 702 731 760 789 818 |
| APG00672 modified | Seq ID 92 | 3' Truncation | PF03945 PF03944 | Endotoxin N Endotoxin C | 98 526 | 335 660 |
| APG00673 | Seq ID 93 | | PF03945 PF00555 PF03944 | Endotoxin N Endotoxin M Endotoxin C | 92 336 567 | 331 556 719 |
| APG00673 modified | Seq ID 94 | Alternate start and 3' Truncation | PF03945 PF00555 PF03944 | Endotoxin N Endotoxin M Endotoxin C | 62 307 538 | 302 527 689 |
| APG00673 modified | Seq ID 95 | Alternate start | PF03945 PF00555 PF03944 | Endotoxin N Endotoxin M Endotoxin C | 63 307 538 | 302 527 690 |
| APG00674 | Seq ID 96 | | PF00652 PF05431 | Ricin B Lectin Toxin 10 | 8 152 | 143 349 |
| APG00675 | Seq ID 97 | | PF12495 | Vip3A N | 10 | 187 |
| APG00677 | Seq ID 98 | | PF03945 PF00555 PF03944 | Endotoxin N Endotoxin M Endotoxin C | 66 304 515 | 299 505 651 |
| APG00679 | Seq ID 99 | | PF03945 PF00555 PF03944 | Endotoxin N Endotoxin M Endotoxin C | 35 258 460 | 253 450 594 |
| APG00679 modified | Seq ID 100 | 3' Truncation | PF03945 PF00555 PF03944 | Endotoxin N Endotoxin M Endotoxin C | 35 258 460 | 253 450 593 |
| APG00687 | Seq ID 101 | | PF03945 PF00555 PF03944 | Endotoxin N Endotoxin M Endotoxin C | 59 330 530 | 322 489 667 |
| APG00687 modified | Seq ID 102 | 3' Truncation | PF03945 PF00555 PF03944 | Endotoxin N Endotoxin M Endotoxin C | 59 330 530 | 322 490 666 |
| APG00687 CryBP1 | Seq ID 103 | | PF07029 | CryBP1 | 1 | 119 |
| APG00688 | Seq ID 104 | | PF03945 PF00555 PF03944 | Endotoxin N Endotoxin M Endotoxin C | 65 305 527 | 300 517 665 |
| APG00688 modified | Seq ID 105 | 3' Truncation | PF03945 PF00555 PF03944 | Endotoxin N Endotoxin M Endotoxin C | 65 305 527 | 300 517 664 |

TABLE 2-continued

| | | | PFAM domains | | | |
|---|---|---|---|---|---|---|
| | | Modification | | Domain | Domain positions | |
| APG ID | Seq ID | Type | PFAM domain | Description | Start | Stop |
| APG00693 | Seq ID 106 | | PF03318 | ETX MTX2 | 91 | 318 |
| APG00693 modified | Seq ID 107 | Signal peptide removed | PF03318 | ETX MTX2 | 12 | 268 |
| APG00693 modified | Seq ID 108 | Alternate start | PF03318 | ETX MTX2 | 35 | 294 |
| APG00695 | Seq ID 109 | | PF03945 | Endotoxin N | 61 | 295 |
| | | | PF00555 | Endotoxin M | 300 | 494 |
| | | | PF03944 | Endotoxin C | 504 | 631 |
| APG00695 modified | Seq ID 110 | Alternate start and 3' Truncation | PF03945 | Endotoxin N | 58 | 292 |
| | | | PF00555 | Endotoxin M | 297 | 491 |
| | | | PF03944 | Endotoxin C | 501 | 627 |
| APG00695 modified | Seq ID 111 | Alternate start | PF03945 | Endotoxin N | 58 | 292 |
| | | | PF00555 | Endotoxin M | 297 | 491 |
| | | | PF03944 | Endotoxin C | 501 | 628 |
| APG00695 Split-Cry C-term | Seq ID 112 | | no PFAM domains | | | |
| APG00701 | Seq ID 113 | | PF05431 | Toxin 10 | 189 | 382 |
| APG00701 modified | Seq ID 114 | Signal peptide removed | PF05431 | Toxin 10 | 160 | 353 |
| APG00702 | Seq ID 115 | | PF03945 | Endotoxin N | 109 | 309 |
| | | | PF14200 | Ricin B Lectin 2 | 487 | 589 |
| APG00702 modified | Seq ID 116 | Signal peptide removed | PF03945 | Endotoxin N | 71 | 271 |
| | | | PF14200 | Ricin B Lectin 2 | 449 | 551 |
| APG00703 | Seq ID 117 | | PF03945 | Endotoxin N | 214 | 352 |
| | | | PF03944 | Endotoxin C | 573 | 723 |
| APG00703 modified | Seq ID 118 | Alternate start | PF03945 | Endotoxin N | 208 | 346 |
| | | | PF03944 | Endotoxin C | 567 | 717 |
| APG00703 modified | Seq ID 119 | Alternate start and 3' Truncation | PF03945 | Endotoxin N | 208 | 346 |
| | | | PF03944 | Endotoxin C | 567 | 716 |
| APG00705 | Seq ID 120 | | PF03945 | Endotoxin N | 100 | 343 |
| | | | PF03944 | Endotoxin C | 535 | 672 |
| APG00705 modified | Seq ID 121 | Alternate start | PF03945 | Endotoxin N | 94 | 337 |
| | | | PF03944 | Endotoxin C | 529 | 666 |
| APG00705 modified | Seq ID 122 | Signal peptide removed and 3' Truncation | PF03945 | Endotoxin N | 65 | 308 |
| | | | PF03944 | Endotoxin C | 500 | 636 |
| APG00705 modified | Seq ID 123 | Signal peptide removed | PF03945 | Endotoxin N | 65 | 308 |
| | | | PF03944 | Endotoxin C | 500 | 637 |
| APG00705 modified | Seq ID 124 | Alternate start and 3' Truncation | PF03945 | Endotoxin N | 94 | 337 |
| | | | PF03944 | Endotoxin C | 529 | 665 |
| APG00705 modified | Seq ID 125 | 3' Truncation | PF03945 | Endotoxin N | 100 | 343 |
| | | | PF03944 | Endotoxin C | 535 | 671 |
| APG00706 | Seq ID 126 | | PF05431 | Toxin 10 | 251 | 446 |
| APG00707 | Seq ID 127 | | PF03318 | ETX MTX2 | 20 | 277 |
| APG00707 modified | Seq ID 128 | Signal peptide removed | PF03318 | ETX MTX2 | 9 | 259 |
| APG00710 | Seq ID 129 | | PF03945 | Endotoxin N | 86 | 336 |
| | | | PF00555 | Endotoxin M | 343 | 533 |
| | | | PF03944 | Endotoxin C | 543 | 679 |
| APG00710 modified | Seq ID 130 | Alternate start | PF03945 | Endotoxin N | 63 | 313 |
| | | | PF00555 | Endotoxin M | 320 | 510 |
| | | | PF03944 | Endotoxin C | 520 | 656 |
| APG00710 modified | Seq ID 131 | Alternate start and 3' Truncation | PF03945 | Endotoxin N | 63 | 313 |
| | | | PF00555 | Endotoxin M | 320 | 510 |
| | | | PF03944 | Endotoxin C | 520 | 655 |
| APG00718 | Seq ID 132 | | PF03318 | ETX MTX2 | 34 | 292 |
| APG00721 | Seq ID 133 | | PF03945 | Endotoxin N | 37 | 270 |
| | | | PF03945 | Endotoxin N | 299 | 346 |
| | | | PF00555 | Endotoxin M | 351 | 462 |
| | | | PF03944 | Endotoxin C | 592 | 729 |
| APG00721 modified | Seq ID 134 | 3' Truncation | PF03945 | Endotoxin N | 37 | 270 |
| | | | PF03945 | Endotoxin N | 299 | 346 |
| | | | PF00555 | Endotoxin M | 351 | 463 |
| | | | PF03944 | Endotoxin C | 592 | 728 |
| APG00721 Split-Cry C-term | Seq ID 135 | | no PFAM domains | | | |

TABLE 2-continued

PFAM domains

| APG ID | Seq ID | Modification Type | PFAM domain | Domain Description | Start | Stop |
|---|---|---|---|---|---|---|
| APG00722 | Seq ID 136 | | PF14200 | Ricin B Lectin 2 | 45 | 146 |
| | | | PF05431 | Toxin 10 | 152 | 348 |
| APG00724 | Seq ID 137 | | PF05431 | Toxin 10 | 209 | 402 |
| APG00724 modified | Seq ID 138 | Signal peptide removed | PF05431 | Toxin 10 | 182 | 375 |
| APG00726 | Seq ID 139 | | PF03945 | Endotoxin N | 86 | 339 |
| | | | PF00555 | Endotoxin M | 350 | 559 |
| | | | PF03944 | Endotoxin C | 569 | 711 |
| APG00726 modified | Seq ID 140 | Alternate start | PF03945 | Endotoxin N | 72 | 325 |
| | | | PF00555 | Endotoxin M | 336 | 545 |
| | | | PF03944 | Endotoxin C | 555 | 697 |
| APG00726 modified | Seq ID 141 | Alternate start and 3' Truncation | PF03945 | Endotoxin N | 72 | 325 |
| | | | PF00555 | Endotoxin M | 336 | 545 |
| | | | PF03944 | Endotoxin C | 555 | 696 |
| APG00729 | Seq ID 142 | | PF05431 | Toxin 10 | 184 | 385 |
| APG00729 modified | Seq ID 143 | Signal peptide removed | PF05431 | Toxin 10 | 157 | 358 |
| APG00735 | Seq ID 144 | | PF14200 | Ricin B Lectin 2 | 69 | 172 |
| | | | PF05431 | Toxin 10 | 178 | 375 |
| APG00735 modified | Seq ID 145 | Alternate start | PF14200 | Ricin B Lectin 2 | 43 | 146 |
| | | | PF05431 | Toxin 10 | 152 | 349 |
| APG00781 | Seq ID 146 | | PF03945 | Endotoxin N | 59 | 294 |
| | | | PF00555 | Endotoxin M | 305 | 509 |
| | | | PF03944 | Endotoxin C | 519 | 656 |
| | | | PF00652 | Ricin B Lectin | 672 | 801 |
| APG00781 modified | Seq ID 147 | 3' Truncation | PF03945 | Endotoxin N | 59 | 294 |
| | | | PF00555 | Endotoxin M | 305 | 509 |
| | | | PF03944 | Endotoxin C | 519 | 652 |
| APG00784 | Seq ID 148 | | PF03945 | Endotoxin N | 67 | 316 |
| | | | PF03944 | Endotoxin C | 531 | 673 |
| APG00784 modified | Seq ID 149 | 3' Truncation | PF03945 | Endotoxin N | 67 | 316 |
| | | | PF03944 | Endotoxin C | 531 | 672 |
| APG00785 | Seq ID 150 | | PF03945 | Endotoxin N | 72 | 302 |
| | | | PF00555 | Endotoxin M | 314 | 501 |
| | | | PF03944 | Endotoxin C | 511 | 670 |
| APG00785 modified | Seq ID 151 | Alternate start | PF03945 | Endotoxin N | 69 | 299 |
| | | | PF00555 | Endotoxin M | 311 | 498 |
| | | | PF03944 | Endotoxin C | 508 | 667 |
| APG00785 modified | Seq ID 152 | Alternate start and 3' Truncation | PF03945 | Endotoxin N | 69 | 299 |
| | | | PF00555 | Endotoxin M | 311 | 498 |
| | | | PF03944 | Endotoxin C | 508 | 666 |
| APG00786 | Seq ID 153 | | PF03945 | Endotoxin N | 67 | 288 |
| | | | PF00555 | Endotoxin M | 293 | 505 |
| | | | PF03944 | Endotoxin C | 516 | 653 |
| APG00786 modified | Seq ID 154 | Alternate start and 3' Truncation | PF03945 | Endotoxin N | 61 | 282 |
| | | | PF00555 | Endotoxin M | 287 | 499 |
| | | | PF03944 | Endotoxin C | 510 | 646 |
| APG00786 modified | Seq ID 155 | Alternate start | PF03945 | Endotoxin N | 61 | 282 |
| | | | PF00555 | Endotoxin M | 287 | 499 |
| | | | PF03944 | Endotoxin C | 510 | 647 |
| APG00787 | Seq ID 156 | | PF03945 | Endotoxin N | 110 | 311 |
| | | | PF01473 | CW binding 1 | 534 | 550 |
| APG00787 modified | Seq ID 157 | Signal peptide removed | PF03945 | Endotoxin N | 72 | 274 |
| | | | PF01473 | CW binding 1 | 496 | 512 |
| APG00799 | Seq ID 158 | | PF03945 | Endotoxin N | 63 | 260 |
| | | | PF03944 | Endotoxin C | 463 | 630 |
| APG00799 modified | Seq ID 159 | 3' Truncation | PF03945 | Endotoxin N | 63 | 260 |
| | | | PF03944 | Endotoxin C | 463 | 629 |
| APG00801 | Seq ID 160 | | PF03945 | Endotoxin N | 67 | 316 |
| | | | PF03944 | Endotoxin C | 527 | 666 |
| APG00801 modified | Seq ID 161 | 3' Truncation | PF03945 | Endotoxin N | 67 | 316 |
| | | | PF03944 | Endotoxin C | 527 | 665 |
| APG00802 | Seq ID 162 | | PF03945 | Endotoxin N | 65 | 285 |
| | | | PF00555 | Endotoxin M | 29 | 498 |
| | | | PF03944 | Endotoxin C | 508 | 653 |
| APG00802 modified | Seq ID 163 | 3' Truncation | PF03945 | Endotoxin N | 65 | 285 |
| | | | PF00555 | Endotoxin M | 295 | 498 |
| | | | PF03944 | Endotoxin C | 508 | 652 |

TABLE 2-continued

PFAM domains

| APG ID | Seq ID | Modification Type | PFAM domain | Domain Description | Domain positions Start | Stop |
|---|---|---|---|---|---|---|
| APG00805 | Seq ID 164 | | PF03945 | Endotoxin N | 75 | 296 |
| | | | PF00555 | Endotoxin M | 301 | 500 |
| | | | PF03944 | Endotoxin C | 511 | 643 |
| APG00805 modified | Seq ID 165 | Alternate start and 3' Truncation | PF03945 | Endotoxin N | 72 | 293 |
| | | | PF00555 | Endotoxin M | 298 | 497 |
| | | | PF03944 | Endotoxin C | 508 | 639 |
| APG00805 modified | Seq ID 166 | Alternate start | PF03945 | Endotoxin N | 72 | 293 |
| | | | PF00555 | Endotoxin M | 298 | 497 |
| | | | PF03944 | Endotoxin C | 508 | 640 |
| APG00806 | Seq ID 167 | | PF05431 | Toxin 10 | 203 | 396 |
| APG00806 modified | Seq ID 168 | Signal peptide removed | PF00652 | Ricin B Lectin | 5 | 100 |
| | | | PF05431 | Toxin 10 | 174 | 367 |
| APG00807 | Seq ID 169 | | PF03318 | ETX MTX2 | 32 | 278 |
| APG00807 modified | Seq ID 170 | Alternate start | PF03318 | ETX MTX2 | 30 | 276 |
| APG00810 | Seq ID 171 | | PF03945 | Endotoxin N | 62 | 286 |
| | | | PF00555 | Endotoxin M | 291 | 489 |
| | | | PF03944 | Endotoxin C | 499 | 635 |
| APG00810 modified | Seq ID 172 | Alternate start and 3' Truncation | PF03945 | Endotoxin N | 59 | 283 |
| | | | PF00555 | Endotoxin M | 288 | 486 |
| | | | PF03944 | Endotoxin C | 496 | 631 |
| APG00810 modified | Seq ID 173 | Alternate start | PF03945 | Endotoxin N | 59 | 283 |
| | | | PF00555 | Endotoxin M | 288 | 486 |
| | | | PF03944 | Endotoxin C | 496 | 632 |
| APG00864 | Seq ID 174 | | PF03945 | Endotoxin N | 74 | 327 |
| | | | PF00555 | Endotoxin M | 332 | 526 |
| | | | PF03944 | Endotoxin C | 543 | 683 |
| APG00912 | Seq ID 175 | | PF03945 | Endotoxin N | 70 | 308 |
| | | | PF00555 | Endotoxin M | 313 | 530 |
| | | | PF03944 | Endotoxin C | 540 | 678 |
| APG00912 modified | Seq ID 176 | Alternate start | PF03945 | Endotoxin N | 64 | 302 |
| | | | PF00555 | Endotoxin M | 307 | 524 |
| | | | PF03944 | Endotoxin C | 534 | 672 |
| APG00912 modified | Seq ID 177 | | PF03945 | Endotoxin N | 64 | 302 |
| | | | PF00555 | Endotoxin M | 307 | 524 |
| | | Alternate start and 3' Truncation | PF03944 | Endotoxin C | 534 | 671 |
| APG00912 CryBP1 | Seq ID 178 | | PF07029 | CryBP1 | 37 | 195 |
| APG00960 | Seq ID 179 | | PF03945 | Endotoxin N | 51 | 277 |
| | | | PF00555 | Endotoxin M | 282 | 491 |
| | | | PF03944 | Endotoxin C | 501 | 644 |
| APG00960 modified | Seq ID 180 | Alternate start and 3' Truncation | PF03945 | Endotoxin N | 36 | 262 |
| | | | PF00555 | Endotoxin M | 267 | 476 |
| | | | PF03944 | Endotoxin C | 486 | 628 |
| APG00960 modified | Seq ID 181 | Alternate start | PF03945 | Endotoxin N | 36 | 262 |
| | | | PF00555 | Endotoxin M | 267 | 476 |
| | | | PF03944 | Endotoxin C | 486 | 629 |
| APG00972 | Seq ID 182 | | PF03945 | Endotoxin N | 91 | 326 |
| | | | PF00555 | Endotoxin M | 332 | 540 |
| | | | PF03944 | Endotoxin C | 550 | 704 |
| APG00972 modified | Seq ID 183 | Alternate start and 3' Truncation | PF03945 | Endotoxin N | 68 | 303 |
| | | | PF00555 | Endotoxin M | 309 | 517 |
| | | | PF03944 | Endotoxin C | 527 | 680 |
| APG00972 modified | Seq ID 184 | Alternate start | PF03945 | Endotoxin N | 68 | 303 |
| | | | PF00555 | Endotoxin M | 309 | 517 |
| | | | PF03944 | Endotoxin C | 527 | 681 |
| APG00980 | Seq ID 185 | | PF03318 | ETX MTX2 | 94 | 315 |
| APG00980 modified | Seq ID 186 | Signal peptide removed | PF03318 | ETX MTX2 | 44 | 265 |
| APG00980 modified | Seq ID 187 | Alternate start | PF03318 | ETX MTX2 | 77 | 298 |
| APG00981 | Seq ID 188 | | PF03945 | Endotoxin N | 71 | 328 |
| | | | PF00555 | Endotoxin M | 333 | 525 |
| | | | PF03944 | Endotoxin C | 535 | 675 |
| APG00981 modified | Seq ID 189 | 3' Truncation | PF03945 | Endotoxin N | 71 | 328 |
| | | | PF00555 | Endotoxin M | 333 | 525 |
| | | | PF03944 | Endotoxin C | 535 | 674 |
| APG00986 | Seq ID 190 | | PF03945 | Endotoxin N | 76 | 305 |
| | | | PF00555 | Endotoxin M | 313 | 488 |
| | | | PF03944 | Endotoxin C | 499 | 635 |

TABLE 2-continued

| | | | PFAM domains | | | |
|---|---|---|---|---|---|---|
| | | Modification | | Domain | Domain positions | |
| APG ID | Seq ID | Type | PFAM domain | Description | Start | Stop |
| APG00986 modified | Seq ID 191 | Alternate start | PF03945 | Endotoxin N | 73 | 302 |
| | | | PF00555 | Endotoxin M | 310 | 485 |
| | | | PF03944 | Endotoxin C | 496 | 632 |
| APG00986 modified | Seq ID 192 | Alternate start and 3' Truncation | PF03945 | Endotoxin N | 73 | 302 |
| | | | PF00555 | Endotoxin M | 310 | 485 |
| | | | PF03944 | Endotoxin C | 496 | 631 |
| APG00986 Split-Cry C-term | Seq ID 193 | | no PFAM domains | | | |
| APG00988 | Seq ID 194 | | PF05431 | Toxin 10 | 190 | 386 |
| APG00988 modified | Seq ID 195 | Signal peptide removed | PF05431 | Toxin 10 | 163 | 359 |
| APG01000 | Seq ID 196 | | PF05431 | Toxin 10 | 57 | 251 |
| APG01000 modified | Seq ID 197 | Alternate start | PF05431 | Toxin 10 | 39 | 233 |
| APG01003 | Seq ID 198 | | PF12495 | Vip3A N | 16 | 188 |
| | | | PF02018 | CBM 4 9 | 545 | 666 |
| APG01003 modified | Seq ID 199 | Alternate start | PF12495 | Vip3A N | 14 | 186 |
| | | | PF02018 | CBM 4 9 | 543 | 664 |
| APG01028 | Seq ID 200 | | PF03945 | Endotoxin N | 80 | 310 |
| | | | PF00555 | Endotoxin M | 315 | 529 |
| | | | PF03944 | Endotoxin C | 539 | 671 |
| APG01028 modified | Seq ID 201 | Alternate start | PF03945 | Endotoxin N | 77 | 307 |
| | | | PF00555 | Endotoxin M | 312 | 526 |
| | | | PF03944 | Endotoxin C | 536 | 668 |
| APG01028 modified | Seq ID 202 | Alternate start and 3' Truncation | PF03945 | Endotoxin N | 77 | 307 |
| | | | PF00555 | Endotoxin M | 312 | 526 |
| | | | PF03944 | Endotoxin C | 536 | 667 |
| APG01028 Split-Cry C-term | Seq ID 203 | | no PFAM domains | | | |
| APG01112 | Seq ID 204 | | PF03945 | Endotoxin N | 2 | 200 |
| APG00556 | Seq ID 205 | | no PFAM domains | | | |
| APG00556 modified | Seq ID 206 | Alternate start | no PFAM domains | | | |
| APG00623 | Seq ID 207 | | no PFAM domains | | | |
| APG01037 | Seq ID 208 | | no PFAM domains | | | |
| APG01037.1 (APG01037 modified) | Seq ID 209 | Alternate start | no PFAM domains | | | |
| APG01037.4 | Seq ID 210 | Alternate start and point mutation (S to T) | no PFAM domains | | | |
| APG01037.5 modified (APG01037 modified) | Seq ID 211 | Alternate start and point mutation (S to T) | no PFAM domains | | | |
| APG01037.6 (APG01037 modified) | Seq ID 212 | Alternate start and point mutation (S to K) | no PFAM domains | | | |
| APG01037.7 (APG01037 modified) | Seq ID 213 | Alternate start and point mutation (T to E) | no PFAM domains | | | |
| APG01037.8 (APG01037 modified) | Seq ID 214 | Alternate start and point mutation (I to E) | no PFAM domains | | | |
| APG01086 | Seq ID 215 | | PF03318 | ETX MTX2 | 34 | 260 |
| APG01086 modified | Seq ID 216 | Alternate start | PF03318 | ETX MTX2 | 28 | 253 |
| APG06508 | Seq ID 217 | | no PFAM domains | | | |
| APG09801 | Seq ID 218 | | no PFAM domains | | | | ii. Variants and Fragments of Pesticidal Proteins and Polynucleotides Encoding the Same Pesticidal proteins or polypeptides of the invention include those set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218 and fragments and variants thereof. By "pesticidal toxin" or "pesticidal protein" or "pesticidal polypeptide" is intended a toxin or protein or polypeptide that has activity against one or more pests, including, insects, fungi, nematodes, and the like such that the pest is killed or controlled.

An "isolated" or "purified" polypeptide or protein, or biologically active portion thereof, is substantially or essentially free from components that normally accompany or interact with the polypeptide or protein as found in its naturally occurring environment. Thus, an isolated or purified polypeptide or protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The term "fragment" refers to a portion of a polypeptide sequence of the invention. "Fragments" or "biologically active portions" include polypeptides comprising a sufficient number of contiguous amino acid residues to retain the biological activity, i.e., have pesticidal activity. Fragments of the pesticidal proteins include those that are shorter than the full-length sequences, either due to the use of an alternate downstream start site, or due to processing that produces a shorter protein having pesticidal activity. Processing may occur in the organism the protein is expressed in, or in the pest after ingestion of the protein. Examples of fragments of the proteins can be found in Table 1. A biologically active portion of a pesticidal protein can be a polypeptide that is, for example, 10, 25, 50, 100, 150, 200, 250 or more amino acids in length of any one of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218. Such biologically active portions can be prepared by recombinant techniques and evaluated for pesticidal activity. As used here, a fragment comprises at least 8 contiguous amino acids of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218.

Bacterial genes, including those encoding the pesticidal proteins disclosed herein, quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined apriori which of these codons are used naturally in the bacterium. Thus, it is understood that use of one of the alternate methionine codons may also lead to generation of pesticidal proteins. These pesticidal proteins are encompassed in the present invention and may be used in the methods disclosed herein. It will be understood that, when expressed in plants, it will be necessary to alter the alternate start codon to ATG for proper translation.

In various embodiments the pesticidal proteins provided herein include amino acid sequences deduced from the full-length nucleotide sequences and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an alternate start site.

It is recognized that modifications may be made to the pesticidal polypeptides provided herein creating variant proteins. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the pesticidal proteins. Alternatively, modifications may be made that improve the activity of the toxin. Modification of Cry toxins by domain III swapping has resulted in some cases in hybrid toxins with improved toxicities against certain insect species. Thus, domain III swapping could be an effective strategy to improve toxicity of Cry toxins or to create novel hybrid toxins with toxicity against pests that show no susceptibility to the parental Cry toxins. Site-directed mutagenesis of domain II loop sequences may result in new toxins with increased insecticidal activity. Domain II loop regions are key binding regions of initial Cry toxins that are suitable targets for the mutagenesis and selection of Cry toxins with improved insecticidal properties. Domain I of the Cry toxin may be modified to introduce protease cleavage sites to improve activity against certain pests. Strategies for shuffling the three different domains among large numbers of cry genes and high through output bioassay screening methods may provide novel Cry toxins with improved or novel toxicities.

As indicated, fragments and variants of the polypeptides disclosed herein will retain pesticidal activity. Pesticidal activity comprises the ability of the composition to achieve an observable effect diminishing the occurrence or an activity of the target pest, including for example, bringing about death of at least one pest, or a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater. The pesticidal activity against one or more of the various pests provided herein, including, for example, pesticidal activity against Coleoptera, Diptera, Hymenoptera, Lepidoptera, Mallophaga, Homoptera, Hemiptera, Orthroptera, Nematodes, Thysanoptera, Dermaptera, Isoptera, Anoplura, Siphonaptera, Trichoptera, etc., or any other pest described herein. It is recognized that the pesticidal activity may be different or improved relative to the activity of the native protein, or it may be unchanged, so long as pesticidal activity is retained. Methods for measuring pesticidal activity are provide elsewhere herein. See also, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

By "variants" is intended polypeptides having an amino acid sequence that is at least about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98% or about 99% identical to the amino acid sequence of any of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218 and retain pesticidal activity. Note, Table 1 provides non-limiting examples of variant polypeptides (and polynucleotide encoding the same) for each of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218. A biologically active variant of a pesticidal polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50 amino acids or more from either the N or C terminal of the polypeptide.

Recombinant or synthetic nucleic acids encoding the pesticidal polypeptides disclosed herein are also provided. Of particular interest are nucleic acid sequences that have been designed for expression in a plant of interest. That is, the nucleic acid sequence can be optimized for increased expression in a host plant. A pesticidal protein of the invention can be back-translated to produce a nucleic acid comprising codons optimized for expression in a particular host, for example, a crop plant. In another embodiment, the polynucleotides encoding the polypeptides provided herein may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Expression of such a coding sequence by the transformed plant (e.g., dicot or monocot) will result in the production of a pesticidal polypeptide and confer increased resistance in the plant to a pest. Recombinant and synthetic nucleic acid molecules encoding the pesticidal proteins of the invention do not include the naturally occurring bacterial sequence encoding the protein.

A "recombinant polynucleotide" or "recombinant nucleic acid" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or a variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides include chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide or nucleic acid" comprises at least one of a combination of two or more chemically linked amino acid segments which are not found directly joined in nature.

Fragments of a polynucleotide (RNA or DNA) may encode protein fragments that retain activity. In specific embodiments, a fragment of a recombinant polynucleotide or a recombinant polynucleotide construct comprises at least one junction of the two or more chemically linked or operably linked nucleic acid segments which are not found directly joined in nature. A fragment of a polynucleotide that encodes a biologically active portion of a polypeptide that retains pesticidal activity will encode at least 25, 30, 40, 50, 60, 70, 75, 80, 90, 100, 110, 120, 125, 130, 140, 150, 160, 170, 175, 180, contiguous amino acids, or up to the total number of amino acids present in a full-length polypeptide as set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218. In specific embodiments, such polypeptide fragments are active fragment, and in still other embodiments, the polypeptide fragment comprises a recombinant polypeptide fragment. As used herein, a fragment of a recombinant polypeptide comprises at least one of a combination of two or more chemically linked amino acid segments which are not found directly joined in nature.

By "Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218.

Variant polynucleotide and proteins also encompass sequences and proteins derived from a mutagenic and recombinogenic procedure such as DNA shuffling. With such a procedure, one or more different pesticidal protein disclosed herein (SEQ ID NO: 1-218) is manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the pesticidal sequences provided herein and other known pesticidal genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

In one embodiment, a method of obtaining a polynucleotide that encodes an improved polypeptide comprising pesticidal activity is provided, wherein the improved polypeptide has at least one improved property over any one of SEQ ID NOS: 1-218. Such methods can comprises (a) recombining a plurality of parental polynucleotides to produce a library of recombinant polynucleotides encoding recombinant pesticidal polypeptides; (b) screening the library to identify a recombinant polynucleotide that encodes an improved recombinant pesticidal polypeptide that has an enhanced property improved over the parental polynucleotide; (c) recovering the recombinant polynucleotide that encodes the improved recombinant pesticidal polypeptide identified in (b); and, (d) repeating steps (a), (b) and (c) using the recombinant polynucleotide recovered in step (c) as one of the plurality of parental polynucleotides in repeated step (a).

Provided herein are active variants of the polypeptides set forth in SEQ ID NOS: 205, 206, 207, 208, 209, 210, 211, 212, 213, and/or 214. Such polypeptides comprise a sequence having at least 80%, 85%, 86%, 87%, 88%, 89%, 90%, 91%, 92%, 93%, 94%, 95%, 96%, 97%, 98%, or 99% sequence identity to any one of SEQ ID NOS: 205, 206, 207, 208, 209, 210, 211, 212, 213, and/or 214 and further comprises one or more of the modifications set forth in Table 3. Any given variant of SEQ ID NO: 205, 206, 207, 208, 209, 210, 211, 212, 213, and/or 214 can have one or more of any combination of amino acid alterations in the corresponding amino acid position(s) as set forth in Table 3, or fragments thereof. Such, variants will retain pesticidal activity. In specific embodiments, such variants will have improved pesticidal activity against an insect of interest.

Further provided are polypeptides comprising a sequence having at least 80%, 85%, 86%, 87%, 88%, 89%, 90%, 91%, 92%, 93%, 94%, 95%, 96%, 97%, 98%, or 99% sequence identity to any one of SEQ ID NOS: 205, 206, 207, 208, 209, 210, 211, 212, 213, and/or 214 and further comprise at least 1, 2, 3, 4, 5, 6, 7, 8, 9, 10 or more of the modifications set forth in Table 3, wherein the amino acid positions 204-210 corresponding to the positions of SEQ ID NO:208 (DHYFWFL) are not altered.

Table 3 provides protein variants of any one of SEQ ID NO: 205-214 as indicated by amino acid position and change. The amino acid position denoted in Table 3 reflects the amino acid position of SEQ ID NO:208 (APG01037.0). Corresponding amino acid positions in SEQ ID NO: 205-207 and 209-214 can be determined using methods discussed elsewhere herein.

TABLE 3

| Gene name | AA position and change |
|---|---|
| APG01037.1 | K6L, V |
| APG01037.1 | F7T |
| APG01037.1 | S10T |
| APG01037.1 | E11D |
| APG01037.1 | V15L |
| APG01037.1 | G16D |
| APG01037.1 | N18T |
| APG01037.1 | P19T |
| APG01037.1 | N20D |
| APG01037.1 | F26D |
| APG01037.1 | E28D |
| APG01037.1 | R29L |
| APG01037.1 | F30Y |
| APG01037.1 | Y44F |
| APG01037.1 | Y45F |
| APG01037.1 | N46D |
| APG01037.1 | Q55R |
| APG01037.1 | T63M |
| APG01037.1 | E66P |
| APG01037.1 | T68I |
| APG01037.1 | Y69F |
| APG01037.1 | Q70R |
| APG01037.1 | Q75N |
| APG01037.1 | P77G |
| APG01037.1 | S78N |
| APG01037.1 | I81F |
| APG01037.1 | N89Q |
| APG01037.1 | H90P |
| APG01037.1 | S96E |
| APG01037.1 | G103E |
| APG01037.1 | N104Q |
| APG01037.1 | Q114K, Y, F, E |
| APG01037.1 | K124D |
| APG01037.1 | T126I |
| APG01037.1 | L127E |
| APG01037.1 | V130F |
| APG01037.1 | F137Y |
| APG01037.1 | S138N |
| APG01037.1 | V139F |
| APG01037.1 | S147N |
| APG01037.1 | T149E |
| APG01037.1 | S157P |
| APG01037.1 | V159Q |
| APG01037.1 | T160S |
| APG01037.1 | N162K |
| APG01037.1 | K168Q |
| APG01037.1 | K169R, M |
| APG01037.1 | K170E, Y, T |
| APG01037.1 | M177K, R |
| APG01037.1 | Q179K |
| APG01037.1 | M182G, L, V, I |
| APG01037.1 | N183Q |
| APG01037.1 | Q185R, K |
| APG01037.1 | Q191N |
| APG01037.1 | S193M |
| APG01037.1 | F194Y |
| APG01037.1 | R200K |
| APG01037.1 | K201R |
| APG01037.1 | V202A, I |
| APG01037.1 | E203Q, D |
| APG01037.1 | D213E |
| APG01037.1 | N214F |
| APG01037.1 | S218K |
| APG01037.1 | T220D |
| APG01037.1 | T222P |
| APG01037.1 | K228N |
| APG01037.1 | F233Y |

The amino acid position denoted in Table 3 reflects the amino acid position of SEQ ID NO:208 (APG01037.0). The amino acid alterations set forth in Table 3 can be made in the corresponding amino acid positions of any one of SEQ ID NOs: 205, 206, 207, 208, 209, 210, 211, 212, 213, and/or 214. With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO: 208 position 1 is L, position 2 is M, position 3 is P, etc. When a test sequence is optimally aligned with SEQ ID NO: 208, a residue in the test sequence that aligns with the P at position 3 is said to "correspond to position 3" of SEQ ID NO: 208. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

iii. Sequence Comparisons

As used herein, the term "identity" or "percent identity" when used with respect to a particular pair of aligned amino acid sequences, refers to the percent amino acid sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences, refers to the sum of the scores that are obtained from a scoring matrix for each amino acid pair in the alignment divided by the length of the aligned sequences.

Unless otherwise stated, identity and similarity will be calculated by the Needleman-Wunsch global alignment and scoring algorithms (Needleman and Wunsch (1970) *J. Mol. Biol.* 48(3):443-453) as implemented by the "needle" program, distributed as part of the EMBOSS software package (Rice, P. Longden, I. and Bleasby, A., EMBOSS: The European Molecular Biology Open Software Suite, 2000, *Trends in Genetics* 16, (6) pp 276-277, versions 6.3.1 available from EMBnet at embnet.org/resource/emboss and emboss.sourceforge.net, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403. BLAST nucleotide searches can be performed with the BLASTN program (nucleotide query searched against nucleotide sequences) to obtain nucleotide sequences homologous to pesticidal-like nucleic acid molecules of the invention, or with the BLASTX program (translated nucleotide query searched against protein sequences) to obtain protein sequences homologous to pesticidal nucleic acid molecules of the invention. BLAST protein searches can be performed with the BLASTP program (protein query searched against protein sequences) to obtain amino acid sequences homologous to pesticidal protein molecules of the invention, or with the TBLASTN program (protein query searched against translated nucleotide sequences) to obtain nucleotide sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

iv. Antibodies

Antibodies to the polypeptides of the present invention, or to variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of toxin polypeptides. Thus, this disclosure provides kits comprising antibodies that specifically bind to the polypeptides described herein, including, for example, polypeptides having the sequence of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133,134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212,213, 214, 215, 216, 217, and/or 218.

II. Pests

The compositions and methods provided herein are useful against a variety of pests. "Pests" includes but is not limited to, insects, fungi, bacteria, nematodes, acarids, protozoan pathogens, animal-parasitic liver flukes, and the like. Pests of particular interest are insect pests, particularly insect pests that cause significant damage to agricultural plants. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, or nematodes. In non-limiting embodiments, the insect pest comprises Western corn rootworm, *Diabrotica virgifera virgifera*; Fall armyworm, *Spodoptera frugiperda*; Colorado potato beetle, *Leptinotarsa decemlineata*; Corn earworm, *Helicoverpa zea* (in North America same species attacks cotton and called cotton bollworm); European corn borer, *Ostrinia nubilalis*; Black cutworm, *Agrotis ipsilon*; Diamondback moth, *Plutella xylostella*; Velvetbean caterpillar, *Anticarsia gemmatalis*; Southwestern corn borer, *Diatraea grandiosella*; Cotton bollworm, *Helicoverpa armigera* (found other than USA in rest of the world); Southern green stinkbug, *Nezara viridula*; Green stinkbug, *Chinavia halaris*; Brown marmorated stinkbug, *Halyomorpha halys*; and Brown stinbug, *Euschistus servus Euschistus heros* (Neotropical brown stink bug OR soy stink bug); *Piezodorus guildinii* (red-banded stink bug); *Dichelops melacanthus* (no common name) and/or *Dichelops furcatus* (no common name); an aphid, such as a soybean aphid. In other embodiments, the pest comprises a nematode including, but not limited to, *Meloidogyne hapla* (Northern root-knot nematode); *Meloidogyne enterolobii, Meloidogyne arenaria* (peanut root-knot nematode); and *Meloidogyne javanica*.

The term "insect pests" as used herein refers to insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips* sp., *Argyrotaenia* sp., *Athetis mindara, Bombyx mori, Bucculatrix thurberiella, Cadra cautella, Choristoneura* sp., *Cochylls hospes, Colias eurytheme, Corcyra cephalonica, Cydia latiferreanus, Cydia pomonella, Datana integerrima, Dendrolimus sibericus,* Desmiafeneralis, *Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Heli-* *coverpa zea, Heliothis virescens, Hemileuca oliviae, Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia calfornica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails,* and *Yponomeuta padella.*

Insect pests also include insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, Coleoptera. Insect pests of the invention for the major crops include, but are not limited to: Maize: *Ostrinia nubilalis,* European corn borer; *Agrotis ipsilon,* black cutworm; *Helicoverpa zeae,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; western corn rootworm, e.g., *Diabrotica virgifera virgifera;* northern corn rootworm, e.g., *Diabrotica longicornis barberi;* southern corn rootworm, e.g., *Diabrotica undecimpunctata howardi;* Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blotch leafminer; *Anaphothrips obscrurus,* grass thrips; *Solenopsis milesta,* thief ant; *Tetranychus urticae,* two spotted spider mite; Sorghum: *Chilo partellus,* sorghum borer; *Spodoptera frugiperda,* fall armyworm; *Helicoverpa zea,* corn earworm; *Elasmopalpus lignosellus,* leser cornstalk borer; *Feltia subterranea,* granulate cutworm; *Phyllophaga crinita,* white grub; *Eleodes, Conoderus,* and *Aeolus* spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; chinch bug, e.g., *Blissus leucopterus leucopterus; Contarinia sorghicola,* sorghum midge; *Tetranychus cinnabarinus,* carmine spider mite; *Tetranychus urticae,* two-spotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* pale western cutworm; *Elasmopalpus lignosellus,* lesser cornstalk borer; *Oulema melanopus,* cereal leaf beetle; *Hypera punctata,* clover leaf weevil; southern corn rootworm, e.g., *Diabrotica undecimpunctata howardi;* Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis*; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; chinch bug, e.g., *Blissus leucopterus leucopterus*; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus*; *Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus*, *Meligethes nigrescens*, *Meligethes canadianus*, and *Meligethes viridescens*; Potato: *Leptinotarsa decemlineata*, Colorado potato beetle.

The methods and compositions provided herein may be effective against Hemiptera such as *Lygus hesperus, Lygus lineolaris, Lygus pratensis, Lygus rugulipennis* Popp, *Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara viridula, Eurygaster, Coreidae, Pyrrhocoridae, Tinidae, Blostomatidae, Reduviidae*, and *Cimicidae*. Pests of interest also include *Araecerus fasciculatus*, coffee bean weevil; *Acanthoscelides obtectus*, bean weevil; *Bruchus rufmanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Stermechus paludatus*, bean stalk weevil; *Hypera brunnipennis*, Egyptian alfalfa weevil; *Sitophilus granaries*, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; Tribolium castaneum, red flour beetle; *Tenebrio molitor*, yellow mealworm.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests may be tested for pesticidal activity of compositions of the invention in early developmental stages, e.g., as larvae or other immature forms. The insects may be reared in total darkness at from about 20 degree C. to about 30 degree C. and from about 30% to about 70% relative humidity. Bioassays may be performed as described in Czapla and Lang (1990) *J. Econ. Entomol.* 83 (6): 2480-2485. See, also the experimental section herein.

III. Expression Cassettes

Polynucleotides encoding the pesticidal proteins provided herein can be provided in expression cassettes for expression in an organism of interest. The cassette will include 5' and 3' regulatory sequences operably linked to a polynucleotide encoding a pesticidal polypeptide provided herein that allows for expression of the polynucleotide. The cassette may additionally contain at least one additional gene or genetic element to be cotransformed into the organism. Where additional genes or elements are included, the components are operably linked. Alternatively, the additional gene(s) or element(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional and translational initiation region (i.e., a promoter), a pesticidal polynucleotide of the invention, and a transcriptional and translational termination region (i.e., termination region) functional in the organism of interest, i.e., a plant or bacteria. The promoters of the invention are capable of directing or driving expression of a coding sequence in a host cell. The regulatory regions (i.e., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991)*Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, tissue-preferred, or other promoters for expression in the organism of interest. See, for example, promoters set forth in WO 99/43838 and in U.S. Pat. Nos. 8,575,425; 7,790,846; 8,147,856; 8,586,832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730). Inducible promoters include those that drive expression of pathogenesis-related proteins (PR proteins), which are induced following infection by a pathogen. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116; and WO 99/43819, herein incorporated by reference. Promoters that are expressed locally at or near the site of pathogen infection may also be used (Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988)*Mol. Gen. Genet.* 2:93-98; and Yang (1996) *Proc. Natl. Acad. Sci. USA* 93:14972-14977; Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; Cordero et al. (1992) *Physiol. Mol. Plant Path.* 41:189-200; U.S. Pat. No. 5,750,386 (nematode-inducible); and the references cited therein).

Wound-inducible promoters may be used in the constructions of the invention. Such wound-inducible promoters include pin II promoter (Ryan (1990) *Ann. Rev. Phytopath.* 28:425-449; Duan et al. (1996) *Nature Biotechnology* 14:494-498); wun1 and wun2 (U.S. Pat. No. 5,428,148); win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Tissue-preferred promoters for use in the invention include those set forth in Yamamoto et al. (1997) *Plant J.* 12(2):255-265; Kawamata et al. (1997) *Plant Cell Physiol.* 38(7):792-803; Hansen et al. (1997)*Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

Leaf-preferred promoters include those set forth in Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Root-preferred promoters are known and include those in Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element); Sanger et al. (1990) *Plant Mol. Biol.* 14(3):433-443 (mannopine synthase (MAS) gene of *Agrobacterium tumefaciens*); and Miao et al. (1991) *Plant Cell* 3(1):11-22 (cytosolic glutamine synthetase (GS)); Bogusz et al. (1990) *Plant Cell* 2(7):633-641; Leach and Aoyagi (1991) Plant Science (Limerick) 79(1):69-76 (rolC and rolD); Teeri et al. (1989) *EMBO J.* 8(2):343-350; Kuster et al. (1995) *Plant Mol. Biol.* 29(4):759-772 (the VfENOD-GRP3 gene promoter); and, Capana et al. (1994) *Plant Mol. Biol.* 25(4):681-691 (rolB promoter). See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108. Seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed.

For expression in a bacterial host, promoters that function in bacteria are well-known in the art. Such promoters include any of the known crystal protein gene promoters, including the promoters of any of the pesticidal proteins of the invention, and promoters specific for *B. thuringiensis* sigma factors. Alternatively, mutagenized or recombinant crystal protein-encoding gene promoters may be recombinantly engineered and used to promote expression of the novel gene segments disclosed herein.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers are known and any can be used. See, for example, PCT/US2015/066648, filed on Dec. 18, 2015, herein incorporated by reference in its entirety, which discloses glufosinate resistance sequences that can be employed as selectable markers.

IV. Methods, Host Cells and Plant Cells

As indicated, DNA constructs comprising nucleotide sequences encoding the pesticidal proteins or active variants or fragment thereof can be used to transform plants of interest or other organisms of interest. Methods for transformation involve introducing a nucleotide construct into a plant. By "introducing" is intended to introduce the nucleotide construct to the plant or other host cell in such a manner that the construct gains access to the interior of a cell of the plant or host cell. The methods of the invention do not require a particular method for introducing a nucleotide construct to a plant or host cell, only that the nucleotide construct gains access to the interior of at least one cell of the plant or the host organism. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

Transgenic plants" or "transformed plants" or "stably transformed" plants or cells or tissues refers to plants that have incorporated or integrated a polynucleotide encoding at least one pesticidal polypeptide of the invention. It is recognized that other exogenous or endogenous nucleic acid sequences or DNA fragments may also be incorporated into the plant cell. *Agrobacterium*- and biolistic-mediated transformation remain the two predominantly employed approaches. However, transformation may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, Agro and viral mediated (Caulimoriviruses, Geminiviruses, RNA plant viruses), liposome mediated and the like.

Transformation protocols as well as protocols for introducing polypeptides or polynucleotide sequences into plants may vary depending on the type of plant or plant cell, i.e., monocot or dicot, targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5.

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) Proc. Nail. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

In specific embodiments, the sequences provide herein can be targeted to specific cite within the genome of the host cell or plant cell. Such methods include, but are not limited to, meganucleases designed against the plant genomic sequence of interest (D'Halluin et al. 2013 *Plant Biotechnol J*); CRISPR-Cas9, TALENs, and other technologies for precise editing of genomes (Feng, et al. Cell Research 23:1229-1232, 2013, Podevin, et al. *Trends Biotechnology*, online publication, 2013, Wei et al., *J Gen Genomics*, 2013, Zhang et al (2013) WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. *Plant J*(2011) 701: 147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta (2002) *Plant Mol Biol* 48:173-182).

The sequence provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

In another embodiment, the genes encoding the pesticidal proteins can be used to transform insect pathogenic organisms. Such organisms include baculoviruses, fungi, protozoa, bacteria, and nematodes. Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include archaea, bacteria, algae, and fungi. Of particular interest are microorganisms such as bacteria, e.g., *Bacillus, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc,* and *Alcaligenes.* Fungi include yeast, e.g., *Saccharomyces, Cryptococcus, Kluyveromyces, Sporobolomyces, Rhodotorula,* and *Aureobasidium.* Of particular interest are such phytosphere bacterial species as *Pseudomonas syringae, Pseudomonas aeruginosa, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. difluens, C. laurentii, Saccharomyces rosei, S. pretoriensis, S. cerevisiae, Sporobolomyces rosues, S. odorus, Kluyveromyces veronae, Aureobasidium pollulans, Bacillus thuringiensis, Escherichia coli, Bacillus subtilis,* and the like.

Illustrative prokaryotes, both Gram-negative and gram-positive, include Enterobacteriaceae, such as *Escherichia, Erwinia, Shigella, Salmonella,* and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Fungi include Phycomycetes and Ascomycetes, e.g., yeast, such as *Saccharomyces* and *Schizosaccharomyces*; and Basidiomycetes yeast, such as *Rhodotorula, Aureobasidium,* Sporobolomyces, and the like.

Genes encoding pesticidal proteins can be introduced by means of electrotransformation, PEG induced transformation, heat shock, transduction, conjugation, and the like. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria by fusing an appropriate signal peptide to the amino-terminal end of the pesticidal protein. Signal peptides recognized by *E. coli* include the OmpA protein (Ghrayeb et al. (1984) *EMBO J,* 3: 2437-2442).

Pesticidal proteins and active variants thereof can be fermented in a bacterial host and the resulting bacteria processed and used as a microbial spray in the same manner that *Bacillus thuringiensis* strains have been used as insecticidal sprays. In the case of a pesticidal protein(s) that is secreted from *Bacillus,* the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins.

Alternatively, the pesticidal proteins are produced by introducing heterologous genes into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example U.S. Pat. No. 6,468,523 and U.S. Publication No. 20050138685, and the references cited therein. In the present invention, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal or agricultural composition(s) that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Agricultural compositions may comprise a polypeptide, a recombinogenic polypeptide or a variant or fragment thereof, as disclosed herein. The agricultural composition disclosed herein may be applied to the environment of a plant or an area of cultivation, or applied to the plant, plant part, plant cell, or seed.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins, provided herein can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In one aspect, pests may be killed or reduced in numbers in a given area by application of the pesticidal proteins provided herein to the area. Alternatively, the pesticidal proteins may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations or compositions may also vary with respect to climatic conditions, environmental considerations, and/or frequency of application and/or severity of pest infestation.

The active ingredients are normally applied in the form of compositions and can be applied to the crop area, plant, or seed to be treated. Methods are therefore provided for providing to a plant, plant cell, seed, plant part or an area of cultivation, an effective amount of the agricultural composition comprising the polypeptide, recombinogenic polypeptide or an active variant or fragment thereof. By "effective amount" is intended an amount of a protein or composition has pesticidal activity that is sufficient to kill or control the pest or result in a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater.

For example, the compositions may be applied to grain in preparation for or during storage in a grain bin or silo, etc. The compositions may be applied simultaneously or in succession with other compounds. Methods of applying an active ingredient or an agrochemical composition comprising at least one of the polypeptides, recombinogenic polypeptides or variants or fragments thereof as disclosed herein, include but are not limited to, foliar application, seed coating, and soil application.

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides.

Non-limiting embodiments include:

Embodiment 1. An isolated polypeptide having insecticidal activity, comprising:
(a) a polypeptide comprising an amino acid sequence selected from the group consisting of sequences set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218; or
(b) a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218.

Embodiment 2. The polypeptide of embodiment 1, wherein said polypeptide comprises the amino acid sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218.

Embodiment 3. The polypeptide of embodiment 1 or 2, further comprising heterologous amino acid sequences.

Embodiment 4. A composition comprising the polypeptide of any one of embodiments 1-3.

Embodiment 5. A recombinant nucleic acid molecule that encodes the polypeptide of any one of embodiments 1, 2, or 4, wherein said recombinant nucleic acid molecule is not the naturally occurring sequence encoding said polypeptide.

Embodiment 6. The recombinant nucleic acid of embodiment 5, wherein said nucleic acid molecule is a synthetic sequence that has been designed for expression in a plant.

Embodiment 7. The recombinant nucleic acid molecule of embodiments 5 or 6, wherein said nucleic acid molecule is operably linked to a promoter capable of directing expression in a plant cell.

Embodiment 8. The recombinant nucleic acid molecule of embodiment 5, wherein said nucleic acid molecule is operably linked to a promoter capable of directing expression in a bacteria.

Embodiment 9. A host cell that contains the recombinant nucleic acid molecule of any one of embodiments 5-8.

Embodiment 10. The host cell of embodiment 9, wherein said host cell is a bacterial host cell.

Embodiment 11. A DNA construct comprising a promoter that drives expression in a plant cell operably linked to a recombinant nucleic acid molecule comprising:
(a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218; or,
(b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, and/or 218.

Embodiment 12. The DNA construct of embodiment 11, wherein said nucleotide sequence is a synthetic DNA sequence that has been designed for expression in a plant.

Embodiment 13. A vector comprising the DNA construct of embodiments 11 or 12.

Embodiment 14. A host cell that contains the DNA construct of embodiments 11 or 12 or the vector of embodiment 13.

Embodiment 15. The host cell of embodiment 14, wherein the host cell is a plant cell.

Embodiment 16. A transgenic plant comprising the host cell of embodiment 15.

Embodiment 17. A composition comprising the host cell of embodiments 9, 10, 14, or 15.

Embodiment 18. The composition of embodiment 17, wherein said composition is selected from the group consisting of a powder, dust, pellet, granule, spray, emulsion, colloid, and solution.

Embodiment 19. The composition of embodiments 16 or 17, wherein said composition comprises from about 1% to about 99% by weight of said polypeptide.

Embodiment 20. A method for controlling a pest population comprising contacting said population with a pesticidal-effective amount of the composition of any one of embodiments 17-19.

Embodiment 21. A method for killing a pest population comprising contacting said population with a pesticidal-effective amount of the composition of any one of embodiments 17-19.

Embodiment 22. A method for producing a polypeptide with pesticidal activity, comprising culturing the host cell of any one of embodiments 9, 10, 14, or 15 under conditions in which the nucleic acid molecule encoding the polypeptide is expressed.

Embodiment 23. A plant having stably incorporated into its genome a DNA construct comprising a nucleotide sequence that encodes a protein having pesticidal activity, said nucleotide sequence comprising:
(a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218; or,
(b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218.

Embodiment 24. A transgenic seed of the plant of embodiment 23.

Embodiment 25. A method for protecting a plant from an insect pest, comprising expressing in a plant or cell thereof a nucleotide sequence that encodes a pesticidal polypeptide, said nucleotide sequence comprising:
  (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218; or,
  (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218.

Embodiment 26. The method of embodiment 25, wherein said plant produces a pesticidal polypeptide having pesticidal against a lepidopteran or coleopteran pest.

Embodiment 27. A method for increasing yield in a plant comprising growing in a field a plant or seed thereof having stably incorporated into its genome a DNA construct comprising a promoter that drives expression in a plant operably linked to a nucleotide sequence that encodes a pesticidal polypeptide, wherein said nucleotide sequence comprises:
  (a) a nucleotide sequence that encodes a polypeptide comprising the amino acid sequence of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218; or,
  (b) a nucleotide sequence that encodes a polypeptide comprising an amino acid sequence having at least the percent sequence identity set forth in Table 1 to an amino acid sequence selected from the group consisting of sequences set forth in SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, or 218.

Embodiment 28. A method of obtaining a polynucleotide that encodes an improved polypeptide comprising pesticidal activity is provided, wherein the improved polypeptide has at least one improved property over any one of SEQ ID NOS: 1-218 comprising:
  (a) recombining a plurality of parental polynucleotides comprising SEQ ID NO: 1-218 or an active variant or fragment thereof to produce a library of recombinant polynucleotides encoding recombinant pesticidal polypeptides;
  (b) screening the library to identify a recombinant polynucleotide that encodes an improved recombinant pesticidal polypeptide that has an enhanced property improved over the parental polynucleotide;
  (c) recovering the recombinant polynucleotide that encodes the improved recombinant pesticidal polypeptide identified in (b); and,
  (d) repeating steps (a), (b) and (c) using the recombinant polynucleotide recovered in step (c) as one of the plurality of parental polynucleotides in repeated step (a).

Embodiment 29. An isolated polypeptide having insecticidal activity, comprising:
  (a) a polypeptide comprising an amino acid sequence selected from the group consisting of sequences set forth in SEQ ID NOs: 205, 206, 207, 208, 209, 210, 211, 212, 213, or 214, and further comprising at least 1, 2, 3, 4, 5, 6, 7, 8, 9, 10 or more of the modifications set forth in Table 3; or (b) a polypeptide comprising an amino acid sequence having at least 80%, 85%, 86%, 87%, 88%, 89%, 90%, 91%, 92%, 93%, 94%, 95%, 96%, 97%, 98%, or 99% sequence identity to any one of SEQ ID NOS: 205, 206, 207, 208, 209, 210, 211, 212, 213, or 214 and further comprising at least 1, 2, 3, 4, 5, 6, 7, 8, 9, 10, or more of the modifications set forth in Table 3.

Embodiment 30. The polypeptide of embodiment 29, wherein said polypeptide comprises the amino acid sequence set forth in SEQ ID NO:205, 206, 207, 208, 209, 210, 211, 212, 213, or 214, and further comprising at least 1, 2, 3, 4, 5, 6, 7, 8, 9, 10 or more of the modifications set forth in Table 3.

Embodiment 31. The polypeptide of embodiment 29 or 30, further comprising heterologous amino acid sequences.

Embodiment 32. A composition comprising the polypeptide of any one of embodiments 29, 30, or 31.

Embodiment 33. A recombinant nucleic acid molecule that encodes the polypeptide of any one of embodiments 1 to 3, wherein said recombinant nucleic acid molecule is not the naturally occurring sequence encoding said polypeptide.

Embodiment 34. The recombinant nucleic acid of embodiment 33, wherein said nucleic acid molecule is a synthetic sequence that has been designed for expression in a plant.

Embodiment 35. The recombinant nucleic acid molecule of embodiment 33 or 34, wherein said nucleic acid molecule is operably linked to a promoter capable of directing expression in a plant cell.

Embodiment 36. The recombinant nucleic acid molecule of any one of embodiments 33, 34, or 35, wherein said nucleic acid molecule is operably linked to a promoter capable of directing expression in a bacteria.

Embodiment 37. A host cell that contains the recombinant nucleic acid molecule of any one of embodiments 33, 34, 35 or 36.

Embodiment 38. The host cell of embodiment 37, wherein said host cell is a bacterial host cell.

Embodiment 39. A DNA construct comprising a promoter that drives expression in a plant cell operably linked to a recombinant nucleic acid molecule comprising: (a) a nucleotide sequence that encodes a polypeptide, wherein the polypeptide comprises the amino acid sequence of any one of SEQ ID NOS:205, 206, 207, 208, 209, 210, 211, 212, 213, or 214, and further comprises at least 1, 2, 3, 4, 5, 6, 7, 8, 9, 10 or more of the modifications set forth in Table 3; or (b) a nucleotide sequence that encodes a polypeptide, wherein the polypeptide comprises an amino acid sequence having at least 80%, 85%, 86%, 87%, 88%, 89%, 90%, 91%, 92%, 93%, 94%, 95%, 96%, 97%, 98%, or 99% sequence identity to any one of SEQ ID NOS: 205, 206, 207, 208, 209, 210, 211, 212, 213, or 214 and further comprises at least 1, 2, 3, 4, 5, 6, 7, 8, 9, 10, or more of the modifications set forth in Table 3.

Embodiment 40. The DNA construct of embodiment 39, wherein said nucleotide sequence is a synthetic DNA sequence that has been designed for expression in a plant.

Embodiment 41. A vector comprising the DNA construct of embodiment 39 or 40.

Embodiment 42. A host cell that contains the DNA construct of any one of embodiments 39, 40 or 41 or the vector of embodiment 41.

Embodiment 43. The host cell of embodiment 42, wherein the host cell is a plant cell.

Embodiment 44. A transgenic plant comprising the host cell of embodiment 42 or 43.

Embodiment 45. A composition comprising the host cell of any one of embodiments 37, 38, 42 or 43.

Embodiment 46. The composition of embodiment 45, wherein said composition is selected from the group consisting of a powder, dust, pellet, granule, spray, emulsion, colloid, and solution.

Embodiment 47. The composition of embodiment 45 or 46, wherein said composition comprises from about 1% to about 99% by weight of said polypeptide.

Embodiment 48. A method for controlling a pest population comprising contacting said population with a pesticidal-effective amount of the composition of any one of embodiments 32 or 45-47.

Embodiment 49. A method for killing a pest population comprising contacting said population with a pesticidal-effective amount of the composition of any one of embodiments 32 or 45-47.

Embodiment 50. A method for producing a polypeptide with pesticidal activity, comprising culturing the host cell of any one of embodiments 37, 38, 42, or 43 under conditions in which the nucleic acid molecule encoding the polypeptide is expressed.

Embodiment 51. A plant having stably incorporated into its genome a DNA construct comprising a nucleotide sequence that encodes a protein having pesticidal activity, wherein said nucleotide sequence comprises: (a) a nucleotide sequence that encodes a polypeptide, wherein the polypeptide comprises the amino acid sequence of any one of SEQ ID NOS: 205, 206, 207, 208, 209, 210, 211, 212, 213, or 214, and further comprises at least 1, 2, 3, 4, 5, 6, 7, 8, 9, 10, or more of the modifications set forth in Table 3; or (b) a nucleotide sequence that encodes a polypeptide, wherein the polypeptide comprises an amino acid sequence having at least 80%, 85%, 86%, 87%, 88%, 89%, 90%, 91%, 92%, 93%, 94%, 95%, 96%, 97%, 98%, or 99% sequence identity to any one of SEQ ID NOS: 205, 206, 207, 208, 209, 210, 211, 212, 213, or 214 and further comprises at least 1, 2, 3, 4, 5, 6, 7, 8, 9, 10, or more of the modifications set forth in Table 3.

Embodiment 52. A transgenic seed of the plant of embodiment 51.

Embodiment 53. A method for protecting a plant from an insect pest, comprising expressing in a plant or cell thereof a nucleotide sequence that encodes a pesticidal polypeptide, wherein said nucleotide sequence comprises: (a) a nucleotide sequence that encodes a polypeptide comprising the amino acid sequence of any one of SEQ ID NOS: 205, 206, 207, 208, 209, 210, 211, 212, 213, or 214, and further comprising at least 1, 2, 3, 4, 5, 6, 7, 8, 9, 10 or more of the modifications set forth in Table 3; or (b) a nucleotide sequence that encodes a polypeptide comprising an amino acid sequence having at least 80%, 85%, 86%, 87%, 88%, 89%, 90%, 91%, 92%, 93%, 94%, 95%, 96%, 97%, 98%, 99% sequence identity to any one of SEQ ID NOS: 205, 206, 207, 208, 209, 210, 211, 212, 213, or 214 and further comprising at least 1, 2, 3, 4, 5, 6, 7, 8, 9, 10, or more of the modifications set forth in Table 3.

Embodiment 54. The method of embodiment 53, wherein said plant produces a pesticidal polypeptide having pesticidal activity against a lepidopteran or coleopteran pest.

Embodiment 55. A method for increasing yield in a plant comprising growing in a field a plant or seed thereof having stably incorporated into its genome a DNA construct comprising a promoter that drives expression in a plant operably linked to a nucleotide sequence that encodes a pesticidal polypeptide, wherein said nucleotide sequence comprises: (a) a nucleotide sequence that encodes a polypeptide comprising the amino acid sequence of any one of SEQ ID NOS: 205, 206, 207, 208, 209, 210, 211, 212, 213, or 214, and further comprising at least 1, 2, 3, 4, 5, 6, 7, 8, 9, 10 or more of the modifications set forth in Table 3; or (b) a nucleotide sequence that encodes a polypeptide comprising an amino acid sequence having at least 80%, 85%, 86%, 87%, 88%, 89%, 90%, 91%, 92%, 93%, 94%, 95%, 96%, 97%, 98%, 99% sequence identity to any one of SEQ ID NOS: 205, 206, 207, 208, 209, 210, 211, 212, 213, or 214 and further comprising at least 1, 2, 3, 4, 5, 6, 7, 8, 9, 10, or more of the modifications set forth in Table 3.

Embodiment 56. A method of obtaining a polynucleotide that encodes an improved polypeptide comprising pesticidal activity is provided, wherein the improved polypeptide has at least one improved property over any one of SEQ ID NOS: 205, 206, 207, 208, 209, 210, 211, 212, 213, or 214 comprising: (a) recombining a plurality of parental polynucleotides comprising SEQ ID NO: 205, 206, 207, 208, 209, 210, 211, 212, 213, or 214 or an active variant or fragment thereof to produce a library of recombinant polynucleotides encoding recombinant pesticidal polypeptides; (b) screening the library to identify a recombinant polynucleotide that encodes an improved recombinant pesticidal polypeptide that has an enhanced property improved over the parental polynucleotide; (c) recovering the recombinant polynucleotide that encodes the improved recombinant pesticidal polypeptide identified in (b); and (d) repeating steps (a), (b) and (c) using the recombinant polynucleotide recovered in step (c) as one of the plurality of parental polynucleotides in repeated step (a).

The following examples are offered by way of illustration and not by way of limitation.

EXAMPLES

Example 1. Discovery of Novel Genes by Sequencing and DNA Analysis

Microbial cultures were grown in liquid culture in standard laboratory media. Cultures were grown to saturation (16 to 24 hours) before DNA preparation. DNA was extracted from bacterial cells by detergent lysis, followed by binding to a silica matrix and washing with an ethanol buffer. Purified DNA was eluted from the silica matrix with a mildly alkaline aqueous buffer.

DNA for sequencing was tested for purity and concentration by spectrophotometry. Sequencing libraries were prepared using the Nextera XT library preparation kit according to the manufacturer's protocol. Sequence data was generated on a HiSeq 2000 according to the Illumina HiSeq 2000 System User Guide protocol.

Sequencing reads were assembled into draft genomes using the CLC Bio Assembly Cell software package. Following assembly, gene calls were made by several methods and resulting gene sequences were interrogated to identify novel homologs of pesticidal genes. Novel genes were identified by BLAST, by domain composition, and by pairwise alignment versus a target set of pesticidal genes. A summary of such sequences is set forth in Table 1 and as in SEQ ID NOS: 1-218.

Genes identified in the homology search were amplified from bacterial DNA by PCR and cloned into bacterial expression vectors containing fused in-frame purification tags. Cloned genes were expressed in *E. coli* and purified by column chromatography. Purified proteins were assessed in insect diet bioassay studies to identify active proteins.

Example 2. Heterologous Expression in *E. Coli*

The open reading frame set forth in SEQ ID NO: 209 (APG01037.1) was cloned into an *E. coli* expression vector containing a 6×HIS tag (pHIS). The expression vector was transformed into BL21*RIPL. An LB culture supplemented with kanyamycin was inoculated with a single colony and grown overnight at 37° C. using 0.5% of the overnight culture, a fresh culture was inoculated and grown to logarithmic phase at 37 degrees C. The culture was induced using 250 mM IPTG for 18 hours at 16° C. The cells were pelleted and resuspended in 10 mM Tris pH7.4 and 150 mM NaCl supplemented with protease inhibitors. The protein expression was evaluated by SDS-PAGE.

Example 3. Pesticidal Activity Against Coleopteran and Lepidoptera

Protein Expression: The sequence set forth in SEQ ID NO: 209 (APG01037.1) was expressed in *E. coli* as described in Example 2. 400 mL of LB was inoculated and grown to an OD600 of 0.6. The culture was induced with 250 mM IPTG overnight at 16° C. The cells were spun down and the cell pellet was resuspend in 5 mL of buffer. The resuspension was bead beaten for 2 min at 4° C.

Bioassay: Fall army worm (FAW), corn ear worm (CEW), European corn borer (ECB) southwestern corn borer (SWCB) and diamond backed moth (DBM) eggs were purchased from a commercial insectary (Benzon Research Inc., Carlisle, PA). The FAW, CEW, ECB and BCW eggs were incubated to the point that eclosion would occur within 12 hrs of the assay setup. SWCB and DBM were introduced to the assay as neonate larvae. Assays were carried out in 24-well trays containing multispecies lepidopteran diet (SOUTHLAND PRODUCTS INC., Lake Village, AR). Samples of the bead beaten lysate were applied to the surface of the diet (diet overlay) and allowed to evaporate and soak into the diet. For CEW, FAW, BCW, ECB and SWCB, a 125 µl of bead beaten lysate was added to the diet surface and dried. For DBM, 50 µl of a 1:2 dilution of bead beaten lysate was added to the diet surface. The bioassay plates were sealed with a plate sealing film vented with pin holes. The plates were incubated at 26 C at 65% RH on a 16:8 day:night cycle in a Percival for 5 days. The assays were assessed for level of mortality, growth inhibition and feeding inhibition.

For the western corn rootworm bioassay, the protein construct/lysate was evaluated in an insect bioassay by dispensing 60 µl of a 1:6 dilution of bead beaten lysate to the top surface of diet in well/s of 24-well plate (Cellstar, 24-well, Greiner Bio One) and allowed to dry. Each well contains 500 µl diet (Marrone et al., 1985). Fifteen to twenty neonate larvae were introduced in each well using a fine tip paint brush and the plate was covered with membrane (Viewseal, Greiner Bio One). The bioassay was stored at ambient temperature and scored for mortality, and/or growth/feeding inhibition at day 4. FIG. 2 provides the assay scoring guidelines for the corn root worm bioassay.

For Colorado Potato Beetle (CPB) a cork bore size No. 8 leaf disk was excised from potato leaf and is dipped in the protein bead beaten lysate with 0.1% Tween80 until thoroughly wet and placed on top of filter disk (Millipore, glass fiber filter, 13 mm). Sixty µl dH$_2$O was added to each filter disk and placed in each well of 24-well plate (Cellstar, 24-well, Greiner Bio One). The leaf disk was allowed to dry and five to seven first instar larvae were introduced in each well using a fine tip paint brush. The plate is covered with membrane (Viewseal, Greiner Bio One) and a small hole was punctured in each well of the membrane. The construct was evaluated with four replicates, and scored for mortality and leaf damage on day 3.

The data from the various Lepidoptera bioassays is set forth in Table 4, and the scoring chart for the Lepidoptera bioassay is found in Table 5. As shown, SEQ ID NO: 209 has pesticidal activity against Lepidoptera.

TABLE 4

Pesticidal activity of SEQ ID NO: 209 (APG01037.1) against various Lepidoptera

|  | Plutella xylostella (Px) | Corn Earworm (CEW) | Fall Armyworm (FAW) | Black Cutworm (BCW) | Southwestern Corn Borer (SWCB) | European Corn Borer (ECB) |
|---|---|---|---|---|---|---|
| Cry1Ac | 5 | 5 | 3 | 5 | 5 | 5 |
| SEQ ID NO: 209 (APG01037.1) | 5 | 4 | 3 | 5 | 4 | 5 |
| MBP empty vector | 0 | 0 | 1 | 0 | 1 | 0 |

TABLE 5

Scoring scale for Lepidoptera bioassay

| 0 | no effect |
|---|---|
| 1 | slight stunt |
| 2 | stunt, low feeding |
| 3 | stunt, some mortality, low feeding |
| 4 | stunt, some mortality, very low feeding |
| 5 | stunt, complete mortality, very low feeding |

The data from the various Coleopteran bioassays is set forth in Table 6. The CPB assay was run using a leaf disk. The leaf disk was soaked in bead beaten lysate with 0.1% Tween 80 and then CPB was placed on the leaf to look at both mortality and feeding. The more damage to the leaf, the more feeding. APG01037.1 (SEQ ID NO: 209) had 100% mortality with 2% leaf damage in the CPB bioassay. Data not shown. Negative controls (Buffer and empty vector) had 0% mortality with 65% and 70% leaf damage respectively. This demonstrates APG01037.1 SEQ ID NO: 209 has pesticidal activity against coleopteran.

Data from the corn root worm bioassay is set forth in Table 6. As shown, APG01037.1 (SEQ ID NO: 209) had 100% mortality and negative controls (Cry1Ac, MBP empty vector and buffer) had less than 10% mortality. This demonstrates APG01037.1 SEQ ID NO: 209 has pesticidal activity against Coleopteran.

TABLE 6

Corn Root Worm Bioassay

| APG# | % Mortality | CRW Larva size |
|---|---|---|
| APG01037.1 (SEQ ID NO: 209) | 100 | s, m |
| Buffer | 10 | b |
| MBP empty vector | 6 | b |
| Diet | 14 | b |

CRW larva size: big (b), medium (m), and small (s)

Example 4. Pesticidal Activity Against Hemipteran

Protein Expression: The sequence set forth is SEQ ID NO: 209 was expressed in E. coli as described in Example 2. 400 mL of LB was inoculated and grown to an OD600 of 0.6. The culture was induced with 0.25 mM IPTG overnight at 16 C. The cells were spun down and the cell pellet is re-suspend in 5 mL of buffer. The resuspension was bead beaten for 2 min on ice.

Second instar SGSB were obtained from a commercial insectary (Benzon Research Inc., Carlisle, PA). A 50% v/v ratio of bead beaten lysate sample to 20% sucrose was employed in the bioassay. Stretched parafilm was used as a feeding membrane to expose the SGSB to the diet/sample mixture. The plates were incubated at 25 C:21 C, 16:8 day:night cycle at 65% RH for 5 days.

Mortality is scored for each sample. The controls (MPB empty vector and buffer) showed 0% mortality. The sample containing SEQ ID NO: 209 (APG01037.1) resulted in 100% mortality of the SGSB.

Example 5. Heterologous Expression in E. Coli

Each open reading frame set forth in SEQ ID NO: 205, 206, 207, 208, 209 or active variants or fragments thereof or an open reading frame set forth in Table 1 (SEQ ID NO: 1-204 and SEQ ID NOS: 205-218) or an active variant or fragment thereof was cloned into an E. coli expression vector containing a 6×HIS tag (pHIS). The expression vector was transformed into BL21*RIPL. An LB culture supplemented with kanamycin was inoculated with a single colony and grown overnight at 37 degrees C. using 0.5% of the overnight culture, a fresh culture was inoculated and grown to logarithmic phase at 37 degrees C. The culture was induced using 250 mM IPTG for 18 hours at 16 degrees C. The cells were pelleted and resuspended in 10 mM Tris pH7.4 and 150 mM NaCl supplemented with protease inhibitors. The protein expression was evaluated by SDS-PAGE.

Example 6. Pesticidal Activity Against Coleopteran and Lepidoptera

Protein Expression: Each of SEQ ID NO: 205, 206, 207, 208, 209 or active variants or fragments thereof or an open reading frame set forth in sequence set forth in Table 1 (SEQ ID NO: 1-218) is expressed in E. coli as described in Example 5. 400 mL of LB is inoculated and grown to an OD600 of 0.6. The culture is induced with 0.25 mM IPTG overnight at 16 C. The cells are spun down and the cell pellet is resuspend in 5 mL of buffer. The resuspension is bead beaten for 2 min at 4 degrees C.

Bioassay: Fall army worm (FAW), corn ear worm (CEW), European corn borer (ECB) southwestern corn borer (SWCB) and diamond backed moth (DBM) eggs are purchased from a commercial insectary (Benzon Research Inc., Carlisle, PA). The FAW, CEW, ECB and BCW eggs are incubated to the point that eclosion would occur within 12 hrs of the assay setup. SWCB and DBM are introduced to the assay as neonate larvae. Assays are carried out in 24-well trays containing multispecies lepidopteran diet (SOUTHLAND PRODUCTS INCORPORATED, Lake Village, AR). Samples of the sonicated lysate are applied to the surface of the diet (diet overlay) and allowed to evaporate and soak into the diet. For CEW, FAW, BCW, ECB and SWCB, a 125 µl of sonicated lysate is added to the diet surface and dried. For DBM, 50 µl of a 1:2 dilution of sonicated lysate was added to the diet surface. The bioassay plates are sealed with a plate sealing film vented with pin holes. The plates are incubated at 26 C at 65% RH on a 16:8 day:night cycle in a Percival for 5 days. The assays are assessed for level of mortality, growth inhibition and feeding inhibition.

For the western corn rootworm bioassay, the protein construct/lysate is evaluated as set forth in Example 3. FIG. 2 provides the assay scoring guidelines for the corn root worm bioassay.

For Colorado Potato Beetle (CPB), the protein construct/lysate is evaluated as set forth in Example 3.

Example 7. Pesticidal Activity Against Hemipteran

Protein Expression: Each of the sequences of SEQ ID NO: 205, 206, 207, 208, 209 or active variants or fragments thereof or an open reading frame set forth in set forth in Table 1 (SEQ ID NO: 1-218) is expressed in *E. coli* as described in Example 5. 400 mL of LB is inoculated and grown to an OD600 of 0.6. The culture is induced with 250 mM IPTG overnight at 16 C. The cells are spun down and the cell pellet is re-suspend in 5 mL of buffer. The resuspension is bead beaten for 2 min at 4 degree C.

Second instar SGSB are obtained from a commercial insectary (Benzon Research Inc., Carlisle, PA). A 50% v/v ratio of bead beaten lysate sample to 20% sucrose is employed in the bioassay. Stretched parafilm is used as a feeding membrane to expose the SGSB to the diet/sample mixture. The plates are incubated at 25 C:21 C, 16:8 day:night cycle at 65% RH for 5 days.

Mortality is scored for each sample.

Example 8. Transformation of Soybean

DNA constructs comprising SEQ ID NO: 205, 206, 207, 208, 209 or an active variant of fragment thereof or each of SEQ ID NOS: 1-218 or active variants or fragments thereof operably linked to a promoter active in a plant are cloned into transformation vectors and introduced into *Agrobacterium* as described in U.S. Provisional Application No. 62/094,782, filed Dec. 19, 2015, herein incorporated by reference in its entirety.

Four days prior to inoculation, several loops of *Agrobacterium* are streaked to a fresh plate of YEP* medium supplemented with the appropriate antibiotics** (spectinomycin, chloramphenicol and kanamycin). Bacteria are grown for two days in the dark at 28 C. After two days, several loops of bacteria are transferred to 3 ml of YEP liquid medium with antibiotics in a 125 ml Erlenmeyer flask. Flasks are placed on a rotary shaker at 250 RPM at 28 C overnight. One day before inoculation, 2-3 ml of the overnight culture were transferred to 125 ml of YEP with antibiotics in a 500 ml Erlenmeyer flask. Flasks are placed on a rotary shaker at 250 RPM at 28 C overnight.

Prior to inoculation, the OD of the bacterial culture is checked at OD 620. An OD of 0.8-1.0 indicates that the culture is in log phase. The culture is centrifuged at 4000 RPM for 10 minutes in Oakridge tubes. The supernatant is discarded and the pellet is re-suspended in a volume of Soybean Infection Medium (SI) to achieve the desired OD. The cultures are held with periodic mixing until needed for inoculation.

Two or three days prior to inoculation, soybean seeds are surface sterilized using chlorine gas. In a fume hood, a petri dish with seeds is place in a bell jar with the lid off. 1.75 ml of 12 N HCl is slowly added to 100 ml of bleach in a 250 ml Erlenmeyer flask inside the bell jar. The lid is immediately placed on top of the bell jar. Seeds are allowed to sterilize for 14-16 hours (overnight). The top is removed from the bell jar and the lid of the petri dish is replaced. The petri dish with the surface sterilized is then opened in a laminar flow for around 30 minutes to disperse any remaining chlorine gas.

Seeds are imbibed with either sterile DI water or soybean infection medium (SI) for 1-2 days. Twenty to 30 seeds are covered with liquid in a 100×25 mm petri dish and incubated in the dark at 24 C. After imbibition, non-germinating seeds are discarded.

Cotyledonary explants is processed on a sterile paper plate with sterile filter paper dampened using SI medium employing the methods of U.S. Pat. No. 7,473,822, herein incorporated by reference.

Typically, 16-20 cotyledons are inoculated per treatment. The SI medium used for holding the explants is discarded and replaced with 25 ml of *Agrobacterium* culture (OD 620=0.8–20). After all explants are submerged, the inoculation is carried out for 30 minutes with periodic swirling of the dish. After 30 minutes, the *Agrobacterium* culture is removed.

Co-cultivation plates is prepared by overlaying one piece of sterile paper onto Soybean Co-cultivation Medium (SCC). Without blotting, the inoculated cotyledons is cultured adaxial side down on the filter paper. Around 20 explants can be cultured on each plate. The plates are sealed with Parafilm and cultured at 24 C and around 120 umoles m-2 s-1 (in a Percival incubator) for 4-5 days.

After co-cultivation, the cotyledons are washed 3 times in 25 ml of Soybean Wash Medium with 200 mg/l of cefotaxime and timentin. The cotyledons are blotted on sterile filter paper and then transferred to Soybean Shoot Induction Medium (SSI). The nodal end of the explant is depressed slightly into the medium with distal end kept above the surface at about 45 deg. No more than 10 explants are cultured on each plate. The plates are wrapped with Micropore tape and cultured in the Percival at 24 C and around 120 umoles m-2 s-1.

The explants are transferred to fresh SSI medium after 14 days. Emerging shoots from the shoot apex and cotyledonary node are discarded. Shoot induction is continued for another 14 days under the same conditions.

After 4 weeks of shoot induction, the cotyledon is separated from the nodal end and a parallel cut is made underneath the area of shoot induction (shoot pad). The area of the parallel cut is placed on Soybean Shoot Elongation Medium (SSE) and the explants cultured in the Percival at 24 C and around 120 umoles m-2 s-1. This step is repeated every two weeks for up to 8 weeks as long as shoots continue to elongate.

When shoots reach a length of 2-3 cm, they are transferred to Soybean Rooting Medium (SR) in a Plantcon vessel and incubated under the same conditions for 2 weeks or until roots reach a length of around 3-4 cm. After this, plants are transferred to soil.

Note, all media mentioned for soybean transformation are found in Paz et al. (2010) *Agrobacterium*-mediated transformation of soybean and recovery of transgenic soybean plants; Plant Transformation Facility of Iowa State University, which is herein incorporated by reference in its entirety. (See, agron-www.agron.iastate.edu/ptf/protocol/Soybean.pdf.)

Example 9. Transformation of Maize

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000.times. Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25 degree C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842). DNA constructs designed to express the proteins set forth SEQ ID NO: 205, 206, 207, 208, 209 or the proteins set forth in Table 1 (SEQ ID NO: 1-218) in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25 degree C. in the dark. To avoid unduly damaging beamed explants, they are incubated for at least 24 hours prior to transfer to recovery media. Embryos are then spread onto recovery period media, for about 5 days, 25 degree C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Example 10. Pesticidal Activity Against Nematodes

A. *Heterodera glycine's* (Soybean Cyst Nematode) In-Vitro Assay.

Soybean Cyst Nematodes are dispensed into a 96 well assay plate with a total volume of 100 uls and 100 J2 per well. The protein of interest as set forth in SEQ ID NO: 205, 206, 207, 208, 209 or active variant or fragments thereof or the sequences set forth in Table 1 (any one of SEQ ID NOS: 1-218) is dispensed into the wells and held at room temperature for assessment. Finally, the 96 well plate containing the SCN J2 is analyzed for motility. Data is reported as % inhibition as compared to the controls. Hits are defined as greater or equal to 70% inhibition.

B. *Heterodera glycine's* (Soybean Cyst Nematode) On-Plant Assay

Soybean plants expressing one or more of SEQ ID NO: 205, 206, 207, 208, 209 or active variant or fragments thereof or the sequences set forth in SEQ ID NO: 1-218 or active variant or fragment thereof are generated as described elsewhere herein. A 3-week-old soybean cutting is inoculated with 5000 SCN eggs per plant. This infection is held for 70 days and then harvested for counting of SCN cyst that has developed on the plant. Data is reported as % inhibition as compared to the controls. Hits are defined as greater or equal to 90% inhibition.

C. *Meloidogyne incognita* (Root-Knot Nematode) In-Vitro Assay

Root-Knot Nematodes are dispensed into a 96 well assay plate with a total volume of 100 uls and 100 J2 per well. The protein of interest comprising any one of SEQ ID NO: 205, 206, 207, 208, 209 or active variant or fragments thereof or the sequences set forth in SEQ ID NO: 1-218 or active variant or fragment thereof is dispensed into the wells and held at room temperature for assessment. Finally, the 96 well plate containing the RKN J2 is analyzed for motility. Data is reported as % inhibition as compared to the controls. Hits are defined as greater or equal to 70% inhibition.

D. *Meloidogyne incognita* (Root-Knot Nematode) On-Plant Assay

Soybean plants expressing one or more of SEQ ID NO: 205, 206, 207, 208, 209 or active variant or fragments thereof or the sequences set forth in SEQ ID NO: 1-218 or active variants or fragments thereof are generated as described elsewhere herein. A 3-week-old soybean is inoculated with 5000 RKN eggs per plant. This infection is held for 70 days and then harvested for counting of RKN eggs that have developed in the plant. Data is reported as % inhibition as compared to the controls. Hits are defined as greater or equal to 90% inhibition.

Example 11. Additional Assays for Pesticidal Activity

The various polypeptides set forth in SEQ ID NO: 205, 206, 207, 208, 209 or active variant or fragments thereof or the sequences set forth in SEQ ID NO: 1-218 or active variant or fragment thereof can be tested to act as a pesticide upon a pest in a number of ways. One such method is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) Pesticide bioassays with arthropods, CRC, Boca Raton, Fla. Alternatively, assays are commonly described in the journals Arthropod Management Tests and Journal of Economic Entomology or by discussion with members of the Entomological Society of America (ESA). Any one of SEQ ID NO: 205, 206, 207, 208, 209 or active variant or fragments thereof or the sequences set forth in SEQ ID NOS: 1-218 or active variant or fragment thereof can be expressed and employed in an assay as set forth herein.

Example 12. Pesticidal Activity Against Coleopteran and Lepidoptera

Protein Expression: Each sequence set forth in Table 7 was expressed in E. coli as described in Example 2. 400 mL of LB was inoculated and grown to an OD600 of 0.6. The culture was induced with 0.25 mM IPTG overnight at 16° C. The cells were spun down and the cell pellet was resuspend in 5 mL of buffer. The resuspension was sonicated for 2 min on ice.

Bioassay: Fall armyworm (FAW), corn earworm (CEW), European corn borer (ECB) southwestern corn borer (SWCB) and diamond backed moth (DBM or Px) bioassays were performed as described in Example 6.

For the western corn rootworm bioassay, the protein construct/lysate was evaluated as described in Example 3. For Colorado Potato Beetle (CPB), the protein construct/lysate was evaluated as described in Example 3.

Table 7 provides a summary of pesticidal activity against coleopteran and lepidoptera of the various sequences. Table code: "−" indicates no activity seen; "+" indicates pesticidal activity; "NT" indicates not tested; "S" indicates stunt; "SS" indicates slight stunt; "LF" indicates low feeding, "M" indicates mortality.

TABLE 7

Summary of Pesticidal Activity against Coleopteran and Lepidoptera.

| APG | Seq ID | FAW | CEW | BCW | ECB | SWCB | CPB | Px | WCR Mortality (%) |
|---|---|---|---|---|---|---|---|---|---|
| APG01037.1 | 209 | + | + | + | + | + | + | + | 100 |
| APG00623.0 | 207 | + | + | + | + | + | + | + | 100 |
| APG00556.1 | 206 | + | + | + | + | + | + | + | 100 |
| APG01037.4 | 210 | + | + | + | + | + | + | + | 100 |
| APG01037.5 | 211 | + | + | + | + | + | + | + | 100 |
| APG01037.6 | 212 | + | + | + | + | + | + | + | 100 |
| APG01037.7 | 213 | + | + | + | + | + | + | + | 100 |
| APG01037.8 | 214 | + | + | + | + | + | + | + | 100 |

Example 13. Pesticidal Activity Against Hemipteran

Protein Expression: Each of the sequences set forth in Table 8 was expressed in E. coli as described in Example 2. 400 mL of LB was inoculated and grown to an OD600 of 0.6. The culture was induced with 0.25 mM IPTG overnight at 16° C. The cells were spun down and the cell pellet was re-suspend in 5 mL of buffer. The resuspension was sonicated for 2 min on ice.

Bioassay: Second instar SGSB, brown sting bugs (BSB) and brown marmorated stink bugs (BMSB) were obtained from ABI's insectary. A 50% v/v ratio of sonicated lysate sample to 20% sucrose solution was employed in the bioassay. Stretched parafilm was used as a feeding membrane to expose the SBs to the diet/sample mixture. The plates were incubated at 25° C.: 21° C., 16:8 day:night cycle at 65% RH for 7 days.

Mortality was scored for each sample. The results are set forth in Table 8. A dashed line indicates no mortality was detected. The negative controls (empty vector expressed binding domain and buffer only) both showed no mortality (0 stinkbugs out of 4).

TABLE 8

Summary of Pesticidal Activity against Hemipteran

| APG | Seq ID | SGSB (% mortality) | BSB (% mortality) | BMSB (% mortality) |
|---|---|---|---|---|
| APG01037.1 | 209 | 100 | 100 | 100 |
| APG00623.0 | 207 | 100 | NT | NT |
| APG00556.1 | 206 | 100 | NT | NT |
| APG01037.4 | 210 | 100 | NT | NT |
| APG01037.5 | 211 | 100 | 100 | 100 |
| APG01037.6 | 212 | 100 | NT | NT |
| APG01037.7 | 213 | 100 | NT | NT |
| APG01037.8 | 214 | 100 | NT | NT |

Example 14. Time Course Assay of APG01037.1 (SEO ID NO: 209) Against Southern Green Stink Bugs Twenty-four second instar SGSB were exposed to 250 ppm APG01037.1 (SEQ ID NO: 209) at 50% v/v ratio of purified protein in 20% sucrose as described in Example 13. Assays were scored for mortality on days 4 through 10. At day 7, mortality was 50% higher than the control. FIG. 3 provides the results of the time course assay of APG01037.1 (SEQ ID NO: 209) against SGSB.

Figure 4:
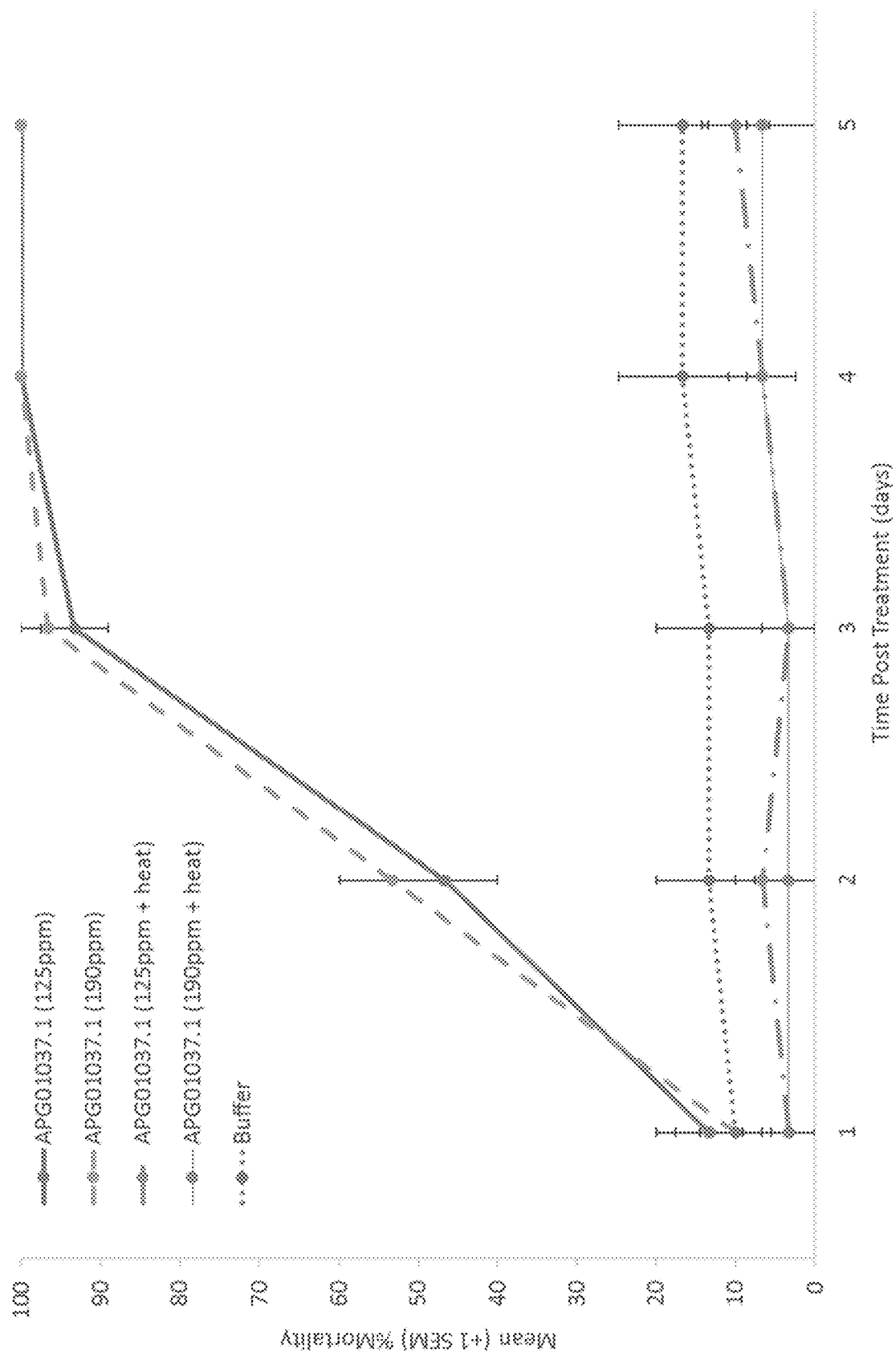
FIG. 4 provides the results of the time course assay of APG01037.1 (SEQ ID NO: 209) against Soybean Aphids.

Example 15. Time Course Assay of APG01037.1 (SEO ID NO: 209) Against Soybean Aphids Five SBA were introduced to each well of a 24-well plate using a paint brush. A membrane was placed over the well and pushed into place with an orifice reducer. APG01037.1 (SEQ ID NO: 209) was pipetted into each orifice reducer through the top opening at a rate of 25% (50 µl sample+150 µl artificial diet). Orifice reducers are sealed using a breathe easy membrane and a yellow plate lid is placed on top of the plate. Reproduction, adult mortality, and honeydew production were recorded on days 1 through 5 post-treatment. The protein was tested at 125 ppm and 190 ppm. At day 3, mortality was at least 80% higher than the control in both concentrations of the protein. FIG. 4 provides the results of the time course assay of APG01037.1 against Soybean Aphids.

Figure 5:
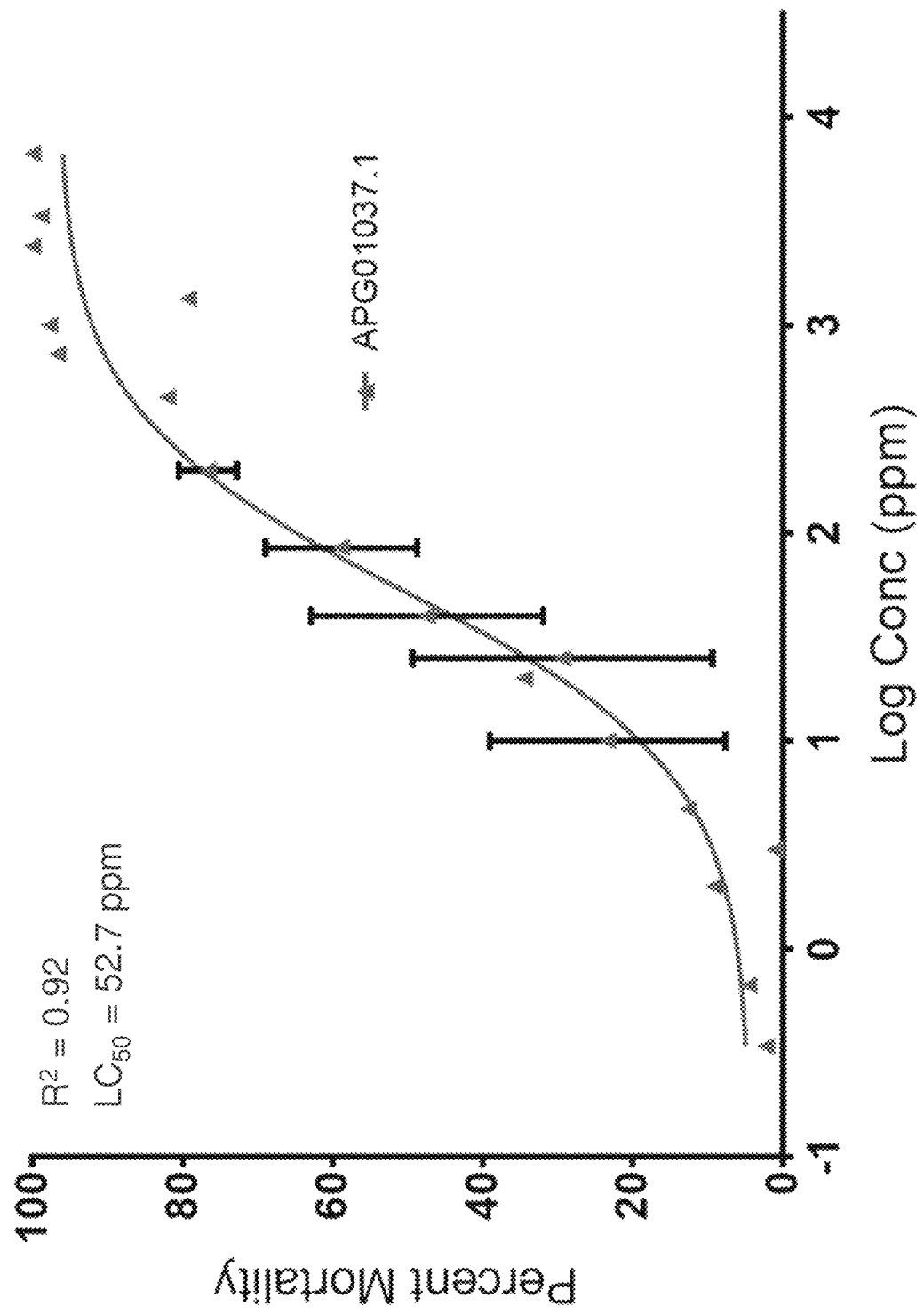
FIG. 5 provides the concentration-response curve of APG01037.1 (SEQ ID NO: 209) against Western Corn Rootworm.

Example 16. Dose-Response Assay of APG01037.1 (SEO ID NO: 209) Against Western Corn Rootworm Approximately 50 WCR neonate larvae were exposed to different doses of APG01037.1 (SEQ ID NO: 209) in the bioassay setup as described in Example 12. The assay was scored at day 5 for mortality. Dose effects were observed. A probit analysis was performed. The LC50 was 52.7 ppm. FIG. 5 provides the concentration-response curve of APG01037.1 (SEQ ID NO: 209) against Western Corn Rootworm.

Figure 6:
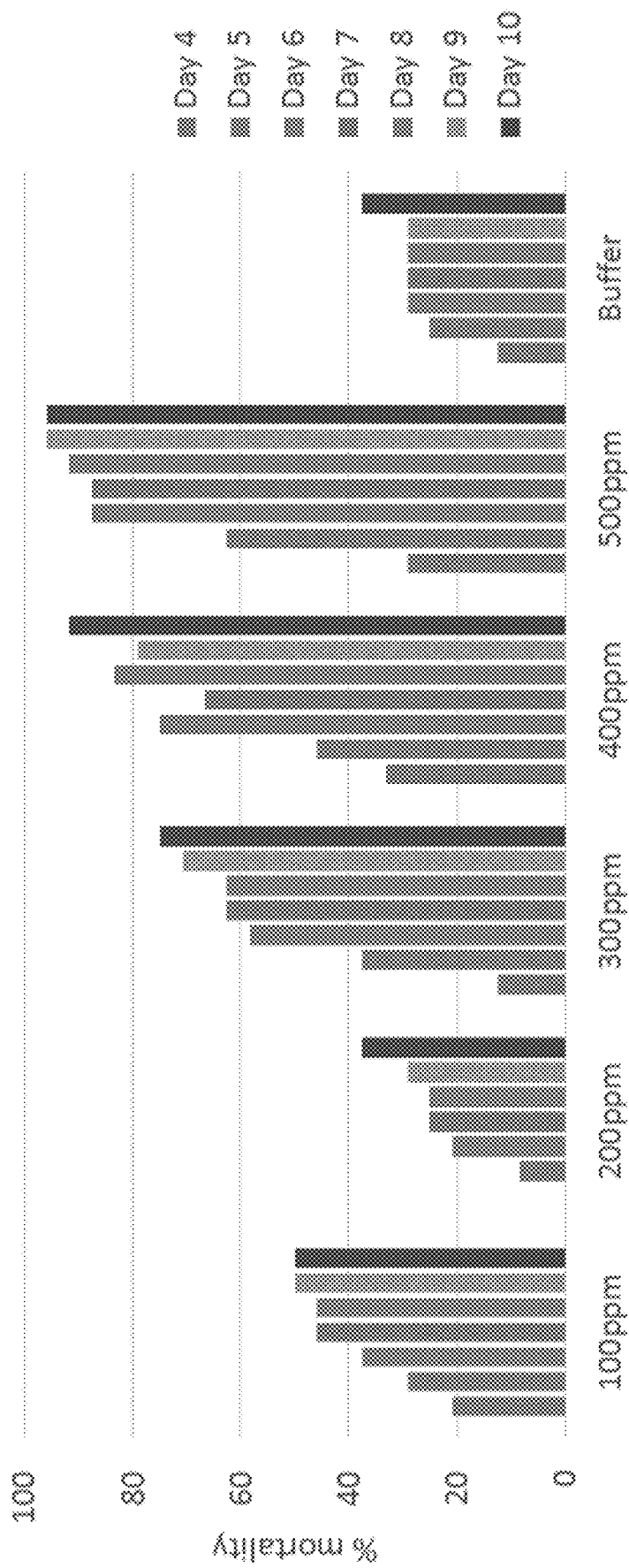
FIG. 6 provides the results of the time course assay of APG01037.5 (SEQ ID NO: 211) against SGSB.

Example 17. Dose-Response Assay of APG01037.5 (SEO ID NO: 211) Against Southern Green Stink Bug Twenty-four second instar SGSB were exposed to different dose of purified APG01037.5 (SEQ ID NO: 211) diluted in 20% sucrose (50% v:v) using the assay format described in Example 13. Assays were scored for mortality on days 5 through 10. Dose effects were observed. FIG. 6 provides the results of the time course assay of APG01037.5 (SEQ ID NO: 211) against SGSB.

Example 18. Pesticidal Activity of APG1037.4-0.8 (SEQ ID NOS: 210, 211, 212, 213, and 214) Against Lygus Bioassay: Lygus eggs were obtained from Ova the Hill Insectary, Columbia, MO. The eggs were incubated to the point that eclosion would occur within 12 hrs of the assay setup. Five to seven eggs were placed into the assay and a 20% v/v ratio of purified protein to diet was employed in the bioassay. Stretched parafilm was used as a feeding membrane to expose the Lygus to the sample/diet mixture. The plates were incubated at 25° C.: 21° C., 16:8 day:night cycle at 65% RH for 5 days.

Figure 7:
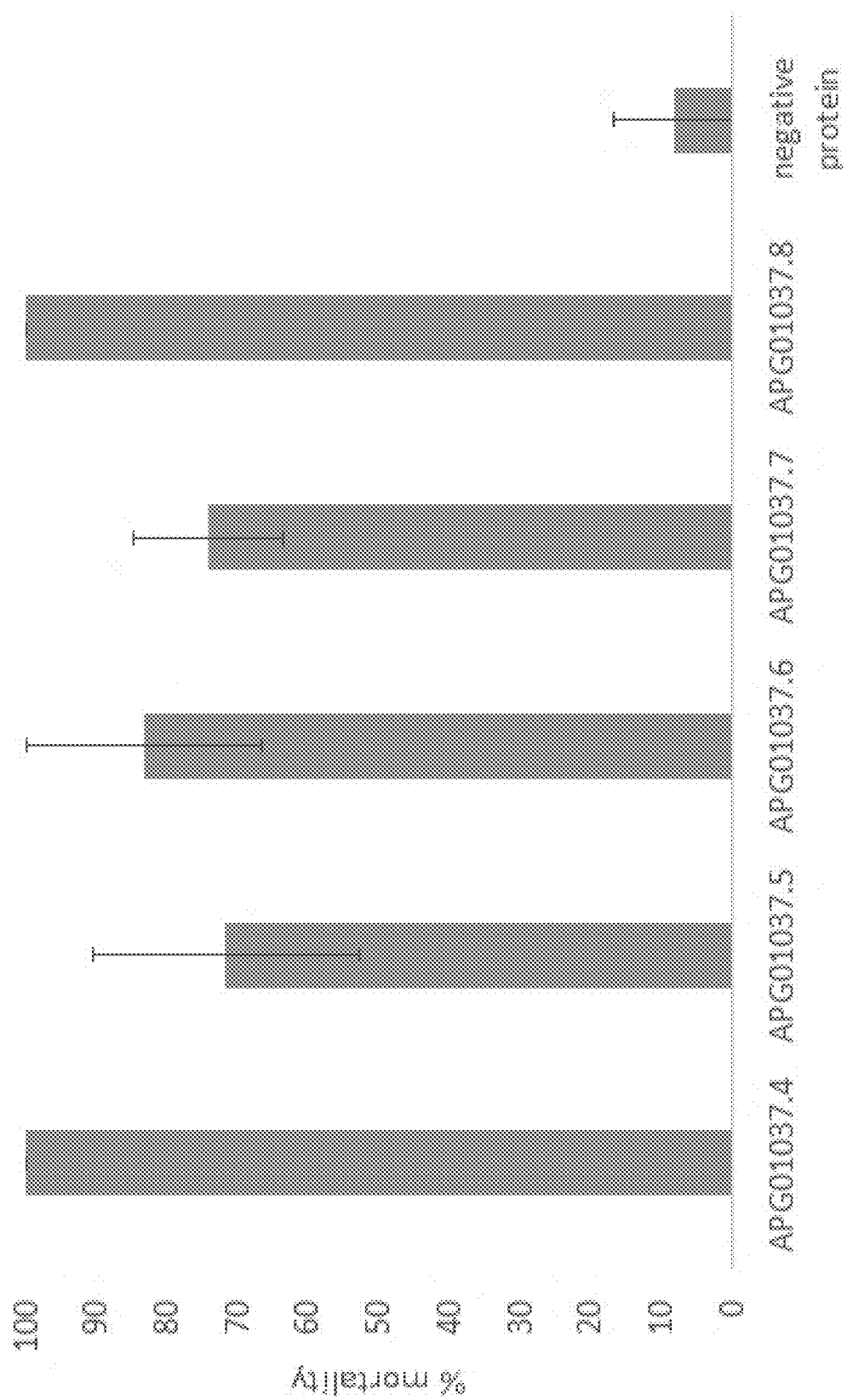
FIG. 7 shows APG1037.4-8 (SEQ ID NO: 210, 211, 212, 213, and 214) had mortality greater than 70% mortality against *Lygus*.

Mortality was scored for each sample. APG1037.4-8 (SEQ ID NO: 210, 211, 212, 213, and 214) had mortality greater than 70% mortality. The results are set forth in FIG. 7.

Example 19. Dose-Response Assay of APG1037.5 Against Fall Armyworm

Newly hatched FAW was introduced to purified APG1037.5 (SEQ ID NO: 211) through diet overlay bioassay as set forth in Example 12. Due to cannibalism only 2 larvae were placed in each well for testing. The assay was scored for mortality, growth inhibition and feeding inhibition. Activity was observed at 300 ppm and greater. The results are set forth in Table 9.

TABLE 9

Dose response APG01037.5 (SEQ ID NO: 211) against Fall armyworm

| Protein dose (ug/cm$^2$) | % Mortality | Mortality rating | Stunting rating |
|---|---|---|---|
| 250 | 0 | 0 | 0 |
| 300 | 75 | 2 | 1 |
| 305 | 75 | 2 | 1 |
| 310 | 67 | 2 | 2 |
| 315 | 100 | 2 | 2 |
| Buffer | 0 | 0 | 0 |

Example 20. Pesticidal Activity Against Coleopteran and Lepidoptera

Protein Expression: The sequence set forth in SEQ ID NO: 1-218 were expressed in E. coli as described in Example 2. 400 mL of LB was inoculated and grown to an OD600 of 0.6. The culture was induced with 250 mM IPTG overnight at 16 C. The cells were spun down and the cell pellet was resuspend in 5 mL of buffer. The resuspension was bead beaten for 2 min at 4 degrees C.

Bioassay: Fall army worm (FAW), corn ear worm (CEW), European corn borer (ECB) southwestern corn borer (SWCB) and diamond backed moth (DBM) eggs were purchased from a commercial insectary (Benzon Research Inc., Carlisle, PA). The FAW, CEW, ECB and BCW eggs were incubated to the point that eclosion would occur within 12 hrs of the assay setup. SWCB and DBM were introduced to the assay as neonate larvae. Assays were carried out in 24-well trays containing multispecies lepidopteran diet (SOUTHLAND PRODUCTS INC., Lake Village, AR). Samples of the bead beaten lysate were applied to the surface of the diet (diet overlay) and allowed to evaporate and soak into the diet. For CEW, FAW, BCW, ECB and SWCB, a 125 µl of bead beaten lysate was added to the diet surface and dried. For DBM, 50 µl of a 1:2 dilution of bead beaten lysate was added to the diet surface. The bioassay plates were sealed with a plate sealing film vented with pin holes. The plates were incubated at 26 C at 65% RH on a 16:8 day:night cycle in a Percival for 5 days. The assays were assessed for level of mortality, growth inhibition and feeding inhibition.

For the western corn rootworm bioassay, the protein construct/lysate was evaluated in an insect bioassay by dispensing 60 µl of a 1:6 dilution of bead beaten lysate to the top surface of diet in well/s of 24-well plate (Cellstar, 24-well, Greiner Bio One) and allowed to dry. Each well contains 500 µl diet (Marrone et al., 1985). Fifteen to twenty neonate larvae were introduced in each well using a fine tip paint brush and the plate was covered with membrane (Viewseal, Greiner Bio One). The bioassay was stored at ambient temperature and scored for mortality, and/or growth/feeding inhibition at day 4. FIG. 2 provides the assay scoring guidelines for the corn root worm bioassay.

For Colorado Potato Beetle (CPB) a cork bore size No. 8 leaf disk was excised from potato leaf and is dipped in the protein bead beaten lysate with 0.1% Tween80 until thoroughly wet and placed on top of filter disk (Millipore, glass fiber filter, 13 mm). Sixty µl dH$_2$O was added to each filter disk and placed in each well of 24-well plate (Cellstar, 24-well, Greiner Bio One). The leaf disk was allowed to dry and five to seven first instar larvae were introduced in each well using a fine tip paint brush. The plate is covered with membrane (Viewseal, Greiner Bio One) and a small hole was punctured in each well of the membrane. The construct was evaluated with four replicates, and scored for mortality and leaf damage on day 3.

The data from the various Lepidoptera and Coleopteran bioassays is set forth in Table 10, and the scoring chart for the Lepidoptera bioassay is found in Table 11. As shown, SEQ ID NO: 209 has pesticidal activity against Lepidoptera.

TABLE 10

Pesticidal activity of the SEQ ID NOS against various Lepidoptera and Coleopterans.

| APG | Seq ID | FAW | CEW | BCW | ECB | SWCB | CPB | Px | WCR Mortality (%) |
|---|---|---|---|---|---|---|---|---|---|
| APG00524.1 | Seq ID 18 | M, SS | — | — | NT | NT | NT | NT | — |
| APG00606.2 | Seq ID 52 | — | — | SS | NT | NT | NT | NT | — |
| APG00785.1 | Seq ID 151 | M, SS | — | SS | NT | NT | NT | NT | — |
| APG00785.2 | Seq ID 152 | M, SS | — | SS | NT | NT | NT | NT | — |
| APG00864.0 | Seq ID 174 | SS | — | SS | NT | NT | NT | NT | — |
| APG00607.0 | Seq ID 54 | M, SS | — | SS | NT | NT | NT | NT | — |
| APG00784.1 | Seq ID 149 | HM, S | — | SS | NT | NT | NT | NT | — |
| APG00960.2 | Seq ID 181 | M, SS | — | SS | NT | NT | NT | NT | — |
| APG00608.1 | Seq ID 56 | SS | — | — | NT | NT | NT | NT | — |
| APG00534.1 | Seq ID 23 | SS | — | SS | NT | NT | NT | NT | — |
| APG00537.1 | Seq ID 29 | M, SS | — | SS | NT | NT | NT | NT | — |
| APG00786.1 | Seq ID 154 | HM, S | — | — | NT | NT | NT | NT | — |
| APG00536.1 | Seq ID 26 | M, SS | — | SS | NT | NT | NT | NT | — |
| APG00536.2 | Seq ID 25 | HM, S | — | SS | NT | NT | NT | NT | — |
| APG00638.0 | Seq ID 65 | SS | SS | SS | NT | NT | NT | NT | — |
| APG00781.0 | Seq ID 146 | — | SS | SS | NT | NT | NT | NT | — |
| APG00528.0 | Seq ID 20 | SS | SS | — | NT | NT | NT | NT | — |
| APG00609.0 | Seq ID 57 | SS | SS | SS | NT | NT | NT | NT | — |
| APG00587.1 | Seq ID 48 | HM, S | SS | — | NT | NT | NT | NT | — |
| APG00637.2 | Seq ID 63 | M, S | SS | — | NT | NI | NT | NT | — |
| APG00735.1 | Seq ID 145 | M, SS | — | SS | NT | NT | NT | NT | — |
| APG00326.1 | Seq ID 2 | M, SS | — | — | NT | NI | NT | NT | — |
| APG00326.2 | Seq ID 3 | M, SS | — | SS | NT | NT | NT | NT | — |
| APG00383.1 | Seq ID 7 | SS | — | — | NT | NI | NT | NT | — |
| APG00687.1 | Seq ID 102 | SS | SS | — | NT | NT | NT | NT | — |
| APG00657.1 | Seq ID 80 | SS | SS | — | NT | NT | NT | NT | — |
| APG00710.2 | Seq ID 131 | SS | — | — | NT | NT | NT | NT | — |
| APG00688.1 | Seq ID 105 | SS | — | — | NT | NT | NT | NT | — |
| APG00805.2 | Seq ID 165 | SS | — | S | NT | NT | NT | NT | — |
| APG00493.1 | Seq ID 9 | HM, S | HM, S | HM, S | NT | NT | +/− | NT | — |
| APG00659.1 | Seq ID 82 | HM, S | M, S | HM, S | NT | NT | — | NT | — |
| APG00494.1 | Seq ID 11 | S | — | SS | NT | NT | NT | NT | — |
| APG01000.1 | Seq ID 197 | S | — | SS | NT | NT | NT | NT | — |
| APG00939.1 | Seq ID 50 | S | — | SS | NT | NT | NT | NT | — |
| APG00661.0 | Seq ID 83 | S | — | — | NT | NT | NT | NT | — |
| APG00513.0 | Seq ID 14 | S | SS | SS | NT | NT | NT | NT | — |
| APG00980.1 | Seq ID 187 | SS | SS | — | NT | NT | NT | NT | — |
| APG00707.1 | Seq ID 128 | SS | — | SS | NT | NT | NT | NT | — |
| APG00495.1 | Seq ID 13 | S | SS | SS | NT | NT | NT | NT | — |
| APG00693.2 | Seq ID 107 | SS | — | — | NT | NT | NT | NT | — |
| APG00679.0 | Seq ID 99 | SS | SS | SS | NT | NT | NT | NT | — |
| APG00679.1 | Seq ID 100 | S | S | — | NT | NT | NT | NT | — |
| APG00514.1 | Seq ID 16 | — | — | SS | NT | NT | NT | NT | — |
| APG00729.1 | Seq ID 143 | HM, S | — | SS | NT | NT | NT | NT | — |
| APG00706.0 | Seq ID 126 | M, SS | — | SS | NT | NT | NT | NT | — |
| APG00622.0 | Seq ID 58 | M, SS | — | M, S | NT | NT | — | NT | — |
| APG00663.0 | Seq ID 87 | SS | — | M, SS | NT | NT | — | NT | — |
| APG00543.0 | Seq ID 31 | M, SS | — | — | NT | NT | NT | NT | — |
| APG00543.1 | Seq ID 32 | M, SS | SS | SS | NT | NT | NT | NT | — |
| APG00705.1 | Seq ID 121 | M, SS | — | M, SS | NT | NT | NT | NT | — |
| APG00705.2 | Seq ID 123 | M, SS | — | M, SS | NT | NT | NT | NT | — |
| APG00705.3 | Seq ID 124 | — | SS | — | NT | NT | NT | NT | — |
| APG00705.4 | Seq ID 122 | M, SS | — | M, SS | NT | NT | NT | NT | — |
| APG00703.2 | Seq ID 119 | M, S | SS | — | NT | NT | NT | NT | — |
| APG01028.1 | Seq ID 201 | — | SS | — | NT | NT | NT | NT | — |
| APG01028.2 | Seq ID 202 | M, SS | SS | — | NT | NT | NT | NT | — |
| APG00695.1 | Seq ID 111 | M, S | SS | — | NT | NT | NT | NT | — |
| APG00695.2 | Seq ID 110 | M, SS | — | — | NT | NT | NT | NT | — |
| APG00555.1 | Seq ID 34 | SS | — | — | NT | NT | NT | NT | — |
| APG00664.1 | Seq ID 90 | M, S | — | — | NT | NT | NT | NT | — |
| APG00677.0 | Seq ID 98 | SS | — | — | NT | NT | NT | NT | — |
| APG01037.1 | Seq ID 209 | M, S | M, S | M, S | M, S | M, S | NT | NT | 80-100 |
| APG00623.0 | Seq ID 207 | M, SS | M, SS | M, S | M, S | HM, S | NT | NT | 80-100 |
| APG00556.1 | Seq ID 206 | M, SS | M, S | M, SS | S | M, S | NT | NT | 80-100 |
| APG00624.1 | Seq ID 61 | SS | — | SS | NT | NT | NT | NT | — |
| APG00675.0 | Seq ID 97 | SS | SS | — | NT | NT | NT | NT | — |
| APG00649.1 | Seq ID 76 | — | — | SS | NT | NT | NT | NT | — |
| APG00988.0 | Seq ID 194 | — | SS | — | NT | NT | NT | NT | — |
| APG00724.0 | Seq ID 137 | — | — | SS | NT | NT | NT | NT | — |
| APG00724.1 | Seq ID 138 | M, SS | SS | SS | NT | NT | NT | NT | — |
| APG00701.1 | Seq ID 114 | — | — | SS | NT | NT | NT | NT | — |
| APG00806.1 | Seq ID 168 | M, SS | — | — | NT | NT | NT | NT | — |
| APG00557.0 | Seq ID 36 | M, S | — | — | NT | NT | NT | NT | — |
| APG00557.1 | Seq ID 37 | SS | — | — | NT | NT | NT | NT | — |

TABLE 10-continued

Pesticidal activity of the SEQ ID NOS against various Lepidoptera and Coleopterans.

| APG | Seq ID | FAW | CEW | BCW | ECB | SWCB | CPB | Px | WCR Mortality (%) |
|---|---|---|---|---|---|---|---|---|---|
| APG00722.0 | Seq ID 136 | HM, S | — | — | NT | NT | NT | NT | — |
| APG00648.0 | Seq ID 73 | SS | — | — | NT | NT | NT | NT | — |
| APG00648.1 | Seq ID 74 | — | — | SS | NT | NT | NT | NT | — |
| APG00674.0 | Seq ID 96 | — | SS | SS | NT | NT | NT | NT | — |
| APG00718.0 | Seq ID 132 | M, S | — | SS | NT | NT | NT | NT | — |
| APG00641.1 | Seq ID 67 | SS | — | — | NT | NT | NT | NT | — |
| APG00912.1 | Seq ID 176 | SS | — | — | NT | NT | NT | NT | — |
| APG00572.0 | Seq ID 46 | S | — | — | NT | NT | NT | NT | — |
| APG00673.1 | Seq ID 95 | — | — | SS | NT | NT | NT | NT | — |
| APG00802.1 | Seq ID 163 | M, S | SS | SS | NT | NT | NT | NT | — |
| APG00810.1 | Seq ID 173 | S | — | — | NT | NT | NT | NT | — |
| APG00644.1 | Seq ID 71 | SS | — | — | NT | NT | NT | NT | — |
| APG00644.2 | Seq ID 72 | M, S | — | SS | NT | NT | NT | NT | — |
| APG01112.0 | Seq ID 204 | HM, S | SS | M, SS | NT | NT | NT | NT | — |
| APG00721.0 | Seq ID 133 | HM, S | SS | M, SS | NT | NT | NT | NT | — |
| APG00721.1 | Seq ID 134 | M, S | SS | SS | NT | NT | NT | NT | — |
| APG00558.1 | Seq ID 39 | HM, S | SS | SS | NT | NT | NT | NT | — |
| APG00558.2 | Seq ID 40 | S | SS | SS | NT | NT | NT | NT | — |

TABLE 11

Scoring scale for Lepidoptera and Coleopteran bioassay

| | |
|---|---|
| — | no effect |
| SS | slight stunt |
| S | Stunt |
| M | Mortality |
| HM | High morality |

Example 21. Pesticidal Activity Against Hemipteran

Protein Expression: The sequence set forth is SEQ ID NO: 160, 9, 82, 58, 59, 87, 209, 207, and 206 was expressed in E. coli as described in Example 2. 400 mL of LB was inoculated and grown to an OD600 of 0.6. The culture was induced with 0.25 mM IPTG overnight at 16 C. The cells were spun down and the cell pellet is re-suspend in 5 mL of buffer. The resuspension was bead beaten for 2 min on ice.

Second instar SGSB were obtained from a commercial insectary (Benzon Research Inc., Carlisle, PA). A 50% v/v ratio of bead beaten lysate sample to 20% sucrose was employed in the bioassay. Stretched parafilm was used as a feeding membrane to expose the SGSB to the diet/sample mixture. The plates were incubated at 25 C:21 C, 16:8 day:night cycle at 65% RH for 5 days.

Mortality is scored for each sample. The controls (MPB empty vector and buffer) showed 0% mortality. The data for SEQ ID NO: 160, 9, 82, 58, 59, 87, 209, 207, and 206 is set forth in Table 12.

TABLE 12

Shows the pesticidal activity of the SEQ ID NOS against Hemipteran

| APG | Seq ID | Tested against SGSB |
|---|---|---|
| APG00801.0 | Seq ID 160 | 50% |
| APG00493.1 | Seq ID 9 | 50% |
| APG00659.1 | Seq ID 82 | 75% |
| APG00622.0 | Seq ID 58 | 75% |
| APG00622.1 | Seq ID 59 | 50% |
| APG00663.0 | Seq ID 87 | 25% |
| APG01037.1 | Seq ID 209 | 100% |
| APG00623.0 | Seq ID 207 | 100% |
| APG00556.1 | Seq ID 206 | 75% |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A polypeptide, comprising:
   (a) a polypeptide comprising an amino acid sequence having at least 95% sequence identity to the amino acid sequence set forth in SEQ ID NO: 82, wherein the polypeptide has pesticidal activity; or
   (b) a polypeptide comprising the amino acid sequence set forth in SEQ ID NO: 82; and
   wherein the polypeptide further comprises a heterologous amino acid sequence chemically linked to the polypeptide.

2. A recombinant nucleic acid molecule encoding a polypeptide comprising:
   (a) an amino acid sequence having at least 95% sequence identity to the amino acid sequence set forth in SEQ ID NO: 82, wherein the polypeptide has pesticidal activity; or
   (b) the amino acid sequence set forth in SEQ ID NO: 82.

3. The recombinant nucleic acid molecule of claim 2, wherein said nucleic acid molecule is a synthetic sequence designed for expression in a plant.

4. A host cell comprising the recombinant nucleic acid molecule of claim 2.

5. The host cell of claim 4, wherein said host cell is a bacterial host cell or a plant cell.

6. A DNA construct comprising a heterologous promoter operably linked to a nucleic acid molecule comprising a nucleotide sequence that encodes a polypeptide comprising
   (a) an amino acid sequence having at least 95% sequence identity to the amino acid sequence set forth in SEQ ID NO: 82, wherein the polypeptide has pesticidal activity; or
   (b) an amino acid sequence set forth in SEQ ID NO: 82.

7. The DNA construct of claim 6, wherein the promoter drives expression in a plant cell or in a bacterial cell.

8. The DNA construct of claim 6, wherein said nucleotide sequence is a synthetic DNA sequence designed for expression in a plant.

9. A vector comprising the DNA construct of claim 6.

10. A host cell comprising the DNA construct of claim 6.

11. A formulation comprising the polypeptide of claim 1.

12. A method for controlling a pest population comprising contacting said pest population with a pesticidal-effective amount of the formulation of claim 11.

13. A method for producing a polypeptide with pesticidal activity comprising culturing the host cell of claim 10 under conditions in which the nucleic acid molecule encoding the polypeptide is expressed.

14. A plant having stably incorporated into its genome a DNA construct comprising the nucleic acid molecule of claim 2.

15. A transgenic seed of the plant of claim 14, wherein said seed has stably incorporated into its genome the DNA construct.

16. The plant of claim 14, wherein the plant is a monocot or a dicot.

17. The plant of claim 16, wherein
   (a) the monocot plant is corn, sorghum, wheat, rice, sugarcane, barley, oats, rye, millet, coconut, pineapple or banana; or
   (b) the dicot plant is sunflower, tomato, crucifers, peppers, potato, cotton, soybean, sugarbeet, tobacco, oilseed rape, sweet potato, alfalfa, safflower, peanuts, cassava, coffee, cocoa, cucumber, lettuce, olive, peas, or tea.

18. A method for protecting a plant from an insect pest, comprising expressing in a plant or cell thereof the nucleic acid molecule of claim 2.

19. The method of claim 18, wherein protecting said plant comprises controlling insect pest damage to said plant.

20. A method for increasing yield in a plant comprising growing in a field a plant or seed thereof having stably incorporated into its genome a DNA construct comprising a promoter that drives expression in a plant operably linked to the nucleic acid molecule of claim 2.

* * * * *